(12) United States Patent
Deciu et al.

(10) Patent No.: US 11,697,849 B2
(45) Date of Patent: *Jul. 11, 2023

(54) METHODS FOR NON-INVASIVE ASSESSMENT OF FETAL GENETIC VARIATIONS THAT FACTOR EXPERIMENTAL CONDITIONS

(71) Applicant: SEQUENOM, INC., San Diego, CA (US)

(72) Inventors: Cosmin Deciu, San Diego, CA (US); Mathias Ehrich, San Diego, CA (US); Dirk J. van den Boom, La Jolla, CA (US); Zeljko Dzakula, San Diego, CA (US)

(73) Assignee: SEQUENOM, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/754,817

(22) Filed: Jan. 30, 2013

(65) Prior Publication Data

US 2013/0150253 A1     Jun. 13, 2013

Related U.S. Application Data

(63) Continuation of application No. PCT/US2013/022290, filed on Jan. 18, 2013, which is a continuation-in-part of application No. PCT/US2012/059123, filed on Oct. 5, 2012.

(60) Provisional application No. 61/589,202, filed on Jan. 20, 2012, provisional application No. 61/709,899, filed on Oct. 4, 2012, provisional application No. 61/663,477, filed on Jun. 22, 2012.

(51) Int. Cl.
  *C40B 20/00* (2006.01)
  *C12Q 1/6883* (2018.01)

(52) U.S. Cl.
  CPC ..... *C12Q 1/6883* (2013.01); *C12Q 2600/156* (2013.01)

(58) Field of Classification Search
  None
  See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,075,212 A | 12/1991 | Rotbart | |
| 5,091,652 A | 2/1992 | Mathies et al. | |
| 5,432,054 A | 7/1995 | Saunders et al. | |
| 5,445,934 A | 8/1995 | Fodor | |
| 5,670,325 A | 9/1997 | Lapidus et al. | |
| 5,720,928 A | 2/1998 | Schwartz et al. | |
| 5,786,146 A | 7/1998 | Herman et al. | |
| 5,928,870 A | 7/1999 | Lapidus et al. | |
| 5,939,598 A | 8/1999 | Kucherlapati et al. | |
| 6,015,714 A | 6/2000 | Baldarelli et al. | |
| 6,090,550 A | 7/2000 | Collinge et al. | |
| 6,100,029 A | 8/2000 | Lapidus et al. | |
| 6,214,558 B1 | 4/2001 | Shuber et al. | |
| 6,214,560 B1 | 4/2001 | Yguerabide et al. | |
| 6,235,475 B1 | 5/2001 | Brenner et al. | |
| 6,258,540 B1 | 7/2001 | Lo et al. | |
| 6,263,286 B1 | 7/2001 | Gilmanshin et al. | |
| 6,403,311 B1 | 6/2002 | Chan | |
| 6,566,101 B1 | 5/2003 | Shuber et al. | |
| 6,617,133 B1 | 9/2003 | Deamer | |
| 6,772,070 B2 | 8/2004 | Gilmanshin et al. | |
| 6,818,395 B1 | 11/2004 | Quake et al. | |
| 6,927,028 B2 | 8/2005 | Dennis et al. | |
| 6,936,422 B2 | 8/2005 | Akeson et al. | |
| 7,005,264 B2 | 2/2006 | Su et al. | |
| 7,169,560 B2 | 1/2007 | Lapidus et al. | |
| 7,279,337 B2 | 10/2007 | Zhu | |
| 7,282,337 B1 | 10/2007 | Harris | |
| 7,947,454 B2 | 5/2011 | Akeson et al. | |
| 7,960,105 B2 | 6/2011 | Schwartz et al. | |
| 7,972,858 B2 | 7/2011 | Meller et al. | |
| 8,195,415 B2* | 6/2012 | Fan .................. | C12Q 1/6869 702/71 |
| 8,688,388 B2 | 4/2014 | Dzakula et al. | |
| 8,700,338 B2* | 4/2014 | Oliphant .............. | C12Q 1/6806 702/19 |
| 2001/0014850 A1 | 8/2001 | Gilmanshin et al. | |
| 2001/0049102 A1 | 12/2001 | Huang et al. | |
| 2002/0006621 A1 | 1/2002 | Bianchi | |
| 2002/0045176 A1 | 4/2002 | Lo et al. | |
| 2002/0110818 A1 | 8/2002 | Chan | |
| 2002/0119469 A1 | 8/2002 | Shuber et al. | |

(Continued)

FOREIGN PATENT DOCUMENTS

| | | |
|---|---|---|
| GB | 2484764 A | 4/2012 |
| WO | WO 00/006770 | 2/2000 |

(Continued)

OTHER PUBLICATIONS

Fan et al. (2010) "Sensitivity of Noninvasive Prenatal Detection of Fetal Aneuploidy from Maternal Plasma Using Shotgun Sequencing Is Limited Only by Counting Statistics" PLoS ONE 5(5):e10439.*
Brown (2001) "A step-by-step guide to non-linear regression analysis of experimental data using a Microsoft Excel spreadsheet" Computer Methods and Programs in Biomedicine 65(3):191-200.*
Leek et al (2010) "Tackling the widespread and critical impact of batch effects in high-throughput data" Nature Reviews Genetics 11:733-739.*
Seo, Songwon (2006) "A Review and Comparison of Methods for Detecting Outliers in Univariate Data Sets" MS Thesis, University of Pittsburgh, available at http://d-scholarship.pitt.edu/7948/.*

(Continued)

*Primary Examiner* — Amy M Bunker
(74) *Attorney, Agent, or Firm* — Loza & Loza, LLP

(57) ABSTRACT

Provided herein are methods, processes and apparatuses for non-invasive assessment of genetic variations.

5 Claims, 16 Drawing Sheets

(56) References Cited

U.S. PATENT DOCUMENTS

| | | |
|---|---|---|
| 2002/0164629 A1 | 11/2002 | Quake et al. |
| 2003/0013101 A1 | 1/2003 | Balasubramanian |
| 2003/0082600 A1 | 5/2003 | Olek et al. |
| 2003/0180779 A1 | 9/2003 | Lofton-Day et al. |
| 2003/0207326 A1 | 11/2003 | Su et al. |
| 2003/0232346 A1 | 12/2003 | Su |
| 2004/0081993 A1 | 4/2004 | Cantor et al. |
| 2004/0110208 A1 | 6/2004 | Chan et al. |
| 2004/0137470 A1 | 7/2004 | Dhallan et al. |
| 2005/0019784 A1 | 1/2005 | Su et al. |
| 2005/0095599 A1 | 5/2005 | Pittaro et al. |
| 2005/0112590 A1 | 5/2005 | Boom et al. |
| 2005/0147980 A1 | 7/2005 | Berlin et al. |
| 2005/0164241 A1 | 7/2005 | Hahn et al. |
| 2005/0227278 A1 | 10/2005 | Wall |
| 2005/0287592 A1 | 12/2005 | Kless |
| 2006/0046258 A1 | 3/2006 | Lapidus et al. |
| 2006/0063171 A1 | 3/2006 | Akeson et al. |
| 2006/0252071 A1 | 11/2006 | Lo et al. |
| 2007/0065823 A1 | 3/2007 | Dressman et al. |
| 2007/0202525 A1 | 8/2007 | Quake et al. |
| 2008/0020390 A1 | 1/2008 | Mitchell et al. |
| 2008/0070792 A1 | 3/2008 | Stoughton et al. |
| 2008/0081330 A1 | 4/2008 | Kahvejian et al. |
| 2008/0138809 A1 | 6/2008 | Kapur et al. |
| 2008/0187915 A1 | 8/2008 | Polonsky et al. |
| 2008/0233575 A1 | 9/2008 | Harris |
| 2009/0026082 A1 | 1/2009 | Berg et al. |
| 2009/0029377 A1 | 1/2009 | Lo et al. |
| 2009/0075252 A1 | 3/2009 | Harris |
| 2009/0129647 A1 | 5/2009 | Dimitrova et al. |
| 2009/0191565 A1 | 7/2009 | Lapidus et al. |
| 2009/0197257 A1 | 8/2009 | Harris |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0112575 A1 | 5/2010 | Fan et al. |
| 2010/0112590 A1 | 6/2010 | Lo et al. |
| 2010/0138165 A1 | 6/2010 | Fan et al. |
| 2010/0151471 A1 | 6/2010 | Faham et al. |
| 2010/0216151 A1 | 8/2010 | Lapidus et al. |
| 2010/0216153 A1 | 8/2010 | Lapidus et al. |
| 2010/0109197 A1 | 9/2010 | Stoddart et al. |
| 2010/0261285 A1 | 10/2010 | Goldstein et al. |
| 2010/0310421 A1 | 12/2010 | Oliver et al. |
| 2010/0330557 A1 | 12/2010 | Yakhini et al. |
| 2011/0086769 A1 | 4/2011 | Oliphant et al. |
| 2011/0159601 A1 | 6/2011 | Golovchenko et al. |
| 2011/0171634 A1 | 7/2011 | Xiao et al. |
| 2011/0174625 A1 | 7/2011 | Akeson et al. |
| 2011/0177498 A1 | 7/2011 | Clarke et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0288780 A1 | 11/2011 | Rabinowitz et al. |
| 2011/0294699 A1 | 12/2011 | Lee et al. |
| 2011/0312503 A1 | 12/2011 | Chuu et al. |
| 2011/0319272 A1 | 12/2011 | Fan et al. |
| 2012/0046877 A1 | 2/2012 | Hyland et al. |
| 2012/0122701 A1 | 5/2012 | Ryan et al. |
| 2012/0165203 A1 | 6/2012 | Quake et al. |
| 2012/0184449 A1* | 7/2012 | Hixson et al. .................. 506/7 |
| 2012/0214678 A1 | 8/2012 | Rava et al. |
| 2012/0264115 A1 | 10/2012 | Rava |
| 2012/0270212 A1 | 10/2012 | Rabinowitz et al. |
| 2012/0270739 A1 | 10/2012 | Rava et al. |
| 2013/0012399 A1 | 1/2013 | Meyers |
| 2013/0022977 A1 | 1/2013 | Lapidus et al. |
| 2013/0034546 A1 | 2/2013 | Rava et al. |
| 2013/0085681 A1 | 4/2013 | Deciu et al. |
| 2013/0096011 A1 | 4/2013 | Rava et al. |
| 2013/0130921 A1 | 5/2013 | Gao et al. |
| 2013/0130923 A1 | 5/2013 | Ehrich et al. |
| 2013/0150253 A1* | 6/2013 | Deciu .................. C12Q 1/6883 506/2 |
| 2013/0196317 A1 | 8/2013 | Lapidus et al. |
| 2013/0237431 A1 | 9/2013 | Lo et al. |
| 2013/0245961 A1 | 9/2013 | Lo et al. |
| 2013/0261983 A1 | 10/2013 | Dzakula et al. |
| 2013/0288244 A1 | 10/2013 | Deciu et al. |
| 2013/0304392 A1 | 11/2013 | Deciu et al. |
| 2013/0309666 A1 | 11/2013 | Deciu et al. |
| 2013/0325360 A1 | 12/2013 | Deciu et al. |
| 2013/0338933 A1 | 12/2013 | Deciu et al. |
| 2014/0065621 A1 | 3/2014 | Mhatre et al. |
| 2014/0100792 A1 | 4/2014 | Deciu et al. |
| 2014/0180594 A1 | 6/2014 | Kim et al. |
| 2014/0235474 A1* | 8/2014 | Tang .................. C12Q 1/6869 506/9 |
| 2014/0242588 A1* | 8/2014 | Van Den Boom ..... G16B 20/00 702/20 |
| 2014/0322709 A1 | 10/2014 | Lapidus et al. |
| 2015/0004601 A1 | 1/2015 | Struble |
| 2015/0005176 A1 | 1/2015 | Kim et al. |
| 2015/0100244 A1 | 4/2015 | Hannum |
| 2015/0167069 A1* | 6/2015 | Schutz .................. C12Q 1/6869 506/2 |
| 2015/0347676 A1 | 12/2015 | Zhao et al. |
| 2016/0034640 A1 | 2/2016 | Zhao et al. |
| 2016/0110497 A1 | 4/2016 | Dzakula et al. |

FOREIGN PATENT DOCUMENTS

| | | |
|---|---|---|
| WO | WO 01/032887 | 5/2001 |
| WO | WO 2002/042496 | 5/2002 |
| WO | WO 03/000920 | 1/2003 |
| WO | WO 03/106620 | 12/2003 |
| WO | WO 05/023091 | 3/2005 |
| WO | WO 06/056480 | 6/2006 |
| WO | WO 07/140417 | 12/2007 |
| WO | WO 07/147063 | 12/2007 |
| WO | WO 08/121828 | 10/2008 |
| WO | WO 09/007743 | 1/2009 |
| WO | WO 09/032779 | 3/2009 |
| WO | WO 09/032781 | 3/2009 |
| WO | WO 09/046445 | 4/2009 |
| WO | WO 10/004265 | 1/2010 |
| WO | WO 10/033578 | 3/2010 |
| WO | WO 10/033639 | 3/2010 |
| WO | WO 10/056728 | 5/2010 |
| WO | WO 10/059731 | 5/2010 |
| WO | WO 10/065470 | 6/2010 |
| WO | WO 10/115016 | 10/2010 |
| WO | WO 11/034631 | 3/2011 |
| WO | WO 11/038327 | 3/2011 |
| WO | WO 11/050147 | 4/2011 |
| WO | WO 2011/057094 | 5/2011 |
| WO | WO 11/087760 | 7/2011 |
| WO | WO 11/090556 | 7/2011 |
| WO | WO 11/090558 | 7/2011 |
| WO | WO 11/090559 | 7/2011 |
| WO | WO 11/091063 | 7/2011 |
| WO | WO 11/102998 | 8/2011 |
| WO | WO 11/143659 | 11/2011 |
| WO | WO 11/146632 | 11/2011 |
| WO | WO 2012/012703 | 1/2012 |
| WO | WO 12/088348 | 6/2012 |
| WO | WO 12/088456 | 6/2012 |
| WO | WO 12/108920 | 8/2012 |
| WO | WO 2012/103031 | 8/2012 |
| WO | WO 2012/118745 | 9/2012 |
| WO | WO 12/177792 | 12/2012 |
| WO | WO 2013/000100 | 1/2013 |
| WO | WO 13/052907 | 4/2013 |
| WO | WO 13/052913 | 4/2013 |
| WO | WO 2013/055817 | 4/2013 |
| WO | WO 13/109981 | 7/2013 |
| WO | WO 2013/177086 | 11/2013 |
| WO | WO 13/192562 | 12/2013 |
| WO | WO 2014/039556 | 3/2014 |
| WO | WO 14/055774 | 4/2014 |

(56) References Cited

FOREIGN PATENT DOCUMENTS

| WO | WO 14/055790 | 4/2014 |
|---|---|---|
| WO | WO 14/116598 | 7/2014 |
| WO | WO 2014/165596 | 10/2014 |
| WO | WO 2014/190286 | 11/2014 |
| WO | WO 2014/205401 | 12/2014 |
| WO | WO 2015/026967 | 2/2015 |
| WO | WO 2015/040591 | 3/2015 |
| WO | WO 2015/051163 | 4/2015 |
| WO | WO 2015/054080 | 4/2015 |
| WO | WO 2015/183872 | 12/2015 |
| WO | WO 16/019042 | 2/2016 |
| WO | WO 2017/087206 | 5/2017 |

OTHER PUBLICATIONS

Chiu et al. (2011) "Non-invasive prenatal assessment of trisomy 21 by multiplexed maternal plasma DNA sequencing: large scale validity study" BMJ 342:c7401 Web Appendices.*
Chiu et al., Noninvasive Prenatal Diagnosis of Fetal Chromosomal Aneuploidy by Massively Parallel Genomic Sequencing of DNA in Maternal Plasma, PNAS, 2008, 105(51), 20458-20463. (Year: 2008).*
Benjamini et al., Summarizing and Correcting the GC Content Bias in High-Throughput Sequencing, Nucleic Acids Research, Feb. 2012, 40(10), 1-14. (Year: 2012).*
Risso et al., GC-Content Normalization for RNA-Seq Data, BMC Bioinformatics, Dec. 2011, 12(480), 1-17. (Year: 2011).*
Hout et al., Multidimensional Scaling, WIREs Cognitive Science, 2012, 4, 93-103. (Year: 2012).*
Holt et al., The New Paradigm of Flow Cell Sequencing, Genome Research, 2008, 18, 839-846. (Year: 2008).*
Lew et al., Instrument-To-Instrument Variability in the Vi-Cell Automated Viability Analyzer, Coulter, 2012, 1-9. (Year: 2012).*
Hansen et al., Removing Technical Variability in RNA-Seq DATA Using Conditional Quantile Normalization, Biostatistics, 2012, 13(2), 204-216. (Year: 2012).*
Risso et al., GC-Content Normalization for RNA-Seq Data, BMC Bioinformatics, 12(480), 1-17. (Year: 2011).*
Chen et al., Noninvasive Prenatal Diagnosis of Fetal Trisomy 18 and Trisomy 13 by Maternal Plasma DNA Sequencing, PLoS One, 2011, 6(7), 1-7. (Year: 2011).*
International Search Report and Written Opinion date Sep. 18, 2013 in International Application No. PCT/US2013/047131, filed on Jun. 21, 2013 and published as WO 2013/192562 dated Dec. 27, 2013.
International Search Report and Written Opinion dated Dec. 13, 2013 in International Application No. PCT/US2013/063287, filed Oct. 3, 2013.
Davanos et al., "Relative quantitation of cell-free fetal DNA in maternal plasma using autosomal DNA markers" Clinica Chimica Acta (2011) 412:1539-1543.
Office Action dated Jan. 17, 2014 in U.S. Appl. No. 13/333,842, filed Dec. 21, 2011 and published as US 2012/0184449 dated Jul. 19, 2012.
Zhou et al., "Detection of DNA number abnormality by microarray expression analysis" Hum. Genet. (2004) 114:464-467.
Office Action dated Jan. 27, 2014 in U.S. Appl. No. 13/829,164, filed Mar. 14, 2013 and published as US 2013-0288244 dated Oct. 31, 2014.
Office Action dated Jan. 30, 2014 in U.S. Appl. No. 13/933,935, filed Jul. 2, 2013 and published as US 2013-0304392 dated Nov. 14, 2013.
International Preliminary Report on Patentability dated Feb. 27, 2014 in International Application No. PCT/US2012/059123, filed on Oct. 5, 2012 and published as WO 2013/052913 dated Apr. 11, 2013.
Office Action dated Dec. 26, 2013 in U.S. Appl. No. 13/797,508, filed Mar. 12, 2013 and published as US 2013-0261983 dated Oct. 3, 2013.
International Preliminary Report on Patentability and Written Opinion dated Jan. 9, 2014 in International Application No. PCT/US2012/043388, filed on Jun. 20, 2012 and published as WO 2012/177792 dated Dec. 27, 2012.
Zhong et al., "Cell-free fetal DNA in the maternal circulation does not stem from the transplacental passage of fetal erythroblasts" Molecular Human Reproduction (2002) 8(9):864-870.
Office Action dated Oct. 16, 2013 in U.S. Appl. No. 13/933,935, filed Jul. 2, 2013 and published as US 2013-0304392 dated Nov. 14, 2013.
Office Action dated Oct. 17, 2013 in U.S. Appl. No. 13/669,136, filed on Nov. 5, 2012 and published as US 2013-0085681 dated Apr. 4, 2013.
Office Action dated Oct. 18, 2013 in U.S. Appl. No. 13/656,328, filed Oct. 19, 2012 and published as US 2013-0103320 dated Apr. 25, 2013.
Invitation to Pay Additional Fees and Partial Search Report dated: Jul. 3, 2013 in International Application No. PCT/US2012/059123 filed: Oct. 5, 2012 and published as: WO/2013/052913 dated Apr. 11, 2013.
International Search Report and Written Opinion dated Jul. 4, 2013 in International Application No. PCT/US2013/022290 filed: Jan. 18, 2013, and published as: WO/2013/109981 dated Jul. 25, 2013.
Office Action dated May 3, 2013 in U.S. Appl. No. 13/333,842, filed Dec. 21, 2011 and published as:-2012/0184449 dated Jul. 19, 2012.
Office Action dated Aug. 22, 2013 in U.S. Appl. No. 13/797,508, filed Mar. 12, 2013.
Aston et al. "Optical mapping: an approach for fine mapping," (1999) Methods Enzymol. 303:55-73.
Aston et al. "Optical mapping and its potential for large-scale sequencing project," (1999) Trends Biotechnol. 17(7):297-302.
Berger et al., "Universal bases for hybridization, replication and chain termination," (2000) Nucleic Acids Res. 28(15): 2911-2914.
Bergstrom et al. "Synthesis, Structure, and Peoxyribonucleic Acid Sequencing with a Universal Nucleoside: 1-(2'-Deoxy-.beta.-D-ribofuranosyl)-3-nitropyrrole," (1995) J. Am. Chem. Soc. 117, 1201-1209.
Brown and Lin "Synthesis and duplex stability of oligonucleotides containing adenine-guanine analogues," (1991) Carbohydrate Research 216, 129-139.
Burlingame et al. Anal. Chem. 70:647R-716R (1998).
Carlson et al., "Molecular Definition of 22q11 Deletions in 151 Velo-Cardio-Facial Syndrome Patients," The American Journal of Human Genetics, vol. 61, Issue 3, 620-629, Sep. 1, 1997.
Chan et al. "Size Distribution of Maternal and Fetal DNA in Maternal Plasma," (2004) Clin. Chem. 50:88-92.
Chiang et al., High-resolution mapping of number alterations with massively parallel sequencing, Nat Methods. Jan. 2009 ; 6(1): 99-103.
Cohen et al. (2005): GC Composition of the Human Genome: In Search of Isochores. Mole Biol. Evol. 22(5):1260-1272.
Dan et al., "Prenatal detection of aneuploidy and imbalanced chromosomal arrangements by massively parallel sequencing," PLoS ONE 7(2): e27835, 2012.
Donoho and Johnstone (1995), "WaveLab and Reproducible Research," Stanford University, Stanford CA 94305, USA, pp. 1-27.
Haar, Alfred (1910) "Zur Theorie der orthogonalen Funktionensysteme", Mathematische Annalen 69 (3): 331-371.
Hsu, S. Self, D. Grove, T. Randolph, K. Wang, J. Delrow, L. Loo, and P. Porter, "Denoising array-based comparative genomic hybridization data using wavelets", Biostatistics (Oxford, England), vol. 6, No. 2, pp. 211-226, 2005.
Husdson et al., "An STA-Based Map of the Human Genome," Science, vol. 270, pp. 1945-1954 (1995).
Hupe,P. et al. (2004) "Analysis of array CGH data: from signal ratio to gain and loss of DNA regions", Bioinformatics, 20, 3413-3422.
Jing et al. (1998) Proc Natl Acad Sci USA. 95(14):8046-51.
Jorgez et al.. "Improving Enrichment of Circulating Fetal DNA for genetic Testing: Size Fractionatiion Followed by Whole Gene Amplification." Fetal Diagnosis and Therapy, Karger Basel, CH, vol. 25, No. 3 Jan. 1, 2009, pp. 314-319.
Jurinke et al. (2004) Mol. Biotechnol. 26, 147-164.
Lai et al. (1999) Nat Genet. 23(3):309-313.

(56) References Cited

OTHER PUBLICATIONS

Lai et al., (2005). Comparative analysis of algorithms for identifying amplifications and deletions in array CGH data. Bioinformatics, 21, 19:3763-3770.
Lin and Brown, "Synthesis and duplex stability of oligonucleotides containing cytosine-thymine analogues.," (1989) Nucleic Acids Res. 17, 10373-10383.
Lin and Brown "Synthesis of oligodeoxyribonucleotides containing degenerate bases and their use as primers in the polymerase chain reaction," (1992) Nucleic Acids Res. 20, 5149-5152.
Lo YM, et al.(1998) Am J Hum Genet 62:768-775.
Loakes and Brown "5-Nitroindole as an universal base analogue," (1994) Nucleic Acids Res. 22, 4039-4043.
WaveThresh (WaveThresh : Wavelets statistics and transforms [online],[retrieved on Apr. 24, 2013], retrieved from the internet <URL:*>http://cran.r-project.org/web/packages/wavethresh/index.html<>) and a detailed description of WaveThresh ( Package 'wavethresh' [online, PDF], Apr. 2, 2013, [retrieved on Apr. 24, 2013], retrieved from the internet <URL:*>http://cran.r-project.org/web/packages/wavethresh/wavethresh.pdf<>).
Nason, G.P. (2008) "Wavelet methods in Statistics", table of contents. R. Springer, New York ISBN: 978-0-387-75960-9 (Print) 978-0-387-75961-6 (Online).
Nichols et al. "A universal nucleoside for use at ambiguous sites in DNA primers," (1994) Nature 369, 492-493.
Olshen et al., "Circular binary segmentation for the analysis of array-based DNA number data," Biostatistics. Oct. 2004;5(4):557-572.
Sambrook and Russell, Molecular Cloning: A Laboratory Manual 3d ed., 2001, Table of Contents.
Schwinger et al., "Clinical utility gene card for: DiGeorge syndrome, velocardiofacial syndrome, Shprintzen syndrome, chromosome 22q11.2 deletion syndrome (22q11.2, TBX1)," European Journal of Human Genetics (2010) 18, published online Feb. 3, 2010.
Srinivasan et al., Noninvasive Detection of Fetal Subchromosome Abnormalities via Deep Sequencing of Maternal Plasma, The American Journal of Human Genetics (2013) Feb. 7, 2013;92(2):167-76.
DNAcopy [online],[retrieved on Apr. 24, 2013], retrieved from the internet <URL:*>http://bioconductor.org/packages/2.12/bioc/html/DNAcopy.html.
Venkatraman, ES, Olshen, AB (2007) "A faster circular binary segmentation algorithm for the analysis of array CGH data", Bioinformatics, 23, 6:657-63.
Verbeck et al. in the Journal of Biomolecular Techniques (vol. 13, Issue 2, 56-61), 2002.
Wang and S. Wang, "A novel stationary wavelet denoising algorithm for array-based DNA number data", International Journal of Bioinformatics Research and Applications, vol. 3, No. 2, pp. 206-222, 2007.
Willenbrock H, Fridlyand J. A comparison study: applying segmentation to array CGH data for downstream analyses. Bioinformatics (2005) Nov. 15;21(22):4084-91.
Wright et al., "The use of cell-free fetal nucleic acids in maternal blood for non-invasive diagnosis," Human Reproduction Update 2009, vol. 15, No. 1, pp. 139-151.
Zhang et al., "A single cell level based method for number variation analysis by low coverage massively parallel sequencing," PLoS ONE 8(1): e54236. doi:10.1371/journal.pone.0054236, 2013.
Adinolfi et al., "Rapid detection of aneuploidies by microsatellite and the quantitative fluorescent polymerase chain reaction." Prenat Diagn. Dec. 1997;17(13):1299-311.
Akeson et al., "Microsecond Time-Scale Discrimination Among Polycytidylic Acid, Polyadenylic Acid, and Polyuridylic Acid as Homopolymers or as Segments Within Single RNA Molecules," Biophysical Journal vol. 77 Dec. 1999 3227-3233.
Alkan, C., et al., Personalized number and segmental duplication maps using nextgeneration sequencing. Nat Genet, 2009. 41(10): p. 1061-7.
Amicucci et al., "Prenatal Diagnosis of Myotonic Dystrophy Using Fetal DNA Obtained from Maternal Plasma," Clin. Chem. 46:301-302, 2000.
Anantha et al., "Porphyrin binding to quadrupled T4G4." Biochemistry. Mar. 3, 1998;37(9):2709-14.
Armour et al., "Measurement of locus number by hybridisation with amplifiable probes." Nucleic Acids Res. Jan. 15, 2000;28(2):605-9.
Armour et al., "The detection of large deletions or duplications in genomic DNA." Hum Mutat. Nov. 2002;20(5):325-37.
Ashkenasy et al., "Recognizing a Single Base in an Individual DNA Strand: A Step Toward Nanopore DNA Sequencing," Angew Chem Int Ed Engl. Feb. 18, 2005; 44(9): 1401-1404.
Ashoor, et al., (2012): Chromosome-selective sequencing of maternal plasma cell-free DNA for first trimester detection of trisomy 21 and trisomy 18, American Journal of Obstetrics and Gynecology, doi: 10.1016/j.ajog.2012.01.029.
Avent et al., "Non-invasive diagnosis of fetal sex; utilization of free fetal DNA in maternal plasma and ultrasound," Prenatal Diagnosis, 2006, 26: 598-603.
Beaucage and Caruthers, Tetrahedron Letts., 22:1859-1862, 1981.
Brizot et al., "Maternal serum hCG and fetal nuchal translucency thickness for the prediction of fetal trisomies in the first trimester of pregnancy." Br J Obstet Gynaecol. Feb. 1995;102(2):127-32.
Brizot et al., "Maternal serum pregnancy-associated plasma protein A and fetal nuchal translucency thickness for the prediction of fetal trisomies in early pregnancy." Obstet Gynecol. Dec. 1994;84(6):918-22.
Brown, L., et al., Validation of QF-PCR for prenatal aneuploidy screening in the United States. Prenat Diagn, 2006. 26(11): p. 1068-74.
Brünger, "Free R value: a novel statistical quantity for assessing the accuracy of crystal structures," Nature 355, 472-475 (Jan. 30, 1992); doi:10.1038/355472a0.
Bullard et al., "Evaluation of statistical methods for normalization and differential expression in mRNA-Seq experiments," Bioinformatics 2010, 11:94, pp. 1-13.
Campbell et al., "Identification of somatically acquired rearrangements in cancer using genome-wide massively parallel paired-end sequencing." Nat Genet. Jun. 2008;40(6):722-9. doi: 10.1038/ng.128. Epub Apr. 27, 2008.
Canick et al., "DNA sequencing of maternal plasma to identify Down syndrome and other trisomies in multiple gestations," Prenat Diagn. May 14, 2012:1-5.
Canick, et al., "A New Prenatal Blood Test for Down Syndrome (RNA)," Jul. 2012 found on the internet at: clinicaltrials.gov/show/A15NCT00877292.
Chen et al., "Noninvasive Prenatal Diagnosis of Fetal Trisomy 18 and Trisomy 13 by Maternal Plasma DNA Sequencing," PLoS ONE, Jul. 2011, vol. 6, Issue 7, e21791, pp. 1-7.
Chim et al. (2008). "Systematic search for placental DNA-methylation markers on chromosome 21: toward a maternal plasma-based epigenetic test for fetal trisomy 21." Clin Chem 54(3): 500-11.
Chiu et al. "Maternal plasma DNA analysis with massively parallel sequencing by ligation for noninvasive prenatal diagnosis of trisomy 21." Clin Chem 56(3): 459-63, 2010.
Chiu et al. (2008). "Noninvasive prenatal diagnosis of fetal chromosomal aneuploidy by massively parallel genomic sequencing of DNA in maternal plasma." Proc Natl Acad Sci U S A 105(51): 20458-20463.
Chiu et al., "Non-invasive prenatal assessment of trisomy 21 by multiplexed maternal plasma DNA sequencing: large scale validity study," BMJ 2011;342:c7401, 1-9.
Chiu et al., "Prenatal exclusion of thalassaemia major by examination of maternal plasma," Lancet 360:998-1000, 2002.
Chu et al. (2009). "Statistical model for whole genome sequencing and its application to minimally invasive diagnosis of fetal genetic disease." Bioinformatics 25(10): 1244-50.
Costa et al., "New Strategy for Prenatal Diagnosis of X-Linked Disorders" N. Engl. J. Med. 346:1502, 2002.
Current Protocols in Molecular Biology, John Wiley&Sons, N.Y. 6.3.1-6.3.6(1989).

(56) References Cited

OTHER PUBLICATIONS

D'Alton ME., "Prenatal diagnostic procedures." Semin Perinatol. Jun. 1994;18(3):140-62.
Data Sheet: Illumina Sequencing: TruSeq RNA and DNA Sample Preparation Kits v2, Publication No. 970-2009-039 Apr. 27, 2011.
Deamer et al., "Nanopores and Nucleic Acids: Prospects for ultrarapid sequencing." Focus Tibtech Apr. 2000, (vol. 18) pp. 147-151.
Derrien et al. (2012) Fast Computation and Applications of Genome Mappability. PLoS ONE 7(1): e30377, doi:10.1371/journal.pone.0030377.
Ding et al., "A high-throughput gene expression analysis technique using competitive PCR and matrix-assisted laser desorption ionization time-of-flight MS." Proc Natl Acad Sci U S A. Mar. 18, 2003;100(6):3059-64. Epub Mar. 6, 2003.
Dohm et al., "Substantial biases in ultra-short read data sets from high-throughput DNA sequencing," Nucleic Acids Res. Sep. 2008;36(16):e105. Epub Jul. 26, 2008.
Edelmann, L., et al., A common molecular basis for rearrangement disorders on chromosome 22q11. Hum Mol Genet, 1999. 8(7): p. 1157-67.
Egger et al., "Reverse transcription multiplex PCR for differentiation between polio- and enteroviruses from clinical and environmental samples." J Clin Microbiol. Jun. 1995;33(6):1442-7.
Ehrich et al., Noninvasive detection of fetal trisomy 21 by sequencing of DNA in maternal blood: a study in a clinical setting, American Journal of Obstetrics and Gynecology—Amer J Obstet Gynecol, vol. 204, No. 3, pp. 205.e1-205.e11, 2011 DOI: 10.1016/j.
Eiben et al., "First-trimester screening: an overview." J Histochem Cytochem. Mar. 2005;53(3):281-3.
Ensenauer, R.E., et al., Microduplication 22q11.2, an emerging syndrome: clinical, cytogenetic, and molecular analysis of thirteen patients. Am J Hum Genet, 2003. 73(5): p. 1027-40.
Fan et al., (2008). "Noninvasive diagnosis of fetal aneuploidy by shotgun sequencing DNA from maternal blood." Proc Natl Acad Sci U S A 105(42): 16266-71.
Gebhard et al., "Genome-wide profiling of CpG methylation identifies novel targets of aberrant hypermethylation in myeloid leukemia." Cancer Res. Jun. 15, 2006;66(12):6118-28.
Goya, R., et al. (2010) SNVMix: predicting single nucleotide variants from nextgeneration sequencing of tumors, *Bioinformatics*, 26, 730-736.
Hahn et al., "Cell-free nucleic acids as potential markers for preeclampsia." Placenta. Feb. 2011;32 Suppl:S17-20. doi: 10.1016/j.placenta.2010.06.018.
Harris et al., "Single-molecule DNA sequencing of a viral genome." Science. Apr. 4, 2008;320(5872):106-9. doi: 10.1126/science.1150427.
Hill, Craig, "Gen-Probe Transcription-Mediated Amplification: System Principles," Jan. 1996 httl://www.gen-probe.com/pdfs/tma_whiteppr.pdf.
Hulten et al., "Rapid and simple prenatal diagnosis of common chromosome disorders: advantages and disadvantages of the molecular methods FISH and QF-PCR." Reproduction. Sep. 2003;126(3):279-97.
Human Genome Mutations, D. N. Cooper and M. Krawczak, BIOS Publishers, 1993.
Innis et al., PCR Protocols: A Guide to Methods and Applications, Innis et al., eds, 1990.
International Human Genome Sequencing Consortium Initial sequencing and analysis of the human genome Nature vol. 409, pp. 860-921 (2001).
James/James "Mathematics Dictionary," Fifth Edition, Chapman & Hall, International Thomson Publishing, 1992, pp. 266-267_270.
Jensen et al. "High-Throughput Massively Parallel Sequencing for Fetal Aneuploidy Detection from Maternal Plasma" Mar. 6, 2013. PLoS ONE 8(3): e57381.
Jensen et al., "Detection of microdeletion 22q11.2 in a fetus by next-generation sequencing of maternal plasma," Clin Chem. Jul. 2012;58(7):1148-1151.

Jiang et al., "FetalQuant: Deducing Fractional Fetal DNA Concentration from Massively Parallel Sequencing of DNA in Maternal Plasma," Bioinformatics, Nov. 15, 2012;28(22):2883-2890.
Kalinina et al., "Nanoliter scale PCR with TaqMan detection." Nucleic Acids Res. May 15, 1997;25(10):1999-2004.
Kitzman et al., (2012): Noninvasive whole-genome sequencing of a human fetus. Science Translational Medicine, 4 (137):137ra76.
Kulkarni et al., "Global DNA methylation patterns in placenta and its association with maternal hypertension in pre-eclampsia." DNA Cell Biol. Feb. 2011;30(2):79-84. doi: 10.1089/dna.2010.1084. Epub Nov. 2, 2010.
Langmead et al., "Ultrafast and memory-efficient alignment of short DNA sequences to the human genome." Genome Biol. 2009;10(3):R25. doi: 10.1186/GB-2009-10-3-r25. Epub Mar. 4, 2009.
Li et al., "Mapping short DNA sequencing reads and calling variants using mapping quality scores." Genome Res. Nov. 2008;18(11):1851-8. doi: 10.1101/gr.078212.108. Epub Aug. 19, 2008.
Liao et al., (2012): Noninvasive Prenatal Diagnosis of Fetal Trisomy 21 by Allelic Ratio Analysis Using Targeted Massively Parallel Sequencing of Maternal Plasma DNA. PLoS ONE, 7(5):e38154, p. 1-7.
Liao, G.J., et al., Targeted massively parallel sequencing of maternal plasma DNA permits efficient and unbiased detection of fetal alleles. Clin Chem, 2010. 57(1): p. 92-101.
Lo "Recent advances in fetal nucleic acids in maternal plasma." J Histochem Cytochem. Mar. 2005;53(3):293-296.
Lo et al. (1997). "Presence of fetal DNA in maternal plasma and serum." Lancet 350(9076): 485-487.
Lo et al. (2007). "Digital PCR for the molecular detection of fetal chromosomal aneuploidy." Proc Natl Acad Sci U S A 104(32): 13116-21.
Lo et al. (2007). "Plasma placental RNA allelic ratio permits noninvasive prenatal chromosomal aneuploidy detection." Nat Med 13(2): 218-23.
Lo et al., "Prenatal Diagnosis of Fetal RhD Status by Molecular Analysis of Maternal Plasma," N. Engl. J. Med. 339:1734-1738, 1998.
Lo et al., "Quantative Abnormalities of Fetal NDA in Maternal Serum in Preeclampsia," Clin. Chem. 45:184-188, 1999.
Lo et al., "Increased Fetal DNA Concentrations in the Plasma of Pregnant Women Carrying Fetuses with Trisomy 21," Clin. Chem. 45:1747-1751, 1999.
Lo, Y.M., et al., Maternal plasma DNA sequencing reveals the genome-wide genetic and mutational profile of the fetus. Sci Transl Med, 2010. 2(61): p. 61ra91.
Lun et al. (2008). "Microfluidics digital PCR reveals a higher than expected fraction of fetal DNA in maternal plasma." Clin Chem 54(10): 1664-72.
Mann et al., "Development and implementation of a new rapid aneuploidy diagnostic service within the UK National Health Service and implications for the future of prenatal diagnosis." Lancet. Sep. 29, 2001;358(9287):1057-61.
Margulies et al., "Genome sequencing in microfabricated high-density picolitre reactors." Nature. Sep. 15, 2005;437(7057):376-80. Epub Jul. 31, 2005.
Mazloom, Amin, "Gender Prediction with Bowtie Alignments using Male Specific Regions," May 10, 2012.
Metzker ML., "Sequencing technologies—the next generation." Nat Rev Genet. Jan. 2010;11(1):31-46. doi: 10.1038/nrg2626. Epub Dec. 8, 2009.
Miller et al., Consensus statement: chromosomal microarray is a first-tier clinical diagnostic test for individuals with developmental disabilities or congenital anomalies. Am J Hum Genet, 2010. 86(5): p. 749-64.
Moudrianakis et al., "Base Sequence Determination in Nucleic Acids with the Electron Microscope, III. Chemistry and Microscopy of Guanine-Labeled DNA." Proc Natl Acad Sci U S A. Mar. 1965;53:564-571.
Nakano et al., "Single-molecule PCR using water-in-oil emulsion." J Biotechnol. Apr. 24, 2003;102(2):117-1+A11024.
Needham-VanDevanter et al., "Characterization of an adduct between CC-1065 and a defined oligodeoxynucleotide duplex." Nucleic Acids Res. Aug. 10, 1984;12(15):6159-68.

(56) References Cited

OTHER PUBLICATIONS

Ng et al. (2003). "mRNA of placental origin is readily detectable in maternal plasma." Proc Natl Acad Sci U S A 100(8): 4748-53.
Nicolaides et al., "One-stop clinic for assessment of risk of chromosomal defects at 12 weeks of gestation." J Matern Fetal Neonatal Med. Jul. 2002;12(1):9-18.
Nolte FS., "Branched DNA signal amplification for direct quantitation of nucleic acid sequences in clinical specimens." Adv Clin Chem. 1998;33:201-35.
Nygren, A. O., J. Dean, et al. (2010) "Quantification of fetal DNA by use of methylation-based DNA discrimination." Clin Chem 56(10): 1627-35.
Ohno, S. (1967). Sex chromosomes and Sex-linked Genes. Berlin, Springer. p. 111.
Old et al. (2007). "Candidate epigenetic biomarkers for non-invasive prenatal diagnosis of Down syndrome." Reprod Biomed Online 15(2): 227-35.
Oudejans et al. (2003). "Detection of chromosome 21-encoded mRNA of placental origin in maternal plasma." Clin Chem 49(9): 1445-9.
Palomaki et al., DNA sequencing of maternal plasma to detect Down syndrome: an international clinical validation study. Genet Med., Nov. 2011;13(11):913-920.
Palomaki, et al. "DNA sequencing of maternal plasma reliably identifies trisomy 18 and trisomy 13 as well as Down syndrome: an international collaborative study" Genet Med 2012;14:296-305.
Pandya et al., "Screening for fetal trisomies by maternal age and fetal nuchal translucency thickness at 10 to 14 weeks of gestation." Br J Obstet Gynaecol. Dec. 1995;102(12):957-62.
Pearson and Regnier, "High-Performance Anion-Exchange Chromatogrtaphy of Oligonucleotides," J. Chrom., 255:137-149, 1983.
Pekalska et al., "Classifiers for dissimilarity-based pattern recognition," 15th International Conference on Pattern Recognition (ICPR'00), vol. 2, Barcelona, Spain, Sep. 3-8, 2000.
Pertl et al., "Rapid molecular method for prenatal detection of Down's syndrome." Lancet. May 14, 1994;343(8907):1197-8.
Peters et al. "Noninvasive Prenatal Diagnosis of a Fetal Microdeletion Syndrome," Correspondence to the Editor, New England Journal of Medicine, 365:19 Nov. 10, 2011, pp. 1847-1848.
Poon et al., "Differential DNA methylation between fetus and mother as a strategy for detecting fetal DNA in maternal plasma." Clin Chem. Jan. 2002;48(1):35-41.
Product Sheet for: Nextera™ DNA Sample Prep Kit (Illumina®-Compatible) Cat. Nos. GA09115, GA091120, GA0911-50, GA0911-96, and GABC0950, from: Epicentre, an Illumina Company, Literature # 307, Jun. 2011.
Qu et al., "Analysis of drug-DNA binding data." Methods Enzymol. 2000;321:353-69.
Robin, N.H. and R.J. Shprintzen, Defining the clinical spectrum of deletion 22q11.2. J Pediatr, 2005. 147(1): p. 90-6.
Romero and Rotbart in Diagnostic Molecular Biology: Principles and Applications pp. 401-406; Persing et al., eds., Mayo Foundation, Rochester, Minn., 1993.
Ross et al., "The DNA sequence of the human X chromosome." Nature. Mar. 17, 2005;434(7031):325-337.
Roth, A., et al. (2012) JointSNVMix: a probabilistic model for accurate detection of somatic mutations in normal/tumour paired next-generation sequencing data, Bioinformatics, 28, 907-913.
Saito et al., "Prenatal DNA diagnosis of a singlegene disorder from maternal plasma," Lancet 356:1170, 2000.
Schouten et al., "Relative quantification of 40 nucleic acid sequences by multiplex ligation-dependent probe amplification." Nucleic Acids Res. Jun. 15, 2002;30(12):e57.
Sehnert et al., "Optimal Detection of Fetal Chromosomal Abnormalities by Massively Parallel DNA Sequencing of Cell-Free Fetal DNA from Maternal Blood," Clinical Chemistry, 57:7, pp. 1042-1049 (2011).

Sekizawa et al., "Cell-free Fetal DNA is increased in Plasma of Women wit Hyperemisis Gravidarum," Clin. Chem. 47:2164-2165, 2001.
Shah, S.P., et al. (2009) Mutational evolution in a lobular breast tumour profiled at single nucleotide resolution, Nature, 461, 809-813.
Shen et al., "A hidden Markov model for number variant prediction from whole genome resequencing data". BMC Bioinformatics, 2011. 12(Suppl 6):54, p. 1-7.
Sherman, S. L., E. G. Allen, et al. (2007). "Epidemiology of Down syndrome." Ment Retard Dev Disabil Res Rev 13(3): 221-7.
Shin, M., L. M. Besser, et al. (2009). "Prevalence of Down syndrome among children and adolescents in 10 regions of the United States." Pediatrics 124(6): 1565-71.
Skaletsy et al., "The male-specific region of the human Y chromosome is a mosaic of discrete sequence classes." Nature. Jun. 19, 2003;423(6942):825-37.
Slater et al., "Rapid, high throughput prenatal detection of aneuploidy using a novel quantitative method (MLPA)." J Med Genet. Dec. 2003;40(12):907-12.
Snijders et al., "Assembly of microarrays for genome-wide measurement of DNA number." Nat Genet. Nov. 2001;29(3):263-4.
Snijders et al., "First-trimester ultrasound screening for chromosomal defects." Ultrasound Obstet Gynecol. Mar. 1996;7(3):216-26.
Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.
Soni et al., "Progress toward ultrafast DNA sequencing using solid-state nanopores." Clin Chem. Nov. 2007;53(11):1996-2001. Epub Sep. 21, 2007.
Sparks et al., (2012): "Selective analysis of cell-free DNA in maternal blood for evaluation of fetal trisomy," Prenatal Diagnosis, 32, 3-9.
Sparks et al., (2012): Non-invasive Prenatal Detection and Selective Analysis of Cell-free DNA Obtained from Maternal Blood: Evaluation for Trisomy 21 and Trisomy 18, American Journal of Obstetrics and Gynecology, pp. 319.e1-319.e9, doi: 10.1016/j.ajog.2012.01.030.
Stagi et al., "Bone density and metabolism in subjects with microdeletion of chromosome 22q11 (del22q11)." Eur J Endocrinol, 2010. 163(2): p. 329-37.
Stanghellini, I., R. Bertorelli, et al. (2006). "Quantitation of fetal DNA in maternal serum during the first trimester of pregnancy by the use of a DAZ repetitive probe." Mol Hum Reprod 12(9): 587-91.
Strachan, The Human Genome, T. BIOS Scientific Publishers, 1992.
Tabor et al. (1986). "Randomised controlled trial of genetic amniocentesis in 4606 low-risk women." Lancet 1(8493): 1287-93.
Timp et al., "Nanopore Sequencing: Electrical Measurements of the Code of Life," IEEE Trans Nanotechnol. May 1, 2010; 9(3): 281-294.
Van den Berghe H, Parloir C, David G et al. A new characteristic karyotypic anomaly in lymphoproliferative disorders. Cancer 1979; 44: 188-95.
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Verma et al., "Rapid and simple prenatal DNA diagnosis of Down's syndrome." Lancet Jul. 4, 1998;352(9121):9-12.
Vincent et al., "Helicase-dependent isothermal PNA amplification." EMBO Rep. Aug. 2004;5(8):795-800. Epub Jul. 9, 2004.
Voelkerding et al., "Next-generation sequencing: from basic research to diagnostics." Clin Chem. Apr. 2009;55(4):641-58. doi: 10.1373/clinchem.2008.112789. Epub Feb. 26, 2009.
Vogelstein et al., "Pigital PCR." Proc Natl Acad Sci U S A. Aug. 3, 1999;96(16):9236-41.
Wapner et al., "First-trimester screening for trisomies 21 and 18." N Engl J Med. Oct. 9, 2003;349(15):1405-13.

(56) References Cited

OTHER PUBLICATIONS

Wu et al., "Genetic and environmental influences on blood pressure and body mass index in Han Chinese: a twin study," (Feb. 2011) Hypertens Res. Hypertens Res 34: 173-179; advance online publication, Nov. 4, 2010.
Zhao et al., "Quantification and application of the placental epigenetic signature of the RASSF1A gene in maternal plasma." Prenat Piagn. Aug. 2010;30(8):778-82.
Zhong et al., "Elevation of both maternal and fetal extracellular circulating deoxyribonucleic acid concentrations in the plasma of pregnant women with preeclampsia," Am. J. Obstet. Gynecol. 184:414-419, 2001.
Zhou et al., "Recent Patents of Nanopore PNA Sequencing Technology: Progress and Challenges," Recent Patents on DNA & Gene Sequences 2010, 4, 192-201.
Zimmermann et al. (2007). "Real-time quantitative polymerase chain reaction measurement of male fetal DNA in maternal plasma." Methods Mol Med 132:43-49.
International Search Report and Written Opinion dated Sep. 26, 2012 in International Application No. PCT/US2011/066639 filed: Dec. 21, 2011 and published as: WO 12/088348 dated Jun. 28, 2012.
International Search Report and Written Opinion dated Apr. 5, 2013 in International Application No. PCT/US2012/043388 filed: Jun. 20, 2012 and published as: WO 12/177792 dated Dec. 27, 2012.
International Search Report and Written Opinion dated Mar. 6, 2013 in International Application No. PCT/US2012/059592 filed: Oct. 10, 2012.
Invitation to Pay Additional Fees and Partial Search Report dated Jan. 18, 2013 in International Application No. PCT/US2012/059592 filed: Oct. 10, 2012.
Office Action dated Feb. 15, 2012 in U.S. Appl. No. 13/669,136, filed Nov. 5, 2012 and published as: US 2013-0085681 dated Apr. 4, 2013.
Office Action dated Feb. 20, 2013 in U.S. Appl. No. 13/656,328, filed Oct. 19, 2012, not yet published.
International Search Report and Written Opinion dated Jul. 14, 2014 in International Application No. PCT/US2014/032687, filed on Apr. 2, 2014.
Office Action dated Jul. 28, 2014 in U.S. Appl. No. 13/797,508, filed Mar. 12, 2013 and published as US 2013-0261983 dated Oct. 3, 2013.
International Preliminary Report on Patentability dated Jul. 31, 2014 in International Application No. PCT/US2013/022290, filed on Jan. 18, 2013 and published as WO 2013/109981 dated Jul. 25, 2013.
Office Action dated Aug. 13, 2014 in U.S. Appl. No. 13/829,164, filed Mar. 14, 2013 and published as US 2013-0288244 dated Oct. 31, 2014.
Office Action dated Aug. 13, 2014 in U.S. Appl. No. 13/669,136, filed Nov. 5, 2012 and published as US 2013-0085681 dated Apr. 4, 2013.
Office Action dated Aug. 14, 2014 in U.S. Appl. No. 13/933,935, filed Jul. 2, 2013 and published as US 2013-0304392 dated Nov. 14, 2013.
Haar, Alfred (1910) "Zur Theorie der orthogonalen Funktionensysteme", Mathematische Annalen 69 (3): 331-371, English translation "On the Theory of Orthogonal Function Systems" 1-37.
Nguyen, Nha, "Denoising of Array-Based DNA Number Data Using The Dual-tree Complex Wavelet Transform," Bioinformatics and Bioengineering, 2007. BIBE 2007. Proceedings of the 7th IEEE International Conference, Boston MA, on Oct. 14-17, 2007, pp. 137-144.
International Preliminary Report on Patentability and Written Opinion dated Apr. 24, 2014 in International Application No. PCT/US2012/059592, filed on Oct. 10, 2012 and published as WO 2013/055817 dated Apr. 18, 2013.
International Search Report and Written Opinion dated Apr. 2, 2014 in International Application No. PCT/US2013/063314, filed on Oct. 3, 2013 and published as WO 2014/055790 dated Apr. 10, 2014.

International Search Report and Written Opinion dated May 9, 2014 in International Application No. PCT/US2014/012369, filed Jan. 21, 2014.
International Preliminary Report on Patentability dated Jun. 9, 2014 in International Application No. PCT/US2012/059114, filed on Oct. 5, 2012 and published as WO 2013/052907 dated Apr. 11, 2013.
International Search Report and Written Opinion dated Feb. 18, 2015 in International Application No. PCT/US2014/058885, filed on Oct. 2, 2014.
Office Action dated Mar. 19, 2015 in U.S. Appl. No. 13/797,508, filed Mar. 12, 2013 and published as US 2013-0261983 dated Oct. 3, 2013.
Shendure et al., "Next-generation DNA sequencing" in Nature Biotechnology (2008) 26:1135-1145.
Chen et al., "A method for noninvasive detection of fetal large deletions/duplications by low coverage massively parallel sequencing" Prenatal Diagnosis (2013) 33(6):584-590, and supplementary material pp. 1-6.
Hsu et al., "A model-based circular binary segmentation algorithm for the analysis of array CGH data" BMC Research Notes (2011) 4:394.
Kim et al., "Identification of significant regional genetic variations using continuous CNV values in aCGH data" Genomics (2009) 94(5):317-323.
Oh et al., "CAM: a web tool for combining array CGH and microarray gene expression data from multiple samples" Computers in Biology and Medicine (2009) 40(9):781-785.
International Search Report and Written Opinion dated Dec. 17, 2014 in International Application No. PCT/US2014/039389, filed on May 23, 2014 and published as WO 2014/190286 dated Nov. 27, 2014.
International Preliminary Report on Patentability dated Dec. 31, 2014 in International Application No. PCT/US2013/047131, filed on Jun. 21, 2013 and published as WO 2013/192562 dated Dec. 27, 2013.
International Search Report and Written Opinion dated Sep. 24, 2014 in International Application No. PCT/US2014/043497, filed on Jun. 20, 2014.
Liu et al., "CUSHAW: a CUDA compatible short read aligner to large genomes based on the Burrows-Wheeler transform" Bioinformatics (2012) 28(14):1830-1837.
Hinds et al., "Whole-genome patterns of common DNA variation in three human populations" Science (2005) 307:1072-1079.
Pushkarev et al., "Single-molecule sequencing of an individual human genome" Nature Biotechnology (2009) 27(9):847-852.
Office Action dated Apr. 16, 2015 in U.S. Appl. No. 13/669,136, filed Nov. 5, 2012 and published as US 2013-0085681 dated Apr. 4, 2013.
Office Action dated Apr. 16, 2015 in U.S. Appl. No. 13/933,935, filed Jul. 2, 2013 and published as US 2013-0304392 dated Nov. 14, 2013.
International Preliminary Report on Patentability dated Apr. 16, 2015 in International Application No. PCT/US2013/063314, filed on Oct. 3, 2013 and published as WO 2014/055790 dated Apr. 10, 2014.
International Preliminary Report on Patentability dated Apr. 16, 2015 in International Application No. PCT/US2013/063287, filed Oct. 3, 2013.
Office Action dated Apr. 17, 2015 in U.S. Appl. No. 13/829,164, filed Mar. 14, 2013 and published as US 2013-0288244 dated Oct. 31, 2014.
Office Action dated May 12, 2015 in U.S. Appl. No. 13/669,136, filed Nov. 5, 2012 and published as US 2013-0085681 dated Apr. 4, 2013.
Office Action dated May 13, 2015 in U.S. Appl. No. 13/333,842, filed on Dec. 21, 2011 and published as US 2012/0184449 dated Jul. 19, 2012.
Fan et al., "Analysis of the size distributions of fetal and maternal cell-free DNA by paired-end sequencing" Clinical Chemistry (2010) 56(8):1279-1286.
Office Action dated Jul. 27, 2015 in U.S. Appl. No. 13/782,857, filed Mar. 1, 2013 and published as US 2013-0310260 dated Nov. 21, 2013.

(56) References Cited

OTHER PUBLICATIONS

Forabosco et al., "Incidence of non-age-dependent chromosomal abnormalities: a population-based study on 88965 amniocenteses" European Journal of Human Genetics (2009) 17:897-903.
Grati, "Chromosomal Mosaicism in Human Feto-Placental Development: Implications for Prenatal Diagnosis" J. Clin. Med. (2014) 3:809-837.
Office Action dated Feb. 23, 2016 in U.S. Appl. No. 14/812,432, filed Jul. 29, 2015 and published as US 2016-0034640 dated Feb. 4, 2016.
Office Action dated Mar. 3, 2016 in U.S. Appl. No. 13/829,373, filed Mar. 14, 2013 and published as US 2013-0338933 dated Dec. 19, 2013.
Office Action dated Mar. 11, 2016 in U.S. Appl. No. 13/782,857, filed Mar. 1, 2013 and published as US 2013-0310260 dated Nov. 21, 2013.
Office Action dated Mar. 22, 2016 in U.S. Appl. No. 12/727,824, filed Mar. 19, 2010 and published as US 2010-0216153 dated Aug. 26, 2010.
Zhao et al., "Detection of fetal subchromosomal abnormalities by sequencing circulating cell-free DNA from maternal plasma" Clinical Chemistry (2015) 61(4):608-616.
Lefkowitz et al., "Clinical validation of a noninvasive prenatal test for genomewide detection of fetal number variants" American Journal of Obstetrics & Gynecology (Dec. 2, 2015) S0002-9378(16)00318-5. doi: 10.1016/j.ajog.2016.02.030. [Epub ahead of print].
Avent, "Refining noninvasive prenatal diagnosis with single-molecule next-generation sequencing" Clin. Chem. (2012) 58(4):657-658.
Boeva et al., "Control-free calling of number alterations in deep-sequencing data using GC-content normalization" Bioinformatics (2011) 27(2):268-269.
Chung et al., "Discovering transcription factor binding sites in highly repetitive regions of genomes with multi-read analysis of ChIP-Seq data" PLoS Computational Biology (2011) 7(7):e1002111.
Chandrananda et al., "Investigating and correcting plasma DNA sequencing coverage bias to enhance aneuploidy discovery" PloS One (2014) 9:e86993.
Benjamini et al., "Summarizing and correcting the GC content bias in high-throughput sequencing" Nucleic Acids Research (2012) 40(10):e72.
International Preliminary Report on Patentability dated Apr. 14, 2016 in International Application No. PCT/US2014/058885, filed on Oct. 2, 2014 and published as WO 2015/051163 dated Apr. 9, 2015.
International Preliminary Report on Patentability dated Apr. 21, 2016 in International Application No. PCT/US2014/059156, filed on Oct. 3, 2014 and published as WO 2015/054080 dated Apr. 16, 2015.
Yuk et al., "Genomic Analysis of Fetal Nucleic Acids in Maternal Blood" Annual Review of Genomics and Human Genetics (2012) 13:285-306.
Office Action dated Apr. 26, 2016 in U.S. Appl. No. 13/797,508, filed Mar. 12, 2013 and published as US 2013-0261983 dated Oct. 3, 2013.
Office Action dated Apr. 27, 2016 in U.S. Appl. No. 13/829,164, filed Mar. 14, 2013 and published as US 2013-0288244 dated Oct. 31, 2014.
Office Action dated Apr. 27, 2016 in U.S. Appl. No. 13/933,935, filed Jul. 2, 2013 and published as US 2013-0304392 dated Nov. 14, 2013.
Bianchi et al., "Isolation of fetal DNA from nucleated erythrocytes in maternal blood," PNAS, 1990,87(9): 3279-3283.
Borsenberger et al., "Chemically Labeled Nucleotides and Oligonucleotides Encode DNA for Sensing with Nanopores," J. Am. Chem. Soc., 131, 7530-7531, 2009.
Branton et al, "The potential and challenges of nanopore sequencing", Nature Biotechnology, 26:1146-1153, 2008.

Braslavsky et al., "Sequence information can be obtained from single DNA molecules," PNAS, 2003, 100(7): 3960-3964.
Brown et al. A step-by-step guide to non-linear regression analysis of experimental data using a Microsoft Excel spreadsheet Computer Methods and Programs in Biomedicine vol. 65, pp. 191-200 (2001).
Bruch et al., Trophoblast-like cells sorted from peripheral maternal blood using flow cytometry: a multiparametric study involving transmission electron microscopy and fetal DNA amplification,: Prenatal Diagnosis 11:787-798, 1991.
Cann et al., "A heterodimeric DNA polymerase: evidence that members of Euryarchaeota possess a distinct DNA polymerase." 1998, Proc. Natl. Acad. Sci. USA 95:14250.
Cariello et al., "Fidelity of Thermococcus litoralis DNA polymerase (Vent) in PCR determined by denaturing gradient gel electrophoresis," Nucleic Acids Res. Aug. 11, 1991;19(15):4193-8.
Chien et al., "Deoxyribonucleic acid polymerase from the extreme thermophile Thermus aquaticus," 1976, J. Bacteoriol, 127: 1550-1557.
Costa et al., "Fetal RHD genotyping in maternal serum during the first trimester of pregnancy" British Journal of Haematology (2002) 119:255-260.
Cunningham et al., in Williams Obstetrics, McGraw-Hill, New York, p. 942, 2002.
Dhallan et al., "Methods to increase the percentage of free fetal DNA recovered from the maternal circulation," J. Am. Med. Soc. 291(9): 1114-1119, Mar. 2004).
Diaz and Sabino, "Accuracy of replication in the polymerase chain reaction. Comparison between Thermotoga maritima DNA polymerase and Thermus aquaticus DNA polymerase." Diaz RS, Sabino EC. 1998 Braz J. Med. Res, 31: 1239.
DNA Replication 2nd edition, Kornberg and Baker, W. H. Freeman, New York, N.Y. (1991).
Drmanac et al., "Sequencing by hybridization: towards an automated sequencing of one million M13 clones arrayed on membranes," Electrophoresis, 13(8): p. 566-573, 1992.
Herzenberg et al., "Fetal cells in the blood of pregnant women: detection and enrichment by fluorescence-activated cell sorting," PNAS 76:1453-1455, 1979.
Hinnisdaels et al., "Direct cloning of PCR products amplified with Pwo DNA polymerase," 1996, Biotechniques, 20: 186-188.
Huber et al. "High-resolution liquid chromatography of DNA fragments on non-porous poly(styrene-divinylbenzene) particles," Nucleic Acids Res. 21(5):1061-1066, 1993.
Huse et al., "Accuracy and quality of massively parallel DNA pyrosequencing" Genome Biology (2007) 8(7):R143.
Johnston et al., "Autoradiography using storage phosphor technology," Electrophoresis. May 1990;11(5):355-360.
Joos et al., "Covalent attachment of hybridizable oligonucleotides to glass supports," Analytical Biochemistry 247:96-101, 1997.
Juncosa-Ginesta et al., "Improved efficiency in site-directed mutagenesis by PCR using a Pyrococcus sp. GB-D polymerase," 1994, Biotechniques, 16(5): pp. 820-823.
Kato et al., "A new packing for separation of DNA restriction fragments by high performance liquid chromatography," J. Biochem, 95(1):83-86, 1984.
Khandjian, "UV crosslinking of RNA to nylon membrane enhances hybridization signals," Mol. Bio. Rep. 11: 107-115, 1986.
Kornberg and Baker, W. H. Freeman, New York, N.Y. (1991).
Lecomte and Doubleday, "Selective inactivation of the 3' to 5' exonuclease activity of Escherichia coli DNA polymerase I by heat," 1983, Polynucleotides Res. 11:7505-7515.
Levin, "It's prime time for reverse transcriptase," Cell 88:5-8 (1997).
Li et al., "Detection of paternally inherited fetal point mutations for beta-thalassemia using size-fractionated cell-free DNA in maternal plasma.," J. Amer. Med. Assoc. 293:843-849, 2005.
Lo et al., "Fetal DNA in maternal plasma: application to non-invasive blood group genotyping of the fetus" Transfus. Clin. Biol. (2001) 8:306-310.
Lundberg et al., "High-fidelity amplification using a thermostable DNA polymerase isolated from Pyrococcus furiosus," 1991 Gene, 108:1-6.

(56) References Cited

OTHER PUBLICATIONS

Mitchell & Howorka, "Chemical tags facilitate the sensing of individual DNA strands with nanopores," Angew. Chem. Int. Ed. 47:5565-5568, 2008.
Myers and Gelfand, "Reverse transcription and DNA amplification by a Thermus thermophilus DNA polymerase," Biochemistry 1991, 30:7661-7666.
Nevin, N.C., "Future direction of medical genetics", The Ulster Medical Journal, vol. 70, No. 1, (2001), pp. 1-2.
Ng et al. "The Concentration of Circulating Corticotropin-releasing Hormone mRNA in Maternal Plasma Is Increased in Preeclampsia," Clinical Chemistry 49:727-731, 2003.
Nordstrom et al., "Characterization of bacteriophage T7 DNA polymerase purified to homogeneity by antithioredoxin immunoadsorbent chromatography," 1981, J. Biol. Chem. 256:3112-3117.
Oroskar et al., "Detection of immobilized amplicons by ELISA-like techniques." Clin. Chem. 42:1547-1555, 1996.
PCT International Search Report and Written Opinion of the international Searching Authority for International Application No. PCT/US11/24132, dated Aug. 8, 2011. 15 pages.
Purnell and Schmidt, "Discrimination of single base substitutions in a DNA strand immobilized in a biological nanopore," ACS Nano, 3:2533, 2009.
Sambrook, Chapter 10 of Molecular Cloning, a Laboratory Manual, S.sup.ed Edition, J. Sambrook, and D. W. Russell, Cold Spring Harbor Press (2001).
Smid et al., "Evaluation of Different Approaches for Fetal DNA Analysis from Maternal Plasma and Nucleated Blood Cells," Clinical Chemistry, 1999, 45(9): 1570-1572.
Smith et al., "Direct mechanical measurements of the elasticity of single DNA molecules by using magnetic beads," Science 258:5085, pp. 1122-1126, Nov. 13, 1992.
Stenesh and McGowan, "DNA polymerase from mesophilic and thermophilic bacteria. III. Lack of fidelity in the replication of synthetic polydeoxyribonucleotides by DNA polymerase from Bacillus licheniformis and Bacillus stearothermophilus," 1977, Biochim Biophys Acta 475:32-41.
Stoddart et al, "Single-nucleotide discrimination in immobilized DNA oligonucleotides with a biological nanopore," Proc. Nat. Acad. Sci. 2009, 106(19): pp. 7702-7707.
Takagi et al., "Characterization of DNA polymerase from Pyrococcus sp. strain KOD1 and its application to PCR," 1997, Appl. Environ. Microbiol. 63(11): pp. 4504-4510.
Taylor et al., "Characterization of chemisorbed monolayers by surface potential measurements," J. Phys. D. Appl. Phys. 24(8):1443-1450, 1991.
Verma, "The reverse transcriptase," Biochim Biophys Acta 473(1):1-38 (Mar. 21, 1977).
Wei, Chungwen et al., "Detection and Quantification by Homogenous PCR of Cell-free Fetal DNA in Maternal Plasma", Clinical Chemistry, vol. 47, No. 2, (2001), pp. 336-338.
Wu et al., "Reverse Transcriptas," CRC Crit. Rev Biochem. 3(3): pp. 289-347 (Jan. 1975).
Yershov et al., "DNA analysis and diagnostics on oligonucleotide microchips," Proc. Natl. Acad. Sci. 93(10): pp. 4913-4918 (May 14, 1996).
Yoon et al., "Sensitive and accurate detection of number variants using read depth of coverage" Genome Research (2009) 19:1586-1592.
Office Action dated Aug. 22, 2013 in U.S. Appl. No. 13/619,039, filed Sep. 14, 2012 and published as: US 2013/0022977 dated Jan. 24, 2013.
Office Action dated Jan. 10, 2013 in U.S. Appl. No. 13/619,039, filed Sep. 14, 2012 and published as: US 2013/0022977 dated Jan. 24, 2013.
Office Action dated Jul. 14, 2014 in U.S. Appl. No. 12/727,824, filed Sep. 13, 2012 and published as: US 2010/0216153 dated Aug. 26, 2010.
Office Action dated Oct. 18, 2011 in U.S. Appl. No. 12/727,824, filed Sep. 13, 2012 and published as: US 2010/0216153 dated Aug. 26, 2010.
Office Action dated May 16, 2011 in U.S. Appl. No. 12/727,824, filed Sep. 13, 2012 and published as: US 2010/0216153 dated Aug. 26, 2010.
Office Action dated Feb. 25, 2015 in U.S. Appl. No. 12/727,824, filed Sep. 13, 2012 and published as: US 2010/0216153 dated Aug. 26, 2010.
Office Action dated May 29, 2015 in U.S. Appl. No. 14/187,876, filed Feb. 24, 2014 and published as US 2014-0322709 dated Oct. 30, 2014.
Kim et al., "Determination of fetal DNA fraction from the plasma of pregnant women using sequence read counts" Prenat. Diagn. (2015) 35(8):810-815.
Extended European Search Report dated Dec. 2, 2015 in European Application No. EP11745050.2, filed on Feb. 9, 2011 and published as EP 2 536 852 dated Dec. 26, 2012.
Omont et al., "Gene-based bin analysis of genome-wide association studies" BMC Proceedings (2008) 2 (Suppl 4):S6.
Trapnell and Salzberg, "How to map billions of short reads onto genomes" Nat. Biotechnol. (2009) 27(5):455-457.
International Search Report and Written Opinion dated Jan. 5, 2016 in International Application No. PCT/US2015/042701, filed on Jul. 29, 2015.
Office Action dated Feb. 1, 2016 in U.S. Appl. No. 13/669,136, filed Nov. 5, 2012 and published as US 2013-0085681 dated Apr. 4, 2013.
Canick et al., "The impact of maternal plasma DNA fetal fraction on next generation sequencing tests for common fetal aneuploidies" Prenat. Diagn. (2013) 33(7):667-674.
Hudecova et al., "Maternal plasma fetal DNA fractions in pregnancies with low and high risks for fetal chromosomal aneuploidies" PLoS One (2014) 9(2):e88484.
Palomaki et al., "DNA sequencing of maternal plasma to detect Down syndrome: an international clinical validation study" Genet Med. (2011) 13:913-920, and Expanded Methods Appendix A, pp. 1-65.
Office Action dated Feb. 12, 2016 in U.S. Appl. No. 13/797,930, filed Mar. 12, 2013 and published as US 2013-0325360 dated Dec. 5, 2013.
International Preliminary Report on Patentability dated Aug. 6, 2015 in International Application No. PCT/US2014/012369, filed Jan. 21, 2014 and published as WO 2014/116598 dated Jul. 31, 2014.
Supplementary Partial European Search Report dated Aug. 10, 2015 in European Application No. EP11745050.2, filed on Feb. 9, 2011 and published as EP 2 536 852 dated Dec. 26, 2012.
Office Action dated Aug. 27, 2015 in U.S. Appl. No. 13/933,935, filed Jul. 2, 2013 and published as US 2013-0304392 dated Nov. 14, 2013.
Office Action dated Sep. 1, 2015 in U.S. Appl. No. 13/829,164, filed Mar. 14, 2013 and published as US 2013-0288244 dated Oct. 31, 2014.
Office Action dated Sep. 8, 2015 in U.S. Appl. No. 13/669,136, filed Nov. 5, 2012 and published as US 2013-0085681 dated Apr. 4, 2013.
Office Action dated Sep. 8, 2015 in U.S. Appl. No. 13/797,508, filed Mar. 12, 2013 and published as US 2013-0261983 dated Oct. 3, 2013.
Office Action dated Sep. 18, 2015 in U.S. Appl. No. 12/727,824, filed Mar. 19, 2010 and published as US 2010-0216153 dated Aug. 26, 2010.
Office Action dated Sep. 22, 2015 in U.S. Appl. No. 13/779,638, filed Feb. 27, 2013 and published as US 2013-0309666 dated Nov. 21, 2013.
Office Action dated Sep. 28, 2015 in U.S. Appl. No. 14/187,876, filed Feb. 24, 2014 and published as US 2014-0322709 dated Oct. 30, 2014.
Office Action dated Oct. 2, 2015 in U.S. Appl. No. 13/782,883, filed Mar. 1, 2013 and published as US 2014-0180594 dated Jun. 26, 2014.

(56) References Cited

OTHER PUBLICATIONS

International Preliminary Report on Patentability dated Oct. 15, 2015 in International Application No. PCT/US2014/032687, filed on Apr. 2, 2014 and published as WO 2014/165596 dated Oct. 9, 2014.
Romiguier et al., "Contrasting GC-content dynamics across 33 mammalian genomes: relationship with life-history traits and chromosome sizes" Genome Research (2010) 20:1001-1009.
National Human Genome Research Institute, Chromosomes fact sheet, (http://www.genome.gov/26524120, downloaded Sep. 9, 2015).
The International SNP Map Working Group "A map of human genome sequence variation containing 1.42 million single nucleotide polymorphisms" Nature (2001) 409:928-933.
Alkan et al., "Personalized number and segmental duplication maps using next-generation sequencing", Nature Genetics, vol. 41, No. 10, Oct. 30, 2009 (Oct. 30, 2009), pp. 1061-1067, and Supplementary Information 1-68.
Office Action dated Oct. 22, 2015 in U.S. Appl. No. 13/781,530, filed Feb. 28, 2013 and published as US 2014-0100792 dated Apr. 10, 2014.
Office Action dated Oct. 27, 2015 in U.S. Appl. No. 13/333,842, filed Dec. 21, 2011 and published as US 2012/0184449 dated Jul. 19, 2012.
Invitation to Pay Additional Fees and Partial International Search Report dated Oct. 14, 2015 in International Application No. PCT/US2015/042701, filed on Jul. 29, 2015.
Yu et al., "Size-based molecular diagnostics using plasma DNA for noninvasive prenatal testing" PNAS USA (2014) 111(23):8583-8588.
International Search Report and Written Opinion dated Oct. 2, 2015 in International Application No. PCT/US2015/032550, filed on May 27, 2015 and published as WO 2015/183872 dated Dec. 3, 2015.
Yu et al., "Noninvasive prenatal molecular karyotyping from maternal plasma" PLoS One (2013) 8(4):e60968.
Bollen, "Bioconductor: Microarray versus next-generation sequencing tool sets" retrieved from the internet: http://dspace.library.uu.nl/bitstream/handle/1874/290489/Sander_Bollen_writing_assignment.pdf, retrieved on Sep. 23, 2015.
International Preliminary Report on Patentability dated Dec. 3, 2015 in International Application No. PCT/US2014/039389, filed on May 23, 2014 and published as WO 2014/190286 dated Nov. 27, 2014.
Agarwal et al., "Commercial landscape of noninvasive prenatal testing in the United States" Prenatal Diagnosis (2013) 33(6):521-531.
Dan et al., "Clinical application of massively parallel sequencing-based prenatal noninvasive fetal trisomy test for trisomies 21 and 18 in 11,105 pregnancies with mixed risk factors" Prenatal Diagnosis (2012) 32:1225-1232.
Holt and Jones, "The new paradigm of flow cell sequencing" Genome Res. (2008) 18:839-846.
Luh and Guo, "A powerful transformation trimmed mean method for one-way fixed effects ANOVA model under non-normality and inequality of variances" British J. Mathematical and Statistical Psychology (1999) 52:303-320.
International Search Report and Written Opinion dated Sep. 9, 2013 in International Application No. PCT/US2012/059123, filed on Oct. 5, 2012 and published as WO/2013/052913 dated Apr. 11, 2013.
International Search Report and Written Opinion dated Sep. 9, 2013 in International Application No. PCT/US2012/059114, filed on Oct. 5, 2012 and published as WO/2013/052907 dated Apr. 11, 2013.
Office Action dated Sep. 11, 2013 in U.S. Appl. No. 13/829,164, filed Mar. 14, 2013.
Office Action dated Sep. 12, 2013 in U.S. Appl. No. 13/669,136, filed Nov. 5, 2012 and published as: US 2013-0085681 dated Apr. 4, 2013.
Office Action dated Sep. 12, 2013 in U.S. Appl. No. 13/656,328, filed Oct. 19, 2012 and published as US 2013-0103320 dated Apr. 25, 2013.
Kim SK, Hannum G, Geis J, Tynan J, Hogg G, Zhao C, Jensen TJ, Mazloom AR, Oeth P, Ehrich M, van den Boom D. Determination of fetal DNA fraction from the plasma of pregnant women using sequence read counts. Prenatal diagnosis. Aug. 2015;35(8):810-5.
Rava RP, Srinivasan A, Sehnert AJ, Bianchi DW. Circulating fetal cell-free DNA fractions differ in autosomal aneuploidies and monosomy X. Clinical chemistry. Jan. 1, 2014;60(1):243-50.

* cited by examiner

METHODS FOR NON-INVASIVE ASSESSMENT OF FETAL GENETIC VARIATIONS THAT FACTOR EXPERIMENTAL CONDITIONS

RELATED PATENT APPLICATIONS

This patent application is a continuation and claims the benefit of International PCT Application No. PCT/US2013/022290 filed Jan. 18, 2013, entitled DIAGNOSTIC PROCESSES THAT FACTOR EXPERIMENTAL CONDITIONS which claims the benefit of U.S. Provisional Patent Application No. 61/589,202 filed on Jan. 20, 2012, entitled DIAGNOSTIC PROCESSES THAT FACTOR EXPERIMENTAL CONDITIONS; PCT/US2013/022290 is also a continuation in part of PCT Application No. PCT/US2012/059123 filed on Oct. 5, 2012, entitled METHODS AND PROCESSES FOR NON-INVASIVE ASSESSMENT OF GENETIC VARIATIONS; which claims the benefit of U.S. Provisional Patent Application No. 61/709,899 filed on Oct. 4, 2012, entitled METHODS AND PROCESSES FOR NON-INVASIVE ASSESSMENT OF GENETIC VARIATIONS; and U.S. Provisional Patent Application No. 61/663,477 filed on Jun. 22, 2012, entitled METHODS AND PROCESSES FOR NON-INVASIVE ASSESSMENT OF GENETIC VARIATIONS.

FIELD

The technology relates in part to methods, processes and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation, fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure.

SUMMARY

Provided herein is a method for detecting the presence or absence of a fetal aneuploidy, including: (a) obtaining nucleotide sequence reads from sample nucleic acid including circulating, cell-free nucleic acid from a pregnant female; (b) mapping the nucleotide sequence reads to reference genome sections; (c) counting the number of nucleotide sequence reads mapped to each reference genome section, thereby obtaining counts; (d) normalizing the counts for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (e) providing an outcome determinative of the presence or absence of a fetal aneuploidy from the normalized sample count. In some embodiments, sequence reads are mapped to a portion of, or all, reference genome sections.

Also provided herein is a method for detecting the presence or absence of a fetal aneuploidy, including: (a) obtaining a sample including circulating, cell-free nucleic acid from a pregnant female; (b) isolating sample nucleic acid from the sample; (c) obtaining nucleotide sequence reads from a sample nucleic acid; (d) mapping the nucleotide sequence reads to reference genome sections, (e) counting the number of nucleotide sequence reads mapped to each reference genome section, thereby obtaining counts; (f) normalizing the counts for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (g) providing an outcome determinative of the presence or absence of a fetal aneuploidy from the normalized sample count.

Provided also herein is a method for detecting the presence or absence of a fetal aneuploidy, including: (a) mapping to reference genome sections nucleotide sequence reads obtained from sample nucleic acid including circulating, cell-free nucleic acid from a pregnant female; (b) counting the number of nucleotide sequence reads mapped to each reference genome section, thereby obtaining counts; (c) normalizing the counts for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (d) providing an outcome determinative of the presence or absence of a fetal aneuploidy from the normalized sample count.

Also provided herein is a method for detecting the presence or absence of a genetic variation, including: (a) obtaining nucleotide sequence reads from sample nucleic acid including circulating, cell-free nucleic acid from a test subject; (b) mapping the nucleotide sequence reads to reference genome sections; (c) counting the number of nucleotide sequence reads mapped to each reference genome section, thereby obtaining counts; (d) normalizing the counts for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (e) providing an outcome determinative of the presence or absence of a genetic variation in the test subject from the normalized sample count.

Provided also herein is a method for detecting the presence or absence of a fetal aneuploidy, including: (a) obtaining a sample including circulating, cell-free nucleic acid from a test subject; (b) isolating sample nucleic acid from the sample; (c) obtaining nucleotide sequence reads from a sample nucleic acid; (d) mapping the nucleotide sequence reads to reference genome sections, (e) counting the number of nucleotide sequence reads mapped to each reference genome section, thereby obtaining counts; (f) normalizing the counts for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (g) providing an outcome determinative of the presence or absence of a genetic variation in the test subject from the normalized sample count.

Also provided herein is a method for detecting the presence or absence of a genetic variation, including: (a) mapping to reference genome sections nucleotide sequence reads obtained from sample nucleic acid including circulating, cell-free nucleic acid from a test subject; (b) counting the number of nucleotide sequence reads mapped to each reference genome section, thereby obtaining counts; (c) normalizing the counts for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (d) providing an outcome determinative of the presence or absence of a genetic variation in the test subject from the normalized sample count.

Provided also herein is a method for detecting the presence or absence of a genetic variation, including: (a) obtaining nucleotide sequence reads from sample nucleic acid including circulating, cell-free nucleic acid from a test subject; (b) mapping the nucleotide sequence reads to reference genome sections; (c) counting the number of nucleotide sequence reads mapped to each reference genome section, thereby obtaining counts; (d) adjusting the counted, mapped sequence reads in (c) according to a selected variable or feature, which selected variable or feature minimizes or eliminates the effect of repetitive sequences and/or over or under represented sequences; (e) normalizing the remaining counts after (d) for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (f) providing an outcome determinative of the presence or absence of a genetic variation in the test subject from the normalized sample count.

Also provided herein is a method for detecting the presence or absence of a genetic variation, including: (a) obtaining a sample including circulating, cell-free nucleic acid from a test subject; (b) isolating sample nucleic acid from the sample; (c) obtaining nucleotide sequence reads from a sample nucleic acid; (d) mapping the nucleotide sequence reads to reference genome sections, (e) counting the number of nucleotide sequence reads mapped to each reference genome section, thereby obtaining counts; (f) adjusting the counted, mapped sequence reads in (e) according to a selected variable or feature, which selected variable or feature minimizes or eliminates the effect of repetitive sequences and/or over or under represented sequences; (g) normalizing the remaining counts after (f) for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (h) providing an outcome determinative of the presence or absence of a genetic variation in the test subject from the normalized sample counts.

Provided also herein is a method for detecting the presence or absence of a genetic variation, including: (a) mapping to reference genome sections nucleotide sequence reads obtained from sample nucleic acid including circulating, cell-free nucleic acid from a test subject; (b) counting the number of nucleotide sequence reads mapped to each reference genome section, thereby obtaining counts; (c) adjusting the counted, mapped sequence reads in (b) according to a selected variable or feature, which selected variable or feature minimizes or eliminates the effect of repetitive sequences and/or over or under represented sequences; (d) normalizing the remaining counts after (c) for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (e) providing an outcome determinative of the presence or absence of a genetic variation in the test subject from the normalized sample counts.

Also provided herein is a method for detecting the presence or absence of a microdeletion, including: (a) obtaining nucleotide sequence reads from sample nucleic acid including circulating, cell-free nucleic acid from a test subject; (b) mapping the nucleotide sequence reads to reference genome sections; (c) counting the number of nucleotide sequence reads mapped to each reference genome section, thereby obtaining counts; (d) adjusting the counted, mapped sequence reads in (c) according to a selected variable or feature, which selected feature or variable minimizes or eliminates the effect of repetitive sequences and/or over or under represented sequences; (e) normalizing the remaining counts after (d) for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (f) providing an outcome determinative of the presence or absence of a genetic variation in the test subject from the normalized sample counts.

Provided herein is a method for detecting the presence or absence of a microdeletion, including: (a) obtaining a sample including circulating, cell-free nucleic acid from a test subject; (b) isolating sample nucleic acid from the sample; (c) obtaining nucleotide sequence reads from a sample nucleic acid; (d) mapping the nucleotide sequence reads to reference genome sections, (e) counting the number of nucleotide sequence reads mapped to each reference genome section, thereby obtaining counts; (f) adjusting the counted, mapped sequence reads in (e) according to a selected variable or feature, which selected feature or variable minimizes or eliminates the effect of repetitive sequences and/or over or under represented sequences; (g) normalizing the remaining counts after (f) for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (h) providing an outcome determinative of the presence or absence of a genetic variation in the test subject from the normalized sample counts.

Also provide herein is a method for detecting the presence or absence of a microdeletion, including: (a) mapping to reference genome sections nucleotide sequence reads obtained from sample nucleic acid including circulating, cell-free nucleic acid from a test subject; (b) counting the number of nucleotide sequence reads mapped to each reference genome section, thereby obtaining counts; (c) adjusting the counted, mapped sequence reads in (b) according to a selected variable or feature, which selected feature or variable minimizes or eliminates the effect of repetitive sequences and/or over or under represented sequences; (d) normalizing the remaining counts after (c) for a first genome section, or normalizing a derivative of the counts for the first genome section, according to an expected count, or derivative of the expected count, thereby obtaining a normalized sample count, which expected count, or derivative of the expected count, is obtained for a group including samples, references, or samples and references, exposed to one or more common experimental conditions; and (f) providing an outcome determinative of the presence or absence of a genetic variation in the test subject from the normalized sample counts.

In some embodiments, the adjusted, counted, mapped sequence reads are further adjusted for one or more experimental conditions prior to normalizing the remaining counts. In certain embodiments, the genetic variation is a microdeletion. In some embodiments, the microdeletion is on Chromosome 22. In certain embodiments, the microdeletion occurs in Chromosome 22 region 22q11.2. In some embodiments, the microdeletion occurs on Chromosome 22 between nucleotide positions 19,000,000 and 22,000,000 according to reference genome hg19.

In some embodiments, the sample nucleic acid is from blood plasma from the test subject, and in certain embodiments, the sample nucleic acid is from blood serum from the test subject. In some embodiments, the test subject is chosen from a human, an animal, and a plant. In certain embodiments, a human test subject includes a female, a pregnant female, a male, a fetus, or a newborn.

In some embodiments, the fetal aneuploidy is trisomy 13. In certain embodiments, the fetal aneuploidy is trisomy 18. In some embodiments, the fetal aneuploidy is trisomy 21.

In certain embodiments, the genetic variation is associated with a medical condition. In some embodiments, the medical condition is cancer. In certain embodiments, the medical condition is an aneuploidy.

In some embodiments, the sequence reads of the cell-free sample nucleic acid are in the form of polynucleotide fragments. In certain embodiments, the polynucleotide fragments are between about 20 and about 50 nucleotides in length. In some embodiments, the polynucleotides are between about 30 to about 40 nucleotides in length. In some embodiments, the term "polynucleotide fragment" is synonymous with, or can be interchanged with the term "sequence information", with reference to sequence reads, or a digital representation of the physical DNA or visa versa.

In certain embodiments, the expected count is a median count. In some embodiments, the expected count is a trimmed or truncated mean, Winsorized mean or bootstrapped estimate. In certain embodiments, the normalized sample count is obtained by a process that includes normalizing the derivative of the counts for the first genome section, which derivative is a first genome section count representation determined by dividing the counts for the first genome section by the counts for multiple genome sections that include the first genome section. In some embodiments, the derivative of the counts for the first genome section is normalized according to a derivative of the expected count, which derivative of the expected count is an expected first genome section count representation determined by dividing the expected count for the first genome section by the expected count for multiple genome sections that include the first genome section. In certain embodiments, the first genome section is a chromosome or part of a chromosome and the multiple genome sections includes autosomes. In some embodiments, the chromosome is chromosome 21, chromosome 18 or chromosome 13.

In certain embodiments, the normalized sample count is obtained by a process including subtracting the expected count from the counts for the first genome section, thereby generating a subtraction value, and dividing the subtraction value by an estimate of the variability of the count. In some embodiments, the normalized sample count is obtained by a process including subtracting the expected first genome section count representation from the first genome section count representation, thereby generating a subtraction value, and dividing the subtraction value by an estimate of the variability of the first genome section count representation. In certain embodiments, the estimate of the variability of the expected count is a median absolute deviation (MAD) of the count. In some embodiments, the estimate of the variability of the count is an alternative to MAD as introduced by Rousseeuw and Croux or a bootstrapped estimate.

In some embodiments, the one or more common experimental conditions include a flow cell. In certain embodiments, the one or more common experimental conditions include a channel in a flow cell. In some embodiments, the one or more common experimental conditions include a reagent plate. In certain embodiments, the reagent plate is used to stage nucleic acid for sequencing. In some embodiments, the reagent plate is used to prepare a nucleic acid library for sequencing. In certain embodiments, the one or more common experimental conditions include an identification tag index.

In certain embodiments, the normalized sample count is adjusted for guanine and cytosine content of the nucleotide sequence reads or of the sample nucleic acid. In some embodiments, methods described herein include subjecting the counts or the normalized sample count to a locally weighted polynomial regression. In certain embodiments, the locally weighted polynomial regression is a LOESS regression or a LOWESS regression. In some embodiments, the normalized sample count is adjusted for nucleotide sequences that repeat in the reference genome sections. In certain embodiments, the counts or the normalized sample count are adjusted for nucleotide sequences that repeat in the reference genome sections. In some embodiments, the method includes filtering the counts before obtaining the normalized sample count.

In some embodiments, the sample nucleic acid includes single stranded nucleic acid. In certain embodiments, the sample nucleic acid includes double stranded nucleic acid. In some embodiments, obtaining the nucleotide sequence reads includes subjecting the sample nucleic acid to a sequencing process using a sequencing device. In certain embodiments, providing an outcome includes factoring the fraction of fetal nucleic acid in the sample nucleic acid. In some embodiments, the method includes determining the fraction of fetal nucleic acid in the sample nucleic acid.

In certain embodiments, the normalized sample count is obtained without adjusting for guanine and cytosine content of the nucleotide sequence reads or of the sample nucleic acid. In some embodiments, the normalized sample count is obtained for one experimental condition. In certain embodiments, the experimental condition is flow cell. In some embodiments, the normalized sample count is obtained for two experimental conditions. In certain embodiments, the experimental conditions are flow cell and reagent plate. In some embodiments, the experimental conditions are flow cell and identification tag index. In some embodiments, the normalized sample count is obtained for three experimental conditions. In certain embodiments, the experimental conditions are flow cell, reagent plate and identification tag index.

In some embodiments, the normalized sample count is obtained after (i) adjustment according to guanine and cytosine content, and after (i), (ii) adjustment according to an experimental condition. In certain embodiments, the normalized sample count is obtained after adjustment according to nucleotide sequences that repeat in the reference genome sections prior to (i). in some embodiments, (ii) consists of adjustment according to flow cell. In certain embodiments, (ii) consists of adjustment according to identification tag index and then adjustment according to flow cell. In some embodiments, (ii) consists of adjustment according to reagent plate and then adjustment according to flow cell. In certain embodiments, (ii) consists of adjustment according to identification tag index and reagent plate and then adjustment according to flow cell.

In certain embodiments, the normalized sample count is obtained after adjustment according to an experimental condition consisting of adjustment according to flow cell. In some embodiments, the normalized sample count is obtained after adjustment according to an experimental condition consisting of adjustment according to identification tag index and then adjustment according to flow cell. In certain embodiments, the normalized sample count is obtained after adjustment according to an experimental condition consisting of adjustment according to reagent plate and then adjustment according to flow cell. In some embodiments, the normalized sample count is obtained after adjustment according to an experimental condition consisting of adjustment according to identification tag index and reagent plate and then adjustment according to flow cell. In certain embodiments, the normalized sample count is obtained after adjustment according to nucleotide sequences that repeat in the reference genome sections prior to adjustment according to the experimental condition.

In certain embodiments, some methods further include evaluating the statistical significance of differences between the normalized sample counts, or a derivative of the normalized sample counts, for the test subject and other samples, references or samples and reference for a first genomic section. In some embodiments, certain methods further include evaluating the statistical significance of differences between the normalized sample counts, or a derivative of the normalized sample counts, for the test subject and other samples, references or samples and reference for one or more genomic sections. In certain embodiments, some methods further include providing an outcome determinative of the presence or absence of a genetic variation in the test subject based on the evaluation. In some embodiments, the genetic variation is chosen from a microdeletion, duplication, and aneuploidy.

Provided also in some embodiments is a computer program product, including a computer usable medium having a computer readable program code embodied therein, the computer readable program code including distinct software modules including a sequence receiving module, a logic processing module, and a data display organization module, the computer readable program code adapted to be executed to implement a method for identifying the presence or absence of a genetic variation in a sample nucleic acid, the method including: (a) obtaining, by the sequence receiving module, nucleotide sequence reads from sample nucleic acid; (b) mapping, by the logic processing module, the nucleotide sequence reads to reference genome sections; (c) counting, by the logic processing module, the number of nucleotide sequence reads mapped to each reference genome section, thereby obtaining counts; (d) normalizing, by the logic processing module, the counts for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; (e) generating, by the logic processing module, an outcome determinative of the presence or absence of a genetic variation in the test subject from the normalized sample count; and (f) organizing, by the data display organization module in response to being determined by the logic processing module, a data display indicating the presence or absence of the genetic variation in the sample nucleic acid.

Also provided in certain embodiments is an apparatus including memory in which a computer program product embodiment described herein is stored. In some embodiments the apparatus includes a processor that implements one or more functions of the computer program product embodiment described herein. In certain embodiments, the one or more functions of the computer program product specified herein, is implemented in a web based environment.

Provided also in certain embodiments, is an apparatus including a web-based system in which a computer program product specified herein is implemented. In some embodiments, the web-based system comprises computers, routers, and telecommunications equipment sufficient for web-based functionality. In certain embodiments, the web-based system comprises network cloud computing, network cloud storage or network cloud computing and network cloud storage.

Provided also in some embodiments is a system including a nucleic acid sequencing apparatus and a processing apparatus, wherein the sequencing apparatus obtains nucleotide sequence reads from a sample nucleic acid, and the processing apparatus obtains the nucleotide sequence reads from the sequencing apparatus and carries out a method including: (a) mapping the nucleotide sequence reads to reference genome sections; (b) counting the number of nucleotide sequence reads mapped to each reference genome section, thereby obtaining counts; (c) normalizing the counts for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; and (d) providing an outcome determinative of the presence or absence of a genetic variation in the sample nucleic acid from the normalized sample count.

Also provided herein is a method of identifying the presence or absence of a 22q11.2 microdeletion between chromosome 22 nucleotide positions 19,000,000 and 22,000,000 according to human reference genome hg19, the method including: (a) obtaining a sample comprising circulating, cell-free nucleic acid from a test subject; (b) isolating sample nucleic acid from the sample; (c) obtaining nucleotide sequence reads from a sample nucleic acid; (d) mapping the nucleotide sequence reads to reference genome sections; (e) counting the number of nucleotide sequence reads mapped to each reference genome section, thereby obtaining counts; (f) adjusting the counted, mapped sequence reads in (e) according to a selected variable or feature, which selected feature or variable minimizes or eliminates the effect of repetitive sequences and/or over or under represented sequences; (g) normalizing the remaining counts after (f) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; (h) evaluating the statistical significance of differences between the normalized counts or a derivative of the normalized counts for the test subject and reference subjects for one or more selected genomic sections corresponding to chromosome 22 between nucleotide positions 19,000,000 and 22,000,000; and (i) providing an outcome determinative of the presence or absence of a genetic variation in the test subject from the evaluation in (h).

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 11A shows a comparison for the standardized library concentration prepared by a semi-automated (n=287) and manual library preparation method. FIG. 14B shows GCRM based z-scores for each of 93 samples. Confirmed euploid samples (n=83) are shown in light grey. Confirmed trisomy 21 samples (n=10) are shown in dark grey.

DETAILED DESCRIPTION

Figure 1:
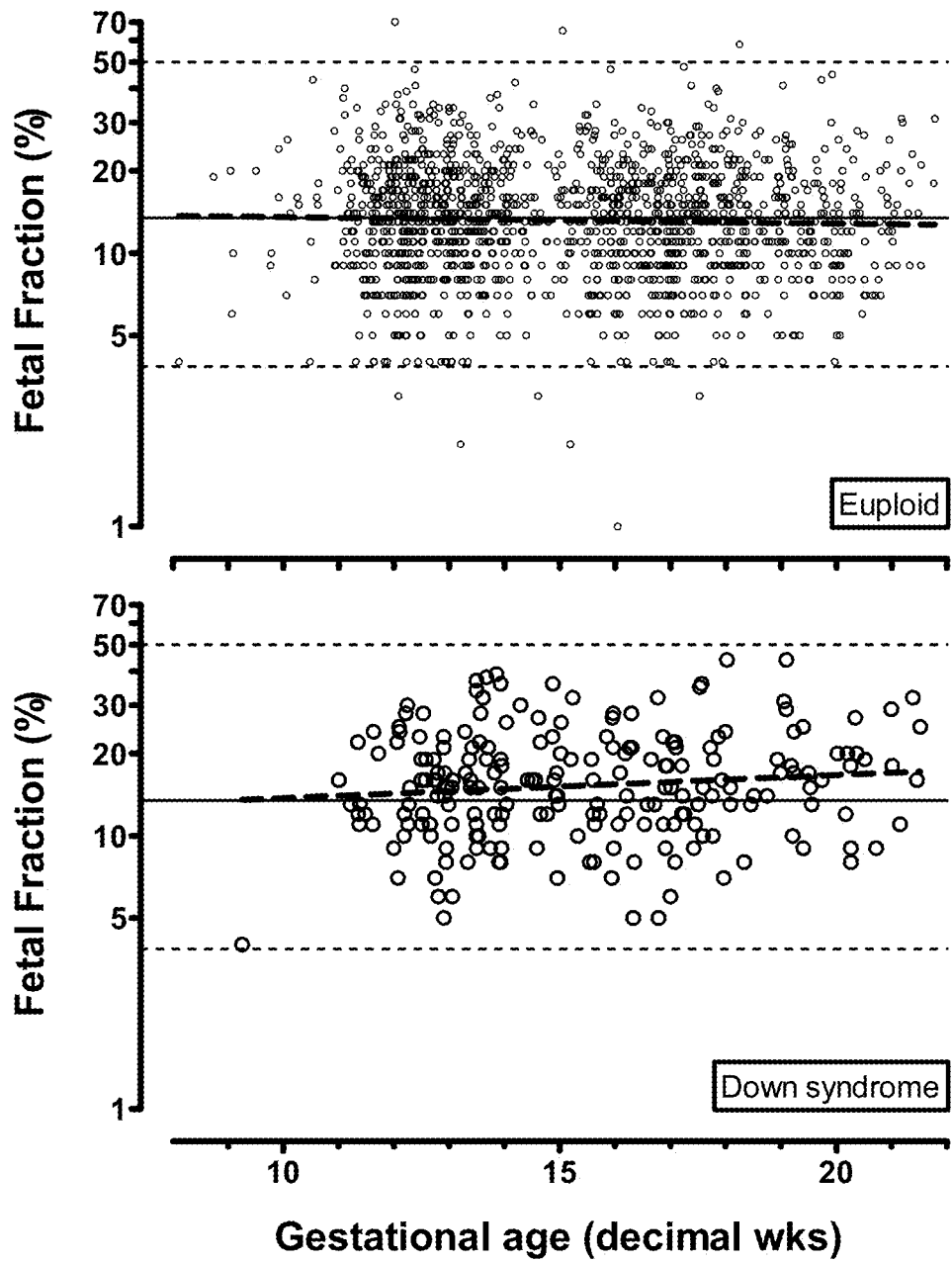
FIG. 1 graphically illustrates the fetal DNA fraction for each of the selected samples plotted as a function of gestational age.

Provided are improved methods, processes and apparatuses useful for identifying genetic variations. Identifying one or more genetic variations or variances can lead to diagnosis of, or determining predisposition to, a particular medical condition. Identifying a genetic variance can result in facilitating a medical decision and/or employing a helpful medical procedure.

Genetic Variations and Medical Conditions

The presence or absence of a genetic variance can be determined using a method or apparatus described herein. In certain embodiments, the presence of absence of one or more genetic variations is determined according to an outcome provided by methods and apparatuses described herein. A genetic variation generally is a particular genetic phenotype present in certain individuals, and often a genetic variation is present in a statistically significant sub-population of individuals. Non-limiting examples of genetic variations include one or more deletions (e.g., micro-deletions), duplications (e.g., micro-duplications), insertions, mutations, polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any observed length, and in some embodiments, is about 1 base or base pair (bp) to 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length). In some embodiments, a genetic variation is a chromosome abnormality (e.g., aneuploidy), partial chromosome abnormality or mosaicism, which are described in greater detail hereafter.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Fetal Gender

In some embodiments, the prediction of fetal gender can be determined by a method or apparatus described herein. Gender determination generally is based on a sex chromosome. In humans, there are two sex chromosomes, the X and Y chromosomes. Individuals with XX are female and XY are male and non-limiting variations include XO, XYY, XXX and XXY.

Chromosome Abnormalities

In some embodiments, the presence or absence of a fetal chromosome abnormality can be determined by using a method or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, deletions and/or duplications of one or more nucleotide sequences (e.g., one or more genes), including deletions and duplications caused by unbalanced translocations. The terms "aneuploidy" and "aneuploid" as used herein refer to an abnormal number of chromosomes in cells of an organism. As different organisms have widely varying chromosome complements, the term "aneuploidy" does not refer to a particular number of chromosomes, but rather to the situation in which the chromosome content within a given cell or cells of an organism is abnormal.

Monosomy generally is a lack of one chromosome of the normal complement. Partial monosomy can occur in unbalanced translocations or deletions, in which only a portion of the chromosome is present in a single copy. Monosomy of sex chromosomes (45, X) causes Turner syndrome, for example.

Disomy generally is the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

Trisomy generally is the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX) or males (e.g., 47, XXY in Klinefelter's syndrome; or 47, XYY).

Tetrasomy and pentasomy generally are the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

A partial monosomy, or partial trisomy, generally is an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the portion that exists on the derivative chromosome) and only one copy of part of the other chromosome involved in the derivative chromosome.

Mosaicism generally is an aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

TABLES 1A and 1B present a non-limiting list of chromosome conditions, syndromes and/or abnormalities that can be potentially identified by methods and apparatus described herein. TABLE 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |

TABLE 1A-continued

| Chromosome | Abnormality | Disease Association |
|---|---|---|
| 9 | monosomy 9p | Rethore syndrome |
| 9 | partial trisomy trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobson Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
| | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |

TABLE 1B-continued

| Syndrome | Chromosome | Start | End | Interval (Mb) | Grade |
| --- | --- | --- | --- | --- | --- |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial/DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |

TABLE 1B-continued

| Syndrome | Chromosome | Start | End | Interval (Mb) | Grade |
|---|---|---|---|---|---|
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | | 21 | 27,037,956 | 27,548,479 | 0.51 |
| Familial Adenomatous Polyposis | | 5 | 112,101,596 | 112,221,377 | 0.12 |
| Hereditary Liability to Pressure Palsies (HNPP) | 17 | 13,968,607 | 15,434,038 | 1.47 | 1 |
| Leri-Weill dyschondrostosis (LWD) - SHOX deletion | X | 751,878 | 867,875 | 0.12 | |
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, Genereviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Genereviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method or apparatus described herein. Preeclampsia is a condition in which hypertension arises in pregnancy (i.e. pregnancy-induced hypertension) and is associated with significant amounts of protein in the urine. In some cases, preeclampsia also is associated with elevated levels of extracellular nucleic acid and/or alterations in methylation patterns. For example, a positive correlation between extracellular fetal-derived hypermethylated RASSF1A levels and the severity of pre-eclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g. strain).

Cancers

In some embodiments, the presence or absence of a cell proliferation disorder (e.g., a cancer) is determined by using a method or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that the methods provided herein can be used to identify a particular type of cancer.

Other Genetic Variations

In some embodiments, the presence or absence of a genetic variation can be determined by using a method or apparatus described herein. In certain embodiments, a genetic variation is one or more conditions chosen from copy number variations (CNV's), microdeletions, duplications, or any condition which causes or results in a genetic dosage variation from an expected genetic dosage observed in an unaffected individual. In some embodiments, copy number variation refers to structural rearrangements of one or more genomic sections, chromosomes, or parts of chromosomes, which rearrangement often is caused by deletions, duplications, inversions, and/or translocations. CNV's can be inherited or caused by de novo mutation, and typically result in an abnormal number of copies of one or more genomic sections (e.g., abnormal gene dosage with respect to an unaffected sample). Copy number variation can occur in regions that range from as small as one kilobase to several megabases, in some embodiments. CNV's can be detected using various cytogenetic methods (FISH, CGH, aCGH, karyotype analysis) and/or sequencing methods.

A microdeletion generally is a decreased dosage, with respect to unaffected regions, of genetic material (e.g., DNA, genes, nucleic acid representative of a particular region) located in a selected genomic section or segment. Microdeletions, and syndromes caused by microdeletions, often are characterized by a small deletion (e.g., generally less than five megabases) of one or more chromosomal segments, spanning one or more genes, the absence of which sometimes confers a disease condition. Microdeletions sometimes are caused by errors in chromosomal crossover during meiosis. In many instances, microdeletions are not detectable by currently utilized karyotyping methods.

A chromosomal duplication, or microduplication or duplication, generally is one or more regions of genetic material (e.g., DNA, genes, nucleic acid representative of a particular region) for which the dosage is increased relative to unaffected regions. Duplications frequently occur as the result of an error in homologous recombination or due to a retrotransposon event. Duplications can range from small regions (thousands of base pairs) to whole chromosomes in some instances. Duplications have been associated with certain types of proliferative diseases. Duplications can be characterized using genomic microarrays or comparative genetic hybridization (CGH). A duplication sometimes is characterized as a genetic region repeated one or more times (e.g., repeated 1, 2, 3, 4, 5, 6, 7, 8, 9 or 10 times).

Samples

Nucleic acid utilized in methods and apparatus described herein often is isolated from a sample obtained from a subject. In some embodiments, a subject is referred to as a test subject, and in certain embodiments a subject is referred to as a sample subject or reference subject. In some embodiments, test subject refers to a subject being evaluated for the presence or absence of a genetic variation. A sample subject, or reference subject, often is a subject utilized as a basis for comparison to the test subject, and a reference subject sometimes is selected based on knowledge that the reference subject is known to be free of, or have, the genetic variation being evaluated for the test subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman).

Nucleic acid may be isolated from any type of suitable biological specimen or sample. Non-limiting examples of specimens include fluid or tissue from a subject, including, without limitation, umbilical cord blood, chorionic villi, amniotic fluid, cerbrospinal fluid, spinal fluid, lavage fluid (e.g., bronchoalveolar, gastric, peritoneal, ductal, ear, athroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample may be blood and sometimes plasma or serum. As used herein, "blood" generally refers to whole blood or any fractions of blood, such as serum and plasma as conventionally defined, for example. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to further preparation. A fluid or tissue sample from which nucleic acid is extracted may be acellular. In some embodiments, a fluid or tissue sample may contain cellular elements or cellular remnants. In some embodiments fetal cells or cancer cells may be included in the sample.

A sample may be heterogeneous, by which is meant that more than one type of nucleic acid species is present in the sample. For example, heterogeneous nucleic acid can include, but is not limited to, (i) fetally derived and maternally derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation).

Nucleic Acid Isolation and Processing

Nucleic acid may be derived from one or more sources (e.g., cells, soil, etc.) by methods known in the art. Cell lysis procedures and reagents are known in the art and may generally be performed by chemical, physical, or electrolytic lysis methods. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

The terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome (e.g., a nucleic acid sample may be from one chromosome of a sample obtained from a diploid organism). Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid can include extracellular nucleic acid in certain embodiments. Extracellular nucleic acid often is nucleic acid isolated from a source having substantially no cells. Extracellular nucleic acid often includes no detectable cells and may contain cellular elements or cellular remnants. Non-limiting examples of acellular sources for extracellular nucleic acid are blood plasma, blood serum and urine. Without being limited by theory, extracellular nucleic acid may be a product of cell apoptosis and cell breakdown, which provides basis for extracellular nucleic acid often having a series of lengths across a large spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid may be extracted, isolated, purified or amplified from the sample(s). As used herein, "isolated" refers to nucleic acid removed from its original environment (e.g., the natural environment if it is naturally occurring, or a host cell if expressed exogenously), and thus is altered by human intervention (e.g., "by the hand of man") from its original environment. An isolated nucleic acid is provided with fewer non-nucleic acid components (e.g., protein, lipid) than the amount of components present in a source sample. A composition comprising isolated nucleic acid can be about 90%, 91%, 92%, 93%, 94%, 95%, 96%, 97%, 98%, 99% or greater than 99% free of non-nucleic acid components. As used herein, "purified" refers to nucleic acid provided that contains fewer nucleic acid species than in the sample source from which the nucleic acid is derived. A composition comprising nucleic acid may be about 90%, 91%, 92%, 93%, 94%, 95%, 96%, 97%, 98%, 99% or greater than 99% free of other nucleic acid species. An amplified nucleic acid often is prepared by subjecting nucleic acid of a sample to a process that linearly or exponentially generates amplicon nucleic acids having the same or substantially the same nucleotide sequence as the nucleotide sequence of the nucleic acid in the sample, or portion thereof.

Nucleic acid also may be processed by subjecting nucleic acid to a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by any suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of nucleotide sequence information.

Nucleic acid fragments may contain overlapping nucleotide sequences, and such overlapping sequences can facilitate construction of a nucleotide sequence of the non-fragmented counterpart nucleic acid, or a portion thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

Nucleic acid can be fragmented by various methods known in the art, which include without limitation, physical, chemical and enzymatic processes. Non-limiting examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected to generate non-specifically cleaved fragments or specifically cleaved fragments. Non-limiting examples of processes that can generate non-specifically cleaved fragment nucleic acid include, without limitation, contacting nucleic acid with apparatus that expose nucleic acid to shearing force (e.g., passing nucleic acid through a syringe needle; use of a French press); exposing nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the portion of an amplified product thereof containing the corresponding nucleotide sequence of a nucleic acid template gene molecule. For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from portions of amplified nucleic acid molecules containing, at least in part, nucleotide sequence information from or based on the representative nucleic acid template molecule.

As used herein, "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel).

Nucleic acid may be specifically cleaved by contacting the nucleic acid with one or more specific cleavage agents. As used herein, a "specific cleavage agent" refers to an agent, sometimes a chemical or an enzyme that can cleave a nucleic acid at one or more specific sites. Specific cleavage agents often cleave specifically according to a particular nucleotide sequence at a particular site.

Examples of enzymatic specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I; glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Nucleic acid may be treated with a chemical agent, and the modified nucleic acid may be cleaved. In non-limiting examples, nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

In some embodiments, fragmented nucleic acid can be subjected to a size fractionation procedure and all or part of the fractionated pool may be isolated or analyzed. Size fractionation procedures are known in the art (e.g., separation on an array, separation by a molecular sieve, separation by gel electrophoresis, separation by column chromatography).

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any form useful for conducting a sequence analysis or manufacture process described herein, such as solid or liquid form, for example. In certain embodiments, nucleic acid may be provided in a liquid form optionally comprising one or more other components, including without limitation one or more buffers or salts.

Obtaining Sequence Reads

Sequencing, mapping and related analytical methods are known in the art (e.g., United States Patent Application Publication US2009/0029377, incorporated by reference). Certain aspects of such processes are described hereafter.

Reads generally are short nucleotide sequences produced by any sequencing process described herein or known in the art. Reads can be generated from one end of nucleic acid fragments ("single-end reads"), and sometimes are generated from both ends of nucleic acids ("double-end reads"). In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.1-fold to about 100-fold coverage, about 0.2-fold to 20-fold coverage, or about 0.2-fold to about 1-fold coverage (e.g., about 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In certain embodiments, a fraction of a nucleic acid pool that is sequenced in a run is further sub-selected prior to sequencing. In certain embodiments, hybridization-based techniques (e.g., using oligonucleotide arrays) can be used to first sub-select for nucleic acid sequences from certain chromosomes (e.g., a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected pool of nucleic acids is sequenced randomly. In some embodiments, the nucleic acid is amplified prior to sequencing. In some embodiments, a portion or subset of the nucleic acid is amplified prior to sequencing.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" representing an individual clonal DNA template or a single DNA molecule. High-throughput sequencing technologies include, for example, sequencing-by-synthesis with reversible dye terminators, sequencing by oligonucleotide probe ligation, pyrosequencing and real time sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in the methods provided herein. Additional sequencing technologies that include the use of developing nucleic acid imaging technologies (e.g. transmission electron microscopy (TEM) and atomic force microscopy (AFM)), are also contemplated herein. Examples of various sequencing technologies are described below.

A nucleic acid sequencing technology that may be used in the methods described herein is sequencing-by-synthesis and reversible terminator-based sequencing (e.g. Illumina's Genome Analyzer and Genome Analyzer II). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adapter primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

In certain sequencing by synthesis procedures, for example, template DNA (e.g., circulating cell-free DNA (ccfDNA)) sometimes is fragmented into lengths of several hundred base pairs in preparation for library generation. In some embodiments, library preparation can be performed without further fragmentation or size selection of the template DNA (e.g., ccfDNA). In certain embodiments, library generation is performed using a modification of the manufacturers protocol, as described in Example 2. Sample isolation and library generation are performed using automated methods and apparatus, in certain embodiments. Briefly, ccfDNA is end repaired by a fill-in reaction, exonuclease reaction or a combination of a fill-in reaction and exonuclease reaction. The resulting blunt-end repaired ccfDNA is extended by a single nucleotide, which is complementary to a single nucleotide overhang on the 3' end of an adapter primer, and often increase ligation efficiency. Any complementary nucleotides can be used for the extension/overhang nucleotides (e.g., A/T, C/G), however adenine frequently is used to extend the end-repaired DNA, and thymine often is used as the 3' end overhang nucleotide.

In certain sequencing by synthesis procedures, for example, adapter oligonucleotides are complementary to the flow-cell anchors, and sometimes are utilized to associate the modified ccfDNA (e.g., end-repaired and single nucleotide extended) with a solid support, the inside surface of a flow cell for example. In some embodiments, the adapter primer includes indexing nucleotides, or "barcode" nucleotides (e.g., a unique sequence of nucleotides usable as an indexing primer to allow unambiguous identification of a sample), one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/indexing, adapter/indexing/sequencing). Indexing primers or nucleotides contained in an adapter primer often are six or more nucleotides in length, and frequently are positioned in the primer such that the indexing nucleotides are the first nucleotides sequenced during the sequencing reaction. In certain embodiments, indexing or barcode nucleotides are associated with a sample but are sequenced in a separate sequencing reaction to avoid compromising the quality of sequence reads. Subsequently, the reads from the barcode sequencing and the sample sequencing are linked together and the reads de-multiplexed. After linking and de-multiplexing the sequence reads can be further adjusted or processed as described herein.

In certain sequencing by synthesis procedures, utilization of index primers allows multiplexing of sequence reactions in a flow cell lane, thereby allowing analysis of multiple samples per flow cell lane. The number of samples that can be analyzed in a given flow cell lane often is dependent on the number of unique index primers utilized during library preparation. Index primers are available from a number of commercial sources (e.g., Illumina, Life Technologies, NEB). Reactions described in Example 2 were performed using one of the few commercially available kits available at the time of the study, which included 12 unique indexing primers. Non limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively). The methods described herein are not limited to 12 index primers and can be performed using any number of unique indexing primers (e.g., 4, 8, 12, 24, 48, 96, or more). The greater the number of unique indexing primers, the greater the number of samples that can be multiplexed in a single flow cell lane. Multiplexing using 12 index primers allows 96 samples (e.g., equal to the number of wells in a 96 well microwell plate) to be analyzed simultaneously in an 8 lane flow cell. Similarly, multiplexing using 48 index primers allows 384 samples (e.g., equal to the number of wells in a 384 well microwell plate) to be analyzed simultaneously in an 8 lane flow cell.

In certain sequencing by synthesis procedures, adapter-modified, single-stranded template DNA is added to the flow cell and immobilized by hybridization to the anchors under limiting-dilution conditions. In contrast to emulsion PCR, DNA templates are amplified in the flow cell by "bridge" amplification, which relies on captured DNA strands "arching" over and hybridizing to an adjacent anchor oligonucleotide. Multiple amplification cycles convert the single-molecule DNA template to a clonally amplified arching "cluster," with each cluster containing approximately 1000 clonal molecules. Approximately $50 \times 10^6$ separate clusters can be generated per flow cell. For sequencing, the clusters are denatured, and a subsequent chemical cleavage reaction and wash leave only forward strands for single-end sequencing. Sequencing of the forward strands is initiated by hybridizing a primer complementary to the adapter sequences, which is followed by addition of polymerase and a mixture of four differently colored fluorescent reversible dye terminators. The terminators are incorporated according to sequence complementarity in each strand in a clonal cluster. After incorporation, excess reagents are washed away, the clusters are optically interrogated, and the fluorescence is recorded. With successive chemical steps, the reversible dye terminators are unblocked, the fluorescent labels are cleaved and washed away, and the next sequencing cycle is performed. This iterative, sequencing-by-synthesis process sometimes requires approximately 2.5 days to generate read lengths of 36 bases. With $50 \times 10^6$ clusters per flow cell, the overall sequence output can be greater than 1 billion base pairs (Gb) per analytical run.

Another nucleic acid sequencing technology that may be used with the methods described herein is 454 sequencing (Roche). 454 sequencing uses a large-scale parallel pyrosequencing system capable of sequencing about 400-600 megabases of DNA per run. The process typically involves two steps. In the first step, sample nucleic acid (e.g. DNA) is sometimes fractionated into smaller fragments (300-800 base pairs) and polished (made blunt at each end). Short adaptors are then ligated onto the ends of the fragments. These adaptors provide priming sequences for both amplification and sequencing of the sample-library fragments. One adaptor (Adaptor B) contains a 5'-biotin tag for immobilization of the DNA library onto streptavidin-coated beads. After nick repair, the non-biotinylated strand is released and used as a single-stranded template DNA (sstDNA) library. The sstDNA library is assessed for its quality and the optimal amount (DNA copies per bead) needed for emPCR is determined by titration. The sstDNA library is immobilized onto beads. The beads containing a library fragment carry a single sstDNA molecule. The bead-bound library is emulsified with the amplification reagents in a water-in-oil mixture. Each bead is captured within its own microreactor where PCR amplification occurs. This results in bead-immobilized, clonally amplified DNA fragments.

In the second step of 454 sequencing, single-stranded template DNA library beads are added to an incubation mix containing DNA polymerase and are layered with beads containing sulfurylase and luciferase onto a device containing pico-liter sized wells. Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing exploits the release of pyrophosphate (PPi) upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed (see, for example, Margulies, M. et al. Nature 437:376-380 (2005)).

Another nucleic acid sequencing technology that may be used in the methods provided herein is Applied Biosystems' SOLiD™ technology. In SOLiD™ sequencing-by-ligation, a library of nucleic acid fragments is prepared from the sample and is used to prepare clonal bead populations. With this method, one species of nucleic acid fragment will be present on the surface of each bead (e.g. magnetic bead). Sample nucleic acid (e.g. genomic DNA) is sheared into fragments, and adaptors are subsequently attached to the 5' and 3' ends of the fragments to generate a fragment library. The adapters are typically universal adapter sequences so that the starting sequence of every fragment is both known and identical. Emulsion PCR takes place in microreactors containing all the necessary reagents for PCR. The resulting PCR products attached to the beads are then covalently bound to a glass slide. Primers then hybridize to the adapter sequence within the library template. A set of four fluorescently labeled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n-1 position for a second round of ligation cycles. Often, five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1.

Another nucleic acid sequencing technology that may be used in the methods described herein is the Helicos True Single Molecule Sequencing (tSMS). In the tSMS technique, a polyA sequence is added to the 3' end of each nucleic acid (e.g. DNA) strand from the sample. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into a sequencing apparatus and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step (see, for example, Harris T. D. et al., Science 320:106-109 (2008)).

Another nucleic acid sequencing technology that may be used in the methods provided herein is the single molecule, real-time (SMRT™) sequencing technology of Pacific Biosciences. With this method, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is then repeated.

Another nucleic acid sequencing technology that may be used in the methods described herein is ION TORRENT (Life Technologies) single molecule sequencing which pairs semiconductor technology with a simple sequencing chemistry to directly translate chemically encoded information (A, C, G, T) into digital information (0, 1) on a semiconductor chip. ION TORRENT uses a high-density array of micro-machined wells to perform nucleic acid sequencing in a massively parallel way. Each well holds a different DNA molecule. Beneath the wells is an ion-sensitive layer and beneath that an ion sensor. Typically, when a nucleotide is incorporated into a strand of DNA by a polymerase, a hydrogen ion is released as a byproduct. If a nucleotide, for example a C, is added to a DNA template and is then incorporated into a strand of DNA, a hydrogen ion will be released. The charge from that ion will change the pH of the solution, which can be detected by an ion sensor. A sequencer can call the base, going directly from chemical information to digital information. The sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection (i.e. detection without scanning, cameras or light), each nucleotide incorporation is recorded in seconds.

Another nucleic acid sequencing technology that may be used in the methods described herein is the chemical-sensitive field effect transistor (CHEMFET) array. In one example of this sequencing technique, DNA molecules are placed into reaction chambers, and the template molecules can be hybridized to a sequencing primer bound to a polymerase. Incorporation of one or more triphosphates into a new nucleic acid strand at the 3' end of the sequencing primer can be detected by a change in current by a CHEMFET sensor. An array can have multiple CHEMFET sensors. In another example, single nucleic acids are attached to beads, and the nucleic acids can be amplified on the bead, and the individual beads can be transferred to individual reaction chambers on a CHEMFET array, with each chamber having a CHEMFET sensor, and the nucleic acids can be sequenced (see, for example, U.S. Patent Publication No. 2009/0026082).

Another nucleic acid sequencing technology that may be used in the methods described herein is electron microscopy. In one example of this sequencing technique, individual nucleic acid (e.g. DNA) molecules are labeled using metallic labels that are distinguishable using an electron microscope. These molecules are then stretched on a flat surface and imaged using an electron microscope to measure sequences (see, for example, Moudrianakis E. N. and Beer M. Proc Natl Acad Sci USA. 1965 March; 53:564-71). In some cases, transmission electron microscopy (TEM) is used (e.g. Halcyon Molecular's TEM method). This method, termed Individual Molecule Placement Rapid Nano Transfer (IMPRNT), includes utilizing single atom resolution transmission electron microscope imaging of high-molecular weight (e.g. about 150 kb or greater) DNA selectively labeled with heavy atom markers and arranging these molecules on ultra-thin films in ultra-dense (3 nm strand-tostrand) parallel arrays with consistent base-to-base spacing. The electron microscope is used to image the molecules on the films to determine the position of the heavy atom markers and to extract base sequence information from the DNA (see, for example, PCT patent publication WO 2009/046445).

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number. In sequencing by hybridization, the method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in the methods described herein. Nanopore sequencing is a single-molecule sequencing technology whereby a single nucleic acid molecule (e.g. DNA) is sequenced directly as it passes through a nanopore. A nanopore is a small hole or channel, of the order of 1 nanometer in diameter. Certain transmembrane cellular proteins can act as nanopores (e.g. alpha-hemolysin). In some cases, nanopores can be synthesized (e.g. using a silicon platform). Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree and generates characteristic changes to the current. The amount of current which can pass through the nanopore at any given moment therefore varies depending on whether the nanopore is blocked by an A, a C, a G, a T, or in some cases, methyl-C. The change in the current through the nanopore as the DNA molecule passes through the nanopore represents a direct reading of the DNA sequence. In some cases a nanopore can be used to identify individual DNA bases as they pass through the nanopore in the correct order (see, for example, Soni G V and Meller A. Clin Chem 53: 1996-2001 (2007); PCT publication no. WO2010/004265).

There are a number of ways that nanopores can be used to sequence nucleic acid molecules. In some embodiments, an exonuclease enzyme, such as a deoxyribonuclease, is used. In this case, the exonuclease enzyme is used to sequentially detach nucleotides from a nucleic acid (e.g. DNA) molecule. The nucleotides are then detected and discriminated by the nanopore in order of their release, thus reading the sequence of the original strand. For such an embodiment, the exonuclease enzyme can be attached to the nanopore such that a proportion of the nucleotides released from the DNA molecule is capable of entering and interacting with the channel of the nanopore. The exonuclease can be attached to the nanopore structure at a site in close proximity to the part of the nanopore that forms the opening of the channel. In some cases, the exonuclease enzyme can be attached to the nanopore structure such that its nucleotide exit trajectory site is orientated towards the part of the nanopore that forms part of the opening.

In some embodiments, nanopore sequencing of nucleic acids involves the use of an enzyme that pushes or pulls the nucleic acid (e.g. DNA) molecule through the pore. In this case, the ionic current fluctuates as a nucleotide in the DNA molecule passes through the pore. The fluctuations in the current are indicative of the DNA sequence. For such an embodiment, the enzyme can be attached to the nanopore structure such that it is capable of pushing or pulling the target nucleic acid through the channel of a nanopore without interfering with the flow of ionic current through the pore. The enzyme can be attached to the nanopore structure at a site in close proximity to the part of the structure that forms part of the opening. The enzyme can be attached to the subunit, for example, such that its active site is orientated towards the part of the structure that forms part of the opening.

In some embodiments, nanopore sequencing of nucleic acids involves detection of polymerase bi-products in close proximity to a nanopore detector. In this case, nucleoside phosphates (nucleotides) are labeled so that a phosphate labeled species is released upon the addition of a polymerase to the nucleotide strand and the phosphate labeled species is detected by the pore. Typically, the phosphate species contains a specific label for each nucleotide. As nucleotides are sequentially added to the nucleic acid strand, the bi-products of the base addition are detected. The order that the phosphate labeled species are detected can be used to determine the sequence of the nucleic acid strand.

The length of the sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median or average length of about 15 bp to 900 bp long (e.g. about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp or more.

In some embodiments, nucleic acids may include a fluorescent signal or sequence tag information. Quantification of the signal or tag may be used in a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

Mapping Reads

Mapping nucleotide sequence reads (i.e., sequence information from a fragment whose physical genomic position is unknown) can be performed in a number of ways, and often comprises alignment of the obtained sequence reads with a matching sequence in a reference genome (e.g., Li et al., "Mapping short DNA sequencing reads and calling variants using mapping quality score," Genome Res., 2008 Aug 19.) In such alignments, sequence reads generally are aligned to a reference sequence and those that align are designated as being "mapped" or a "sequence tag." In some cases, a mapped sequence read is referred to as a "hit". In some embodiments, mapped sequence reads are grouped together according to various parameters and assigned to particular genome sections, which are discussed in further detail below.

Various computational methods can be used to map each sequence read to a genome section. Non-limiting examples of computer algorithms that can be used to align sequences include BLAST, BLITZ, and FASTA, or variations thereof. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate genome sections (described hereafter), for example. Sequence reads generated in Examples 1, 2 and 3 were mapped to the UCSC hg19 human reference genome using CASAVA version 1.6, as described in Examples 2 and 3. In some embodiments, sequence read mapping can be performed before adjustment for repetitive sequences and/or GC content, and in certain embodiments, sequence read mapping can be performed after adjustment for repetitive sequences and/or GC content.

A "sequence tag" is a nucleic acid (e.g. DNA) sequence (i.e. read) assigned specifically to a particular genome section and/or chromosome (i.e. one of chromosomes 1-22, X or Y for a human subject). A sequence tag may be repetitive or non-repetitive within a single portion of the reference genome (e.g., a chromosome). In some embodiments, repetitive sequence tags are eliminated from further analysis (e.g. quantification). In some embodiments, a read may uniquely or non-uniquely map to portions in the reference genome. A read is considered to be "uniquely mapped" if it aligns with a single sequence in the reference genome. A read is considered to be "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read to be mapped to a reference sequence.

A reference sequence, or reference genome, often is an assembled or partially assembled genomic sequence from an individual or multiple individuals. In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of one or more individuals having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

Genome Sections

In some embodiments, mapped sequence reads (i.e. sequence tags) are grouped together according to various parameters and assigned to particular genome sections. Often, the individual mapped sequence reads can be used to identify an amount of a genome section present in a sample. In some embodiments, the amount of a genome section can be indicative of the amount of a larger sequence (e.g. a chromosome) in the sample. The term "genome section" also can be used interchangeably with "sequence window", "section", "bin", "locus", "region", "partition" or "segment". In some embodiments, a genome section is an entire chromosome, portion of a chromosome, multiple chromosome portions, multiple chromosomes, portions from multiple chromosomes, and/or combinations thereof. In some cases, a genome section is delineated based on one or more parameters which include, for example, length or a particular feature or features of the sequence. In some embodiments, a genome section is based on a particular length of genomic sequence. In some embodiments, the methods include analysis of multiple mapped sequence reads to a plurality of genome sections. The genome sections can be approximately the same length or the genome sections can be different lengths. In some embodiments, a genome section is about 10 kilobases (kb) to about 100 kb, about 20 kb to about 80 kb, about 30 kb to about 70 kb, about 40 kb to about 60 kb, and sometimes about 50 kb. In some embodiments, the genome section is about 10 kb to about 20 kb. The genomic sections discussed herein are not limited to contiguous runs of sequence. Thus, genome sections can be made up of contiguous or non-contiguous sequences. The genomic sections discussed herein are not limited to a single chromosome and, in some embodiments, may transcend individual chromosomes. In some cases, genomic sections may span one, two, or more entire chromosomes. In addition, the genomic sections may span joint or disjoint portions of multiple chromosomes.

In some embodiments, genome sections can be particular chromosome sections in a chromosome of interest, such as, for example, chromosomes where a genetic variation is assessed (e.g. an aneuploidy of chromosomes 13, 18 and/or 21). A genome section can also be a pathogenic genome (e.g. bacterial, fungal or viral) or fragment thereof. Genome sections can be genes, gene fragments, regulatory sequences, introns, exons, and the like.

In some embodiments, a genome (e.g. human genome) is partitioned into genome sections based on the information content of the regions. The resulting genomic regions may contain sequences for multiple chromosomes and/or may contain sequences for portions of multiple chromosomes.

In some cases, the partitioning may eliminate similar locations across the genome and only keep unique regions. The eliminated regions may be within a single chromosome or may span multiple chromosomes. The resulting genome is thus trimmed down and optimized for faster alignment, often allowing for focus on uniquely identifiable sequences. In some cases, the partitioning may down weight similar regions. The process for down weighting a genome section is discussed in further detail below. In some embodiments, the partitioning of the genome into regions transcending chromosomes may be based on information gain produced in the context of classification. For example, the information content may be quantified using the p-value profile measuring the significance of particular genomic locations for distinguishing between groups of confirmed normal and abnormal subjects (e.g. euploid and trisomy subjects). In some embodiments, the partitioning of the genome into regions transcending chromosomes may be based on any other criterion, such as, for example, speed/convenience while aligning tags, high or low GC content, uniformity of GC content, presence of repetitive sequences, other measures of sequence content (e.g. fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, level of uncertainty assigned to individual bins, and/or a targeted search for particular features.

Sequence Tag Density

"Sequence tag density" refers to the value of sequence tags or reads for a defined genome section where the sequence tag density is used for comparing different samples and for subsequent analysis. In some embodiments, the value of sequence tags is a normalized value of sequence tags. The value of the sequence tag density sometimes is normalized within a sample, and sometimes is normalized to a median value for a group of samples (e.g., samples processed in a flow lane, samples prepared in a library generation plate, samples collected in a staging plate, the like and combinations thereof).

In some embodiments, normalization can be performed by counting the number of tags falling within each genome section; obtaining a median, mode, average, or midpoint value of the total sequence tag count for each chromosome; obtaining a median, mode, average or midpoint value of all of the autosomal values; and using this value as a normalization constant to account for the differences in total number of sequence tags obtained for different samples. In certain embodiments, normalization can be performed by counting the number of tags falling within each genome section for all samples in a flow cell; obtaining a median, mode, average or midpoint value of the total sequence tag count for each chromosome for all samples in a flow cell, obtaining a median, mode, average or midpoint value of all of the autosomal values for all samples in a flow cell; and using this value as a normalization constant to account for the differences in total number of sequence tags obtained for different samples processed in parallel in a flow cell. In some embodiments, normalization can be performed by counting the number of tags falling within each genome section for all samples prepared in a plate (e.g., reagent plate, microwell plate); obtaining a median, mode, average or midpoint value of the total sequence tag count for each chromosome for all samples prepared in a plate, obtaining a median, mode, average or midpoint value of all of the autosomal values for all samples prepared in a plate; and using this value as a normalization constant to account for the differences in total number of sequence tags obtained for different samples processed in parallel in a plate.

A sequence tag density sometimes is about 1 for a disomic chromosome. Sequence tag densities can vary according to sequencing artifacts, most notably G/C bias, batch processing effects (e.g., sample preparation), and the like, which can be corrected by use of an external standard or internal reference (e.g., derived from substantially all of the sequence tags (genomic sequences), which may be, for example, a single chromosome, a calculated value from all autosomes, a calculated value from all samples analyzed in a flow cell (single chromosome or all autosomes), or a calculated value from all samples processed in a plate and analyzed in one or more flow cells, in some embodiments). Thus, dosage imbalance of a chromosome or chromosomal regions can be inferred from the percentage representation of the locus among other mappable sequenced tags of the specimen. Dosage imbalance of a particular chromosome or chromosomal regions therefore can be quantitatively determined and be normalized. Methods for sequence tag density normalization and quantification are discussed in further detail below.

In some embodiments, a proportion of all of the sequence reads are from a chromosome involved in an aneuploidy (e.g., chromosome 13, chromosome 18, chromosome 21), and other sequence reads are from other chromosomes. By taking into account the relative size of the chromosome involved in the aneuploidy (e.g., "target chromosome": chromosome 21) compared to other chromosomes, one could obtain a normalized frequency, within a reference range, of target chromosome-specific sequences, in some embodiments. If the fetus has an aneuploidy in the target chromosome, then the normalized frequency of the target chromosome-derived sequences is statistically greater than the normalized frequency of non-target chromosome-derived sequences, thus allowing the detection of the aneuploidy. The degree of change in the normalized frequency will be dependent on the fractional concentration of fetal nucleic acids in the analyzed sample, in some embodiments.

Outcomes and Determination of the Presence or Absence of a Genetic Variation

Some genetic variations are associated with medical conditions. Genetic variations often include a gain, a loss and/or alteration (e.g., duplication, deletion, fusion, insertion, mutation, reorganization, substitution or aberrant methylation) of genetic information (e.g., chromosomes, portions of chromosomes, polymorphic regions, translocated regions, altered nucleotide sequence, the like or combinations of the foregoing) that result in a detectable change in the genome or genetic information of a test subject with respect to a reference subject free of the genetic variation. The presence or absence of a genetic variation can be determined by analyzing and/or manipulating sequence reads that have been mapped to genomic sections (e.g., genomic bins) as known in the art and described herein. In some embodiments, the presence or absence of a known condition, syndrome and/or abnormality, non-limiting examples of which are provided in TABLES 1A and 1B, can be detected and/or determined utilizing methods described herein.

Counting

Sequence reads that have been mapped or partitioned based on a selected feature or variable can be quantified to determine the number of reads that were mapped to each genomic section (e.g., bin, partition, genomic segment and the like), in some embodiments. In certain embodiments, the total number of mapped sequence reads is determined by counting all mapped sequence reads, and in some embodiments the total number of mapped sequence reads is determined by summing counts mapped to each bin or partition. In some embodiments, counting is performed in the process of mapping reads. In certain embodiments, a subset of mapped sequence reads is determined by counting a predetermined subset of mapped sequence reads, and in some embodiments a predetermined subset of mapped sequence reads is determined by summing counts mapped to each predetermined bin or partition. In some embodiments, predetermined subsets of mapped sequence reads can include from 1 to n sequence reads, where n represents a number equal to the sum of all sequence reads generated from a test subject sample, one or more reference subject samples, all samples processed in a flow cell, or all samples prepared in a plate for analysis using one or more flow cells. Sequence reads that have been mapped and counted for a test subject sample, one or more reference subject samples, all samples processed in a flow cell, or all samples prepared in a plate sometimes are referred to as a sample count. Sample counts sometimes are further distinguished by reference to the subject from which the sample was isolated (e.g., test subject sample count, reference subject sample count, and the like).

In some embodiments, a test sample also is used as a reference sample. A test sample sometimes is used as reference sample and a median expected count and/or a derivative of the median expected count for one or more selected genomic sections (e.g., a first genomic section, a second genomic section, a third genomic section, 5 or more genomic sections, 50 or more genomic sections, 500 or more genomic sections, and the like) known to be free from genetic variation (e.g., do not have any microdeletions, duplications, aneuploidies, and the like in the one or more selected genomic sections) is determined. The median expected count or a derivative of the median expected count for the one or more genomic sections free of genetic variation can be used to evaluate the statistical significance of counts obtained from other selected genomic sections (e.g., different genomic sections than those utilized as the reference sample sections) of the test sample. In some embodiments, the median absolute deviation also is determined, and in certain embodiments, the median absolute deviation also is used to evaluate the statistical significance of counts obtained from other selected genomic sections of the test sample.

In certain embodiments, a normalization process that normalizes counts includes use of an expected count. In some embodiments, sample counts are obtained from pre-determined subsets of mapped sequence reads. In certain embodiments, predetermined subsets of mapped sequence reads can be selected utilizing any suitable feature or variable. In some embodiments, a predetermined set of mapped sequence reads is utilized as a basis for comparison, and can be referred to as an "expected sample count" or "expected count" (collectively an "expected count"). An expected count often is a value obtained in part by summing the counts for one or more selected genomic sections (e.g., a first genomic section, a second genomic section, a third genomic section, five or more genomic sections, 50 or more genomic sections, 500 or more genomic sections, and the like). Sometimes the selected genomic sections are chosen as a reference, or basis for comparison, due to the presence or absence of one or more variables or features. Sometimes an expected count is determined from counts of a genomic section (e.g., one or more genomic sections, a chromosome, genome, or part thereof) that is free of a genetic variation (e.g., a duplication, deletion, insertions, a fetal aneuploidy, trisomy). In certain embodiments an expected count is derived from counts of a genomic section (e.g., one or more genomic sections, a chromosome, genome, or part thereof) that comprises a genetic variation (e.g., a duplication, deletion, insertions, a fetal aneuploidy, trisomy). Sometimes an expected count is determined from counts of one or more genomic sections where some of the genomic sections comprise a genetic variation and some of the genomic sections are substantially free of a genetic variation. An expected count often is determined using data (e.g., counts of mapped sequence reads) from a group of samples obtained under at least one common experimental condition. An expected count sometimes is determined by applying to counts one or more mathematical or statistical manipulations described herein or otherwise known in the art. Non-limiting examples of expected count or expected sample count values resulting from such mathematical or statistical manipulations include median, mean, mode, average and/or midpoint, median absolute deviation, an alternative to median absolute deviation as introduced by Rousseeuw and Croux, a boot-strapped estimate, the like and combinations thereof. In some embodiments, an expected count is a median, mode, average and/or midpoint of counts (e.g., counts of a genomic section, chromosome, genome or part thereof). An expected count sometimes is a median, mode, average and/or midpoint or mean of counts or sample counts. Non-limiting examples of counts and expected counts include filtered counts, filtered expected counts, normalized counts, normalized expected counts, adjusted counts and adjusted expected counts. Filtering, normalization and adjustment processes are described in further detail herein.

In some embodiments, a derivative of an expected count is an expected count derived from counts that have been normalized and/or manipulated (e.g., mathematically manipulated). Counts that have been normalized and/or manipulated (e.g., mathematically manipulated) are sometimes referred to as a derivative of counts. A derivative of counts sometimes is a representation of counts from a first genomic section, which representation often is counts from a first genomic section relative to (e.g., divided by) counts from genomic sections that include the first genomic section. Sometimes a derivative of counts is express as a percent representation or ratio representation. Sometimes the representation is of one genomic section to multiple genomic sections, where the multiple genomic sections are from all or part of a chromosome. Sometimes the representation is of multiple genomic sections to a greater number of genomic sections, where the multiple genomic sections are from all or part of a chromosome and the greater number of genomic sections is from multiple chromosomes, substantially all autosomes or substantially the entire genome. In some embodiments a normalization process that normalizes a derivative of counts includes use of a derivative of an expected count. An expected count obtained from a derivative of counts is referred to herein as a "derivative of the expected count". Sometimes a derivative of an expected count is an expected count derived from a representation of counts (e.g., a percent representation, a chromosomal representation). In some embodiments, a derivative of an expected count is a median, mode, average and/or midpoint of a count representation (e.g., a percent representation, a chromosomal representation). In certain embodiments, a median is a median, mean, mode, midpoint, average or the like.

Sometimes an estimate of variability is determined for counts, expected counts or a derivative of an expected count. Non-limiting examples of an estimate of variability include a median absolute deviation (MAD) of the counts, expected counts or derivative of the expected counts; an alternative to MAD as introduced by Rousseeuw and Croux; a boot-strapped estimate; a standard deviation of the counts, expected counts or derivative of the expected counts; the like and combinations thereof. An estimate of variability sometimes is utilized in a normalization process for obtaining a normalized sample count.

In certain embodiments, a normalization process for obtaining a normalized sample count includes subtracting an expected count from counts for a first genome section, thereby generating a subtraction value, and dividing the subtraction value by an estimate of the variability of the counts or expected counts. Non-limiting examples of the variability of the counts or expected counts is a median absolute deviation (MAD) of the counts or expected counts, an alternative to MAD as introduced by Rousseeuw and Croux or a bootstrapped estimate. In some embodiments, a normalization process for obtaining a normalized sample count includes subtracting the expected first genome section count representation from the first genome section count representation, thereby generating a subtraction value, and dividing the subtraction value by an estimate of the variability of the first genome section count representation or the expected first genome section count representation. Non-limiting examples of the variability of the count representation or the expected count representation are a median absolute deviation (MAD) of the count representation or the expected count representation, an alternative to MAD as introduced by Rousseeuw and Croux or a bootstrapped estimate. In some embodiments an expected count is a median, mode, average, mean and/or midpoint of the counts of the first genome section, and sometimes an expected count representation is a median, mean, mode, average and/or midpoint of the count representation of the first genomic section.

In some embodiments, an expected count, a derivative of an expected count (e.g., an expected count representation), or an estimate of variability of counts, a derivative of counts, an expected count or derivative of an expected count, independently is determined according to sample data acquired under one or more common experimental conditions. An estimate of variability sometimes is obtained for sample data generated from one or more common experimental conditions; an estimate of variability sometimes is obtained for sample data not generated from one or more common experimental conditions; an expected count sometimes is obtained for sample data generated from one or more common experimental conditions; an expected count sometimes is obtained for sample data not generated from one or more common experimental conditions; and an estimate of variability and an expected count sometimes are obtained for sample data generated from one or more common experimental conditions. An estimate of variability of a derivative of an expected count (e.g., an expected count representation) sometimes is obtained for sample data generated from one or more common experimental conditions; an estimate of variability of a derivative of an expected count (e.g., an expected count representation) sometimes is obtained for sample data not generated from one or more common experimental conditions; a derivative of an expected count (e.g., an expected count representation) sometimes is obtained for sample data generated from one or more common experimental conditions; a derivative of an expected count (e.g., an expected count representation) sometimes is obtained for sample data not generated from one or more common experimental conditions; and an estimate of variability of a derivative of an expected count (e.g., an expected count representation) and a derivative of an expected count (e.g., an expected count representation) sometimes are obtained for sample data generated from one or more common experimental conditions.

In some embodiments, an expected count or a derivative of an expected count (e.g., an expected count representation), is determined using sample data acquired under one or more common experimental conditions, and an estimate of variability of counts, a derivative of counts, an expected count or derivative of an expected count is determined using sample data not acquired under a common experimental condition. In certain embodiments, an estimate of variability of counts, a derivative of counts, an expected count or derivative of an expected count is determined using sample data acquired for a first number of samples, and not acquired under under a common experimental condition, and an expected count or a derivative of an expected count (e.g., an expected count representation), is determined using sample data acquired under one or more common experimental conditions and acquired for a second number of samples less than the first number of samples. The second number of samples sometimes is acquired in a time frame shorter than the time frame in which the first number of samples was acquired.

Sample data acquired under one or more common experimental conditions sometimes is acquired under 1 to about 5 common experimental conditions (e.g., 1, 2, 3, 4 or 5 common experimental conditions). Non-limiting examples of common experimental conditions include a channel in a flow cell, a flow cell unit, flow cells common to a container, flow cells common to a lot or manufacture run; a reagent plate unit, reagent plates common to a container, reagent plates common to a lot or manufacture run; an operator; an instrument (e.g., a sequencing instrument); humidity, temperature; identification tag index; the like and combinations thereof. Reagent plates sometimes are utilized for nucleic acid library preparation and/or nucleic acid sequencing.

Quantifying or counting sequence reads can be performed in any suitable manner including but not limited to manual counting methods and automated counting methods. In some embodiments, an automated counting method can be embodied in software that determines or counts the number of sequence reads or sequence tags mapping to each chromosome and/or one or more selected genomic sections. Software generally are computer readable program instructions that, when executed by a computer, perform computer operations, as described herein.

The number of sequence reads mapped to each bin and the total number of sequence reads for samples derived from test subject and/or reference subjects can be further analyzed and processed to provide an outcome determinative of the presence or absence of a genetic variation. Mapped sequence reads that have been counted sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, genomic section or bin specific], experimental condition based [e.g., index based, flow cell based, plate based] the like and combinations thereof). In certain embodiments, data or data sets can be organized and/or stratified into a matrix having two or more dimensions based on one or more features or variables (e.g., fetal fraction and maternal age; fetal fraction and geographic location; percent chromosome 21 representation and flow cell number; chromosome 21 z-score and maternal weight; chromosome 21 z-score and gestational age, and the like). Data organized and/or stratified into matrices can be organized and/or stratified using any suitable features or variables. A non-limiting example of data in a matrix includes data that is organized by maternal age, maternal ploidy, and fetal contribution. Non-limiting examples of data stratified using features or variables are presented in FIGS. 4 to 45. In certain embodiments, data sets characterized by one or more features or variables sometimes are processed after counting.

Elevations

In some embodiments, a value is ascribed to an elevation (e.g., a number). An elevation can be determined by a suitable method, operation or mathematical process (e.g., a processed elevation). An elevation often is, or is derived from, counts (e.g., normalized counts) for a set of genomic sections. Sometimes an elevation of a genomic section is substantially equal to the total number of counts mapped to a genomic section (e.g., normalized counts). Often an elevation is determined from counts that are processed, transformed or manipulated by a suitable method, operation or mathematical process known in the art. Sometimes an elevation is derived from counts that are processed and non-limiting examples of processed counts include weighted, removed, filtered, normalized, adjusted, averaged, derived as a mean (e.g., mean elevation), added, subtracted, transformed counts or combination thereof. Sometimes an elevation comprises counts that are normalized (e.g., normalized counts of genomic sections). An elevation can be for counts normalized by a suitable process, non-limiting examples of which include bin-wise normalization, normalization by GC content, linear and nonlinear least squares regression, GC LOESS, LOWESS, PERUN, RM, GCRM, cQn, the like and/or combinations thereof. An elevation can comprise normalized counts or relative amounts of counts. Sometimes an elevation is for counts or normalized counts of two or more genomic sections that are averaged and the elevation is referred to as an average elevation. Sometimes an elevation is for a set of genomic sections having a mean count or mean of normalized counts which is referred to as a mean elevation. Sometimes an elevation is derived for genomic sections that comprise raw and/or filtered counts. In some embodiments, an elevation is based on counts that are raw. Sometimes an elevation is associated with an uncertainty value. An elevation for a genomic section is sometimes referred to as a "genomic section elevation" and is synonymous with a "genomic section level" herein.

Normalized or non-normalized counts for two or more elevations (e.g., two or more elevations in a profile) can sometimes be mathematically manipulated (e.g., added, multiplied, averaged, normalized, the like or combination thereof) according to elevations. For example, normalized or non-normalized counts for two or more elevations can be normalized according to one, some or all of the elevations in a profile. Sometimes normalized or non-normalized counts of all elevations in a profile are normalized according to one elevation in the profile. Sometimes normalized or non-normalized counts of a fist elevation in a profile are normalized according to normalized or non-normalized counts of a second elevation in the profile.

Non-limiting examples of an elevation (e.g., a first elevation, a second elevation) are an elevation for a set of genomic sections comprising processed counts, an elevation for a set of genomic sections comprising a mean, median, mode, midpoint or average of counts, an elevation for a set of genomic sections comprising normalized counts, the like or any combination thereof. In some embodiments, a first elevation and a second elevation in a profile are derived from counts of genomic sections mapped to the same chromosome. In some embodiments, a first elevation and a second elevation in a profile are derived from counts of genomic sections mapped to different chromosomes.

In some embodiments an elevation is determined from normalized or non-normalized counts mapped to one or more genomic sections. In some embodiments, an elevation is determined from normalized or non-normalized counts mapped to two or more genomic sections, where the normalized counts for each genomic section often are about the same. There can be variation in counts (e.g., normalized counts) in a set of genomic sections for an elevation. In a set of genomic sections for an elevation there can be one or more genomic sections having counts that are significantly different than in other genomic sections of the set (e.g., peaks and/or dips). Any suitable number of normalized or non-normalized counts associated with any suitable number of genomic sections can define an elevation.

Sometimes one or more elevations can be determined from normalized or non-normalized counts of all or some of the genomic sections of a genome. Often an elevation can be determined from all or some of the normalized or non-normalized counts of a chromosome, or segment thereof. Sometimes, two or more counts derived from two or more genomic sections (e.g., a set of genomic sections) determine an elevation. Sometimes two or more counts (e.g., counts from two or more genomic sections) determine an elevation. In some embodiments, counts from 2 to about 100,000 genomic sections determine an elevation. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 genomic sections determine an elevation. In some embodiments counts from about 10 to about 50 genomic sections determine an elevation. In some embodiments counts from about 20 to about 40 or more genomic sections determine an elevation. In some embodiments, an elevation comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more genomic sections. In some embodiments, an elevation corresponds to a set of genomic sections (e.g., a set of genomic sections of a reference genome, a set of genomic sections of a chromosome or a set of genomic sections of a segment of a chromosome).

In some embodiments, an elevation is determined for normalized or non-normalized counts of genomic sections that are contiguous. Sometimes genomic sections (e.g., a set of genomic sections) that are contiguous represent neighboring segments of a genome or neighboring segments of a chromosome or gene. For example, two or more contiguous genomic sections, when aligned by merging the genomic sections end to end, can represent a sequence assembly of a DNA sequence longer than each genomic section. For example two or more contiguous genomic sections can represent of an intact genome, chromosome, gene, intron, exon or segment thereof. Sometimes an elevation is determined from a collection (e.g., a set) of contiguous genomic sections and/or non-contiguous genomic sections.

Significantly Different Elevations

In some embodiments, a profile of normalized counts comprises an elevation (e.g., a first elevation) significantly different than another elevation (e.g., a second elevation) within the profile. A first elevation may be higher or lower than a second elevation. In some embodiments, a first elevation is for a set of genomic sections comprising one or more reads comprising a copy number variation (e.g., a maternal copy number variation, fetal copy number variation, or a maternal copy number variation and a fetal copy number variation) and the second elevation is for a set of genomic sections comprising reads having substantially no copy number variation. In some embodiments, significantly different refers to an observable difference. Sometimes significantly different refers to statistically different or a statistically significant difference. A statistically significant difference is sometimes a statistical assessment of an observed difference. A statistically significant difference can be assessed by a suitable method in the art. Any suitable threshold or range can be used to determine that two elevations are significantly different. In some cases two elevations (e.g., mean elevations) that differ by about 0.01 percent or more (e.g., 0.01 percent of one or either of the elevation values) are significantly different. Sometimes two elevations (e.g., mean elevations) that differ by about 0.1 percent or more are significantly different. In some cases, two elevations (e.g., mean elevations) that differ by about 0.5 percent or more are significantly different. Sometimes two elevations (e.g., mean elevations) that differ by about 0.5, 0.75, 1, 1.5, 2, 2.5, 3, 3.5, 4, 4.5, 5, 5.5, 6, 6.5, 7, 7.5, 8, 8.5, 9, 9.5 or more than about 10% are significantly different. Sometimes two elevations (e.g., mean elevations) are significantly different and there is no overlap in either elevation and/or no overlap in a range defined by an uncertainty value calculated for one or both elevations. In some cases the uncertainty value is a standard deviation expressed as sigma. Sometimes two elevations (e.g., mean elevations) are significantly different and they differ by about 1 or more times the uncertainty value (e.g., 1 sigma). Sometimes two elevations (e.g., mean elevations) are significantly different and they differ by about 2 or more times the uncertainty value (e.g., 2 sigma), about 3 or more, about 4 or more, about 5 or more, about 6 or more, about 7 or more, about 8 or more, about 9 or more, or about 10 or more times the uncertainty value. Sometimes two elevations (e.g., mean elevations) are significantly different when they differ by about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 times the uncertainty value or more. In some embodiments, the confidence level increases as the difference between two elevations increases. In some cases, the confidence level decreases as the difference between two elevations decreases and/or as the uncertainty value increases. For example, sometimes the confidence level increases with the ratio of the difference between elevations and the standard deviation (e.g., MADS).

In some embodiments, a first set of genomic sections often includes genomic sections that are different than (e.g., non-overlapping with) a second set of genomic sections. For example, sometimes a first elevation of normalized counts is significantly different than a second elevation of normalized counts in a profile, and the first elevation is for a first set of genomic sections, the second elevation is for a second set of genomic sections and the genomic sections do not overlap in the first set and second set of genomic sections. In some cases, a first set of genomic sections is not a subset of a second set of genomic sections from which a first elevation and second elevation are determined, respectively. Sometimes a first set of genomic sections is different and/or distinct from a second set of genomic sections from which a first elevation and second elevation are determined, respectively.

Sometimes a first set of genomic sections is a subset of a second set of genomic sections in a profile. For example, sometimes a second elevation of normalized counts for a second set of genomic sections in a profile comprises normalized counts of a first set of genomic sections for a first elevation in the profile and the first set of genomic sections is a subset of the second set of genomic sections in the profile. Sometimes an average, mean, median, mode or midpoint elevation is derived from a second elevation where the second elevation comprises a first elevation. Sometimes, a second elevation comprises a second set of genomic sections representing an entire chromosome and a first elevation comprises a first set of genomic sections where the first set is a subset of the second set of genomic sections and the first elevation represents a maternal copy number variation, fetal copy number variation, or a maternal copy number variation and a fetal copy number variation that is present in the chromosome.

In some embodiments, a value of a second elevation is closer to the mean, average mode, midpoint or median value of a count profile for a chromosome, or segment thereof, than the first elevation. In some embodiments, a second elevation is a mean elevation of a chromosome, a portion of a chromosome or a segment thereof. In some embodiments, a first elevation is significantly different from a predominant elevation (e.g., a second elevation) representing a chromosome, or segment thereof. A profile may include multiple first elevations that significantly differ from a second elevation, and each first elevation independently can be higher or lower than the second elevation. In some embodiments, a first elevation and a second elevation are derived from the same chromosome and the first elevation is higher or lower than the second elevation, and the second elevation is the predominant elevation of the chromosome. Sometimes, a first elevation and a second elevation are derived from the same chromosome, a first elevation is indicative of a copy number variation (e.g., a maternal and/or fetal copy number variation, deletion, insertion, duplication) and a second elevation is a mean elevation or predominant elevation of genomic sections for a chromosome, or segment thereof.

In some cases, a read in a second set of genomic sections for a second elevation substantially does not include a genetic variation (e.g., a copy number variation, a maternal and/or fetal copy number variation). Often, a second set of genomic sections for a second elevation includes some variability (e.g., variability in elevation, variability in counts for genomic sections). Sometimes, one or more genomic sections in a set of genomic sections for an elevation associated with substantially no copy number variation include one or more reads having a copy number variation present in a maternal and/or fetal genome. For example, sometimes a set of genomic sections include a copy number variation that is present in a small segment of a chromosome (e.g., less than 10 genomic sections) and the set of genomic sections is for an elevation associated with substantially no copy number variation. Thus a set of genomic sections that include substantially no copy number variation still can include a copy number variation that is present in less than about 10, 9, 8, 7, 6, 5, 4, 3, 2 or 1 genomic sections of an elevation.

Sometimes a first elevation is for a first set of genomic sections and a second elevation is for a second set of genomic sections and the first set of genomic sections and second set of genomic sections are contiguous (e.g., adjacent with respect to the nucleic acid sequence of a chromosome or segment thereof). Sometimes the first set of genomic sections and second set of genomic sections are not contiguous.

Relatively short sequence reads from a mixture of fetal and maternal nucleic acid can be utilized to provide counts which can be transformed into an elevation and/or a profile. Counts, elevations and profiles can be depicted in electronic or tangible form and can be visualized. Counts mapped to genomic sections (e.g., represented as elevations and/or profiles) can provide a visual representation of a fetal and/or a maternal genome, chromosome, or a portion or a segment of a chromosome that is present in a fetus and/or pregnant female.

Data Processing

Mapped sequence reads that have been counted are referred to herein as raw data, since the data represent unmanipulated counts (e.g., raw counts). In some embodiments, sequence read data in a data set can be adjusted and/or processed further (e.g., mathematically and/or statistically manipulated) and/or displayed to facilitate providing an outcome. Adjusted sequence read data often results from manipulation of a portion of, or all, sequences reads, data in a data set, and/or sample nucleic acid. Any suitable manipulation can be used to adjust a portion of or all sequence reads, data in a data set and/or sample nucleic acid. In some embodiments, an adjustment to sequence reads, data in a data set and/or sample nucleic acid is a process chosen from filtering (e.g., removing a portion of the data based on a selected feature or variable; removing repetitive sequences, removing uninformative bins or bins having zero median counts, for example), adjusting (e.g., rescaling and/or re-weighting a portion of or all data based on an estimator; re-weighting sample counts based on G/C content, rescaling and/or re-weighting a portion of or all data based on fetal fraction, for example), normalizing using one or more estimators or statistical manipulations (e.g., normalizing all data in a given flow cell to the median absolute deviation of all data in the flow cell), and the like. In some embodiments, the estimator is a robust estimator. In certain embodiments, a portion of the sequence read data is adjusted and/or processed, and in some embodiments, all of the sequence read data is adjusted and/or processed.

Adjusted or processed sequence reads, data in a data set and/or sample nucleic acid sometimes are referred to as a derivative (e.g., a derivative of the counts, derivative data, derivative of the sequence reads, and the like). A derivative of counts, data or sequence reads often is generated by the use of one or more mathematical and/or statistical manipulations on the counts, data or sequence reads. Any suitable mathematic and/or statistical manipulation described herein or known in the art can be used to generate a derivative counts, data, or sequence reads. Non-limiting examples of mathematical and/or statistical manipulations that can be utilized to filter, adjust, normalize or manipulate counts, data, or sequence reads to generate a derivative include, average, mean, median, mode, midpoint, median absolute deviation, alternate to median absolute deviation as introduced by Rousseeuw and Croux, bootstrapped estimate, other methods described herein and known in the art, the like or combinations thereof.

In certain embodiments, data sets, including larger data sets, may benefit from pre-processing to facilitate further analysis. Pre-processing of data sets sometimes involves removal of redundant and/or uninformative genomic sections or bins (e.g., bins with uninformative data, redundant mapped reads, genomic sections or bins with zero median counts, over represented or under represented sequences [e.g., G/C sequences], repetitive sequences). Without being limited by theory, data processing and/or preprocessing may (i) remove noisy data, (ii) remove uninformative data, (iii) remove redundant data, (iv) reduce the complexity of larger data sets, (v) reduce or eliminate experimental condition induced data variability, (vi) rescale and/or re-weight a portion of or all data in a data set, and/or (vii) facilitate transformation of the data from one form into one or more other forms. The terms "pre-processing" and "processing" when utilized with respect to data or data sets are collectively referred to herein as "processing". Processing can render data more amenable to further analysis, and can generate an outcome in some embodiments.

Noisy data often is (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being over represented when prepared using PCR-based methods. Methods described herein can reduce or eliminate the contribution of noisy data, and therefore reduce the effect of noisy data on the provided outcome.

Uninformative data, uninformative bins, and uninformative genomic sections often are genomic sections, or data derived therefrom, having a numerical value that is significantly different from a predetermined cutoff threshold value or falls outside a predetermined cutoff range of values. A cutoff threshold value or range of values often is calculated by mathematically and/or statistically manipulating sequence read data (e.g., from a reference, subject, flow cell and/or plate), in some embodiments, and in certain embodiments, sequence read data manipulated to generate a threshold cutoff value or range of values is sequence read data (e.g., from a reference, subject, flow cell and/or plate). In some embodiments, a threshold cutoff value is obtained by calculating the standard deviation and/or median absolute deviation (e.g., MAD or alternative to MAD as introduced by Rousseeuw and Croux, or bootstrapped estimate) of a raw or normalized count profile and multiplying the standard deviation for the profile by a constant representing the number of standard deviations chosen as a cutoff threshold (e.g., multiply by 3 for 3 standard deviations), whereby a value for an uncertainty is generated. In certain embodiments, a portion or all of the genomic sections exceeding the calculated uncertainty threshold cutoff value, or outside the range of threshold cutoff values, are removed as part of, prior to, or after the normalization process. In some embodiments, a portion or all of the genomic sections exceeding the calculated uncertainty threshold cutoff value, or outside the range of threshold cutoff values or raw data points, are weighted as part of, or prior to the normalization or classification process. Examples of weighting are described herein. In some embodiments, redundant data, and redundant mapped reads refer to sample derived sequence reads that are identified as having already been assigned to a genomic location (e.g., base position) and/or counted for a genomic section.

Experimental Conditions

Samples sometimes are affected by common experimental conditions. Samples processed at substantially the same time or using substantially the same conditions and/or reagents sometimes exhibit similar experimental condition (e.g., common experimental condition) induced data variability when compared to other samples processed at a different time and/or at the same time using different conditions and/or reagents. There often are practical considerations that limit the number of samples that can be prepared, processed and/or analyzed at any given time during an experimental procedure. In certain embodiments, the time frame for processing a sample from raw material to generating an outcome sometimes is days, weeks or even months. Due to the time between isolation and final analysis, high throughput experiments that analyze large numbers of samples sometimes generate batch effects or experimental condition-induced data variability.

Experimental condition-induced data variability often includes any data variability that is a result of sample isolation, storage, preparation and/or analysis. Non-limiting examples of experimental condition induced variability include flow-cell based variability and/or plate based variability that includes: over or under representation of sequences; noisy data; spurious or outlier data points, reagent effects, personnel effects, laboratory condition effects and the like. Experimental condition induced variability sometimes occurs to subpopulations of samples in a data set (e.g., batch effect). A batch often is samples processed using substantially the same reagents, samples processed in the same sample preparation plate (e.g., microwell plate used for sample preparation; nucleic acid isolation, for example), samples staged for analysis in the same staging plate (e.g., microwell plate used to organize samples prior to loading onto a flow cell), samples processed at substantially the same time, samples processed by the same personnel, and/or samples processed under substantially the same experimental conditions (e.g., temperature, $CO_2$ levels, ozone levels, the like or combinations thereof). Experimental condition batch effects sometimes affect samples analyzed on the same flow cell, prepared in the same reagent plate or microwell plate and/or staged for analysis (e.g., preparing a nucleic acid library for sequencing) in the same reagent plate or microwell plate. Additional sources of variability can include, quality of nucleic acid isolated, amount of nucleic acid isolated, time to storage after nucleic acid isolation, time in storage, storage temperature, the like and combinations thereof. Variability of data points in a batch (e.g., subpopulation of samples in a data set which are processed at the same time and/or using the same reagents and/or experimental conditions) sometimes is greater than variability of data points seen between batches. This data variability sometimes includes spurious or outlier data whose magnitude can effect interpretation of some or all other data in a data set. A portion or all of a data set can be adjusted for experimental conditions using data processing steps described herein and known in the art; normalization to the median absolute deviation calculated for all samples analyzed in a flow cell, or processed in a microwell plate, for example.

Experimental condition-induced variability can be observed for data obtained over a period of weeks to months or years. (e.g., 1 week, 1-4 weeks, 1 month, 1-3 months, 1-6 months). Sometimes multiple experiments are conducted over a period of weeks to months where one or more experimental conditions are common experimental conditions. Non-limiting examples of common experimental conditions include use of the same instrument, machine or part thereof (e.g., a sequencer, a liquid handling device, a spectrophotometer, photocell, etc.), use of the same device (e.g., flow cell, flow cell channel, plate, chip, the like, or part thereof), use of the same protocol (operating procedure, standard operating procedure, recipe, methods and/or conditions (e.g., time of incubations, temperature, pressure, humidity, volume, concentration), the same operator (e.g., a technician, scientist), and same reagents (e.g., nucleotides, oligonucleotides, sequence tag, identification tag index, sample (e.g., ccf DNA sample), proteins (e.g., enzymes, buffers, salts, water), the like).

Use of the same device, apparatus or reagent can include a device, apparatus, reagent or part thereof from the same manufacturer, the same manufacturing run, same lot (e.g., a material originating from the same plant, manufacturer, manufacturing run or location, a collection labeled with the same date), same cleaning cycle, same preparation protocol, same container (bag, box, package, storage bin, pallet, trailer), same shipment (e.g., same date of delivery, same order, having the same invoice), same manufacturing plant, same assembly line, the like or combinations thereof. Use of the same operator, in some embodiments, means one or more operators of a machine, apparatus or device are the same.

Adjusting data in a data set often can reduce or eliminate the effect of outliers on a data set, rescale or re-weight data to facilitate providing an outcome, and/or reduce the complexity and/or dimensionality of a data set. In certain embodiments, data can be sorted (e.g., stratified, organized) according to one or more common experimental conditions (e.g., reagents used, flow cell used, plate used, personnel that processed samples, index sequences used, the like or combinations thereof). In some embodiments, data can be normalized or adjusted according to one or more common experimental conditions.

Data may be rescaled or re-weighted using robust estimators. A robust estimator often is a mathematical or statistical manipulation that minimizes or eliminates the effect of spurious or outlier data, whose magnitude may effect providing an outcome (e.g., making a determination of the presence or absence of a genetic variation). Any suitable robust estimator can be used to adjust a data set. In some embodiments, a robust estimator is a robust estimator of scale (e.g., variability; similar to and/or includes the median absolute deviation [MAD] or alternative to MAD as introduced by Rousseeuw and Croux, or bootstrapped estimate), and in certain embodiments, a robust estimator is a robust estimator of location (e.g., expected value; similar to an average or median). Non-limiting examples of robust estimators of scale and location are described in Example 2 and also are known in the art (e.g., median, ANOVA, and the like). In some embodiments, a portion of, or all data in a data set can be adjusted using an expected count or derivative of an expected count obtained using a robust estimator. In some embodiments an expected count is a count derived from a reference or reference sample (e.g., a known euploid sample).

Any suitable procedure can be utilized for adjusting and/or processing data sets described herein. Non-limiting examples of procedures that can be used to adjust data sets include experimental condition-based adjustments (e.g., plate-based normalization, flow-cell based normalization [e.g., flow-cell based median comparisons], repeat masking adjustment (e.g., removal of repetitive sequences); G/C content adjustment; locally weighted polynomial (e.g., LOESS) regression adjustment, normalization using robust estimators (e.g., estimate of location [e.g., expected value; similar to average], estimate of scale [e.g., variability]; and analysis of variability [e.g., ANOVA]). Additionally, in certain embodiments, data sets can be further processed utilizing one or more of the following data processing methods filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, sliding window processing (e.g., sliding window normalization), static window processing (e.g., static window normalization), the like and combinations of the foregoing, and in certain embodiments, a processing method can be applied to a data set prior to an adjustment step. In some embodiments, data sets are adjusted and/or processed based on various features (e.g., GC content, redundant mapped reads, centromere regions, telomere regions, repetitive sequences, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject. Data adjustment and/or processing can be performed in any number of steps, in certain embodiments, and in those embodiments with more than one step, the steps can be performed in any order. For example, data may be adjusted and/or processed using only a single adjustment/processing procedure in some embodiments, and in certain embodiments data may be adjusted/processed using 1 or more, 5 or more, 10 or more or 20 or more adjustment/processing steps (e.g., 1 or more adjustment/processing steps, 2 or more adjustment/processing steps, 3 or more adjustment/processing steps, 4 or more adjustment/processing steps, 5 or more adjustment/processing steps, 6 or more adjustment/processing steps, 7 or more adjustment/processing steps, 8 or more adjustment/processing steps, 9 or more adjustment/processing steps, 10 or more adjustment/processing steps, 11 or more adjustment/processing steps, 12 or more adjustment/processing steps, 13 or more adjustment/processing steps, 14 or more adjustment/processing steps, 15 or more adjustment/processing steps, 16 or more adjustment/processing steps, 17 or more adjustment/processing steps, 18 or more adjustment/processing steps, 19 or more adjustment/processing steps, or 20 or more adjustment/processing steps). In some embodiments, adjustment/processing steps may be the same step repeated two or more times (e.g., filtering two or more times, normalizing two or more times), and in certain embodiments, adjustment/processing steps may be two or more different adjustment/processing steps (e.g., repeat masking, flow-cell based normalization; bin-wise G/C content adjustment, flow-cell based normalization; repeat masking, bin-wise G/C content adjustment, plate-based normalization; filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different adjustment/processing steps can be utilized to process sequence read data to facilitate providing an outcome. In certain embodiments, adjusting and/or processing data sets by the criteria described herein may reduce the complexity and/or dimensionality of a data set.

In some embodiments, one or more adjustment/processing steps can comprise adjustment for one or more experimental conditions described herein. Non-limiting examples of experimental conditions that sometimes lead to data variability include: over or under representation of sequences (e.g., biased amplification based variability); noisy data; spurious or outlier data points; flow cell-based variability (e.g., variability seen in samples analyzed on one flow cell, but not seen in other flow cells used to analyze samples from the same batch (e.g., prepared in the same reagent plate or microwell plate)); and/or plate-based variability (e.g., variability seen in some or all samples prepared in the same reagent plate or microwell plate and/or staged for analysis in the same microwell plate regardless of the flow cell used for analysis).

In some embodiments percent representation is calculated for a genomic section (e.g., a genomic section, chromosome, genome, or part thereof). In some embodiments a percent representation is determined as a number of counts mapped to a genomic section normalized to (e.g., divided by) the number of counts mapped to multiple genomic sections. Sometimes the determination of a percent representation excludes genomic sections and/or counts derived from sex chromosomes (e.g., X and/or Y chromosomes). Sometimes the determination of a percent representation includes only genomic sections and/or counts derived from autosomes. Sometimes the determination of a percent representation includes genomic sections and/or counts derived from autosomes and sex chromosomes. For example for $perc_i$ denoting the percent representation for a selected genomic section i, $$perc_i = \frac{counts_i}{\sum_{j=1}^{22} counts_j}$$

where $counts_i$ are counts of reads mapped to the selected genomic section i and $counts_j$ are the number of counts of reads mapped to multiple genomic sections j (e.g., multiple genomic sections on chromosome j, genomic sections of all autosomes j, genomic sections of genome j). For example, for $chr_i$ denoting the chromosomal representation for chromosome i, $$chr_i = \frac{counts_i}{\sum_{j=1}^{22} counts_j}$$

where $counts_j$ are the number of aligned reads on chromosome j. In some embodiments a percent representation is a "genome section count representation". Sometimes a percent representation is a "genomic section representation" or a "chromosome representation".

In certain embodiments, one or more adjustment/processing steps can comprise adjustment for experimental condition-induced variability. Variability can be adjusted by using a robust estimator of scale and/or location. In some embodiments, z-scores can be adjusted for experimental condition-induced variability by determining (1) the percent representation of a selected genomic section (e.g., a first genome section count representation; chromosome, chromosome 21 for example), (2) the median, mean, mode, average and/or midpoint of all values of percent representation for a selected genomic section, (3) the median absolute deviation (MAD) of all values of percent representation, and adjusting the z-score using a flow cell-based robust estimator that minimizes or eliminates the effect of outliers. In certain embodiments, a robust flow cell-based z-score adjustment for a target chromosome, target genomic region or target genomic section (e.g., chromosome 21) is calculated utilizing the formula below.

$$Z\ robust = \frac{perc_i - \text{Median}(\{perc_{iec}\})}{MAD(\{perc_{iec'}\})}$$

The formula as written is configured to calculate a robust Z-score for a genomic section, where perc is percent representation (e.g., first genome section count representation, chromosome representation) of a selected genomic section i (e.g., any suitable genomic section, chromosome, genome, or part thereof). In some embodiments, the Median is calculated from one or more percent representation values for the selected genomic section i obtained for experimental conditions ec. A MAD is calculated from one or more percent representation values for the selected genomic section i obtained for experimental conditions ec'. The generalized formula can be utilized to obtain robust z-scores for any genomic section by substituting the equivalent values for the chosen target genomic section in certain embodiments. In some embodiments, a Median, mean, mode, average, mdipoint and/or MAD is calculated for a selected set of samples or a subset of samples. Sometimes a Median and/or MAD is calculated for the same set of samples. In some embodiments a Median and/or MAD is calculated for a different set of samples. In some embodiments the experimental conditions ec are the same. In some embodiments the experimental conditions ec can comprise or consist of one or more common experimental conditions. In some embodiments the experimental conditions ec are different. In some embodiments the experimental conditions ec' are the same. In some embodiments the experimental conditions ec' can comprise or consist of one or more common experimental conditions. In some embodiments the experimental conditions ec' are different. Sometimes the experimental conditions ec and ec' are different. In some embodiments the experimental conditions ec and ec' can comprise or consist of one or more common experimental conditions. For example, a robust Z-score for a selected genomic section can be calculated from (a) a Mean derived from a selected set of data collected from a selected set of samples and where the data was obtained under one or more common experimental conditions (e.g., from the same flow cell), and (b) a MAD derived from another selected set of data collected from another selected set of samples and where the data was obtained under one or more common experimental conditions (e.g., using different flow cells and the same lot of selected reagents). In some embodiments a Mean and a MAD are derived from data sharing at least one common experimental condition. Sometimes a Mean and a MAD are derived from data that do not share a common experimental condition.

In some embodiments a normalized sample count (e.g., a Z-score) is obtained by a process comprising subtracting an expected count (e.g., a median of counts, a median of percent representations) from counts of a first genomic section (e.g., counts, a percent representation) thereby generating a subtraction value, and dividing the subtraction value by an estimate of the variability of the count (e.g., a MAD, a MAD of counts, a MAD of percent representations). In some embodiments an expected count (e.g., a median of counts, a median of percent representations) and an estimate of the variability of the count (e.g., a MAD, a MAD of counts, a MAD of percent representations) are derived from data sharing at least one common experimental condition. Sometimes an expected count (e.g., a median of counts, a median of percent representations) and an estimate of the variability of the count (e.g., a MAD, a MAD of counts, a MAD of percent representations) are derived from data that do not share a common experimental condition. In some embodiments a median can be a median, mean, mode, average and/or midpoint.

In certain embodiments, one or more adjustment/processing steps can comprise adjustment for flow cell-based variability. Flow cell-based variability can be adjusted by using a robust estimator of scale and/or location. In some embodiments, z-scores can be adjusted for flow cell-based variability by determining (1) the percent representation of a selected chromosome (e.g., a first genome section count representation; chromosome 21 for example), (2) the median of all values of chromosome representation observed in a flow cell, (3) the median absolute deviation of all values of chromosome representation observed in a flow cell, and adjusting the z-score using a flow cell-based robust estimator that minimizes or eliminates the effect of outliers. In certain embodiments, a robust flow cell-based z-score adjustment for a target chromosome, target genomic region or target genomic section (e.g., chromosome 21) is calculated utilizing the formula below.

$$z_{robust_{FC}} = \frac{perc.chr21 - \mathrm{median}(\{perc.chr21\})_{FC}}{MAD(\{perc.chr21\})_{FC}}$$

The formula as written is configured to calculate a robust Z-score for chromosome 21, where perc.chr21 is percent chromosome 21 representation (e.g., first genome section count representation), MAD represents median absolute deviation and FC represents flow cell. The generalized formula can be utilized to obtain robust z-scores for any chromosome by substituting the equivalent values for the chosen target chromosome, target genomic region or target genomic section where the chromosome 21 reference is designated (e.g., .chr21), in certain embodiments.

In some embodiments, one or more adjustment/processing steps can comprise adjustment for plate-based variability. Plate-based variability can be adjusted by using a robust estimator of scale and/or location. In certain embodiments, z-scores can be adjusted for plate-based variability by determining (1) the percent representation of a selected chromosome (e.g., a first genome section count representation; chromosome 21 for example), (2) the median of all values of chromosome representation observed in one or more plates, (3) the median absolute deviation of all values of chromosome representation observed in one or more plates, and adjusting the z-score using a plate-based robust estimator that minimizes or eliminates the effect of outliers. In certain embodiments, a robust plate-based z-score adjustment for a target chromosome, target genomic region or target genomic section (e.g., chromosome 21) is calculated utilizing the formula below.

$$z_{robust_{PLATE}} = \frac{perc.chr21 - \mathrm{median}(\{perc.chr21\})_{PLATE}}{MAD(\{perc.chr21\})_{PLATE}}$$

The formula as written is configured to calculate a robust Z-score for chromosome 21, where perc.chr21 is percent chromosome 21 representation (e.g., first genome section count representation), MAD represents median absolute deviation and PLATE represents one or more plates of samples (e.g., reagent plate or plates, sample preparation plate or plates, staging plate or plates). The generalized formula can be utilized to obtain robust z-scores for any chromosome by substituting the equivalent values for the chosen target chromosome, target genomic region or target genomic section where the chromosome 21 reference is designated (e.g., .chr21), in certain embodiments.

Median absolute deviation (MAD) sometimes is calculated using the formula:

$$MAD=1.4826*median(\{|X-median(\{X\})|\})$$

where, X represents any random variable for which the median absolute deviation is calculated, and the normalization constant 1.4826 represents 1/Inv[Phi](¾) and where Phi is the cumulative distribution function for the standard Gaussian (e.g., normal) distribution, and Inv[Phi] is its inverse (e.g., related to a quantile function). Inv[Phi] is evaluated at X=¾, and is equal to 1/1.4826. In "R code", the equation for calculating the normalization constant is: 1/qnorm (¾)=1.4826. "R code" is a non-proprietary open source programming language used for a variety of statistical analysis substantially similar to the S programming language (e.g., R Development Core Team (2010). R: A language and environment for statistical computing. R Foundation for Statistical Computing, Vienna, Austria. ISBN 3-900051-07-0, URL world wide web.R-project.org/). The normalization constant 1.4826 is chosen such that the median absolute deviation (e.g., MAD) of normally distributed data is equal, for large samples, to the standard deviation (e.g., STDEV) of the same data, which effectively puts the MAD and STDEV on the same scale. A quantile function often is utilized to prescribe a probability distribution. A quantile function of a probability distribution is the inverse of its integral, and often specifies the value which the random variable will be at, or below, for a given probability, in some embodiments.

In certain embodiments, one or more adjustment/processing steps can comprise adjustment for over or under representation of sequences. As noted herein, amplification procedures utilized in some preparation and/or sequencing steps sometimes generate over or under representation of sequences due to sequence content and/or structure. Over or under representation of sequences sometimes reduces the confidence in a provided outcome. The effect of over or under sequence representation can be minimized or eliminated by adjusting or normalizing a portion of, or all of a data set with reference to an expected value using a robust estimator, in certain embodiments. In some embodiments, an expected value is calculated for a portion of, or all chromosomes using one or more estimators chosen from; an average, a median, average, midpoint, mode, a median absolute deviation (MAD), an alternate to MAD as introduced by Rousseeuw and Croux, bootstrapped estimate, standard deviations, z-scores, robust z-score, ANOVA, LOESS regression analysis (e.g., LOESS smoothing, LOWESS smoothing) and the like. Adjusting a portion of or all of a data set to reduce or eliminate the effect of over or under representation of sequences can facilitate providing an outcome, and/or reduce the complexity and/or dimensionality of a data set.

In some embodiments, one or more adjustment/processing steps can comprise adjustment for G/C content. As noted herein, sequences with high G/C content sometimes are over or under represented in a raw or processed data set. In certain embodiments, G/C content for a portion of or all of a data set (e.g., selected bins, selected portions of chromosomes, selected chromosomes) is adjusted to minimize or eliminate G/C content bias by adjusting or normalizing a portion of, or all of a data set with reference to an expected value using a robust estimator. In some embodiments, the expected value is the G/C content of the nucleotide sequence reads, and in certain embodiments, the expected value is the G/C content of the sample nucleic acid. In some embodiments, the expected value is calculated for a portion of, or all chromosomes using one or more estimators chosen from; average, median, mean, mode, midpoint, median absolute deviation, (MAD), an alternate to MAD as introduced by Rousseeuw and Croux, bootstrapped estimate, standard deviation, z-score, robust z-score, ANOVA, LOESS regression analysis (e.g., LOESS smoothing, LOWESS smoothing) and the like. Adjusting a portion of or all of a data set to reduce or eliminate the effect of G/C content bias can facilitate providing an outcome, and/or reduce the complexity and/or dimensionality of a data set, in some embodiments.

PERUN

A particularly useful normalization methodology for reducing error associated with nucleic acid indicators is referred to herein as Parameterized Error Removal and Unbiased Normalization (PERUN). PERUN methodology can be applied to a variety of nucleic acid indicators (e.g., nucleic acid sequence reads) for the purpose of reducing effects of error that confound predictions based on such indicators.

For example, PERUN methodology can be applied to nucleic acid sequence reads from a sample and reduce the effects of error that can impair nucleic acid elevation determinations (e.g., genomic section elevation determinations). Such an application is useful for using nucleic acid sequence reads to assess the presence or absence of a genetic variation in a subject manifested as a varying elevation of a nucleotide sequence (e.g., genomic section). Non-limiting examples of variations in genomic sections are chromosome aneuploidies (e.g., trisomy 21, trisomy 18, trisomy 13) and presence or absence of a sex chromosome (e.g., XX in females versus XY in males). A trisomy of an autosome (e.g., a chromosome other than a sex chromosome) can be referred to as an affected autosome. Other non-limiting examples of variations in genomic section elevations include microdeletions, microinsertions, duplications and mosaicism.

In certain applications, PERUN methodology can reduce experimental bias by normalizing nucleic acid indicators for particular genomic groups, the latter of which are referred to as bins. Bins include a suitable collection of nucleic acid indicators, a non-limiting example of which includes a length of contiguous nucleotides, which is referred to herein as a genomic section or portion of a reference genome. Bins can include other nucleic acid indicators as described herein. In such applications, PERUN methodology generally normalizes nucleic acid indicators at particular bins across a number of samples in three dimensions. A detailed description of particular PERUN applications is described in Example 4 and Example 5 herein.

In certain embodiments, PERUN methodology includes calculating a genomic section elevation for each bin from a fitted relation between (i) experimental bias for a bin of a reference genome to which sequence reads are mapped and (ii) counts of sequence reads mapped to the bin. Experimental bias for each of the bins can be determined across multiple samples according to a fitted relation for each sample between (i) the counts of sequence reads mapped to each of the bins, and (ii) a mapping feature fore each of the bins. This fitted relation for each sample can be assembled for multiple samples in three dimensions. The assembly can be ordered according to the experimental bias in certain embodiments (e.g., FIG. 82, Example 4), although PERUN methodology may be practiced without ordering the assembly according to the experimental bias.

A relation can be generated by a method known in the art. A relation in two dimensions can be generated for each sample in certain embodiments, and a variable probative of error, or possibly probative of error, can be selected for one or more of the dimensions. A relation can be generated, for example, using graphing software known in the art that plots a graph using values of two or more variables provided by a user. A relation can be fitted using a method known in the art (e.g., graphing software). Certain relations can be fitted by linear regression, and the linear regression can generate a slope value and intercept value. Certain relations sometimes are not linear and can be fitted by a non-linear function, such as a parabolic, hyperbolic or exponential function, for example.

In PERUN methodology, one or more of the fitted relations may be linear. For an analysis of cell-free circulating nucleic acid from pregnant females, where the experimental bias is GC bias and the mapping feature is GC content, the fitted relation for a sample between the (i) the counts of sequence reads mapped to each bin, and (ii) GC content for each of the bins, can be linear. For the latter fitted relation, the slope pertains to GC bias, and a GC bias coefficient can be determined for each bin when the fitted relations are assembled across multiple samples. In such embodiments, the fitted relation for multiple samples and a bin between (i) GC bias coefficient for the bin, and (ii) counts of sequence reads mapped to bin, also can be linear. An intercept and slope can be obtained from the latter fitted relation. In such applications, the slope addresses sample-specific bias based on GC-content and the intercept addresses a bin-specific attenuation pattern common to all samples. PERUN methodology can significantly reduce such sample-specific bias and bin-specific attenuation when calculating genomic section elevations for providing an outcome (e.g., presence or absence of genetic variation; determination of fetal sex).

Thus, application of PERUN methodology to sequence reads across multiple samples in parallel can significantly reduce error caused by (i) sample-specific experimental bias (e.g., GC bias) and (ii) bin-specific attenuation common to samples. Other methods in which each of these two sources of error are addressed separately or serially often are not able to reduce these as effectively as PERUN methodology. Without being limited by theory, it is expected that PERUN methodology reduces error more effectively in part because its generally additive processes do not magnify spread as much as generally multiplicative processes utilized in other normalization approaches (e.g., GC-LOESS).

Additional normalization and statistical techniques may be utilized in combination with PERUN methodology. An additional process can be applied before, after and/or during employment of PERUN methodology. Non-limiting examples of processes that can be used in combination with PERUN methodology are described hereafter.

In some embodiments, a secondary normalization or adjustment of a genomic section elevation for GC content can be utilized in conjunction with PERUN methodology. A suitable GC content adjustment or normalization procedure can be utilized (e.g., GC-LOESS, GCRM). In certain embodiments, a particular sample can be identified for application of an additional GC normalization process. For example, application of PERUN methodology can determine GC bias for each sample, and a sample associated with a GC bias above a certain threshold can be selected for an additional GC normalization process. In such embodiments, a predetermined threshold elevation can be used to select such samples for additional GC normalization.

In certain embodiments, a bin filtering or weighting process can be utilized in conjunction with PERUN methodology. A suitable bin filtering or weighting process can be utilized and non-limiting examples are described herein. Examples 4 and 5 describe utilization of R-factor measures of error for bin filtering.

GC Bias Module

Determining GC bias (e.g., determining GC bias for each of the portions of a reference genome (e.g., genomic sections)) can be provided by a GC bias module (e.g., by an apparatus comprising a GC bias module). In some embodiments, a GC bias module is required to provide a determination of GC bias. Sometimes a GC bias module provides a determination of GC bias from a fitted relationship (e.g., a fitted linear relationship) between counts of sequence reads mapped to each of the portions of a reference genome and GC content of each portion. An apparatus comprising a GC bias module can comprise at least one processor. In some embodiments, GC bias determinations (i.e., GC bias data) are provided by an apparatus that includes a processor (e.g., one or more processors) which processor can perform and/or implement one or more instructions (e.g., processes, routines and/or subroutines) from the GC bias module. In some embodiments, GC bias data is provided by an apparatus that includes multiple processors, such as processors coordinated and working in parallel. In some embodiments, a GC bias module operates with one or more external processors (e.g., an internal or external network, server, storage device and/or storage network (e.g., a cloud)). In some embodiments, GC bias data is provided by an apparatus comprising one or more of the following: one or more flow cells, a camera, fluid handling components, a printer, a display (e.g., an LED, LCT or CRT) and the like. A GC bias module can receive data and/or information from a suitable apparatus or module. Sometimes a GC bias module can receive data and/or information from a sequencing module, a normalization module, a weighting module, a mapping module or counting module. A GC bias module sometimes is part of a normalization module (e.g., PERUN normalization module). A GC bias module can receive sequencing reads from a sequencing module, mapped sequencing reads from a mapping module and/or counts from a counting module, in some embodiments. Often a GC bias module receives data and/or information from an apparatus or another module (e.g., a counting module), transforms the data and/or information and provides GC bias data and/or information (e.g., a determination of GC bias, a linear fitted relationship, and the like). GC bias data and/or information can be transferred from a GC bias module to an expected count module, filtering module, comparison module, a normalization module, a weighting module, a range setting module, an adjustment module, a categorization module, and/or an outcome module, in certain embodiments.

Other Data Processing

In certain embodiments, one or more adjustment/processing steps can comprise adjustment for repetitive sequences. As noted herein, repetitive sequences often are uninformative data and/or can contribute to noisy data, which sometimes reduces the confidence in a provided outcome. Any suitable method for reducing the effect of repetitive sequences (e.g., removal of repetitive sequences) described herein or known in the art can be used. Non-limiting examples of resources available for removal of repetitive sequences can be found in the following publications: URL world wide web repeatmasker.org/papers.html and world wide web biomedcentral.com/1471-2105/11/80. The effect of the presence of repetitive sequences on a provided outcome can be minimized or eliminated by adjusting or normalizing a portion of, or all of a data set with reference to an expected value using a robust estimator, in certain embodiments. In some embodiments, the expected value is calculated for a portion of, or all chromosomes using one or more estimators chosen from; an average, a median, mode, midpoint, mean, a median absolute deviation, (MAD), an alternate to MAD as introduced by Rousseeuw and Croux, bootstrapped estimate, standard deviations, z-scores, robust z-score, ANOVA, LOESS regression analysis (e.g., LOESS smoothing, LOWESS smoothing) and the like. Adjusting a portion of or all of a data set to reduce or eliminate the effect of repetitive sequences can facilitate providing an outcome, and/or reduce the complexity and/or dimensionality of a data set.

In some embodiments, one or more adjustment/processing steps can comprise an index sequence adjustment. As noted herein, adaptor primers utilized in embodiments described herein frequently include index sequences. If all indexes have substantially the same performance, chromosome representation, or some other genomic-relevant equivalent metric would be distributed the same way across substantially all samples labeled by different indexes. However in practice, some indexes work better than others, which in turn causes some fragments to be preferentially analyzed (e.g., up-weighted) with respect to other fragments by an algorithm. Additionally, some indexes can lead to a smaller number of detected and/or aligned reads, which in turn effects the resolution for samples tagged with those index sequences, when compared to samples tagged with other indexes. A portion of or all of a data set can be adjusted or normalized using an estimator, with respect to one or more index sequences, in certain embodiments, and in certain embodiments the estimator is chosen from: an average, a median, mean, mode, midpoint, a median absolute deviation (MAD), an alternate to MAD as introduced by Rousseeuw and Croux, bootstrapped estimate, standard deviations, z-scores, robust z-score, ANOVA, LOESS regression analysis (e.g., LOESS smoothing, LOWESS smoothing) and the like. Adjusting a portion of or all of a data set to reduce with respect to one or more index sequences can facilitate providing an outcome, and/or reduce the complexity and/or dimensionality of a data set.

A portion of or all of a data set also can be additionally processed using one or more procedures described below.

In some embodiments, one or more processing steps can comprise one or more filtering steps. Filtering generally removes genomic sections or bins from consideration. Bins can be selected for removal based on any suitable criteria, including but not limited to redundant data (e.g., redundant or overlapping mapped reads), non-informative data (e.g., bins with zero median counts), bins with over represented or under represented sequences, noisy data, the like, or combinations of the foregoing. A filtering process often involves removing one or more bins from consideration and subtracting the counts in the one or more bins selected for removal from the counted or summed counts for the bins, chromosome or chromosomes, or genome under consideration. In some embodiments, bins can be removed successively (e.g., one at a time to allow evaluation of the effect of removal of each individual bin), and in certain embodiments all bins marked for removal can be removed at the same time. In some embodiments, genomic sections characterized by a variance above or below a certain level are removed, which sometimes is referred to herein as filtering "noisy" genomic sections. In certain embodiments, a filtering process comprises obtaining data points from a data set that deviate from the mean profile elevation of a genomic section, a chromosome, or portion of a chromosome by a predetermined multiple of the profile variance, and in certain embodiments, a filtering process comprises removing data points from a data set that do not deviate from the mean profile elevation of a genomic section, a chromosome or portion of a chromosome by a predetermined multiple of the profile variance. In some embodiments, a filtering process is utilized to reduce the number of candidate genomic sections analyzed for the presence or absence of a genetic variation. Reducing the number of candidate genomic sections analyzed for the presence or absence of a genetic variation (e.g., microdeletion, micro-duplication) often reduces the complexity and/or dimensionality of a data set, and sometimes increases the speed of searching for and/or identifying genetic variations and/or genetic aberrations by two or more orders of magnitude.

In some embodiments, one or more processing steps can comprise one or more normalization steps. Normalization can be performed by a suitable method known in the art. Sometimes normalization comprises adjusting values measured on different scales to a notionally common scale. Sometimes normalization comprises a sophisticated mathematical adjustment to bring probability distributions of adjusted values into alignment. In some cases normalization comprises aligning distributions to a normal distribution. Sometimes normalization comprises mathematical adjustments that allow comparison of corresponding normalized values for different datasets in a way that eliminates the effects of certain gross influences (e.g., error and anomalies). Sometimes normalization comprises scaling. Normalization sometimes comprises division of one or more data sets by a predetermined variable or formula. Non-limiting examples of normalization methods include bin-wise normalization, normalization by GC content, linear and nonlinear least squares regression, LOESS, GC LOESS, LOWESS (locally weighted scatterplot smoothing), PERUN (see below), repeat masking (RM), GC-normalization and repeat masking (GCRM), cQn and/or combinations thereof. In some embodiments, the determination of a presence or absence of a genetic variation (e.g., an aneuploidy) utilizes a normalization method (e.g., bin-wise normalization, normalization by GC content, linear and nonlinear least squares regression, LOESS, GC LOESS, LOWESS (locally weighted scatterplot smoothing), PERUN, repeat masking (RM), GC-normalization and repeat masking (GCRM), cQn, a normalization method known in the art and/or a combination thereof).

For example, LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relation between fragment count (e.g., sequence reads, counts) and GC composition for genomic sections. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

In certain embodiments, normalization refers to division of one or more data sets by a predetermined variable. Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference genomic sections to the total number of counts mapped to the chromosome or the entire genome on which the selected genomic section or sections are mapped; normalizing raw count data for one or more selected genomic segments to a median reference count for one or more genomic sections or the chromosome on which a selected genomic segment or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable.

Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing genomic sections, or bins, with respect to a normalizing value sometimes is referred to as "bin-wise normalization".

In certain embodiments, a processing step comprising normalization includes normalizing to a static window, and in some embodiments, a processing step comprising normalization includes normalizing to a moving or sliding window. A "window" often is one or more genomic sections chosen for analysis, and sometimes used as a reference for comparison (e.g., used for normalization and/or other mathematical or statistical manipulation). Normalizing to a static window often involves using one or more genomic sections selected for comparison between a test subject and reference subject data set in a normalization process. In some embodiments the selected genomic sections are utilized to generate a profile. A static window generally includes a predetermined set of genomic sections that do not change during manipulations and/or analysis. Normalizing to a moving window, or normalizing to a sliding window, often is a normalization performed on genomic sections localized to the genomic region (e.g., immediate genetic surrounding, adjacent genomic section or sections, and the like) of a selected test genomic section, where one or more selected test genomic sections are normalized to genomic sections immediately surrounding the selected test genomic section. In certain embodiments, the selected genomic sections are utilized to generate a profile. A sliding or moving window normalization often includes repeatedly moving or sliding to an adjacent test genomic section, and normalizing the newly selected test genomic section to genomic sections immediately surrounding or adjacent to the newly selected test genomic section, where adjacent windows have one or more genomic sections in common. In certain embodiments, a plurality of selected test genomic sections and/or chromosomes can be analyzed by a sliding window process.

In some embodiments, normalizing to a sliding or moving window can generate one or more values, where each value represents normalization to a different set of reference genomic sections selected from different regions of a genome (e.g., chromosome). In certain embodiments, the one or more values generated are cumulative sums (e.g., a numerical estimate of the integral of the normalized count profile over the selected genomic section, domain (e.g., part of chromosome), or chromosome). The values generated by the sliding or moving window process can be used to generate a profile and facilitate arriving at an outcome. In some embodiments, cumulative sums of one or more genomic sections can be displayed as a function of genomic position. Moving or sliding window analysis sometimes is used to analyze a genome for the presence or absence of micro-deletions and/or micro-insertions. In certain embodiments, displaying cumulative sums of one or more genomic sections is used to identify the presence or absence of regions of genetic variation (e.g., micro-deletions, micro-duplications). In some embodiments, moving or sliding window analysis is used to identify genomic regions containing micro-deletions and in certain embodiments, moving or sliding window analysis is used to identify genomic regions containing micro-duplications.

In some embodiments, a processing step comprises a weighting. Weighting, or performing a weight function, often is a mathematical manipulation of a portion or all of a data set sometimes utilized to alter the influence of certain data set features or variables with respect to other data set features or variables (e.g., increase or decrease the significance and/or contribution of data contained in one or more genomic sections or bins, based on the quality or usefulness of the data in the selected bin or bins). A weighting function can be used to increase the influence of data with a relatively small measurement variance, and/or to decrease the influence of data with a relatively large measurement variance, in some embodiments. For example, bins with under represented or low quality sequence data can be "down weighted" to minimize the influence on a data set, whereas selected bins can be "up weighted" to increase the influence on a data set. A non-limiting example of a weighting function is $[1/(\text{standard deviation})^2]$. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak elevations, determination of peak edge locations, calculation of peak area ratios, analysis of median chromosomal elevation, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median elevations, mean elevations, count distribution within a genomic region, relative representation of nucleic acid species, the like or combinations thereof.

In some embodiments, a processing step can include the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median elevations, mean elevations, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

In some embodiments, an adjustment/processing step optionally comprises generating one or more profiles (e.g., profile plot) from various aspects of a data set or derivation thereof (e.g., product of one or more mathematical and/or statistical data processing steps known in the art and/or described herein). Generating a profile often involves employing a mathematical and/or statistical manipulation of data that facilitates identification of patterns and/or correlations in large quantities of data. A profile often is values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a portion or subset of a data set. A profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a genomic section. In certain embodiments, a data point in a profile represents the results of data manipulation for groups of genomic sections. In some embodiments, groups of genomic sections may be adjacent to one another, and in certain embodiments, groups of genomic sections may be from different parts of a chromosome or genome.

Data points in a profile derived from a data set can be representative of any suitable data categorization. Non-limiting examples of categories into which data can be grouped to generate profile data points include: genomic sections based on sized, genomic sections based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile frequently is presented as a plot, and non-limiting examples of profile plots that can be generated include raw count (e.g., raw count profile or raw profile), normalized count (e.g., normalized count profile or normalized profile), bin-weighted, z-score, p-value, area ratio versus fitted ploidy, median elevation versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median elevation versus ratio between fitted and measured fetal fraction, principle components). A raw count profile plot, or raw profile plot, often is a plot of counts in each genomic section in a region normalized to total counts in a region (e.g., genome, chromosome, portion of chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected genomic section is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or range of values indicative of the presence or absence of a genetic variation can vary while still providing an outcome useful for determining the presence or absence of a genetic variation. In some embodiments, a profile is indicative of and/or representative of a phenotype.

By way of a non-limiting example, an adjusted/normalized dataset can be generated from raw sequence read data by (a) obtaining total counts for all chromosomes, selected chromosomes, genomic sections and/or portions thereof for all samples from one or more flow cells, or all samples from one or more plates; (b) adjusting, filtering and/or removing one or more of (i) uninformative or repetitive genomic sections (e.g., repeat masking; described in Example 2) (ii) G/C content bias (iii) over or under represented sequences, (iv) noisy data; and (c) adjusting/normalizing a portion of or all remaining data in (b) with respect to an expected value using a robust estimator for the selected chromosome or selected genomic location, thereby generating an adjusted/normalized value. In certain embodiments, the data in (c) is optionally adjusted with respect to one or more index sequences, one or more additional estimators, one or more additional processing steps, the like or combinations thereof. In some embodiments, adjusting, filtering and/or removing one or more of i) uninformative and/or repetitive genomic sections (e.g., repeat masking) (ii) G/C content bias (iii) over or under represented sequences, (iv) noisy data can be performed in any order (e.g.,(i); (ii); (iii); (iv); (i), (ii), (ii), (i); (iii), (i); (ii), (iii), (i); (i), (iv), (iii); (ii), (i) (iii); (i), (ii), (iii), (iv); (ii), (i), (iii), (v); (ii), (iv), (iii), (i); and the like). In certain embodiments, remaining data can be adjusted based on one or more experimental conditions described herein.

In some embodiments, sequences adjusted by one method can impact a portion of sequences substantially completely adjusted by a different method (e.g., G/C content bias adjustment sometimes removes up to 50% of sequences removed substantially completely by repeat masking).

An adjusted/normalized dataset can be generated by one or more manipulations of counted mapped sequence read data. Sequence reads are mapped and the number of sequence tags mapping to each genomic bin are determined (e.g., counted). In some embodiments, datasets are repeat masking adjusted to remove uninformative and/or repetitive genomic sections prior to mapping, and in certain embodiments, the reference genome is repeat masking adjusted prior to mapping. Performing either masking procedure yields substantially the same results. In certain embodiments, datasets are adjusted for G/C content bias by bin-wise G/C normalization with respect to a robust estimator of the expected G/C sequence representation for a portion of or all chromosomes. In some embodiments, a dataset is repeat masking adjusted prior to G/C content adjustment, and in certain embodiments, a dataset is G/C content adjusted prior to repeat masking adjustment. After adjustment, the remaining counts typically are summed to generate an adjusted data set. In certain embodiments, dataset adjustment facilitates classification and/or providing an outcome. In some embodiments, an adjusted data set profile is generated from an adjusted dataset and utilized to facilitate classification and/or providing an outcome.

After sequence read data have been counted and adjusted for repetitive sequences, G/C content bias, or repetitive sequences and G/C content bias, datasets can be adjusted for one or more index sequences, in some embodiments. Samples from multiple patients can be labeled with different index sequences and mixed together on a flow cell. Sequence read mapping between patients and indices is homomorphic (unique in both directions), in some embodiments. After sequencing measurements are completed, different sequenced fragments can be assigned to the individual patients from which they originate. Separation between different sequence fragments often is achieved based on the index (barcode) portions of the fragment sequences. Substantially all the fragments that bear the same index (barcode) are grouped together and ascribed to the patient associated with that index. The same procedure is repeated for each patient sample, in certain embodiments. A few fragments may have no index or an unrecognized index (due to experimental errors). Fragments which have no index or an unrecognized index are left unassigned, unless the unrecognized index looks similar to one of the expected indices, in which case one can optionally admit those fragments as well. Only the fragments that are assigned to a given patient are aligned against the reference genome and counted toward the chromosomal representation of that particular patient. After adjustment, the remaining counts typically are summed to generate an adjusted data set. In certain embodiments, dataset adjustment facilitates classification and/or providing an outcome. In some embodiments, an adjusted data set profile is generated from an adjusted dataset and utilized to facilitate classification and/or providing an outcome.

After sequence read data have been counted, adjusted for repetitive sequences, G/C content bias, or repetitive sequences and G/C content bias, and/or index sequences, datasets can be adjusted to minimize or eliminate the effect of flow cell-based and/or plate-based experimental condition bias. In certain embodiments, dataset adjustment facilitates classification and/or providing an outcome. In some embodiments, an adjusted data set profile is generated from an adjusted dataset and utilized to facilitate classification and/or providing an outcome.

After datasets are adjusted as described herein, a portion of or all of a data set also can be additionally processed using one or more procedures described below. In some embodiments, additional processing of a portion of or all of a data set comprises generating a Z-score as described herein, or as known in the art. In certain embodiments, a Z-score is generated as a robust Z-score that minimizes the effects of spurious or outlier data.

Data sets can be optionally normalized to generate normalized count profiles. A data set can be normalized by normalizing one or more selected genomic sections to a suitable normalizing reference value. In some embodiments, a normalizing reference value is representative of the total counts for the chromosome or chromosomes from which genomic sections are selected. In certain embodiments, a normalizing reference value is representative of one or more corresponding genomic sections, portions of chromosomes or chromosomes from a reference data set prepared from a set of reference subjects know not to possess a genetic variation. In some embodiments, a normalizing reference value is representative of one or more corresponding genomic sections, portions of chromosomes or chromosomes from a test subject data set prepared from a test subject being analyzed for the presence or absence of a genetic variation. In certain embodiments, the normalizing process is performed utilizing a static window approach, and in some embodiments the normalizing process is performed utilizing a moving or sliding window approach. In certain embodiments, a normalized profile plot is generated to facilitate classification and/or providing an outcome. An outcome can be provided based on normalized profile plots.

Data sets can be optionally filtered and normalized, the processed data sets can be further manipulated by one or more filtering and/or normalizing procedures, in some embodiments. A data set that has been further manipulated by one or more filtering and/or normalizing procedures can be used to generate a profile, in certain embodiments. The one or more filtering and/or normalizing procedures sometimes can reduce data set complexity and/or dimensionality, in some embodiments. An outcome can be provided based on a data set of reduced complexity and/or dimensionality.

Data sets can be further manipulated by weighting, in some embodiments. One or more genomic sections can be selected for weighting to reduce the influence of data (e.g., noisy data, uninformative data) contained in the selected genomic sections, in certain embodiments, and in some embodiments, one or more genomic sections can be selected for weighting to enhance or augment the influence of data (e.g., data with small measured variance) contained in the selected genomic segments. In some embodiments, a data set is weighted utilizing a single weighting function that decreases the influence of data with large variances and increases the influence of data with small variances. A weighting function sometimes is used to reduce the influence of data with large variances and augment the influence of data with small variances (e.g., $[1/(\text{standard deviation})^2]$). In some embodiments, a profile plot of processed data further manipulated by weighting is generated to facilitate classification and/or providing an outcome. An outcome can be provided based on a profile plot of weighted data Data sets can be further manipulated by one or more mathematical and/or statistical (e.g., statistical functions or statistical algorithm) manipulations, in some embodiments. In certain embodiments, processed data sets can be further manipulated by calculating Z-scores for one or more selected genomic sections, chromosomes, or portions of chromosomes. In some embodiments, processed data sets can be further manipulated by calculating P-values. Formulas for calculating Z-scores and P-values are known in the art. In certain embodiments, mathematical and/or statistical manipulations include one or more assumptions pertaining to ploidy and/or fetal fraction. In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fetal fraction.

In certain embodiments, multiple manipulations are performed on processed data sets to generate an N-dimensional space and/or N-dimensional point, after data sets have been counted, optionally filtered and normalized. An outcome can be provided based on a profile plot of data sets analyzed in N-dimensions.

Data sets can be further manipulated by utilizing one or more processes chosen from peak elevation analysis, peak width analysis, peak edge location analysis, peak lateral tolerances, the like, derivations thereof, or combinations of the foregoing, as part of or after data sets have processed and/or manipulated. In some embodiments, a profile plot of data processed utilizing one or more peak elevation analysis, peak width analysis, peak edge location analysis, peak lateral tolerances, the like, derivations thereof, or combinations of the foregoing is generated to facilitate classification and/or providing an outcome. An outcome can be provided based on a profile plot of data that has been processed utilizing one or more peak elevation analysis, peak width analysis, peak edge location analysis, peak lateral tolerances, the like, derivations thereof, or combinations of the foregoing.

In some embodiments, the use of one or more reference samples known to be free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for the selected genomic section or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected genomic section or sections is expected to vary significantly from the predetermined value for affected genomic locations.

In some embodiments, analysis and processing of data can include the use of one or more assumptions. Any suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. A normalized count profile often is a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

As noted above, data sometimes is transformed from one form into another form. Transformed data, or a transformation, often is an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion or genomic deletion; represent the presence or absence of a variation in the physical amount of a sequence associated with medical conditions). A virtual representation sometimes is further transformed into one or more numerical values or graphical representations of the digital representation of the starting material. These procedures can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). Any suitable feature or variable can be utilized to adjust and/or reduce data set complexity and/or dimensionality. Non-limiting examples of features that can be chosen for use as a target feature for data adjustment/processing include flow-cell based and/or plate based experimental conditions, GC content, repetitive sequences, index sequences, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, robust Z-scores, p-values, median absolute deviations, or alternates to MAD described herein); reduction of multiple analysis methods to probability plots or single points; principle component analysis of derived quantities; and the like or combinations thereof.

Outcome

Analysis, adjustment and processing of data can provide one or more outcomes. An outcome often is a result of data adjustment and processing that facilitates determining whether a subject was, or is at risk of having, a genetic variation. An outcome often comprises one or more numerical values generated using an adjustment/processing method described herein in the context of one or more considerations of probability or estimators. A consideration of probability includes but is not limited to: measure of variability, confidence level, sensitivity, specificity, standard deviation, coefficient of variation (CV) and/or confidence level, Z-scores, robust Z-scores, percent chromosome representation, median absolute deviation, or alternates to median absolute deviation, Chi values, Phi values, ploidy values, fetal fraction, fitted fetal fraction, area ratios, median elevation, the like or combinations thereof. A consideration of probability can facilitate determining whether a subject is at risk of having, or has, a genetic variation, and an outcome determinative of a presence or absence of a genetic disorder often includes such a consideration.

In some embodiments, an outcome comprises factoring the fraction of fetal nucleic acid in the sample nucleic acid (e.g., adjusting counts, removing samples or not making a call). Determination of fetal fraction sometimes is performed using a fetal quantifier assay (FQA), as described herein in the Examples and known in the art (e.g., United States Patent Application Publication NO: US 2010-0105049 A1, entitled "PROCESSES AND COMPOSITIONS FOR METHYLATION-BASED ENRICHMENT OF FETAL NUCLEIC ACIDS" which is incorporated herein by reference in its entirety).

An outcome often is a phenotype with an associated level of confidence (e.g., fetus is positive for trisomy 21 with a confidence level of 99%, test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. A score, or call, often is generated by calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or genomic section from a data set, with respect to a reference genome can lead to an identification of the presence or absence of a genetic variation, which genetic variation sometimes is associated with a medical condition (e.g., cancer, preeclampsia, trisomy, monosomy, and the like). In certain embodiments, an outcome is generated from an adjusted data set. In some embodiments, a provided outcome that is determinative of the presence or absence of a genetic variation and/or fetal aneuploidy is based on a normalized sample count. In some embodiments, an outcome comprises a profile. In those embodiments in which an outcome comprises a profile, any suitable profile or combination of profiles can be used for an outcome. Non-limiting examples of profiles that can be used for an outcome include z-score profiles, robust Z-score profiles, p-value profiles, chi value profiles, phi value profiles, the like, and combinations thereof.

An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in any suitable form, which form comprises without limitation, a probability (e.g., odds ratio, p-value), likelihood, value in or out of a cluster, value over or under a threshold value, value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. An outcome also can describe any assumptions used in data processing. In certain embodiments, an outcome comprises a value that falls within or outside a predetermined range of values and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. A true positive refers to a subject correctly diagnosed as having a genetic variation. A false positive refers to a subject wrongly identified as having a genetic variation. A true negative refers to a subject correctly identified as not having a genetic variation. A false negative refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative. Sensitivity generally is the number of true positives divided by the number of true positives plus the number of false negatives, where sensitivity (sens) may be within the range of $0 \leq sens \leq 1$. Ideally, the number of false negatives equal zero or close to zero, so that no subject is wrongly identified as not having at least one genetic variation when they indeed have at least one genetic variation. Conversely, an assessment often is made of the ability of a prediction algorithm to classify negatives correctly, a complementary measurement to sensitivity. Specificity generally is the number of true negatives divided by the number of true negatives plus the number of false positives, where sensitivity (spec) may be within the range of $0 \leq spec \leq 1$. Ideally, the number of false positives equal zero or close to zero, so that no subject is wrongly identified as having at least one genetic variation when they do not have the genetic variation being assessed.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein.

A method that has sensitivity and specificity equaling one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

In some embodiments, an outcome based on counted mapped sequence reads or derivations thereof is determinative of the presence or absence of one or more conditions, syndromes or abnormalities listed in TABLE 1A and 1B. In certain embodiments, an outcome generated utilizing one or more data processing methods described herein is determinative of the presence or absence of one or more conditions, syndromes or abnormalities listed in TABLE 1A and 1B. In some embodiments, an outcome determinative of the presence or absence of a condition, syndrome or abnormality is, or includes, detection of a condition, syndrome or abnormality listed in TABLE 1A and 1B.

In certain embodiments, an outcome is based on a comparison between: a test sample and reference sample; a test sample and other samples; two or more test samples; the like; and combinations thereof. In some embodiments, the comparison between samples facilitates providing an outcome. In certain embodiments, an outcome is based on a Z-score generated as described herein or as is known in the art. In some embodiments, a Z-score is generated using a normalized sample count. In some embodiments, the Z-score generated to facilitate providing an outcome is a robust Z-score generated using a robust estimator. In certain embodiments, an outcome is based on a normalized sample count.

After one or more outcomes have been generated, an outcome often is used to provide a determination of the presence or absence of a genetic variation and/or associated medical condition. An outcome typically is provided to a health care professional (e.g., laboratory technician or manager; physician or assistant). In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in any suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described in the Examples.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A healthcare professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient.

Receiving a report often involves obtaining, by a communication means, a text and/or graphical representation comprising an outcome, which allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by any other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file. Outcome information also can be obtained from a laboratory file. A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

A healthcare professional or qualified individual, can provide any suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Software can be used to perform one or more steps in the process described herein, including but not limited to; counting, data processing, generating an outcome, and/or providing one or more recommendations based on generated outcomes.

Machines, Software and Interfaces

Apparatuses, software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by any suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A user may, for example, place a query to software which then may acquire a data set via internet access, and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, one or more robust estimator algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, any suitable configuration and control may be utilized for mapping and/or processing data using multiple machines, such as in local network, remote network and/or "cloud" computing platforms.

In some embodiments, an apparatus may comprise a web-based system in which a computer program product described herein is implemented. A web-based system sometimes comprises computers, telecommunications equipment (e.g., communications interfaces, routers, network switches), and the like sufficient for web-based functionality. In certain embodiments, a web-based system includes network cloud computing, network cloud storage or network cloud computing and network cloud storage. Network cloud storage generally is web-based data storage on virtual servers located on the internet. Network cloud computing generally is network-based software and/or hardware usage that occurs in a remote network environment (e.g., software available for use for a few located on a remote server). In some embodiments, one or more functions of a computer program product described herein is implemented in a web-based environment.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by any suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, simulated data is generated by an in silico process and the simulated data serves as data that can be input via an input device. As used herein, "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., data acquisition module, data processing module, data display module). Software often is computer readable program instructions that, when executed by a computer, perform computer operations. A module often is a self-contained functional unit that can be used in a larger software system. For example, a software module is a part of a program that performs a particular process or task.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically adjusts and/or processes the data (e.g., a processing module that adjusts and/or processes received data (e.g., filters, normalizes, provides an outcome and/or report). Obtaining and/or receiving input information often involves receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

In some embodiments, provided are computer program products, such as, for example, a computer program product comprising a computer usable medium having a computer readable program code embodied therein, the computer readable program code adapted to be executed to implement a method comprising: (a) obtaining sequence reads of sample nucleic acid from a test subject; (b) mapping the sequence reads obtained in (a) to a known genome, which known genome has been divided into genomic sections; (c) counting the mapped sequence reads within the genomic sections; (d) generating an adjusted data set by adjusting the counts or a derivative of the counts for the genomic sections obtained in (c); and (e) providing an outcome determinative of the presence or absence of a genetic variation from the adjusted count profile in (d).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational geometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative adjusted and/or processed data set or outcome. An adjusted or processed data set sometimes is of reduced complexity compared to the parent data set that was processed. Based on an adjusted and/or processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data adjustment and/or processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified result, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for providing an outcome determinative of the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

Transformations

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These procedures can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

Genomic Section Normalization Systems, Apparatus and Computer Program Products

In certain aspects provided is a system comprising one or more processors and memory, which memory comprises instructions executable by the one or more processors and which memory comprises counts of sequence reads of circulating, cell-free sample nucleic acid from a test subject mapped to genomic sections of a reference genome; and which instructions executable by the one or more processors are configured to: (a) normalize the counts for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; and (b) determine the presence or absence of a fetal aneuploidy based on the normalized sample count.

In certain aspects provided is a system comprising one or more processors and memory, which memory comprises instructions executable by the one or more processors and which memory comprises counts of sequence reads of circulating, cell-free sample nucleic acid from a test subject mapped to genomic sections of a reference genome; and which instructions executable by the one or more processors are configured to: (a) adjust the counted, mapped sequence reads in according to a selected variable or feature, which selected feature or variable minimizes or eliminates the effect of repetitive sequences and/or over or under represented sequences; (b) normalize the remaining counts in (a) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; (c) evaluate the statistical significance of differences between the normalized counts or a derivative of the normalized counts for the test subject and reference subjects for one or more selected genomic sections; and (d) determine the presence or absence of a genetic variation in the test subject based on the evaluation in (c).

Provided also in certain aspects is an apparatus comprising one or more processors and memory, which memory comprises instructions executable by the one or more processors and which memory comprises counts of sequence reads of circulating, cell-free sample nucleic acid from a test subject mapped to genomic sections of a reference genome; and which instructions executable by the one or more processors are configured to: (a) normalize the counts for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; and (b) determine the presence or absence of a fetal aneuploidy based on the normalized sample count.

Provided also in certain aspects is an apparatus comprising one or more processors and memory, which memory comprises instructions executable by the one or more processors and which memory comprises counts of sequence reads of circulating, cell-free sample nucleic acid from a test subject mapped to genomic sections of a reference genome; and which instructions executable by the one or more processors are configured to: (a) adjust the counted, mapped sequence reads in according to a selected variable or feature, which selected feature or variable minimizes or eliminates the effect of repetitive sequences and/or over or under represented sequences; (b) normalize the remaining counts in (a) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; (c) evaluate the statistical significance of differences between the normalized counts or a derivative of the normalized counts for the test subject and reference subjects for one or more selected genomic sections; and (d) determine the presence or absence of a genetic variation in the test subject based on the evaluation in (c).

Also provided in certain aspects is a computer program product tangibly embodied on a computer-readable medium, comprising instructions that when executed by one or more processors are configured to: (a) access counts of sequence reads of circulating, cell-free sample nucleic acid from a test subject mapped to genomic sections of a reference genome, (b) normalize the counts for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; and (c) determine the presence or absence of a fetal aneuploidy based on the normalized sample count.

Also provided in certain aspects is a computer program product tangibly embodied on a computer-readable medium, comprising instructions that when executed by one or more processors are configured to: (a) access counts of sequence reads mapped to portions of a reference genome, which sequence reads are reads of circulating cell-free nucleic acid from a test sample; (b) adjust the counted, mapped sequence reads in according to a selected variable or feature, which selected feature or variable minimizes or eliminates the effect of repetitive sequences and/or over or under represented sequences; (c) normalize the remaining counts in (b) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions; (d) evaluate the statistical significance of differences between the normalized counts or a derivative of the normalized counts for the test subject and reference subjects for one or more selected genomic sections; and (e) determine the presence or absence of a genetic variation in the test subject based on the evaluation in (d).

In certain embodiments, the system, apparatus and/or computer program product comprises a: (i) a sequencing module configured to obtain nucleic acid sequence reads; (ii) a mapping module configured to map nucleic acid sequence reads to portions of a reference genome; (iii) a weighting module configured to weight genomic sections, (iv) a filtering module configured to filter genomic sections or counts mapped to a genomic section, (v) a counting module configured to provide counts of nucleic acid sequence reads mapped to portions of a reference genome; (vi) a normalization module configured to provide normalized counts; (vii) an expected count module configured to provide expected counts or a derivative of expected counts; (viii) a plotting module configured to graph and display an elevation and/or a profile; (ix) an outcome module configured to determine an outcome (e.g., outcome determinative of the presence or absence of a fetal aneuploidy); (x) a data display organization module configured to indicate the presence or absence of a segmental chromosomal aberration or a fetal aneuploidy or both; (xi) a logic processing module configured to perform one or more of map sequence reads, count mapped sequence reads, normalize counts and generate an outcome; or (xii) combination of two or more of the foregoing.

In some embodiments the sequencing module and mapping module are configured to transfer sequence reads from the sequencing module to the mapping module. The mapping module and counting module sometimes are configured to transfer mapped sequence reads from the mapping module to the counting module. The counting module and filtering module sometimes are configured to transfer counts from the counting module to the filtering module. The counting module and weighting module sometimes are configured to transfer counts from the counting module to the weighting module. The mapping module and filtering module sometimes are configured to transfer mapped sequence reads from the mapping module to the filtering module. The mapping module and weighting module sometimes are configured to transfer mapped sequence reads from the mapping module to the weighting module. Sometimes the weighting module, filtering module and counting module are configured to transfer filtered and/or weighted genomic sections from the weighting module and filtering module to the counting module. The weighting module and normalization module sometimes are configured to transfer weighted genomic sections from the weighting module to the normalization module. The filtering module and normalization module sometimes are configured to transfer filtered genomic sections from the filtering module to the normalization module. In some embodiments, the normalization module and/or expected count module are configured to transfer normalized counts to an outcome module or plotting module.

Modules

Modules sometimes are part of an apparatus, system or software and can facilitate transfer and/or processing of information and data. Non-limiting examples of modules are described hereafter.

Sequencing Module

Sequencing and obtaining sequencing reads can be provided by a sequencing module or by an apparatus comprising a sequencing module. A "sequence receiving module" as used herein is the same as a "sequencing module". An apparatus comprising a sequencing module can be any apparatus that determines the sequence of a nucleic acid from a sequencing technology known in the art. In certain embodiments, an apparatus comprising a sequencing module performs a sequencing reaction known in the art. A sequencing module generally provides a nucleic acid sequence read according to data from a sequencing reaction (e.g., signals generated from a sequencing apparatus). In some embodiments, a sequencing module or an apparatus comprising a sequencing module is required to provide sequencing reads. In some embodiments a sequencing module can receive, obtain, access or recover sequence reads from another sequencing module, computer peripheral, operator, server, hard drive, apparatus or from a suitable source. Sometimes a sequencing module can manipulate sequence reads. For example, a sequencing module can align, assemble, fragment, complement, reverse complement, error check, or error correct sequence reads. An apparatus comprising a sequencing module can comprise at least one processor. In some embodiments, sequencing reads are provided by an apparatus that includes a processor (e.g., one or more processors) which processor can perform and/or implement one or more instructions (e.g., processes, routines and/or subroutines) from the sequencing module. In some embodiments, sequencing reads are provided by an apparatus that includes multiple processors, such as processors coordinated and working in parallel. In some embodiments, a sequencing module operates with one or more external processors (e.g., an internal or external network, server, storage device and/or storage network (e.g., a cloud)).

Sometimes a sequencing module gathers, assembles and/or receives data and/or information from another module, apparatus, peripheral, component or specialized component (e.g., a sequencer). In some embodiments, sequencing reads are provided by an apparatus comprising one or more of the following: one or more flow cells, a camera, a photo detector, a photo cell, fluid handling components, a printer, a display (e.g., an LED, LCT or CRT) and the like. Often a sequencing module receives, gathers and/or assembles sequence reads. Sometimes a sequencing module accepts and gathers input data and/or information from an operator of an apparatus. For example, sometimes an operator of an apparatus provides instructions, a constant, a threshold value, a formula or a predetermined value to a module. Sometimes a sequencing module can transform data and/or information that it receives into a contiguous nucleic acid sequence. In some embodiments, a nucleic acid sequence provided by a sequencing module is printed or displayed. In some embodiments, sequence reads are provided by a sequencing module and transferred from a sequencing module to an apparatus or an apparatus comprising any suitable peripheral, component or specialized component. In some embodiments, data and/or information are provided from a sequencing module to an apparatus that includes multiple processors, such as processors coordinated and working in parallel. In some cases, data and/or information related to sequence reads can be transferred from a sequencing module to any other suitable module. A sequencing module can transfer sequence reads to a mapping module or counting module, in some embodiments.

Mapping Module

Sequence reads can be mapped by a mapping module or by an apparatus comprising a mapping module, which mapping module generally maps reads to a reference genome or segment thereof. A mapping module can map sequencing reads by a suitable method known in the art. In some embodiments, a mapping module or an apparatus comprising a mapping module is required to provide mapped sequence reads. An apparatus comprising a mapping module can comprise at least one processor. In some embodiments, mapped sequencing reads are provided by an apparatus that includes a processor (e.g., one or more processors) which processor can perform and/or implement one or more instructions (e.g., processes, routines and/or subroutines) from the mapping module. In some embodiments, sequencing reads are mapped by an apparatus that includes multiple processors, such as processors coordinated and working in parallel. In some embodiments, a mapping module operates with one or more external processors (e.g., an internal or external network, server, storage device and/or storage network (e.g., a cloud)). An apparatus may comprise a mapping module and a sequencing module. In some embodiments, sequence reads are mapped by an apparatus comprising one or more of the following: one or more flow cells, a camera, fluid handling components, a printer, a display (e.g., an LED, LCT or CRT) and the like. A mapping module can receive sequence reads from a sequencing module, in some embodiments. Mapped sequencing reads can be transferred from a mapping module to a counting module or a normalization module, in some embodiments.

Counting Module

Counts can be provided by a counting module or by an apparatus comprising a counting module.

A counting module can determine, assemble, and/or display counts according to a counting method known in the art. A counting module generally determines or assembles counts according to counting methodology known in the art. In some embodiments, a counting module or an apparatus comprising a counting module is required to provide counts. An apparatus comprising a counting module can comprise at least one processor. In some embodiments, counts are provided by an apparatus that includes a processor (e.g., one or more processors) which processor can perform and/or implement one or more instructions (e.g., processes, routines and/or subroutines) from the counting module. In some embodiments, reads are counted by an apparatus that includes multiple processors, such as processors coordinated and working in parallel. In some embodiments, a counting module operates with one or more external processors (e.g., an internal or external network, server, storage device and/or storage network (e.g., a cloud)). In some embodiments, reads are counted by an apparatus comprising one or more of the following: a sequencing module, a mapping module, one or more flow cells, a camera, fluid handling components, a printer, a display (e.g., an LED, LCT or CRT) and the like. A counting module can receive data and/or information from a sequencing module and/or a mapping module, transform the data and/or information and provide counts (e.g., counts mapped to genomic sections). A counting module can receive mapped sequence reads from a mapping module. A counting module can receive normalized mapped sequence reads from a mapping module or from a normalization module. A counting module can transfer data and/or information related to counts (e.g., counts, assembled counts and/or displays of counts) to any other suitable apparatus, peripheral, or module. Sometimes data and/or information related to counts are transferred from a counting module to a normalization module, a plotting module, a categorization module and/or an outcome module.

Normalization Module

Normalized data (e.g., normalized counts) can be provided by a normalization module (e.g., by an apparatus comprising a normalization module). In some embodiments, a normalization module is required to provide normalized data (e.g., normalized counts) obtained from sequencing reads. A normalization module can normalize data (e.g., counts, filtered counts, raw counts) by one or more normalization procedures known in the art. A normalization module can provide an estimate of the variability of the expected counts (e.g., a MAD of the expected counts and/or a MAD of an expected count representation). In some embodiments a normalization module can provide a MAD of expected counts by deriving multiple median values from expected counts obtained from multiple experiments (e.g., sometimes different experiments, sometimes experiments exposed to one or more common experimental conditions), deriving an absolute error (e.g., deviation, variability, standard deviation, standard error) of the multiple median values and determining a mean, average, or median of the calculated absolute errors. In some embodiments a normalization module can provide a MAD of an expected count representation by deriving multiple median values from expected count representations obtained from multiple experiments (e.g., sometimes different experiments, sometimes experiments exposed to one or more common experimental conditions) and then deriving an absolute error (e.g., deviation, variability, standard deviation, standard error) of the multiple median values. An apparatus comprising a normalization module can comprise at least one processor. In some embodiments, normalized data is provided by an apparatus that includes a processor (e.g., one or more processors) which processor can perform and/or implement one or more instructions (e.g., processes, routines and/or subroutines) from the normalization module. In some embodiments, normalized data is provided by an apparatus that includes multiple processors, such as processors coordinated and working in parallel. In some embodiments, a normalization module operates with one or more external processors (e.g., an internal or external network, server, storage device and/or storage network (e.g., a cloud)). In some embodiments, normalized data is provided by an apparatus comprising one or more of the following: one or more flow cells, a camera, fluid handling components, a printer, a display (e.g., an LED, LCT or CRT) and the like. A normalization module can receive data and/or information from a suitable apparatus or module. Sometimes a normalization module can receive data and/or information from a sequencing module, a normalization module, a mapping module or counting module. A normalization module can receive sequencing reads from a sequencing module, mapped sequencing reads from a mapping module and/or counts from a counting module, in some embodiments. Often a normalization module receives data and/or information from another apparatus or module, transforms the data and/or information and provides normalized data and/or information (e.g., normalized counts, normalized values, normalized reference values (NRVs), and the like). Normalized data and/or information can be transferred from a normalization module to a comparison module, a normalization module, a range setting module, an adjustment module, a categorization module, and/or an outcome module, in certain embodiments. Sometimes normalized counts (e.g., normalized mapped counts) are transferred to an expected representation module and/or to an experimental representation module from a normalization module.

Expected Count Module

An expected count or a derivative of an expected count (e.g., a percent representation) can be provided by an expected count module (e.g., by an apparatus comprising an expected count module). In some embodiments, an expected count module is required to provide expected counts or a derivative of expected counts obtained from sequencing reads (e.g., counts of mapped sequence reads, a predetermined subsets of mapped sequence reads). An expected count module can sum the counts for one or more selected genomic sections. Sometimes an expected count module applies one or more mathematical or statistical manipulations to sequence reads and/or counts. An expected count module can determine a derivative of an expected count by determining a percent representation (e.g., a count representation). An apparatus comprising an expected count module can comprise at least one processor. In some embodiments, an expected count or a derivative of an expected count is provided by an apparatus that includes a processor (e.g., one or more processors) which processor can perform and/or implement one or more instructions (e.g., processes, routines and/or subroutines) from the expected count module. In some embodiments, an expected count or a derivative of an expected count is provided by an apparatus that includes multiple processors, such as processors coordinated and working in parallel. In some embodiments, an expected count module operates with one or more external processors (e.g., an internal or external network, server, storage device and/or storage network (e.g., a cloud)). In some embodiments, an expected count or a derivative of an expected count is provided by an apparatus comprising one or more of the following: one or more flow cells, a camera, fluid handling components, a printer, a display (e.g., an LED, LCT or CRT) and the like. An expected count module can receive data and/or information from a suitable apparatus or module. Sometimes an expected count module can receive data and/or information from a sequencing module, an expected count module, a mapping module, a normalization module or counting module. An expected count module can receive sequencing reads from a sequencing module, mapped sequencing reads from a mapping module and/or counts from a counting module, in some embodiments. Often an expected count module receives data and/or information from another apparatus or module, transforms the data and/or information and provides an expected count or a derivative of an expected count. An expected count or a derivative of an expected count can be transferred from an expected count module to a comparison module, an expected count module, a normalization module, a range setting module, an adjustment module, a categorization module, and/or an outcome module, in certain embodiments.

Outcome Module

The presence or absence of a genetic variation (an aneuploidy, a fetal aneuploidy, a copy number variation) can be identified by an outcome module or by an apparatus comprising an outcome module. Sometimes a genetic variation is identified by an outcome module. Often a determination of the presence or absence of an aneuploidy is identified by an outcome module. In some embodiments, an outcome determinative of a genetic variation (an aneuploidy, a copy number variation) can be identified by an outcome module or by an apparatus comprising an outcome module. An outcome module can be specialized for determining a specific genetic variation (e.g., a trisomy, a trisomy 21, a trisomy 18). For example, an outcome module that identifies a trisomy 21 can be different than and/or distinct from an outcome module that identifies a trisomy 18. In some embodiments, an outcome module or an apparatus comprising an outcome module is required to identify a genetic variation or an outcome determinative of a genetic variation (e.g., an aneuploidy, a copy number variation). An apparatus comprising an outcome module can comprise at least one processor. In some embodiments, a genetic variation or an outcome determinative of a genetic variation is provided by an apparatus that includes a processor (e.g., one or more processors) which processor can perform and/or implement one or more instructions (e.g., processes, routines and/or subroutines) from the outcome module. In some embodiments, a genetic variation or an outcome determinative of a genetic variation is identified by an apparatus that may include multiple processors, such as processors coordinated and working in parallel. In some embodiments, an outcome module operates with one or more external processors (e.g., an internal or external network, server, storage device and/or storage network (e.g., a cloud)). Sometimes an apparatus comprising an outcome module gathers, assembles and/or receives data and/or information from another module or apparatus. Sometimes an apparatus comprising an outcome module provides and/or transfers data and/or information to another module or apparatus. Sometimes an outcome module transfers, receives or gathers data and/or information to or from a component or peripheral. Often an outcome module receives, gathers and/or assembles counts, elevations, profiles, normalized data and/or information, reference elevations, expected elevations, expected ranges, uncertainty values, adjustments, adjusted elevations, plots, categorized elevations, comparisons and/or constants. Sometimes an outcome module accepts and gathers input data and/or information from an operator of an apparatus. For example, sometimes an operator of an apparatus provides a constant, a threshold value, a formula or a predetermined value to an outcome module. In some embodiments, data and/or information are provided by an apparatus that includes multiple processors, such as processors coordinated and working in parallel. In some embodiments, identification of a genetic variation or an outcome determinative of a genetic variation is provided by an apparatus comprising a suitable peripheral or component. An apparatus comprising an outcome module can receive normalized data from a normalization module, an expected count module, expected elevations and/or ranges from a range setting module, comparison data from a comparison module, categorized elevations from a categorization module, plots from a plotting module, and/or adjustment data from an adjustment module. An outcome module can receive data and/or information, transform the data and/or information and provide an outcome. An outcome module can provide or transfer data and/or information related to a genetic variation or an outcome determinative of a genetic variation to a suitable apparatus and/or module. A genetic variation or an outcome determinative of a genetic variation identified by methods described herein can be independently verified by further testing (e.g., by targeted sequencing of maternal and/or fetal nucleic acid).

After one or more outcomes have been generated, an outcome often is used to provide a determination of the presence or absence of a genetic variation and/or associated medical condition. An outcome typically is provided to a health care professional (e.g., laboratory technician or manager; physician or assistant). Often an outcome is provided by an outcome module. Sometimes an outcome is provided by a plotting module. Sometimes an outcome is provided on a peripheral or component of an apparatus. For example, sometimes an outcome is provided by a printer or display. In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in a suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described in the Examples.

Generating an outcome can be viewed as a transformation of nucleic acid sequence read data, or the like, into a representation of a subject's cellular nucleic acid, in certain embodiments. For example, analyzing sequence reads of nucleic acid from a subject and generating a chromosome profile and/or outcome can be viewed as a transformation of relatively small sequence read fragments to a representation of relatively large chromosome structure. In some embodiments, an outcome results from a transformation of sequence reads from a subject (e.g., a pregnant female), into a representation of an existing structure (e.g., a genome, a chromosome or segment thereof) present in the subject (e.g., a maternal and/or fetal nucleic acid). In some embodiments, an outcome comprises a transformation of sequence reads from a first subject (e.g., a pregnant female), into a composite representation of structures (e.g., a genome, a chromosome or segment thereof), and a second transformation of the composite representation that yields a representation of a structure present in a first subject (e.g., a pregnant female) and/or a second subject (e.g., a fetus).

EXAMPLES

The examples set forth below illustrate certain embodiments and do not limit the technology.

Example 1

Determination of the Presence or Absence of a Genetic Variation Using Blind Samples Effective prenatal screening tests for Down syndrome often combine maternal age with information from sonographic measurement of nuchal translucency in the first trimester and/or measurements of several maternal serum screening markers obtained in the first and second trimesters. These prenatal screening tests often detect up to about 90% of substantially all cases at a false-positive rate of about 2%. Given the prevalence of Down syndrome, 1 of every 16 screen positive women offered invasive diagnostic testing (e.g., amniocentesis or chorionic villus sampling) will have an affected pregnancy and 15 will not. As many as 1 in 200 such invasive procedures are associated with fetal loss, a significant adverse consequence of prenatal diagnosis. The significant adverse consequence of fetal loss sometimes has led to screening cutoffs being adjusted to minimize the false-positive rate. In practice, false-positive rates of about 5% are common.

Discovery that about 3-6% of cell-free DNA in maternal blood was of fetal origin prompted studies to determine whether Down syndrome could be detected noninvasively. Fetal Down syndrome was identified using massively parallel shotgun sequencing (MPSS), a technique that sequences the first 36 bases of millions of DNA fragments to determine their specific chromosomal origin. If a fetus has a third chromosome 21, the percentage of chromosome 21 fragments is slightly higher than expected. Subsequent reports have extended these observations and suggest that a detection rate of at least about 98% can be achieved at a false-positive rate of about 2% or lower. Although promising, these studies were limited by the following factors; the studies were performed utilizing relatively small patient groups (range 13-86 Down syndrome cases and 34-410 euploid control samples); DNA sequencing was not performed in CLIA-certified laboratories; and throughput and turnaround times did not simulate clinical practice.

Methods, processes and apparatuses described herein can be utilized to provide an outcome determinative of the presence or absence of a genetic variation (e.g., trisomy, Down's syndrome) using blind samples, and without the need for a reference genome data set to which test subject data is normalized, in some embodiments.

Materials and Methods

Overall Study Design

The study presented herein (see world wide web URL clinicaltrials.gov NCT00877292) involved patients enrolled at 27 prenatal diagnostic centers worldwide (e.g., referred to hereinafter as Enrollment Sites). Women at high risk for Down syndrome based on maternal age, family history or a positive serum and/or sonographic screening test provided consent, plasma samples, demographic and pregnancy-related information. Institutional Review Board approval (or equivalent) was obtained at each enrollment site. Identification of patients and samples was by study code. Samples were drawn immediately before invasive testing, processed within 6 hours, stored at −80° C., and shipped on dry ice to the Coordinating Center. Within this cohort, a nested case-control study was developed, with blinded DNA testing for Down syndrome. Seven euploid samples were matched to each case, based on gestational age (nearest week; same trimester), Enrollment Site, race (self-declared), and time in freezer (within 1 month). Assuming no false-negative results, 200 Down syndrome pregnancies (cases) had 80% power to reject 98% as the lower confidence interval (CI). The cases were distributed equally between first and second trimesters. For this study, Down syndrome was defined as 47, XY, +21 or 47, XX, +21; mosaics and twin pregnancies with Down syndrome were excluded. Study coordination and sample storage were based at an independent academic medical center (e.g., Women & Infants Hospital). Frozen, coded samples (4 mL) were sent to the Sequenom Center for Molecular Medicine (SCMM, San Diego, Calif.) for testing. SCMM had no knowledge of the karyotype and simulated clinical testing, including quantifying turnaround time. A subset of samples was sent for testing at the Orphan Disease Testing Center at University of California at Los Angeles (UCLA; Los Angeles, Calif.), an independent academic laboratory experienced in DNA sequencing. Both laboratories were CLIA-certified, and both provided clinical interpretations using a standardized written protocol originally developed by SCMM.

Study Integrity

The highest priority was given to ensuring integrity, reliability, and independence of this industry-funded study. A three person Oversight Committee (see Acknowledgments) was created and charged with assessing and providing recommendations on study design, conduct, analysis, and interpretation. The study protocol included Enrollment Site inspections, isolation of Enrollment Sites from the study sponsor, confirmatory testing by an independent academic laboratory, blinding of diagnostic test results on multiple levels, no remote computer access to outcome data, access to all raw data by the academic testing site, immediate file transfer of sequencing and interpretation results to the Coordinating Center, and use of file checksums to identify subsequent changes. SCMM provided the independent laboratory with similar equipment, training, interpretive software, and standard operating protocols.

The Laboratory-Developed Test

As noted previously MPSS was utilized to sequence cell-free DNA. In brief, circulating cell-free DNA fragments are isolated from maternal plasma and quantified with an assay that determines the fetal contribution (fetal fraction). The remaining isolate was used to generate sequencing libraries, normalized and multiplexed to allow four samples to be run in a single flow cell lane (e.g., eight lanes per flow cell). DNA libraries were quantified using a microfluidics platform (Caliper Life Sciences, Hopkinton, Mass.) and generated clusters using the cBot platform (Illumina, Inc, San Diego, Calif.). Flow cells were sequenced on the Illumina HiSeq 2000 platform and analyzed resulting data using Illumina software. Computer interpretation provided a robust estimate of the standard deviations (e.g., SD's) above or below the central estimate (z-score); z-scores at or above 3 were considered to be consistent with Down syndrome. The Director of the primary CLIA Laboratory (SCMM) reviewed results, initiated calls for testing second aliquots, and provided a final "signed out" interpretation for all pregnancies tested. The Director of the independent CLIA Laboratory (UCLA) did the same but without the ability to call for second sample aliquots. Each laboratory only had access to its own results.

Statistical Analysis

The study would be paused if an interim analysis showed that more than 3 of 16 cases or 6 of 112 controls were misclassified. Although a matched study, the analysis was planned to be unmatched. Differences were examined among groups and associations using $X^2$ test, t-test, analysis of variance (ANOVA), and linear regression (after appropriate transformations) using SAS™ Analytics Pro (Cary, N.C.; formerly known as Statistical Analysis System) and True Epistat (Richardson, Tex.). Confidence intervals (CIs) of proportions were computed using a binomial distribution. P values were two-sided, and significance was at the 0.05 level.

Results

Sample Population

Between April 2009 and February 2011, 27 Enrollment Sites (see TABLE 1 below) identified eligible pregnant women, obtained informed consent, and collected samples. Among 4664 enrollees, 218 singleton Down syndrome and 3930 singleton euploid pregnancies occurred. FIG. 1 provides details on fetal outcomes, plasma sample status, and reasons why 279 women (6%) were excluded. None of the samples was included in previous publications or studies. A total of 4385 women (94%) had a singleton pregnancy, at least two suitable plasma samples and diagnostic test results. Of these, 97% were between 11 and 20 weeks' gestation, inclusive; 34% were in the first trimester. Fetal karyotypes (or equivalent) were available for all but 51 enrolled women. For 116 women, the plasma samples were not considered adequate for testing (e.g., thawed during transit, more than 6 hours before being frozen, only one aliquot, and insufficient volume). An additional 112 women were excluded because of multiple gestations or existing fetal death. Among the 4385 viable singleton pregnancies, 34% were obtained in the late first trimester and 66% in the early second trimester. A total of 212 Down syndrome cases were selected for testing. For each case, seven matched euploid pregnancies were chosen (e.g., 1484; 7:1 ratio of euploid to Down syndrome cases). Among the 237 other outcomes were additional autosomal aneuploidies, sex chromosome aneuploidies, mosaics, and other chromosomal abnormalities. One control was later discovered to be trisomy 18 but was included as a "euploid" control.

Fetal Contribution to Circulating Free DNA

Before MPSS, extracted DNA was tested to determine the proportion of free DNA of fetal origin in maternal plasma (fetal fraction). Nearly all (1687/1696; 99.5%) had a final fetal fraction within acceptable limits (4-50%); the geometric mean was 13.4%. The lower cutoff was chosen to minimize false negative results. The upper cutoff was chosen to alert the Laboratory Director that this represents a rare event. Nine had unacceptable levels; six below the threshold and three above. As the success of MPSS in identifying Down syndrome is highly dependent on the fetal fraction, 16 potential covariates (see FIGS. 4-19, Example 2) were explored (processing time, hemolysis, geographic region, indication for diagnostic testing, Enrollment Site, gestational age, maternal age, maternal weight, vaginal bleeding, maternal race, Caucasian ethnicity, fetal sex, freezer storage time, and effect of fetal fraction on DNA library concentration, number of matched sequences, and fetal outcome). A strong negative association of fetal fraction with maternal weight was observed in case and control women (see FIG. 11, Example 2), with weights of 100, 150, and 250 pounds associated with predicted fetal fractions of 17.8%, 13.2%, and 7.3%, respectively. No association was found for gestational age, maternal race, or indication for testing. Other associations were small and usually nonsignificant.

TABLE 1

Clinical sites enrolled in the study, along with related enrollment and outcome information

| Enrollment site | Location | Clinical investigator | Down syndrome | Normal karyotype | Other | Patients enrolled |
|---|---|---|---|---|---|---|
| North York General Hospital | Toronto, Canada | Wendy S. Meschino, MD | 41 | 651 | 86 | 778 |
| Istituto G. Gaslini | Genoa, Italy | Pierangela De Biasio, MD | 27 | 492 | 35 | 554 |
| Hospital Clinic Barcelona | Barcelona, Spain | Antoni Borrell, MD, PhD | 24 | 291 | 44 | 359 |
| Centrum Lekarske Genetiky | Ceske Budejovice, Czech Republic | David Cutka, MD | 14 | 362 | 19 | 395 |
| Hospital Italiano | Buenos Aires, Argentina | Lucas Otario, MD, PhD | 13 | 68 | 14 | 95 |
| Dalhousie University | Halifax, Canada | Michiel Van den Hof, MD | 12 | 115 | 18 | 145 |
| Rotunda Hospital | Dublin, Ireland | Fergal Malone, MD | 12 | 70 | 12 | 94 |
| Semmelweis University | Budapest, Hungary | Csaba Papp, MD, PhD | 10 | 64 | 9 | 83 |
| IMALAB s.r.o. Medical Laboratories | Zlin, Czech Republic | Jaroslav Loucky, RNDr | 9 | 238 | 8 | 255 |
| CEMIC | Buenos Aires, Argentina | Maria Laura Igarzabal, MD | 8 | 224 | 49 | 281 |
| University of Iowa | Iowa City, IA | Kristi Borowski, MD | 8 | 135 | 30 | 173 |
| Women & Infants Hospital | Providence, RI | Barbara O'Brien, MD | 6 | 99 | 21 | 126 |
| University of Pecs | Pecs, Hungary | Béla Veszprémi, MD, PhD | 4 | 172 | 31 | 207 |
| University of Alabama at Birmingham | Birmingham, AL | Joseph Biggio, MD | 4 | 169 | 20 | 193 |
| Rambam Medical Center | Haifa, Israel | Zeev Weiner, MD | 4 | 133 | 10 | 147 |
| Cedars Sinai PDC | Los Angeles, CA | John Williams, MD | 3 | 192 | 28 | 223 |
| Northwestern University | Chicago, IL | Jeffrey Dungan, MD | 3 | 88 | 11 | 102 |
| Henry Ford Hospital | Detroit, MI | Jacquelyn Roberson, MD | 3 | 74 | 14 | 91 |
| University of Virginia | Charlottesville, VA | Devereux N. Saller, Jr, MD | 3 | 21 | 8 | 32 |
| University of British Columbia | Vancouver, Canada | Sylvie Langlois, MD | 2 | 67 | 14 | 83 |
| Intermountain Healthcare | Salt Lake City, UT | Nancy Rose, MD | 2 | 67 | 9 | 78 |
| Brigham and Women's Hospital | Boston, MA | Louise Wilkins-Haug, MD | 2 | 21 | 8 | 31 |
| Baylor College of Medicine | Houston, TX | Anthony Johnson, DO | 2 | 20 | 0 | 22 |
| Yale University | New Haven, CT | Maurice J. Mahoney, MD, JD | 1 | 31 | 9 | 41 |
| New Beginnings Perinatal Consultants | Providence, RI | Marshall Carpenter, MD | 1 | 7 | 4 | 12 |
| University of Calgary | Calgary, Canada | Jo-Ann Johnson, MD | 0 | 52 | 5 | 57 |
| Royal North Shore Hospital | Sydney, Australia | Vitomir Tasevski, PhD | 0 | 7 | 0 | 7 |
| All | | | 218 | 3,930 | 516 | 4,664 |

TABLE 2

Demographics and pregnancy-related information for the selected Down syndrome and matched euploid samples tested

| Characteristic | Down syndrome | Euploid | P |
|---|---|---|---|
| Number of samples | 212 | 1,484 | |
| Maternal age in years (average, SD) | 37.0, 5.0 | 36.6, 5.1 | 0.36 |
| Maternal age 35 years or older (N, %) | 160 (75%) | 1,036 (70%) | 0.12 |
| Gestational age (average, range) | 15.3 (9.2-21.3) | 15.0 (8.1-21.5) | 0.21 |
| Gestational age in first trimester/second trimester (%) | 50%/50% | 50%/50% | 1.0 |
| Maternal weight in pounds (average, SD) | 149 (30) | 152 (33) | 0.33 |
| Bleeding (%) | 17% | 15% | 0.44 |
| Maternal race (N, %) | 188 (89%) | 1,316 (89%) | 1.0 |
| Caucasian | 5 (2%) | 35 (2%) | |
| Black | 15 (7%) | 105 (7%) | |
| Asian | 4 (2%) | 28 (2%) | |
| Unknown | 39 (18%) | 303 (20%) | |
| Caucasian Hispanic (N, %) | 3 (1%) | 42 (3%) | 0.92 |
| Ashkenazi Jewish (N, %) | | | 0.13 |
| Main indication for enrollment (N, %) | 48 (23%) | 327 (22%) | <0.001 |
| Screen positive by first trimester test | 11 (5%) | 118 (8%) | |
| Screen positive by second trimester test | 38 (18%) | 192 (13%) | |
| Screen positive by integrated test | 51 (24%) | 130 (9%) | |
| Ultrasound anomaly identified | 24 (12%) | 543 (37%) | |
| Advanced maternal age | 39 (18%) | 112 (8%) | |
| Two or more indications | 0 (0%) | 44 (3%) | |
| Family history of aneuploidy | 1 (<1%) | 18 (1%) | |
| Other or Not Indicated | | 787 (53%) | 0.79 |
| Diagnostic procedure (N, %) | 114 (54%) | 697 (47%) | |
| Amniocentesis | 97 (46%) | 0 (0%) | |
| Chorionic villus sampling | 1 (<1%) | | |
| Examination of products of conception | | 805 (54%) | <0.001 |
| Diagnostic test (N, %) | 95 (46%) | 679 (45%) | |
| Karyotype alone | 115 (53%) | 0 (0%) | |
| karyotype and other | | | |

TABLE 2-continued

Demographics and pregnancy-related information for the selected Down syndrome and matched euploid samples tested

| Characteristic | Down syndrome | Euploid | P |
|---|---|---|---|
| QF-PCR or FISH alone | 2 (<1%) | 45 (3%) | |
| Hemolysis moderate to gross (N, %) | 8 (4%) | 1.2 (0.1-6) | 0.60 |
| Sample processing, in hours (mean, range) | 1.1 (0.1-6) | | 0.63 |

TABLE 2 above compares demographic and pregnancy-related information between cases and controls. Matching was successful. Median age was about 37 years in both groups; all were 18 years or older. Indications for diagnostic testing differed, with cases more likely to have an ultrasound abnormality or multiple indications. Samples were collected, processed, and frozen, on average, within 1 hour; all within 6 hours. Outcomes were based on karyotyping, except for two first trimester cases (quantitative polymerase chain reaction in one, and fluorescence in situ hybridization in the other, of products of conception after termination of a viable fetus with severe ultrasound abnormalities).

Massively Parallel Shotgun Sequencing Testing for Down Syndrome

Testing was performed over 9 weeks (January to March, 2011) by 30 scientists, molecular technicians/technologists with training on the assay protocols, and related instrumentation. Historical reference ranges were to be used for interpretation, 9 with real-time review of new data a requirement. Review of the first few flow cells by the Laboratory Director (before sign out) revealed that adjustments to the reference data were necessary (see Example 2 and FIGS. 20-22). After data from six flow cells were generated, results were assessed by the Oversight Committee according to the interim criteria, and the confidential decision was made to allow the testing to continue. At the conclusion of testing, but before unblinding, SCMM requested a second aliquot for 85 of the 90 test failures among the 1696 enrollees (5.3%; 95% CI, 4.3-6.5; see Example 2). The second result was used for final interpretation.

Down syndrome samples showed a clear and significant positive relationship with fetal fraction; 208 of the samples are above the cutoff and four are below. Four Down syndrome samples had z-scores below the cutoff of 3; all had fetal fractions of <7%. (e.g., 7%, 7%, 5%, and 4%). A strong positive association between fetal fraction and z-score existed for cases (after logarithmic transformation, slope=0.676, P<0.001) but not for controls (slope=0.0022, P=0.50). One of the low fetal fraction Down syndrome samples had an initial z-score of 5.9 with one borderline quality failure; the repeat sample z-score was 2.9 (a borderline value consistent with the initial positive result). Combining the information from the repeated sample with a 5.9 score on the initial sample (e.g., a borderline failure), allowed the Laboratory Director to make the correct call. All other clinical interpretations agreed with the computer interpretation. Therefore, signed out results correctly identified 209 of 212 Down syndrome fetuses (detection rate of 98.6%; 95% CI, 95.9-99.7).

Clinical interpretation of all Down syndrome and euploid samples used in the study are as follows: Among the euploid pregnancies, 1471 were negative, 3 were positive, and 13 failed on the second aliquot as well. Among the Down syndrome pregnancies, 209 were positive and 3 were negative. Among the 1471 euploid samples, 3 had z-scores >3 over a range of fetal fractions and were incorrectly classified as Down syndrome, yielding a false-positive rate of 0.2% (95% CI, <0.1-0.6). For 13 women (13/1696 or 0.8%; 95% CI, 0.4-1.3), interpretation was not provided due to quality control failures on initial and repeat samples (six had fetal fractions <4%, one >50%), although their test results were available and usually "normal" (see FIG. 2B). Laboratory results, sample handling, and pregnancy outcomes for the misclassified pregnancies were extensively checked for potential errors; none were identified (see TABLE 3, Example 2). Analysis of the first 15 covariates versus z-score was performed (see FIGS. 7-10, Example 2). A strong negative association existed for maternal weight among cases; this association was weaker in controls. There was a small, but significant, positive association with gestational age in cases (see FIG. 7, Example 2), with regressed z-scores at 11 and 19 weeks gestation of 7.2 and 9.9, respectively. Other associations were small and usually not significant.

Confirmation by an Independent Laboratory of Testing Performance

An independent university laboratory (e.g., UCLA) performed cluster generation, DNA sequencing, and interpretation for a subset of 605 initial sample aliquots originally processed and tested by SCMM. This subset was randomly selected by the Coordinating Center from all complete groups of 92 patient samples (e.g., plates). A total of 578 samples were successfully tested at both sites (96%). Computer-interpreted MPSS results are expressed as a z-score, with SCMM values. A total of 77 Down syndrome and 501 euploid pregnancies were successfully tested at both sites. The 27 samples that failed on the initial test at one or both sites are not included. A z-score cutoff of 3 was used. Among these samples, only one disagreement occurred. A euploid sample was misclassified by UCLA (z-score=3.46) but correctly classified by SCMM (z-score=2.02). Both groups misclassified one Down syndrome sample. Correlations were high among both 77 Down syndrome and 501 euploid pregnancies (e.g., R=0.80 and 0.83, respectively). In this subset of 578, the detection, false-positive, and initial failure rates for SCMM were 98.7%, 0.0%, and 4.4%, respectively. The corresponding rates for UCLA were 98.7%, 0.2%, and 3.9% (see TABLE 3, Example 2). In another subset of 56 enrollees, duplicate 4 mL plasma samples were tested by each laboratory. One euploid sample failed at both sites due to low fetal fraction. Two additional euploid samples failed sequencing at UCLA; their protocol did not allow retesting. Failure rates at SCMM and UCLA were 1.8% and 5.3%, respectively. Among 53 remaining samples, the two sites agreed on all quality parameters and interpretive results (Example 2). At both laboratories, the detection and false-positive rates were 100% and 0%, respectively.

Post Hoc Analysis

The large sample size provided an opportunity to investigate alternative methods of interpreting the MPSS results. After sign out, but before laboratory unblinding, chromosome 21 percent results were adjusted by the SCMM laboratory for GC content, a process shown to improve MPSS performance, as well as filtered with respect to The Repeat Mask (URL world wide web repeatmasker.org/PreMaskedGenomes.html) and the results forwarded to the Coordinating Center to determine whether alternative interpretive algorithms might perform better, be more robust, or both. Analysis showed that control results varied by flow cell or by plate (three flow cells that are batch processed) (ANOVA, F=13.5, P<0.001), but the SD was constant (ANOVA, F=1.2, P=0.23), allowing conversion of the GC-adjusted results to multiples of the plate median. Multiples of the plate median values in Down syndrome and euploid pregnancies were completely separate, except for one persistent false-negative result (see Example 2). Adjusting flow-cell specific z-scores also improved performance, with two false negative and one false positive result remaining (see Example 2). The post hoc analyses were not available at the time clinical interpretations were made.

Clinical Implications

Two thousand one hundred and sixteen initial patient samples (1696 reported here and 420 other patient samples) were tested with a throughput of 235 patients per week using two HiSeq 2000 platforms. Turnaround time (e.g., sample thaw to sign out) improved over the 9 weeks of testing, meeting a 10-day target for 18 of the final 20 flow cells (see Example 2). This does not include the 5% of samples that required a second aliquot, although turnaround time for the samples that required a second aliquot did not double because failures often were detected early in the testing process.

To assess utility, a simple model (see Example 2) compares current diagnostic protocols for Down syndrome with one that inserts MPSS between identification of high-risk pregnancy and invasive diagnosis. Assume 100,000 women at high risk for Down syndrome, with one affected pregnancy for every 32 normal pregnancies, diagnostic testing costs of $1,000 per patient (see Example 2), and a procedure-related fetal loss rate of 1 in 200. Complete uptake of invasive testing by high-risk women would detect 3,000 cases at a cost of $100 million and 500 procedure-related losses. Complete uptake of MPSS testing by all high-risk women, followed by invasive testing in those with positive MPSS results (along with those who failed testing), would detect 2,958 cases (42 missed) at a cost of $3.9 million and 20 losses. The difference in financial costs for the two protocols could help offset MPSS testing costs. Assigning a dollar value to the 480 potentially avoidable procedure-related losses is difficult, but they are an equally important consideration. If the procedure-related loss rate were lower than 1 in 200, the absolute number of losses would decrease, but the proportional reduction would remain the same.

Discussion

A total of 350 Down syndrome and 2061 control pregnancies have been reported, including those reported herein. The total reported Down syndrome and control pregnancies document 99.0% sensitivity and specificity (e.g., 95% CI, 98.2-99.8%, $I^2$=0%; See TABLE 5, Example 2), providing definitive evidence of the clinical validity of a test for Down syndrome based on MPSS. A positive result sometimes increased Down syndrome risk by 490-fold (e.g., 98.6% detection/0.2% false-positive rate), and a negative result sometimes reduced risk by 72-fold (e.g., 99.8%/1.4%). Testing was successful in 992 of every 1000 women. Although 5.3% of initial tests failed quality checks, 82% of these were resolved after testing second aliquots. Remaining test failures often were associated with a low fetal fraction, which sometimes can be resolved by repeat sampling a week or two later in the pregnancy. MPSS performance was confirmed by the independent laboratory (e.g., see TABLE 5 in Example 2) using original plasma samples and plasma DNA preparations.

The current study handled large numbers of samples (collection, processing, freezing, and shipping) by 27 Enrollment Sites; simulating expected clinical practice. Our findings support MPSS performance across a broad gestational age range, among various racial/ethnic groups, for all maternal ages and for all diagnostic testing indications (see Example 2). Performance is not affected by vaginal bleeding or sample hemolysis and is robust to sample processing time up to 6 hours. Because of the well-described dilution effect of increased blood volume, 15 test failures are more common in heavier women. Accounting for fetal fraction in the interpretation may be warranted. Overall, most women with false-positive screening results will avoid invasive testing, while nearly all affected pregnancies will be confidently diagnosed by conventional invasive means. The present study supports offering MPSS to women identified as being at high risk for Down syndrome, taking into account the test's complexity and resources required. Were testing to occur at least twice a week, the turnaround time for 95% of patient results would be comparable with that currently available for cytogenetic analysis of amniotic fluid cells and chorionic villus sampling. Availability of MPSS could also justify lowering serum/ultrasound screening cutoffs, resulting in higher Down syndrome detection. This study documents, for the first time, an inherent variability from flow-cell to flow-cell. Accounting for these changes improves clinical performance. How best to perform such adjustments needs more study.

Post hoc analyses resulted in reduced false-negative and false-positive results, mostly because of adjustments for GC content. This constitutes strong evidence that MPSS performance will be better when testing is introduced into practice. This study also provides evidence that MPSS can be translated from research to a clinical setting with reasonable turnaround and throughput. Certain implementation issues deserve attention. A collection tube that allows storage and shipment at ambient temperature without affecting cell-free DNA levels would be helpful. Currently, samples must be processed, frozen, and shipped on dry ice, similar to the protocol followed in our study. As this was an observational study, a demonstration project showing efficacy in clinical settings is warranted. Educational materials for both patients and providers need to be developed and validated to help ensure informed decision making. Additional concerns include reimbursement and development of relevant professional guidelines. Some have suggested that testing fetal DNA raises new ethical questions. In the recommended setting of MPSS testing of women at high risk, many of these questions are not relevant.

A major goal in the field of prenatal screening has been to reduce the need for invasive procedures. MPSS testing cannot yet be considered diagnostic. However, offering MPSS testing to women already at high risk for Down syndrome can reduce procedure-related losses by up to 96%, while maintaining high detection. Confirmation by invasive testing is still needed. This study, along with previous reports, documents high performance, but we extend the evidence by performing the testing in a CLIA-certified laboratory, having second aliquots available for initial failures, monitoring turnaround time, assessing operator to operator and machine to machine variability, validating a subset of sample results in an independent academic clinical laboratory, and integrating a medical geneticist/laboratory director into the reporting process. This report does not address other chromosome abnormalities 13 or events such as twin pregnancies. As the technology moves forward, such refinements will become available. Although some implementation issues still need to be addressed, the evidence warrants introduction of this test on a clinical basis to women at high risk of Down syndrome, before invasive diagnostic testing.

Example 2

Determination of the Presence or Absence of a Genetic Variation Using Blind Samples: Additional Materials, Methods and Results Study Integrity The study Oversight Committee was created in February 2009 to help assure continuing study independence and integrity. Committee composition was designed to represent the obstetrics and genetics academic community, with expertise in both clinical and laboratory aspects of prenatal testing and molecular genetic methods. The Committee met with the study Co-Principal Investigators (Co-PI's), either in person or by phone, an average of three times a year during 2009 and 2010, and completed its mission and held its last conference call with the end of active study enrollment in February 2011. Committee members chose not to sign confidentiality agreements with the study sponsor (Sequenom) so that they would not have knowledge of proprietary methods or results and did not directly interact with Sequenom personnel during the course of the study. Oversight Committee input was essential in implementing 1) secure methods in coding and selecting samples for testing, 2) the interim check on test results, and 3) rules to maintain separation between the study sponsor and coordinating center and recruitment site activities.

Inspections of each Enrollment Site by a study Co-PI or Coordinator involved an on-site visit to review and evaluate adherence to procedures, examine the working space and resources, validate submitted data and answer questions about the study's aims, methods and timelines. Summaries of each inspection were generated, signed by the particular study PI and Enrollment Site PI, and copies containing no patient identifiers or data were sent to the study sponsor. Enrollment Sites did not contact the study sponsor directly and had a proportion of samples tested by an independent laboratory.

Procedures were also put in place to ensure that raw data could not be changed without detection, and that all raw results could be reanalyzed by the independent laboratory. Blinding of diagnostic test results was accomplished on two levels. Within the Coordinating Center, samples and demographic information were stored in Rhode Island, while outcome data were stored at a second branch of the Coordinating Center (e.g., in Maine), for merging with demographic data at the appropriate time. None of this information was accessible from remote locations as the server was not connected to the internet.

Coordinating Center

Woman & Infants Hospital (WIH) acted as the Coordinating Center and had overall responsibility for the study. Responsibilities included implementing and adhering to the study design, recruiting and establishing communications with Enrollment Sites, maintaining the secure study database and website, collecting and verifying patient data, maintaining the processed plasma sample bank, and organizing and utilizing the Oversight Committee. The Center was located at two sites, one in Standish, Me., where computerized data were held under the supervision of a Co-PI and a study coordinator, and one in Providence, R.I., where samples were received from the Enrollment sites, stored at −80° C., and shipped to the testing laboratories as needed, and where administrative and supply support for the Enrollment Sites was located. The study was administered by WIH according to Federal guidelines. A non-disclosure agreement was signed between WIH and the study sponsor, allowing the Co-PIs access to interim data and research results throughout the study.

Enrollment Sites

Sites were preferentially sought that offered services to large numbers of patients, integrated screening, or first trimester diagnostic testing. The 27 participating Enrollment Sites (see TABLE 1, Example 1) provided diagnostic testing for Down syndrome (or other autosomal aneuploidies) in the late first and/or early second trimester. All had the capacity to collect, process, store and ship plasma samples according to a stringent protocol. The sites secured institutional review board (or equivalent) approval, and obtained informed consent of each woman who enrolled in the study.

Laboratory Sites

The Sequenom Center for Molecular Medicine in San Diego (SCMM-SD) is CLIA-certified as a high complexity molecular genetics laboratory. The laboratory has two Illumina HiSeq 2000 Next Generation Sequencers, both of which were used in this study. The Orphan Disease Testing Center at the University of California, Los Angeles School of Medicine (UCLA), also a CLIA-certified high complexity genetics laboratory, had one Illumina HiSeq 2000 platform during this study. UCLA collaborated with SCMM-SD in performing massively parallel sequencing of blinded study samples and provided clinical interpretations according to a standardized written protocol, updated for use on the Illumina HiSeq 2000 platform, created at SCMM-SD.

Study Population

Information about pregnant women who were scheduled for diagnostic testing was reviewed at each Enrollment Site to identify those with a high risk for aneuploidy according to study criteria, and whose fetuses were 21 weeks' 6 days gestation or less. High risk was defined as being screen positive for Down syndrome or other trisomy by serum and/or ultrasound testing, maternal age of 38 years or more at delivery (during the early part of the study this was set at 40 years or older), or a family history of aneuploidy. Women who qualified were informed about the study by genetic counselors or physicians and provided signed informed consent if they chose to participate. Each woman's signature and full consent form were stored locally. Selected demographic and pregnancy-related information was obtained on a standardized form, along with at least two (and up to five) 10 mL purple top tubes of venous blood, drawn prior to the diagnostic procedure. Participants were identified only by a study code on the data forms and on the processed plasma tubes. Pregnancies with multiple gestations and existing fetal deaths were eligible, provided that diagnostic testing was planned for all fetuses.

Power Analysis

The study was intended to determine whether existing practice should change. Therefore, a high level of confidence was needed in estimating both the detection rate (proportion of Down syndrome pregnancies with a positive test, or sensitivity) and the false positive rate (proportion of unaffected pregnancies with a positive test, or 1-specificity). Under the assumption of no false negatives, sufficient cases should be included to have at least 80% power to find the detection rate significantly higher than 98%. Analyzing 200 cases would provide 90% power to reject this lower limit. For each of these cases, seven euploid pregnancies (controls) would be selected to ensure reasonable confidence in the false positive rate.

Sample/Data Collection

Plasma samples were drawn prior to amniocentesis or chorionic villus sampling and processed according to the protocol of Ehrich et al., (Am. J. Obstet. Gynecol. (2011) 204:205.e1-11). Briefly, 10 mL plasma tubes (EDTA-containing, purple top) were centrifuged at 2,500×g for 10 minutes at 4° C., the plasma pooled in a 50 mL centrifuge tube, and centrifuged at 15,500×g for 10 minutes at 4° C. The plasma was then transferred to two or more 15 mL conical tubes, 4 mL per tube, with the last tube containing any residual volume. These tubes were placed in a −70° C. or colder freezer for longer term storage at the Enrollment Site or at −20° C. for no more than 24 hours prior to shipment on dry ice for 1 to 2 day delivery to the Coordinating Center. If stored at −80° C., samples were shipped in batches on dry ice, usually on a monthly basis, for 1 to 2 day delivery to the Coordinating Center. All plasma tubes were identified using a pre-printed bar coded label with the site-specific study ID affixed. Quick International Courier, Inc., was used for international shipments to ensure proper tracking, maintenance of dry ice in packages, and delivery.

A standardized multipart form was used for data collection and included a pre-printed bar-coded study label, collection date, gestational age, maternal age, weight, race and ethnicity, indication for the procedure, number of fetuses, fetal sex, sample draw date and time, number of tubes drawn, time received in the laboratory, and time placed in the freezer. One copy was retained at the site, while the other was shipped with the samples to the Coordinating Center. To obtain karyotype information, an electronic request form was generated for each woman, where each request form included: procedure date, gestational age, procedure (e.g., amniocentesis, CVS), diagnostic test (e.g., karyotype, qfPCR), the interpreted test result (as well as fetal sex), and sufficient space to include results for additional fetuses and comments. For both the processed plasma tubes and the data forms, participants were identified only by a study code.

Selection of Samples for Analysis

Selection criteria included access to a full 4 mL processed sample, woman's age at least 18 years and no, or limited, important data missing. The last few enrolled cases from the late first trimester (≤14 weeks' gestation) and the early second trimester (15-22 weeks' gestation) were not included because the target of 100 cases per trimester had been reached with a reasonable cushion. Matching was based on gestational age, maternal race, maternal ethnicity, Enrollment Site, and time in the freezer. Samples were shipped in dry ice for processing and testing, only after the laboratory developed test (LDT) had been through final internal validation, a publication submitted, and Oversight Committee consent. In select circumstances (e.g., broken aliquot, failed extraction), a second aliquot could be requested. The number of second aliquots and indications for sending was tracked.

Laboratory Testing

Library Preparation

The extracted circulating cell-free (ccf) DNA was used for library preparation without further fragmentation or size selection. ccf DNA generally is naturally fragmented with an average length of about 160 base pairs. Fifty-five µL of DNA eluent was stored at 4° C. in low-binding Eppendorf tubes following extraction until the library preparation began. Storage times ranged from 24 to 72 hours. The library preparation was carried out according to the manufacturer's specifications (Illumina), with some modifications as noted herein. Enzymes and buffers were sourced from Enzymatics, MA (End Repair Mix—LC; dNTP Mix (25 mM each); Exo(−) Klenow polymerase; 10× Blue Buffer; 100 mM dATP; T4 DNA Ligase; 2× Rapid Ligation Buffer) and New England Biolabs, MA (Phusion PCR MM). Adapter oligonucleotides, indexing oligonucleotides, and PCR primers were obtained from Illumina Inc, CA.

Library preparation was initiated by taking 40 µL of ccf DNA for end repair, retaining 15 µL for fetal quantifier assay (FQA) Quality Control (QC). End repair of the sample was performed with a final concentration of 1× End Repair buffer, 24.5 µM each dNTPs, and 1 µL of End Repair enzyme mix. The end repair reaction was carried out at room temperature for 30 minutes and the products were cleaned with Qiagen Qiaquick columns, eluting in 36 µL of elution buffer (EB). 3' mono-adenylation of the end repaired sample was performed by mixing the end repaired sample with a final concentration of 1× Blue Buffer, 192 µM dATP, and 5U of Exo(−) Klenow Polymerase. The reaction was incubated at 37° C. for 30 minutes and cleaned up with Qiagen MinElute columns, eluting the products in 14 µL of EB. Adapters were ligated to the fragments by incubating for 10 minutes at room temperature with 1× Rapid Ligation buffer, 48.3 nM Index PE Adapter Oligos, and 600U T4 DNA Ligase. The ligation reaction was cleaned up with QiaQuick columns, and the sample eluted in 23 µL of EB. The adapter modified sample was enriched by amplifying with a high-fidelity polymerase. The entire 23 µL eluent of each sample was mixed with 1× Phusion MM, Illumina PE 1.0 and 2.0 primers, and 1 of 12 index primers for a total PCR reaction volume of 50 µL. The methods and processes described herein are not limited to the use of 12 index primers. Any number of additional index primers can be used with methods and processes described herein, depending on platform and/or manufacturer availability. The greater the number of index primers, the greater the number of samples that can be run in a flow cell lane. The methods and processes described herein utilized index primers commercially available at the time of the study. The sample was amplified in a 0.65-mL PCR tube using an AB GeneAmp PCR System 9700 thermal cycler. The PCR conditions utilized for amplification included an initial denaturation at 98° C. for 30 seconds, 15 cycles of denaturation at 98° C. for 10 seconds, annealing at 65° C. for 30 seconds, and extension at 72° C. for 30 seconds. A final extension at 72° C. for 5 minutes was followed by a 4° C. hold. The PCR products were cleaned with MinElute columns and the libraries eluted in 17 µL of EB.

Quality Control of Sequencing Library (Lab Chip GX)

The libraries were quantified via electrophoretic separation on a microfluidics platform. Each library was diluted 1:100 and analyzed in triplicate using the Caliper LabChip GX instrument with HT DNA 1K LabChip, v2 and HiSens Reagent kit (Caliper Life Sciences, Hopkinton, Mass.). Concentrations were calculated by Caliper LabChip GX software v2.2 using smear analysis from 200-400 bp.

Clustering and Sequencing

Clustering and sequencing was performed according to standard Illumina protocols. Individual libraries were normalized to a 2 nM concentration and then clustered in 4-plex format to a final flow cell loading concentration of 1.2 µM per sample or 4.8 µM per flow cell lane. The cBOT instrument and v4 Single-Read cBOT reagent kits were used. Thirty-six cycles of single-read multiplexed sequencing was performed on the HiSeq 2000 using v1 HiSeq Sequencing Reagent kits and supplemental Multiplex Sequencing Primer kits. Image analysis and base calling were performed with Illumina's RTA1.7/HCS1.1 software. Sequences were aligned to the UCSC hg19 human reference genome (non repeat-masked) using CASAVA version 1.6. Clustering and sequencing can also be performed using 8-plex, 12-plex, 16-plex, 24 plex, 48 plex, 96 plex or more, depending on availability of unique indexing primers.

Data Analysis

For classification of samples as chromosome 21 trisomic versus disomic, a method similar to that described in Chiu et al., (BMJ (2011) 342:c7401) and Ehrich et al., (Am. J. Obstet. Gynecol. (2011) 204:205.e1-11) was utilized, the entire contents of which are incorporated herein by reference in their entirety. Unlike the methods used for those studies, the classification applied herein was done in an "on-line" fashion to simulate clinical practice. Samples were called as soon as one flow cell was processed. This "on-line" version of the classification predictions used all the data associated with a flow cell in order to establish a standardized chromosomal representation (e.g., a flow cell-robust z-score, or FC-robust z-score), by using robust estimates of the location and scale of the chromosome representation. With $chr_i$ denoting the chromosomal representation for chromosome i, $$chr_i = \frac{counts_i}{\sum_{j=1}^{22} counts_j}$$

where $counts_j$ are the number of aligned reads on chromosome j, the equation of the FC-robust chromosome z-score for sample N associated with the chromosome i is $$z_N = \frac{chr_{i_N} - \mathrm{median}(chr_i)}{MAD(chr_i)}$$

A normalized form of the median absolute deviation (MAD) was used for a robust estimate of the scale, $$MAD(X) = \frac{1}{\Phi^{-1}(3/4)} \cdot \mathrm{median}(|X - \mathrm{median}(X)|),$$

with the multiplicative constant chosen to approximate the standard deviation of a normally distributed random variable. Samples were called trisomic with respect to chromosome 21 if $z_N > 3$ and disomic otherwise.

Filtering Repeat Regions and GC Normalization

In the human genome, repeated genomic sequences which can be inferred with the current detection methods represent up to half of the entire genome. These repetitive regions can take the forms of simple repeats, or tandem repeats (e.g., satellite, minisatellite, microsatellite DNA mostly found at centromeres and telomeres of chromosomes), or segmental duplications and interspersed repeats (e.g., SINES, LINES, DNA transposons). The size of such duplications can range from few base pairs (bp), to hundreds of bp, and all the way up to 10-300 kilobase pairs. The repetitive nature of these regions is believed to be a source of variance in the PCR amplification step that is present in some of the next-generation sequencing techniques, Massively Parallel Shotgun Sequencing for example.

In order to evaluate the impact of reads mapped to such repetitive regions on the classification accuracy, all samples were analyzed with or without such reads included in the tabulation of chromosomal representation. Samples were analyzed with or without the benefit of removing the contribution of repeated genomic sequences. For efficient computational processing, the reference genome used for the alignment of the short reads was not a 'repeat-masked' version but rather one that included such repetitive regions. Post-alignment, a filtering procedure based was utilized on the information contained in the Repeat Library 20090604 (URL world wide web repeatmasker.org). For Repeat-Mask-aware classification, only reads which do not overlap with the repeated regions were then considered for the estimation of chromosomal representation.

The different GC content of genomic sequences sometimes leads to different amplification efficiency during PCR steps, which in turn sometimes can lead to a biased sampling of the original genomic material. To compensate for this potential amplification bias, the counts for each 50 Kb bin were summarized and further normalized with respect to the bin-specific GC content by using a LOESS technique similar to that described in Alkan et al. (Nat. Genet. (2009) 41:1061-1067) The filtered counts normalized with respect to the estimated GC bias were then used for determination of chromosomal representation.

The read filtering and count normalization procedures described herein were not used for the "on-line" classification of chromosome 21 ploidy, but were used as part of a subsequent analysis and data sets for all samples were delivered by SCMM to the Coordinating Center prior to unblinding. The chromosome representation calculated after applying both the filtering with respect to the Repeat Mask as well as the GC normalization procedures are referred to in this study as 'GC-adjusted chromosome representation', z-scores calculated from such chromosome representation are referred to as 'GC-adjusted z-scores'.

The SCMM-SD laboratory performed all of the steps for all 1,640 samples. The UCLA laboratory received library preparations for about 40% of these samples, and then completed the testing protocol. For one set of samples (e.g., 1 plate; 3 flow cells; about 96 samples) containing seven Down syndrome cases and controls, separate 4 mL processed plasma samples were shipped to both the SCMM-SD and UCLA laboratories and the entire LDT was performed in duplicate. For any sample having test results from both laboratories, the result from SCMM-SD was considered the primary result.

Results and Discussion

Figure 2:
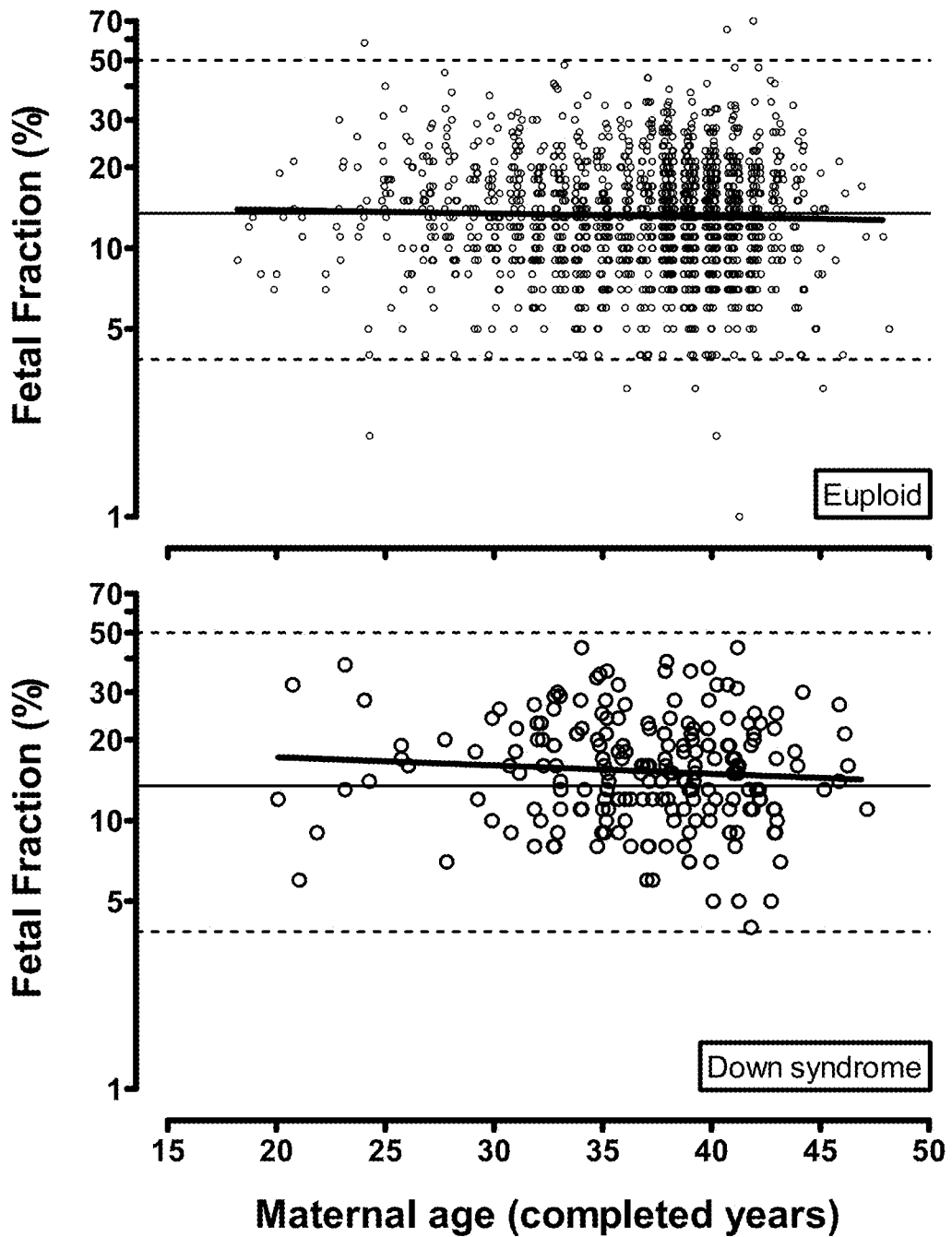
FIG. 2 graphically illustrates the fetal DNA fraction for each of the selected samples plotted as a function of maternal age.
Figure 3:
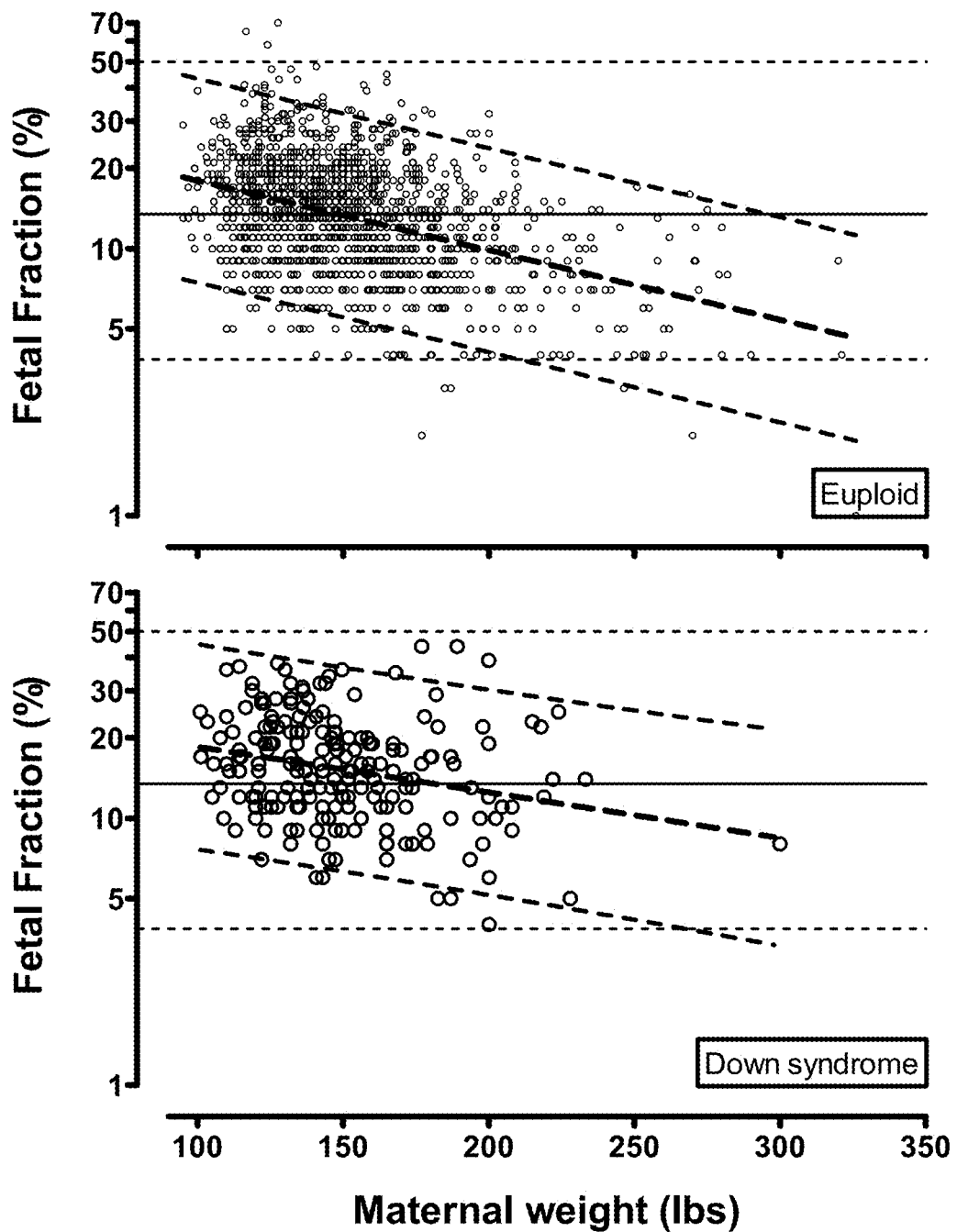
FIG. 3 graphically illustrates the fetal DNA fraction for each of the selected samples plotted as a function of maternal weight.

The tabularized and graphical data presented herein for FIGS. 4 to 19 includes covariate analysis of the fetal fractions (percentage of fetally derived free circulating DNA) for all 212 Down syndrome pregnancies and 1,484 euploid pregnancies. In order to improve visibility of the data, categorical data were 'dithered' to the left and right of the labeled tick mark. All of the pregnancies studied were viable at time of sampling, and all were verified singleton pregnancies with diagnostic test results available (e.g., karyotype). Dithering often is a random jittering or slight shifting of data points to avoid over-plotting. The X axis coordinate was varied slightly to allow visualization of individual points for that category, without changing the overall view of the plot. Since the fetal fraction test results were available prior to sequencing, they were used to determine sample adequacy. Acceptable fetal fractions were between 4% and 50%, inclusive (horizontal thin dashed lines in the graphs). In clinical practice, samples outside of this range may be considered unacceptable for sequencing. The overall median fetal fraction of 14.0% (geometric mean 13.4%, arithmetic mean 15.0%) is shown in FIGS. 1 to 3 as a thin solid horizontal line. If the fetal fraction is lower than 4%, it becomes difficult to resolve the small difference between circulating DNA from Down syndrome and euploid pregnancies. Higher levels indicate potential problems with sample handling. The distribution of fetal fractions is right-skewed. For this reason, the presentation and analysis is after a logarithmic transformation. For covariates explored using regression analyses, only the regression line is shown if results do not reach statistical significance. Otherwise, 95% prediction limits are shown, as well.

Fetal fraction was analyzed according to time between sample draw and freezer storage. Using the results of the analysis for euploid pregnancies, the expected fetal fractions for 1, 2, 3, 4 and 5 hours to freezer would be 13.5%, 13.2%, 12.8%, 12.5% and 12.2%, respectively.

Sample hemolysis status was evaluated by the Enrollment site prior to freezing. A standard scheme of none, slight, moderate and gross was used. None and slight were subsequently grouped into a 'No' category, with moderate and gross grouped into a 'Yes' category. There was no significant difference in fetal fraction for those with hemolysis (mean=13.2% and 13.6% for No and Yes, respectively, t=−0.46, p=0.64). For Down syndrome pregnancies there was little if any difference for those with hemolysis (mean=15.4% and 15.0%, respectively, t=0.14, p=0.89).

There was no significant relationship for the percent fetal fraction (euploid pregnancies), stratified by geographic region; (mean fetal fractions of 13.9%, 13.1%, 12.8% and 13.4%, from left to right, ANOVA F=1.93, p=0.12) or among the Down syndrome pregnancies (mean fetal fractions of 17.4%, 15.0%, 14.5% and 15.9%, from left to right, ANOVA F=1.45, p=0.23).

There was no significant association for the percent fetal fraction stratified by indication for diagnostic testing; (mean fetal fractions of 13.0%, 13.2%, 13.4%, 12.7%, 13.1%, 14.1%, 15.6%, and 13.3%, from left to right, ANOVA F=0.61, p=0.75) or among the Down syndrome pregnancies, again showing no association (mean fetal fractions of 14.9%, 15.0%, 15.6%, 15.3%, 14.8%, NA, 13.0%, and 15.7%, from left to right, ANOVA F=0.11, p=0.99).

For the percent fetal fraction stratified by Enrollment sites with at least 50 samples, there is a significant difference (mean fetal fractions range from 10.2% to 18.7%, ANOVA F=5.59, p<0.0001) and for the same analysis among the Down syndrome pregnancies there is not a significant difference (mean fetal fractions range from 12.7% to 16.9%, ANOVA F=0.35, p=0.97). This is not explained by different maternal weights (see FIG. B8), as the average weight in the five Enrollment Sites with the highest fetal fractions was 151 pounds compared to 150 pounds in the six Sites with the lower fetal fractions.

FIG. 1: The x-axis shows the gestational age at the time of sample draw. The top panel (Euploid pregnancies) shows the fetal fraction by gestational age. Linear regression did not find a significant relationship (thick dashed line, p=0.23, slope=−0.0024). An analysis of Down syndrome pregnancies (bottom panel) found a similar result, (p=0.10, slope=0.0084).

FIG. 2: The x-axis shows the maternal age at the estimated delivery date. The top panel (Euploid pregnancies) shows the fetal fraction by maternal age. Linear regression did not find a significant relationship (thick dashed line, p=0.23, slope=−0.0013). An analysis of Down syndrome pregnancies (bottom panel) found a similar result (p=0.26, slope=−0.0031).

FIG. 3: The x-axis shows maternal weight in pounds at the time of sample draw. The top panel (Euploid pregnancies) shows the fetal fraction by maternal weight from euploid pregnancies. Linear regression found a significant relationship (thick dashed line, with 95% predication limits shown by thin dashed lines, p<0.0001, slope=−0.0026). A similar result (bottom panel) was found for the Down syndrome pregnancies (p=0.0002, slope=−0.0017). Using the euploid results as an example, women weighing 100, 150, 200, 250 and 300 pounds would be expected to have average fetal fractions of 17.8%, 13.2%, 9.8%, 7.3% and 5.4%, respectively.

There was a slight, but significant, decrease in fetal fraction for those (Euploid pregnancies) reporting vaginal bleeding (mean=13.3% and 12.3% for No and Yes, respectively, t=2.04, p=0.04). For the same analysis among the Down syndrome pregnancies there was a significant increase for those reporting bleeding (mean=14.7% and 17.6%, respectively, t=−2.07, p=0.04).

There was no difference in fetal fraction between male and female euploid fetuses (mean of 13.4% and 12.9%, respectively, t=1.68, p=0.094) or among the Down syndrome pregnancies (mean=15.2% and 15.3%, respectively, t=−0.05, p=0.96).

Down syndrome pregnancies have a higher fetal fraction that is statistically significant (mean 15.2% versus 13.2%, t=−4.11, p<0.0001) than euploid pregnancies. If this were to be used as a screening test for Down syndrome, then at false positive rates of 5% and 10%, the corresponding detection rates would be 9.0% and 17.5%, respectively. These correspond to a cumulative odds ratio of about 1.8.

Covariate analysis of fetal fraction revealed that maternal weight was a significant factor in the determination of genetic variation. At average weights of 100 and 250 pounds, the expected fetal fractions are 17.8% and 7.3%, respectively. The maternal weight effect may explain the small but significant effects found for fetal fraction versus maternal race and ethnicity. Time from sample draw to freezer storage also has a significant effect on fetal fraction, with longer times resulting in slightly lower fetal fractions. The effect seen for sample draw to freezer storage is, however, substantially smaller than for maternal weight. The remaining associations are generally small, and usually nonsignificant.

Figure 4:
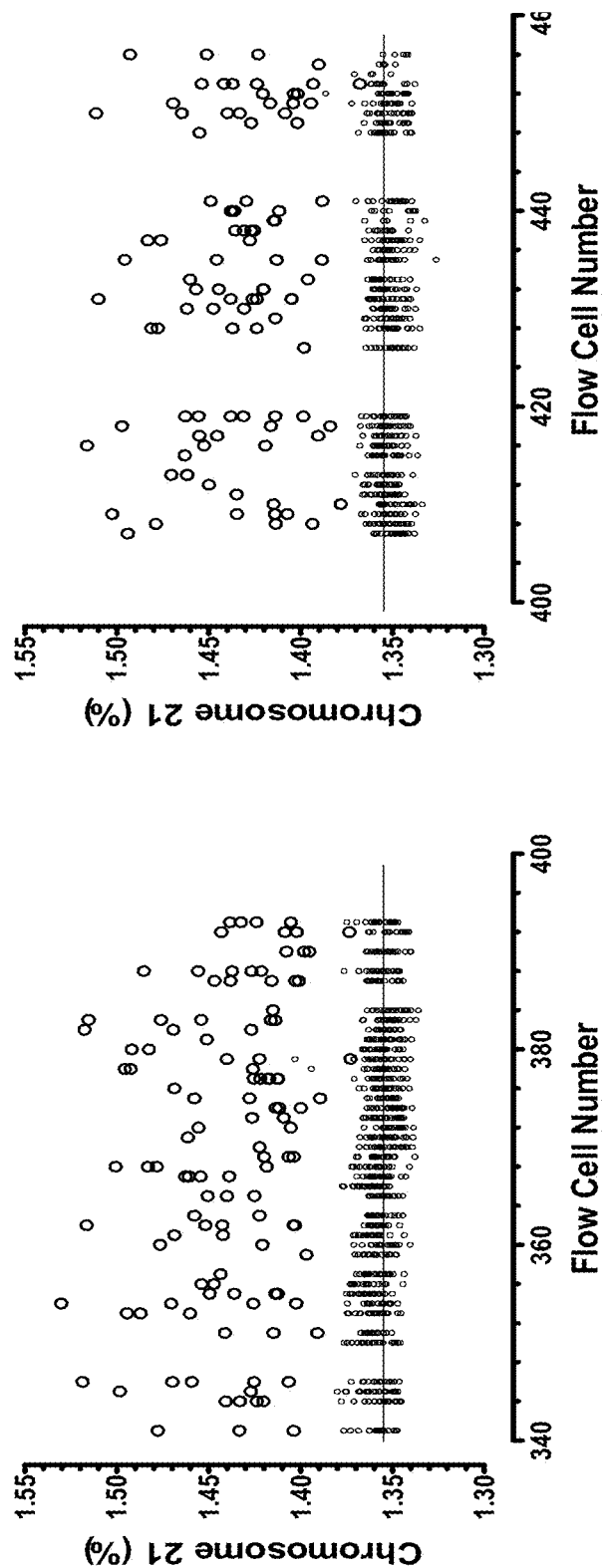
FIG. 4 graphically illustrates chromosome 21 percentage for each of the selected samples plotted as a function of chromosome 21 matched reads by flow cell.
Figure 5:
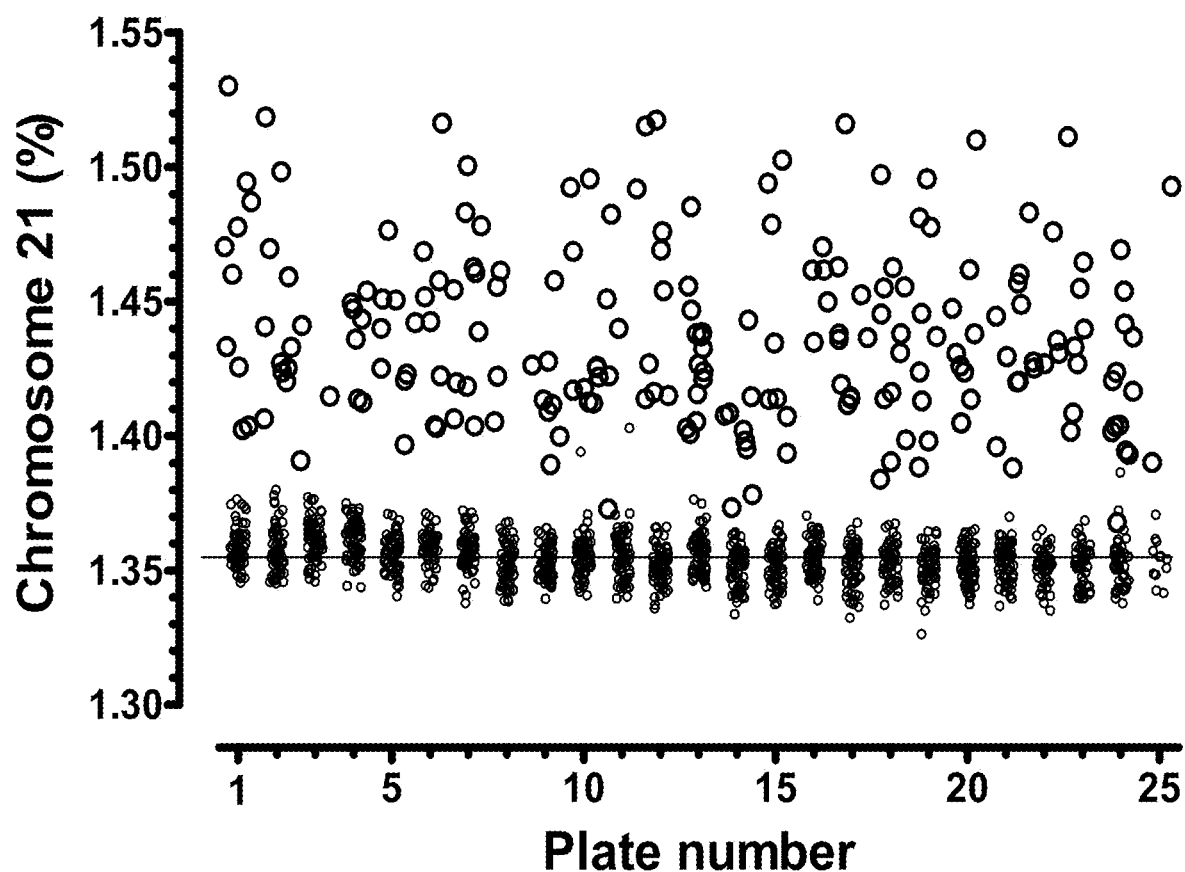
FIG. 5 graphically illustrates the chromosome 21 percentage for each of the selected samples plotted as a function of chromosome 21 matched reads by plate number.
Figure 6:
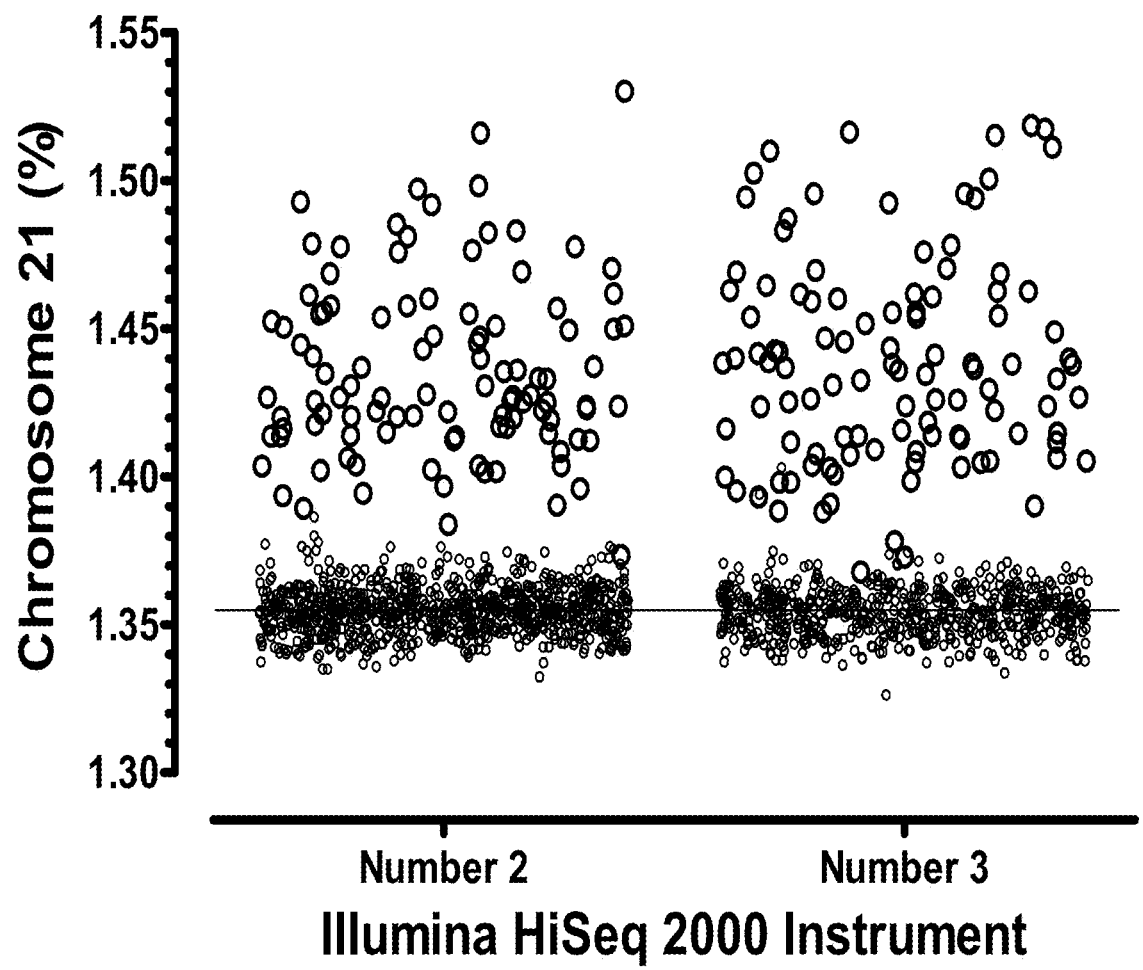
FIG. 6 graphically illustrates the chromosome 21 percentage for each of the selected samples plotted as a function of the Illumina instrument used for sequencing.

The data presented graphically in FIGS. 4 to 6 summarize the relationships between the chromosome 21 representation (e.g., percent chromosome 21) and assay variability. Samples from four patients generally were quad-plexed in a single flow cell lane (e.g., 8 lanes equates to 32 patients). However, only 30 patient samples usually were run, with the additional positions holding controls. 92 patients were processed together in 96 well plates. Each plate was run on 3 flow cells (e.g., 1 sample plate was run on 3 flow cells when using quad-plexing and 4 index primers per lane). Generally, 7 plates of data were grouped together to form a batch. Each batch contained the allotted samples in random order. Thus, cases and controls within a batch were not necessarily run on the same sample plate or flow cell. Running cases and controls together sometimes can under-estimate total variance in matched analyses. All 212 Down syndrome and all but 13 of the 1,484 euploid results are shown in FIGS. 4 to 6. In instances in which a sample initially failed, but the second result was successful, the second result is shown. Those samples that failed to produce a useable result on the repeated sample are not shown. All the pregnancies studied were viable at the time of sampling, and all were verified singleton pregnancies with diagnostic test results available (e.g., karyotype analysis).

FIG. 4 shows C21% results by flow cell. The percentage of chromosome 21 matched reads divided by the total autosomal reads is plotted for both euploid (small circles) and Down syndrome (larger circles) by the flow cell number (x-axis). Each flow cell can test 32 samples (in quad-plex), resulting in 28 to 30 patient samples along with control samples (not all patient samples run in each flow cell are included in this report). Generally, 20 to 25 euploid and 2 to 7 Down syndrome pregnancies are shown for each. In some instances (e.g., a flow cell with repeats), the numbers are much smaller. Overall, 76 flow cells contained data relevant to the current study, including testing of additional aliquots. Flow cells were consecutively numbered, and missing flow cells were used for other studies, including testing at the independent laboratory. Flow cell-to-flow cell changes in the mean level can be seen. Also, there is a clear tendency for early flow cells to be above the euploid mean of 1.355%, while the later flow cells tend to be lower. There is no difference in the standard deviations of the euploid results among flow cells. A reference line is drawn at 1.355%, the overall average fetal fraction for the euploid samples. Flow cell to flow cell variability in mean levels can be seen (ANOVA, F=4.93, p<0.001), but the standard deviation is constant (F=1.1, p=0.31).

FIG. 5 contains the same data as FIG. 4, but the data are stratified by plate rather than flow cell. Processing is performed in 96 well plates. The processed samples from one plate are then run on three flow cells. The reference line is at 1.355%. Plate to plate variability in mean levels can be seen (ANOVA, F=13.5, p<0.001), but the standard deviation is constant (F=1.2, p=0.23). The same tendencies can be seen in this figure that were evident in FIG. 4. The reduction in overall variance is somewhat less when accounting for plate-to-plate differences compared to flow cell-to-flow cell. However, once plate differences are accounted for, there is no significant effect for flow cell differences. As seen in FIG. 4, there is no difference in the standard deviations of the euploid results among plates.

FIG. 6 contains the same data as FIGS. 4 and 5, but the data are stratified according to which Illumina instrument was used for sequencing. 42 and 34 plates were processed on Number 2 and Number 3, respectively. The reference line is at 1.355%. There is no difference in the chromosome 21 percent by instrument in Euploid (means of 1.355 and 1.354, respectively, t=2.0, p=0.16) or Down syndrome pregnancies (means of 1.436 and 1.438, respectively, t=0.32, p=0.57). There is no systematic difference in C21% results from the two machines.

Fifteen potential covariates for all 212 Down syndrome and all but 13 of the 1,484 euploid results were summarized versus the clinically reported chromosome 21 z-score. All the pregnancies studied were viable at the time of sampling, and all were verified singleton pregnancies with diagnostic test results available (e.g., karyotype analysis). One Down syndrome sample had a z-score slightly over 25, but was plotted at 24.9. The range of euploid samples is between −3 and +3. Among cases, a cut-off level of 3 was used. The distribution of z-scores is right-skewed in cases, but Gaussian in controls. The data, however, were still plotted on a linear scale. Regression analysis in cases was after a logarithmic transformation.

All samples selected for testing were processed and stored in the freezer within six hours of collection. For chromosome 21 z-score by time from sample draw to freezer storage, linear regression does not find a significant relationship for either the euploid or Down syndrome pregnancies (p=0.90, slope=−0.0025; and p=0.50, slope=−0.20, respectively).

Hemolysis status was evaluated by the Enrollment site prior to freezing. There was no significant difference in the z-score after stratification by hemolysis status for either group (t=−0.01, p=0.99 and t=−0.12, p=0.90 for euploid and Down syndrome pregnancies, respectively).

There was no significant relationship for z-scores stratified by geographic region for euploid pregnancies (mean z-scores of −0.22, −0.14, −0.12 and −0.01, from left to right, ANOVA F=1.84, p=0.14) or among the Down syndrome pregnancies (mean z-scores of 10.1, 9.9, 8.9 and 10.2, from left to right, ANOVA F=1.00, p=0.39).

There was a slight but significant effect for z-scores stratified by indication for diagnostic testing for Euploid pregnancies (mean z-scores of −0.15, −0.14, −0.24, −0.05, −0.11, 0.20, −0.52 and −0.20, from left to right, ANOVA F=2.02, p=0.049) but no significant effect for Down syndrome pregnancies (mean z-scores of 8.9, 9.1, 9.7, 9.8, 10.0, n/a, 10.7 and 9.5, from left to right, ANOVA F=0.25, p=0.96).

For z-score stratified by Enrollment site and sites with at least 50 samples, there is no effect for Euploid pregnancies (mean z-scores range from −0.21 to 0.02, ANOVA F=0.57, p=0.84) or Down syndrome pregnancies (mean z-scores range from 6.90 to 12.34, ANOVA F=1.45, p=0.16).

Figure 7:
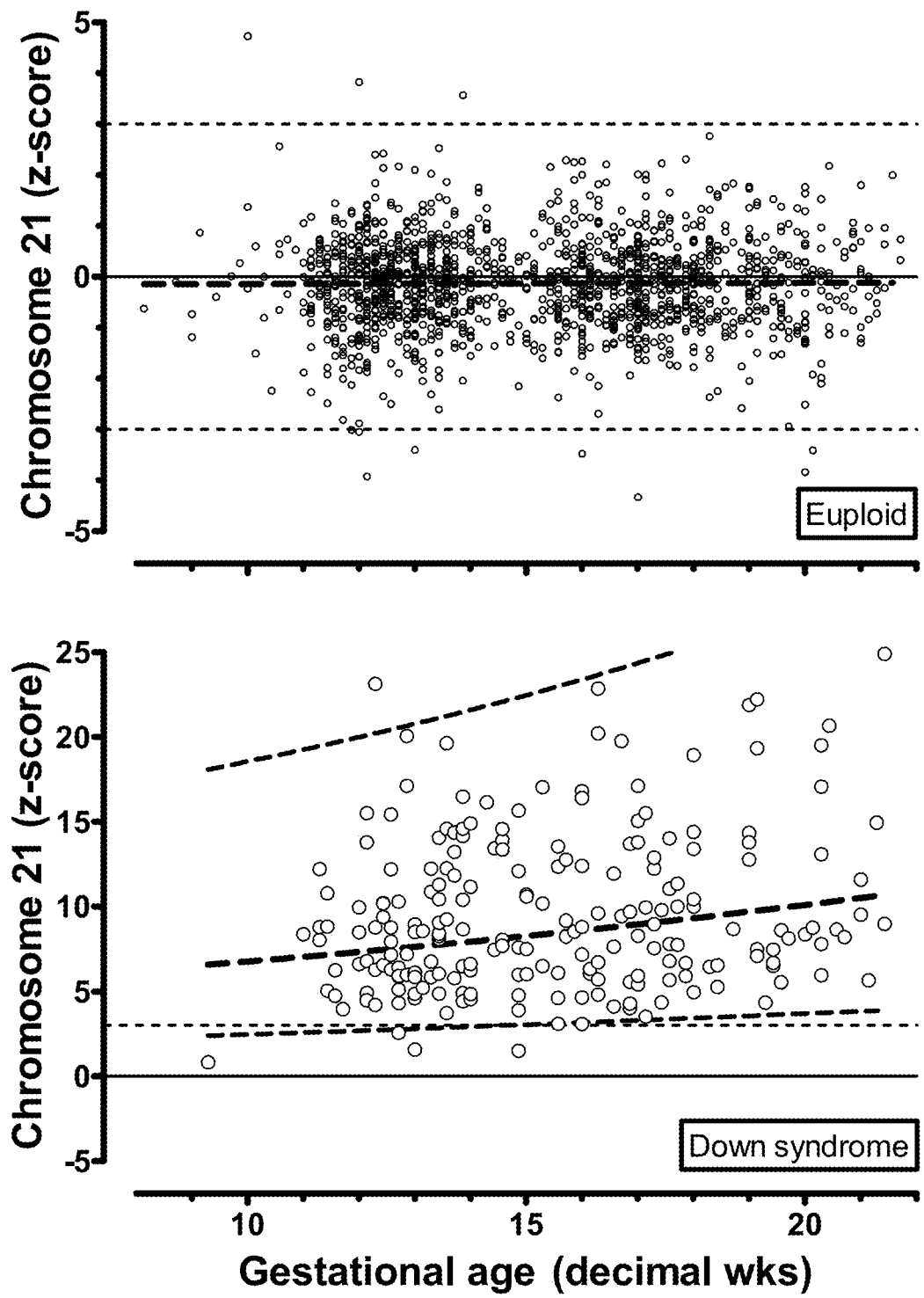
FIG. 7 graphically illustrates the chromosome 21 z-score for each of the selected samples plotted as a function of gestational age.

FIG. 7: The x-axis shows the gestational age at the time of sample draw. The top panel (Euploid pregnancies) shows the z-score by gestational age. Linear regression did not find a significant relationship (p=0.79, slope=0.0023). An analysis of Down syndrome pregnancies (see lower panel) found a significant positive association with gestational age (p=0.0023, slope=0.017 on the log of the z-score).

Figure 8:
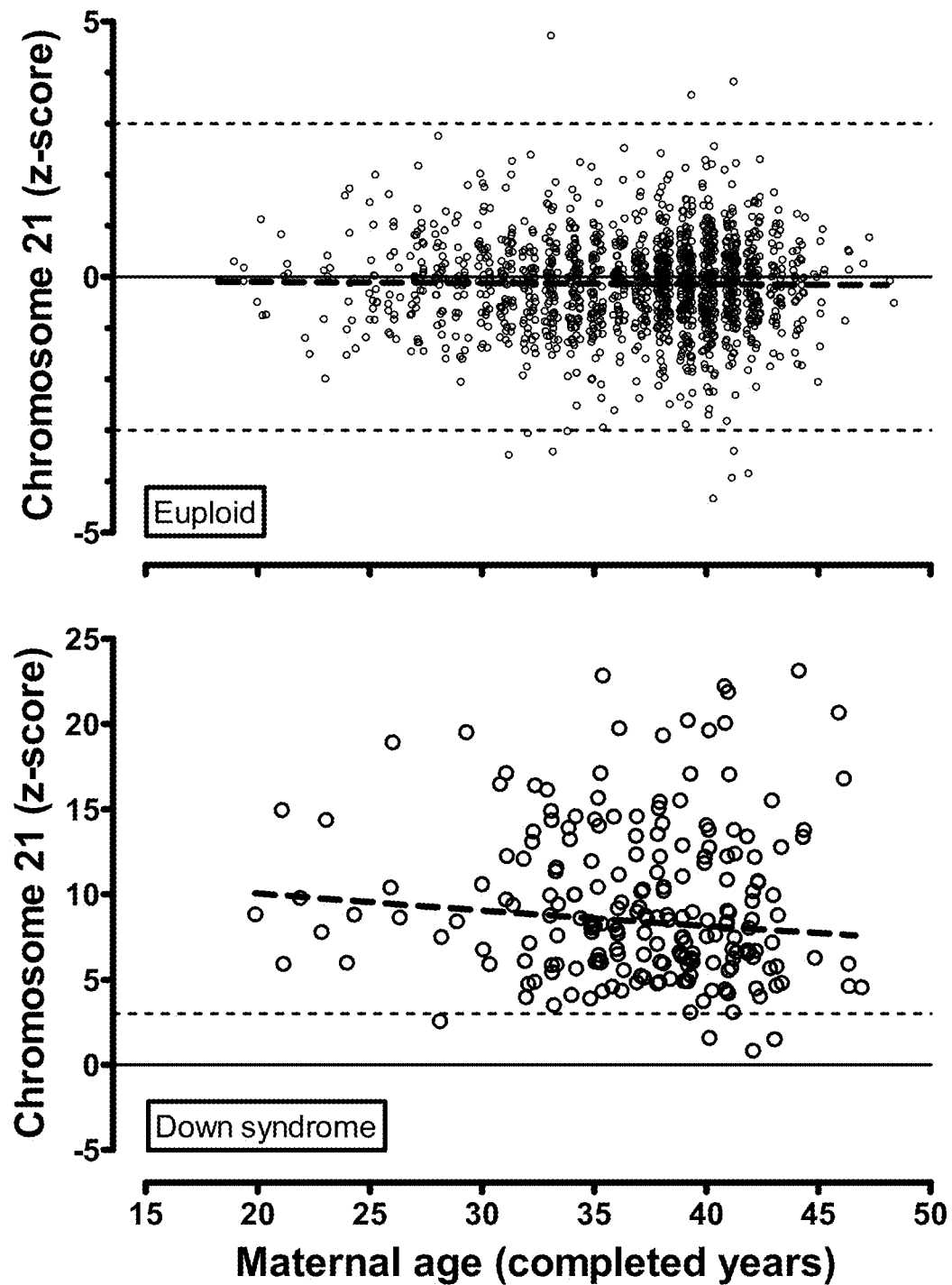
FIG. 8 graphically illustrates the chromosome 21 z-score for each of the selected samples plotted as a function of maternal age.

FIG. 8: The x-axis shows the maternal age at the estimated delivery date. The top panel (Euploid pregnancies) shows the z-score by maternal age. Linear regression did not find a significant relationship (thick dashed line, p=0.62, slope=−0.0023. An analysis of Down syndrome pregnancies (bottom panel) found a similar result (p=0.14, slope=−0.0046).

Figure 9:
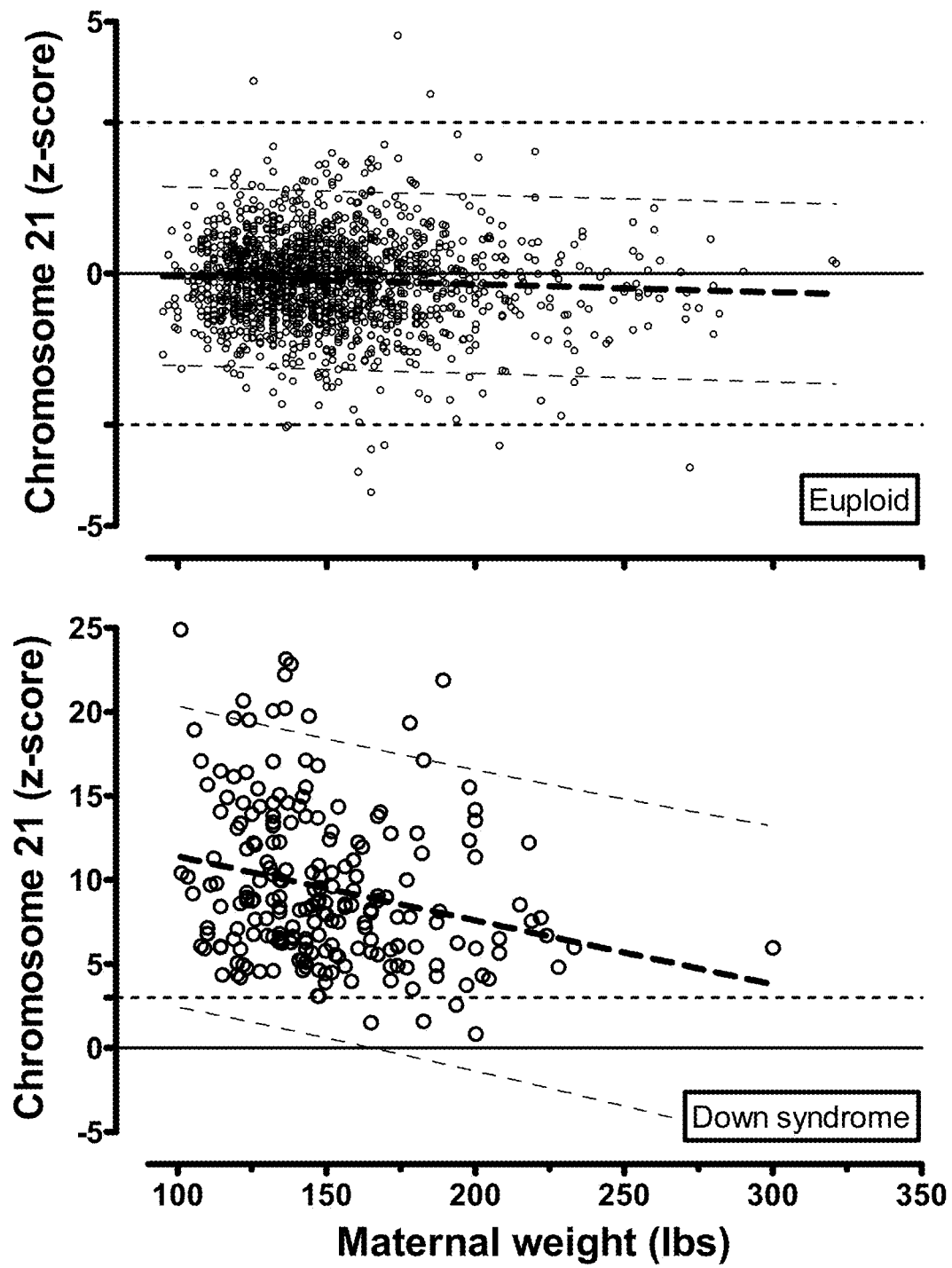
FIG. 9 graphically illustrates the chromosome 21 z-score for each of the selected samples plotted as a function of maternal weight.

FIG. 9: The x-axis shows the maternal weight in pounds at the time of sample draw. The top panel (Euploid pregnancies) shows the z-score by maternal weight for samples for euploid pregnancies. Linear regression found a significant negative slope (thick dashed line, with 95% prediction limits shown by thin dashed lines, p=0.029, slope=−0.0016). A similar, but much larger, effect is seen for Down syndrome pregnancies (lower panel, p=0.0003, slope=−0.038). This latter effect is likely due to the maternal weight effect on fetal fraction (see FIG. 11).

There was no significant difference in z-scores by reported vaginal bleeding status for Euploid pregnancies (mean=−0.14 and −0.09, for No and Yes, respectively, t=−0.65, p=0.52). For the same analysis among the Down syndrome pregnancies there was a significant increase for those reporting bleeding (mean=9.03 and 11.70, respectively, t=−3.14, p=0.0019).

There is no significant effect for z-score stratified by maternal race for Euploid pregnancies (mean z-scores of −0.14, −0.15, 0.28 and −0.21, from left to right; ANOVA F=2.44, p=0.063) or Down syndrome pregnancies (mean z-scores of 9.55, 8.90, 9.63 and 10.24, from left to right, ANOVA F=0.12, p=0.95).

There is no significant effect for z-score stratified by Caucasian ethnicity for Euploid pregnancies (mean z-scores of −0.16, −0.06 and 0.00, from left to right, ANOVA F=1.70, p=0.18) or Down syndrome pregnancies (mean z-scores of 9.5, 9.4 and 11.9, from left to right, ANOVA F=0.38, p=0.68).

There is no difference in z-scores stratified by fetal sex between males and females for Euploid pregnancies (mean=−0.13 and mean=−0.13, respectively, t=−0.04, p=0.97) or for Down syndrome pregnancies (mean=9.25 and mean=9.80, respectively, t=−0.85, p=0.39).

For z-scores by freezer storage time, linear regression did not find a significant slope for Euploid (thick dashed line, p=0.72, slope=0.000057) or Down syndrome pregnancies (lower panel, p=0.25, slope=−0.0022).

Figure 10:
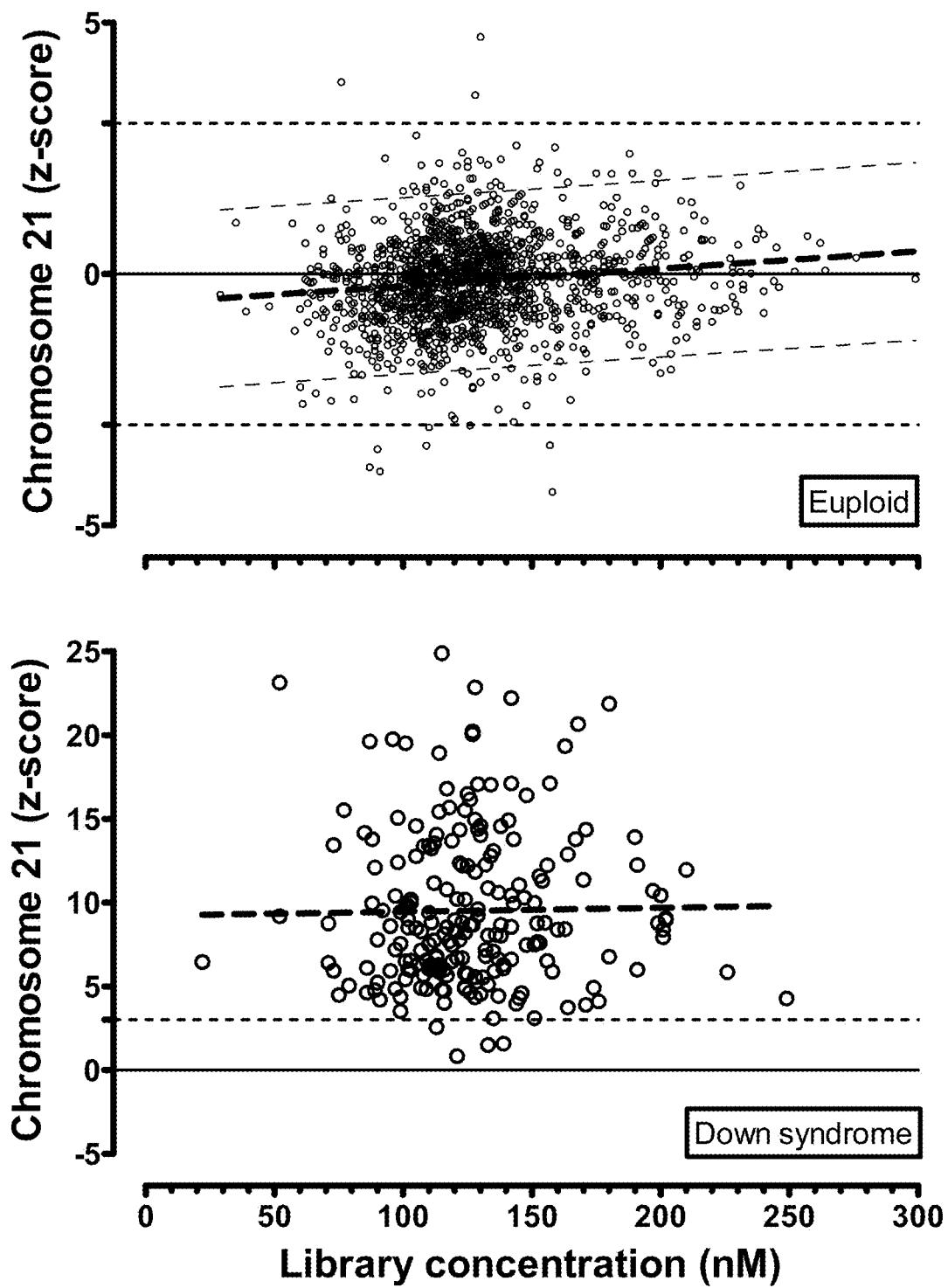
FIG. 10 graphically illustrates the chromosome 21 z-score for each of the selected samples plotted as a function of library concentration.
Figure 11:
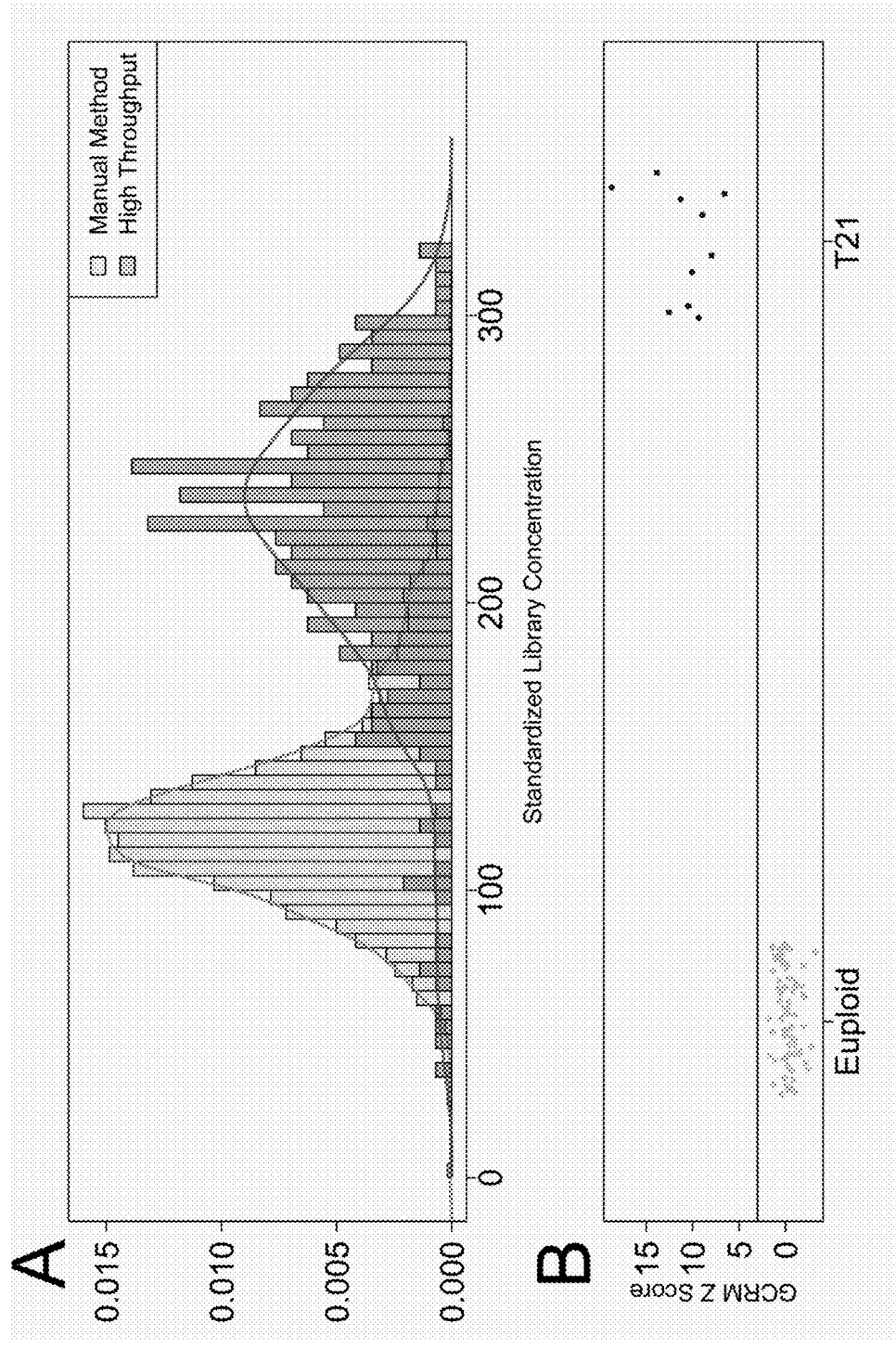
FIG. 11 illustrates a library preparation optimization.

FIG. 10: The top panel (Euploid pregnancies) shows the z-score versus DNA library concentration. Linear regression shows a statistically significant positive slope (thick dashed line, with 95% predication limits shown by thin dashed lines, p<0.0001, slope=0.0034). A similar but nonsignificant effect is seen for Down syndrome pregnancies (lower panel, p=0.82, slope=0.0024).

Linear regression for z-score by millions of matched DNA sequences finds a nonsignificant positive slope for Euploid pregnancies (thick dashed line, p=0.47, slope=0.0072) and for Down syndrome pregnancies (lower panel, p=0.94, slope=0.0099). As noted for covariate analysis of fetal fraction, covariate analysis of chromosome 21 z-scores revealed that maternal weight also was a significant factor in the determination of genetic variation, but the effect seen was greater among Down syndrome pregnancies. Gestational age also has a significant positive association in some cases. However, the effect seen with gestational age is significantly smaller than that seen for maternal weight. The remaining associations are generally small, and usually nonsignificant.

TABLE 3 below provides additional detailed information regarding six samples originally misclassified by MPSS testing. In three cases, subjects who were confirmed as Down syndrome were initially classified as not having Down syndrome (see sample ID numbers 162, 167 and 371), and in three cases subjects who were confirmed as healthy children were initially classified as having Down syndrome.

Total turn-around time (TAT) in days by flow cell for the entire process of massively parallel shotgun sequencing was analyzed. For the first third of flow cells processed, total turn-around time (TAT) was dominated by the computer interpretation time due to modifications made in the algorithm prior to clinical sign-out described in our publication. The process of clinical sign-out improved over time. Two flow cells (about two-thirds of the way through the study) needed to be completely re-sequenced and this resulted in an increased TAT. During the last 20 flow cells, the TAT was within the 10 day target for 18 (90%). The TATs in a true clinical setting may be somewhat better, based on two potential improvements: in the current study, samples were not processed over the weekend, and a dedicated clinician was not always available for sign-out on a given day. About 5% of samples were repeated, roughly doubling the TAT for those samples.

The success/failure rate for identifying euploid and Down syndrome samples resulted in a rate of successful interpretation (92%) as well as reasons for test failures among the 212 samples from Down syndrome pregnancies. Repeat testing of a new aliquot from these 17 women resulted in 100% of samples having a successful interpretation. The analysis was repeated for the 1,484 euploid pregnancies tested. A total of 13 samples were considered test failures, even after a second aliquot was tested. Overall, the success rate in performing MPSS was 99.2%, with 5% of initial samples needing a second aliquot.

TABLE 3

Detailed information regarding six misclassifications by MPSS testing

|  | ID = 162 | ID = 167 | ID = 371 | ID = 22 | ID = 221 | ID = 249 |
|---|---|---|---|---|---|---|
| T21 z-score | +0.83 | +1.50 | +1.57 | +3.82 | +4.72 | +3.56 |
| MPSS interpretation | Not DS | Not DS | Not DS | DS | DS | DS |
| Karyotype | 47, XX + 21 | 47, XY + 21 | 47, XY + 21 | 46, XY | 46, XX | 46, XX |
| Confirmation | Karyotype confirmed False Neg | Confirmed at autopsy False Neg | Confirmed by provider False Neg | Confirmed "healthy boy" False Pos | Confirmed "healthy girl" False Pos | Confirmed "healthy girl" False Pos |
| Gestational age (wks) | 9.2 | 14.6 | 13.0 | 12.1 | 10.0 | 13.6 |
| Maternal age (yrs) | 42 | 43 | 40 | 41 | 33 | 39 |
| Maternal Weight (lbs) | 200 | 165 | 182 | 125 | 174 | 185 |
| Race/Ethnicity | White | White | White | White, Hispanic | White | White |
| Bleeding | No | No | No | Yes | Yes | No |
| Referral Reason | Mat age and hx aneuploidy | Mat age and integrated screen | First trimester screen | Maternal age 38 or older | Mat age and hx aneuploidy | First trimester screen |
| Processing Time (hrs) | 1 | 3 | 3 | 1 | 1 | 1 |
| Sample volume (mL) | 4.0 | 4.0 | 3.8 | 3.9 | 4.0 | 4.0 |
| Hemolysis | Slight | NR | None | None | Slight | Slight |
| Fetal Fraction (%) | 4 | 7 | 5 | 19 | 24 | 11 |
| Note | 1$^{st}$ sample failed - low fetal DNA |  |  | 1$^{st}$ sample failed - high fetal DNA |  |  |

TABLE 4 presented below provides additional detailed information on a comparison of the final MPSS interpretations for 79 Down syndrome and 526 euploid samples tested at the SCMM and UCLA laboratories. Mixed libraries for 605 samples were prepared at Sequenom Center for Molecular Medicine (SCMM), tested, frozen, and then shipped to the independent UCLA laboratory for retesting. Detection and false positive rates at SCMM (98.7% and 0%, respectively), were slightly, but not significantly, better than those at UCLA (97.5% and 0.2%, respectively). However, failure rates were slightly, but not significantly, lower at UCLA versus SCMM (0% and 2.5% in Down syndrome; 3.9% and 4.4% in euploid pregnancies, respectively).

The impact of adjusting chromosome 21 percent representation scores for GC content and plate based experimental conditions was analyzed. GC adjustment reduced the presence of high (and low) outliers among the euploid pregnancies, while reducing the spread of data. Without any adjustments (x-axis), a cut-off of 1.38% results in four false negatives and three false positive results. With GC adjustment two of the four false negatives and all three false positive results are resolved using the same cut-off of 1.38%. However, one of the false negative results and a new false positive result fall on the cut-off line. The interpretation of the remaining, fourth, false negative is unchanged. By adding the plate adjustment to create the MoM, all three false positives and three of four false negatives are potentially resolved by any cut-off falling within the grey zone horizontal rectangle.

For 1,471 euploid and 212 Down syndrome cases, the use of chromosome 21 z-scores adjusted for GC content and flow-cell variability leads to the resolution of two false negative and the three original false positives using the z-score cut-off 3 (equivalent to the 'on-line' calling algorithm). However, one new false positive is generated.

TABLE 4

Comparison of the final MPSS interpretations for 79 Down syndrome and 526 euploid samples tested at two laboratories.

| | SCMM | | | | | | |
|---|---|---|---|---|---|---|---|
| | Down syndrome | | | Euploid | | | |
| UCLA | True Positive | False Negative | Failure | True Negative | False Positive | Failure | Totals |
| Down syndrome | | | | | | | |
| True Pos | 76 | 0 | 1 | | | | 77 |
| False Neg | 0 | 1 | 1 | | | | 2 |
| Test failure | 0 | 0 | 0 | | | | 0 |
| Euploid | | | | | | | |
| True Neg | | | | 500 | 0 | 4 | 504 |
| False Pos | | | | 1 | 0 | 0 | 1 |
| Test Failure | | | | 2 | 0 | 19 | 21 |
| Totals | 76 | 1 | 2 | 503 | 0 | 23 | 605 |

Table 5 presented below compares this study protocol and results with previously published studies that also used massively parallel sequencing of maternal plasma to screen for Down syndrome.

TABLE 5 presented below compares this study protocol and results with previously published studies that also used massively parallel sequencing of maternal plasma to screen for Down syndrome.

| Characteristics | Current Study | Ehrich 2011 | Chiu 2011 | Sehnert 2011 |
|---|---|---|---|---|
| Multiplexing | 4-plex | 4-plex | 2-plex[1] | NR |
| Down syndrome (N) | 212 | 39 | 86 | 13 |
| Euploid/non-Down syndrome | 1,484 | 410 | 146 | 34 |
| Illumina Platform | HiSeq 2000 | GAIIx | GAIIx | x |
| Performed in CLIA laboratory | Yes | No | No | No |
| Simulate Practice? | Yes | No | No | No |
| Flow cells | 76 | >15 | >16 | NR |
| Study Population | N Amer, S Amer, Europe, Australia | US | Hong Kong, Netherlands, UK | US |
| Gestational age in weeks (mean, range) | 15 (8-22) | 16 (8-36) | 13 (NR) | 15 (10-28) |
| Trimester 1st/2nd (%) | 50/50 | NR | 88/12 | 58/42 |
| Failures (n/N, %) | 13/1696 (<1) | 18/467 (3.9) | 11/764 (1.4) | 0/47 |
| Detection Rate (%) | 209/212 (98.6) | 39/39 (100) | 86/86 (100) | 13/13 (100) |
| False Positive rate (%) | 3/1471 (0.2) | 1/410 (0.2) | 3/146 (2.1) | 0/34 (0) |
| Throughput (samples/week) | 250 | NR | NR | NR |
| Required volume | >3.5 mL | >3.5 mL | >2 mL | ~4 mL[3] |
| Available 2$^{nd}$ sample | Yes | No | No | Yes |
| Fetal fraction estimated | All | All | Males only | NR |
| Turn-around time[2] (days) | 8.8[4] | 10[5] | NR | NR |

[1]Report also included 8-plex, but only the results for 2-plex are shown
[2]from start of processing to sequencing completion (does not include alignment or sign-out)
[3]Authors state, "plasma from a single [10 mL] blood tube was sufficient for sequencing"
[4]Mean of last 20 flow cells [32 samples each]
[5]Authors state, "each batch [96 samples] required approximately 10 days from DNA extraction to the final sequencing result"

Example 3

Detection of Microdeletions Utilizing Circulating Cell-Free DNA

The field of prenatal diagnostics has advanced through the implementation of techniques that enable the molecular characterization of circulating cell free (ccf) fetal DNA isolated from maternal plasma. Using next generation sequencing methodologies, it has been shown that chromosomal abberations can be detected. The detection of trisomy 21 has been validated both analytically and in large-scale clinical studies. Similar validation of trisomies 13 and 18, sex aneuploidies, and other rare chromosomal aberrations likely will follow in the near future.

One facet of genetic annomalies that has not yet been thoroughly addressed using ccf fetal DNA as the analyte are sub-chromosomal copy number variations (CNVs). Approximatly 12% of individuals with unexplained developmental delay/intellectual disability (DD/ID), autism spectrum disorder (ASD) or multiple congentital anomalities (MCA) have been diagnosed with a clinically relevant CNV. One example of such a clinically relevant condition is 22q11.2 Deletion Syndrome, a disorder comprised of multiple conditions including DiGeorge Syndrome, Velocardiofacial Syndrome, and Conotruncal Anomaly Face Syndrome. While the exact manifestation of these conditions varies slightly, each have been linked to a heterozygous deletion of a gene rich region of about 3 million base pairs (bp) on chromosome 22, which has been shown to be prone to high levels of both duplications and microdeletions due to the presence of repetitive elements which enable homologous recombination. Chromosome 22q11.2 deletion syndrome effects approximately 1 in 4000 live births and is characterized by frequent heart defects, cleft palate, developmental delays, and learning disabilities.

Described herein are the results of investigations performed to determine the technical feasibility of detecting a sub-chromosomal CNV by sequencing ccf DNA from maternal plasma. Maternal plasma from two women each carrying a fetus confirmed by karyotype analysis to be affected by 22q11.2 Deletion Syndrome and 14 women at low risk for fetal aneuploidies as controls was examined. The ccf DNA from each sample was sequenced using two individual lanes on a HiSeq2000 instrument resulting in approximately 4× genomic coverage. A statistically significant decrease in the representation of a region of 3 million bp on chromosome 22 corresponding to the known affected area in the two verified cases was detected, as compared to the controls, confirming the technical feasability of detecting a sub-chromosomal CNV by sequencing ccf DNA from maternal plasma.

Materials and Methods

Sample Acquisition

Samples were collected under two separate Investigational Review Board (IRB) approved clinical protocols (Western Institutional Review Board ID 20091396 and Compass IRB 00462). The two affected blood samples were collected prior to an invasive procedure. The presence of a 22q11.2 microdeletion was confirmed in these samples by karyotype analysis on material obtained by non-transplacental amniocentesis. The 14 control samples were collected without a subsequent invasive procedure, thus no karyotype information was available for the control samples. All subjects provided written informed consent prior to undergoing any study related procedures including venipuncture for the collection of 30 to 50 mL of whole blood into EDTA-K2 spray-dried 10 mL Vacutainers (Becton Dickinson, Franklin Lakes, N.J.). Samples were refrigerated or stored on wet ice until processing. Within 6 hours of blood draw maternal whole blood was centrifuged using an Eppendorf 5810R plus swing out rotor at 4° C. and 2500 g for 10 minutes and the plasma collected (e.g., about 4 mL). The plasma was centrifuged a second time using an Eppendorf 5810R plus fixed angle rotor at 4° C. and 15,000 g for 10 minutes. After the second spin, the plasma was removed from the pellet that formed at the bottom of the tube and distributed into 4-mL plasma bar-coded aliquots and immediately stored frozen at −80° C. until DNA extraction.

Nucleic Acid Extraction ccfDNA was extracted from maternal plasma using the QIAamp Circulating Nucleic Acid Kit according to the manufacturer's protocol (Qiagen) and eluted in 55 μL of Buffer AVE (Qiagen).

Fetal Quantifier Assay

The relative quality and quantity of ccfDNA was assessed by a Fetal Quantifier Assay (FQA), according to methods known in the art. FQA uses differences in DNA methylation between maternal and fetal ccfDNA as the basis for quantification. FQA analysis was performed upon each of the 16 analyzed samples as previously described in Ehrich et al. and Palomaki et al. (Genet Med. (2011)13(11):913-20 and Genetics in Medicine(2012)14:296-305) which are hereby incorporated by refencence in their entirety.

Sequencing Library Preparation

Libraries were created using a modified version of the recommended manufacturer's protocol for TruSeq library preparation (Illumina). Extracted ccfDNA (e.g., about 40 μL) was used as the template for library preparation. All libraries were created with a semi-automated process that employed liquid handler instrumentation (Caliper Zephyr; Caliper LifeSciences) with a magnetic bead-based (Beckman Coulter) cleanup step after the end repair, ligation, and PCR biochemical processes. Since ccfDNA has been well characterized to exist in maternal plasma within a small range of fragment sizes, no size selection was performed upon either the extracted ccfDNA or the prepared libraries. The size distribution and quantity of each library was measured using capillary electrophoresis (Caliper LabChip GX; Caliper) and each library was normalized to a standard concentration of about 2 nM prior to clustering using a CBot instrument (Illumina). Each sample was subjected to 36 cycles of sequencing by synthesis using two lanes of a HiSeq2000 v3 flowcell (Illumina).

Data Analysis

Sequencing data analysis was performed as described in Palomaki et al (Genet Med. (2011)13(11):913-20 and Genetics in Medicine (2012)14:296-305) which are hereby incorporated by refencence in their entirety. Briefly, all output files (e.g., .bcl files) from the HiSeq2000 instrument were converted to fastq format and aligned to the February, 2009 build of the human genome (hg19) using CASAVA v1.7 (Illumina). All reads which overlapped with repetitive regions of the genome were removed after alignment based upon the information contained within Repeat Library 20090604 (Universal Resource Locator (URL) world wide web repeatmasker.org) to minimize the effect of repeat sequences on subsequent calculations. For analysis purposes, each chromosome was divided into distinct 50 kb bins and the number of reads mapped to each of these bins were summed. Reads within each bin were normalized with respect to the bin-specific GC content using a LOESS method, as known in the art to minimize the effect of G/C content bias on subsequent calculations. The repeat-masked, GC normalized read counts by bin were then used for calculation of statistical significance and coverage.

Statistical significance was determined by calculating a z-score for the fraction of total aligned autosomal reads mapping to the region of interest relative to the total number of aligned autosomal reads. Z-scores were calculated using a robust method whereby a z-score for a given sample was calculated by using the formula $Z_{Sample}=($Fraction$_{Sample}-$Median Fraction$_{Population})/$Median Absolute Deviation$_{Population}$. Coverage was calculated by the formula Coverage=LN/G where L is read length (36 bp), N is the number of repeat masked, GC normalized reads, and G is the size of the repeat-masked haploid genome.

Results

Next generation sequencing was performed upon ccf DNA isolated from the plasma of the 16 pregnant females, of which two were confirmed by karyotype analysis after amniocentesis to be carrying a fetus affected by chromosome 22q11.2 Deletion Syndrome. Karyotype information for the fetuses of the 14 control samples was not available. Plasma was collected from the two affected samples at a similar gestational age (19 and 20 weeks) when compared to the control samples (median=20 weeks; see TABLE 6 below). Prior to sequencing, the fetal contribution to the total ccfDNA was measured as known in the art. All samples contained more than 10% fetal DNA with a median contribution of 18%; the two samples carrying the fetal microdeletion contained 17 and 18% fetal DNA (see TABLE 6 below).

region across all analyzed samples and is the classification cutoff traditionally used in fetal aneuploidy detection.

Because the exact location of the genomic deletion might vary slightly from case to case, we chose to test an area of 3 million basepairs located between Chr22:19000000-22000000 (see TABLE 6 above). A method analogous to that used for chromosomal aneuploidy detection was used to calculate the fraction of all autosomal reads that mapped to the target region. The control samples contained 0.075% of the reads located in 22q11 while the affected samples with the known fetal microdeletion only showed 0.073% of reads in this region. To test for statistical significance of this difference, a z-score for each sample was calculated using a robust method. Both affected samples showed z-scores lower than −3 (e.g., −5.4 and −7.1, respectively) while all low risk control samples had a z-score higher than −3 (see FIG. 47). One of the low risk samples showed a z-score higher than +3. The genomic region of 22q11 has previously been associated with genomic instability and this result might indicate a potential duplication which has been reported to occur previously, however, because karyotype information was not available for the low risk samples it remains unclear whether the observed result is linked to a fetal CNV.

Discussion

Recent advances in the field of non-invasive prenatal diagnostics have enabled the ability to detect fetal aneuploidies by sequencing the ccfDNA present in maternal plasma. Using a similar approach to that used for anueploidy

TABLE 6

| Sample ID | Sample Group | Plasma Vol (mL) | Fetal Fraction | Gestational Age (Weeks) | Total GC Norm Reads | Genomic Coverage | GC Norm Fraction in Affected Region |
|---|---|---|---|---|---|---|---|
| 12800 | Low Risk | 4 | 0.42 | 19 | 202890379 | 4.43 | 0.000755 |
| 12801 | Microdeletion | 4 | 0.17 | 20 | 188214827 | 4.11 | 0.000732 |
| 12802 | Low Risk | 3.9 | 0.24 | 24 | 164976211 | 3.60 | 0.000752 |
| 12803 | Low Risk | 4 | 0.13 | 12 | 190397481 | 4.16 | 0.000753 |
| 12804 | Low Risk | 4 | 0.16 | 24 | 175708269 | 3.84 | 0.000747 |
| 12805 | Low Risk | 4 | 0.35 | 17 | 192035852 | 4.19 | 0.000755 |
| 12806 | Low Risk | 3.9 | 0.13 | 12 | 189438328 | 4.14 | 0.000757 |
| 12807 | Low Risk | 3.9 | 0.18 | 20 | 185562643 | 4.05 | 0.000755 |
| 12808 | Microdeletion | 4 | 0.18 | 19 | 146700048 | 3.20 | 0.000726 |
| 12809 | Low Risk | 4 | 0.54 | 21 | 154878242 | 3.38 | 0.000750 |
| 12810 | Low Risk | 4 | 0.15 | 16 | 188121991 | 4.11 | 0.000768 |
| 12811 | Low Risk | 4 | 0.16 | 24 | 172366695 | 3.76 | 0.000757 |
| 12812 | Low Risk | 4 | 0.10 | 12 | 180005977 | 3.93 | 0.000751 |
| 12813 | Low Risk | 4 | 0.23 | 25 | 151510852 | 3.31 | 0.000752 |
| 12814 | Low Risk | 4 | 0.20 | 20 | 143687629 | 3.14 | 0.000752 |
| 12815 | Low Risk | 3.9 | 0.18 | 12 | 177482109 | 3.88 | 0.000754 |

Each sample was sequenced using two lanes of a HiSeq2000 flowcell, resulting in between about 3.1× to about 4.4× genomic coverage (See TABLE 6 above). Reads were binned using a bin size of 50 kb and bins were visualized across chromosome 22 for the affected microdeletion samples to identify the location of the microdeletion for the affected samples. Both samples that carried the confirmed 22q11.2 microdeletion exhibited a decreased representation in this genomic area (see FIG. 47). Z-scores were calculated for each sample relative to the median of all samples for the region affected on chromosome 22. Values corresponding to plasma from low risk females are shown in black while values representing known cases of 22q11.2 Deletion Syndrome are shown in gray. The dashed line at −3 represents a z-score that is 3 times the median absolute deviation lower than the median representation for this detection, the results presented herein confirm the feasibility of non-invasively detecting sub-chromosome level CNVs in a developing fetus by sequencing the corresponding ccfDNA in maternal plasma. The data presented herein, albeit with a small number of cases, shows that regions smaller than a single chromosome can reliably be detected from maternal plasma, in this case a deletion of 22q11.2. Peters et al (2011) reported a 4.2 Mb deletion on chromosome 12 that was detected using similar methodology. Peters et al. examined a single case of a fetal microdeletion detected at a late gestational age (35 weeks) and compared it to seven samples known to be diploid for chromosomes 12 and 14. In contrast, the results presented herein, which were obtained prior to the publication of the aforementioned study, examined affected samples at an earlier gestational age (19 and 20 weeks), utilized twice the number of affected and unaffected samples, and detected a microdeletion 28% smaller (3 Mb) than previously described. Additionlly, the results presented herein utilized 4× genomic coverage to successfully detect the 3 Mb fetal deletion, which is an increase in coverage of approximatly 20 fold over current standard aneuploidy detection. Smaller deletions, potentially down to 0.5 Mb, or samples containing less fetal ccfDNA may require even higher coverage.

Example 4

Automating Library Preparation, Increasing Multiplexing Level and Bioinformatics Provided below are implementations of a set of process changes that led to a three-fold increase in throughput and a 4-fold reduction in hands-on time while maintaining clinical accuracy. The three main changes of this modified assay include: higher multiplexing levels (from 4-plex to 12-plex), automated sequencing library preparation, and the implementation of new bioinformatic methods. The results confirm that the protocol yields a more simplified workflow amenable to higher throughput while maintaining high sensitivity and specificity for the detection of trisomies 21, 18 and 13.

Material and Methods

Sample Acquisition and Blood Processing.

Samples for the initial evaluation of the high-throughput assay (library preparation development and assay verification) were collected under three separate Investigational Review Board (IRB) approved clinical protocols (BioMed IRB 301-01, Western IRB 20091396, and Compass IRB 00462). All subjects provided written informed consent prior to undergoing any study related procedures including venipuncture for the collection of up to 20 mL of whole blood into EDTA-K2 spray-dried 10 mL Vacutainers (EDTA tubes; Becton Dickinson, Franklin Lakes, N.J.) and 30 mL of whole blood into Cell-Free DNA BCT 10 mL Vacutainers (BCT tubes; Streck, Omaha, Nebr.). Samples collected in EDTA tubes were refrigerated or stored on wet ice and were processed to plasma within 6 hours of the blood draw. Samples collected in BCT tubes were stored at ambient temperature and processed to plasma within 72 hours of the blood draw. The maternal whole blood in EDTA tubes was centrifuged (Eppendorf 5810R plus swing out rotor), chilled (4° C.) at 2500 g for 10 minutes, and the plasma was collected. The EDTA plasma was centrifuged a second time (Eppendorf 5810R plus fixed angle rotor) at 4° C. at 15,500 g for 10 minutes. After the second spin, the EDTA plasma was removed from the pellet that formed at the bottom of the tube and distributed into 4 mL barcoded plasma aliquots and immediately stored frozen at −70° C. until DNA extraction. The maternal whole blood in BCT tubes was centrifuged (Eppendorf 5810R plus swing out rotor), warmed (25° C.) at 1600 g for 15 minutes and the plasma was collected. The BCT plasma was centrifuged a second time (Eppendorf 5810R plus swing out rotor) at 25° C. at 2,500 g for 10 minutes. After the second spin, the BCT plasma was removed from the pellet that formed at the bottom of the tube and distributed into 4 mL barcoded plasma aliquots and immediately stored frozen at −70° C. until DNA extraction.

Samples for multiplexing development and clinical evaluation were collected as previously described (Palomaki G E, et al. (2012) Genet. Med. 14: 296-305 & Palomaki G E, et al. (2011)) Briefly, whole blood was collected from enrolled patients prior to an invasive procedure. All samples were collected from pregnant females at an increased risk for fetal aneuploidy in their first or second gestational trimester as part of an international collaboration (ClinicalTrials.gov NCT00877292). IRB approval (or equivalent) was obtained for this collaboration at each of 27 collection sites. Some data generated in 4plex format and used herein have been previously presented herein, however, all data from 12plex sequencing was generated using the same libraries now sequenced independently in 12plex format. In addition, for independent confirmation of the high-throughput method, a plasma aliquot from each of 1269 patients was processed. Each of these patients contributed a distinct plasma aliquot to the previously published studies and the fetal karyotype was known. Only samples from singleton pregnancies confirmed to be simple trisomies 21, 18, and 13 or from euploid controls were used. Circulating cell-free DNA was extracted from maternal plasma using the QIAamp Circulating Nucleic Acid Kit (Qiagen) as described herein. The quantity of ccf DNA was assessed for each sample by the Fetal Quantifier Assay (FQA). Extracted ccf DNA (40 μL) was used as the template for all library preparation. Libraries for the initial increased (12plex) multiplex experimentation were prepared using previously described methods. Briefly, ccf DNA was extracted and sequencing libraries prepared using oligonucleotides (Illumina), enzymes (Enzymatics), and manual purification processes between each enzymatic reaction using column-based methods (Qiagen). All newly created libraries used in this study were created in 96-well plate format using a modified version of the manufacturer's protocol for TruSeq library preparation (Illumina) and a semi-automated process that utilized liquid handler instrumentation (Caliper Zephyr; Caliper LifeSciences) with a magnetic bead-based (AMPure XP; Beckman Coulter) cleanup step after the end repair, ligation, and PCR biochemical processes. Since ccf DNA has been well characterized to exist in maternal plasma within a small range of fragment sizes, no size selection was performed upon either the extracted ccf DNA or the prepared libraries. Evaluation of library size distribution and quantification was performed as previously described herein. Twelve isomolar sequencing libraries were pooled and sequenced together on the same lane (12-plex) of an Illumina v3 flowcell on an Illumina HiSeq2000. Sequencing by synthesis was performed for 36 cycles followed by 7 cycles to read each sample index. Sequencing libraries were prepared from pooled ccf DNA isolated from the plasma of two adult male volunteers diagnosed with trisomy 21 or non-pregnant euploid females. Libraries were quantified and mixed at two concentrations (4% trisomy 21 and 13% trisomy 21) to approximate the contribution of ccf fetal DNA in maternal plasma. Library performance was tested prior to the implementation of these controls into the clinical evaluation study.

Data Analysis

All BCL (base call) output files from the HiSeq2000 were converted to FASTQ format and aligned to the February, 2009 build of the human genome (hg19). Since the libraries for multiplex development were prepared manually with the previous version of biochemistry, analysis methods were applied as previously described (Palomaki et al., 2012 and herein). For all subsequent studies, reads were aligned to hg19 allowing for only perfect matches within the seed sequence using Bowtie 2 (Langmead B, Salzberg S L (2012) Nat. Methods 9:357-359). For analysis purposes, the reads mapped to each chromosome were quantified using standard histograms comprising adjacent, non-overlapping 50 kbp long genomic segments. After binning, selection of included 50 kbp genomic segments was determined using a previously described cross validation method (Brunger A T (1992) Nature 355: 472-475). Regions were excluded from further analysis based upon exhibiting high inter-sample variance, low mappability (Derrien T, et al. (2012) PLoS One 7: e30377), or high percentage of repetitive elements (Repeat Library 20090604; http://www.repeatmasker.org). Finally, aligned reads corresponding to the remaining 50 kbp genomic segments were normalized to account for GC bias (Alkan C, et al. (2009) Nat Genet. 41: 1061-1067) and used to calculate the fraction of aligned reads derived from each chromosome. A robust z-score was calculated as described using the formula $Z_{Chromosome}=(\text{Chromosome Fraction}_{Sample}-\text{Median ChromosomeFraction}_{Flow\ Cell})/\text{Median Absolute Deviation}_{population}$. The median chromosome fraction was calculated specific to each flow cell while the Median Absolute Deviation (MAD) was a constant value derived from a static MAD.

Results

Some clinical studies using MPSS for noninvasive fetal aneuploidy detection have shown a range of 92-100% detection rate while maintaining a false positive rate of less than 1%. Our goal was to maintain or improve upon this performance while streamlining the protocol and increasing sample throughput. Improvements focused on three aspects: I) optimizing library preparation to enable robust yield and increased throughput, II) increasing the number of individually molecularly indexed samples pooled together in a single flowcell lane (multiplex level), and III) improving analytical methods for aneuploidy classification.

Traditional sequencing library preparation is labor intensive, time consuming, and sensitive to operator-to-operator variability. To alleviate these issues, we developed a semi-automated process utilizing a 96-channel liquid handling platform. TruSeq library preparation biochemistry was optimized for the low abundance of ccf DNA recovered from 4 mL of plasma (10-20 ng), which was a 50-fold reduction from the 1 μg recommended input quantity for the TruSeq library preparation kit. In addition, manual purification procedures were replaced with an automated AMPure XP bead purification process optimized for speed, reproducibility and ccf DNA recovery. Comparison of a set of 287 libraries prepared using this method to libraries produced using the manual method as described (herein and Palomaki et al. 2011 and Palomaki et al. 2012) revealed an increase in median library concentration from 124 to 225 nM after standardization for elution volume (FIG. 11A). The combined semi-automated process produced 96 libraries in 5 hours, requiring only a single technician and 1.5 hours of hands-on labor time. This resulted in a 4-fold increase in throughput coincident with a 4-fold decrease in labor without sacrificing library yield or quality. Ninety three libraries (83 confirmed euploid samples and 10 confirmed trisomy 21 samples; TABLE 7) were prepared using this method, sequenced, analyzed and demonstrated accurate classification performance in this small data set (FIG. 11B; TABLE 8).

Figure 12:
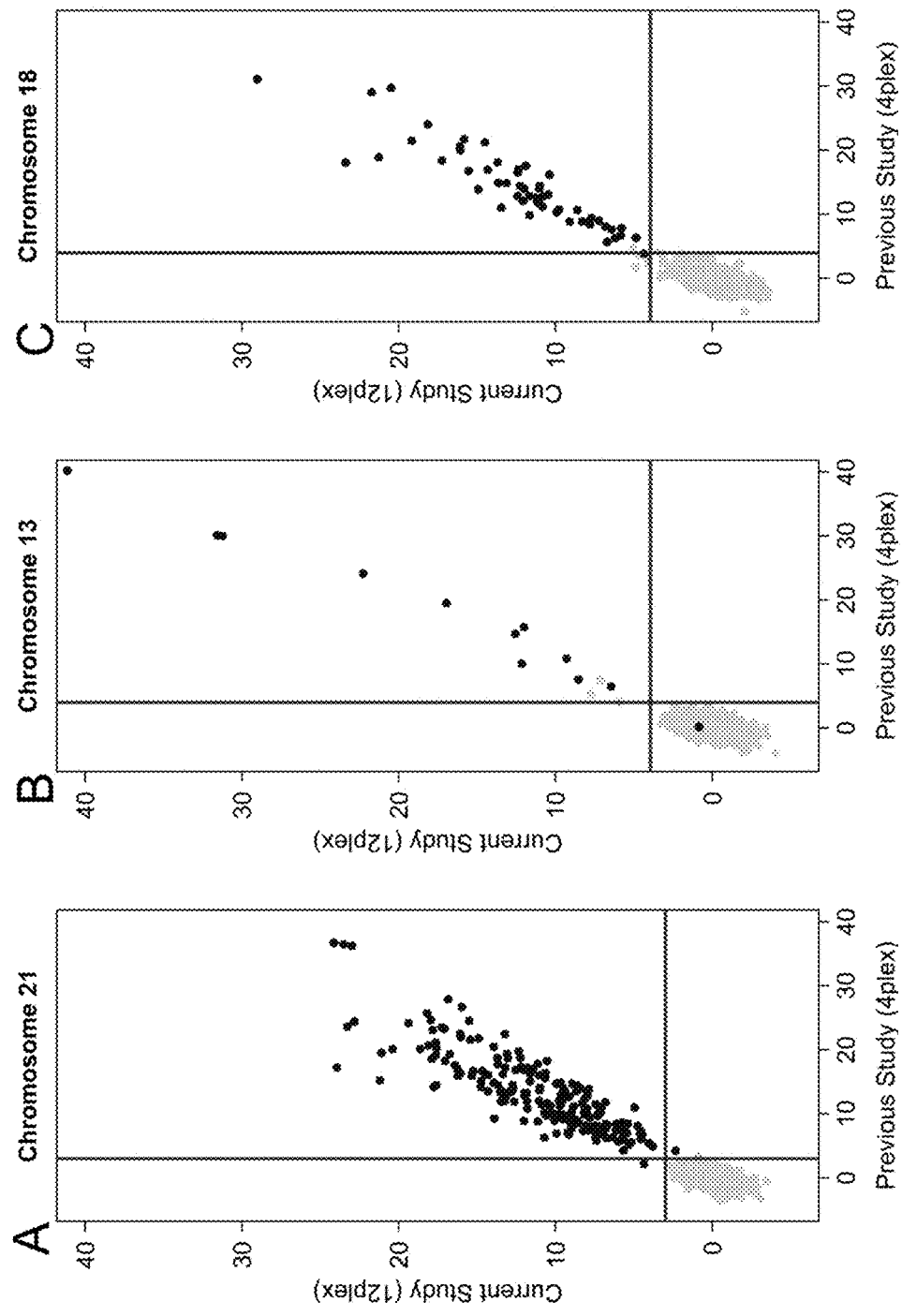
FIG. 12. shows a paired comparison of z-scores. Z-scores were calculated for paired samples with previously described GC normalized, repeat masked z-scores on the x-axis and z-scores from the same libraries sequenced in 12-plex on the y-axis. Samples classified by karyotype analysis as trisomies for FIG. 12A (Chromosome 21), FIG. 12B (Chromosome 13), or FIG. 12C (Chromosome 18) are shown in dark grey. Unaffected samples for each aneuploidy condition are shown in light gray. Horizontal and vertical lines in each plot represent the respective classification cutoff for that chromosome (z=3 for chromosome 21, z=3.95 for chromosomes 13 and 18).
Figure 13:
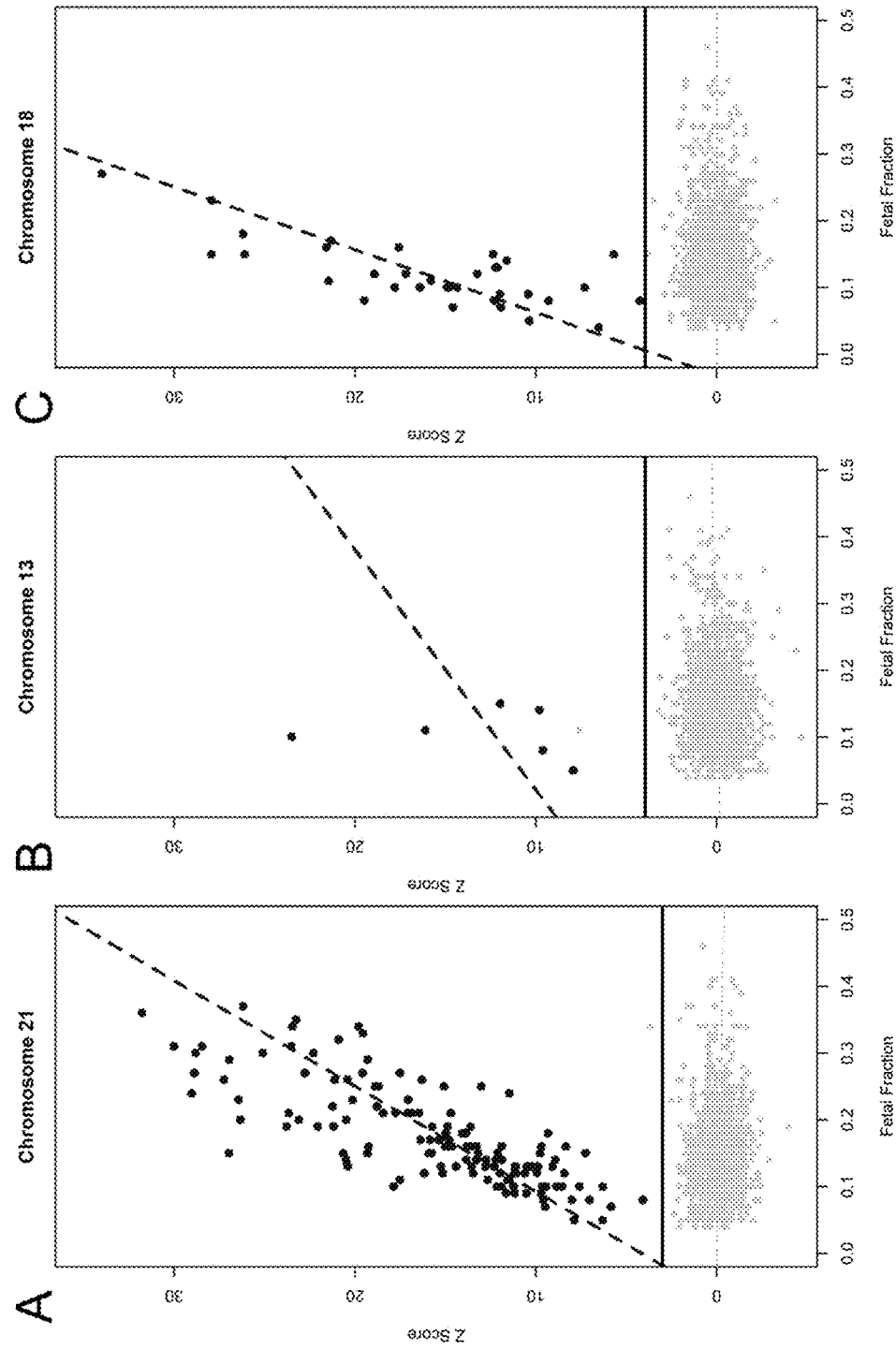
FIG. 13 shows Z-scores (x-axis) verse fetal fraction (y-axis). The chromosome specific z-score for each aneuploid chromosome is plotted against the proportion of fetal DNA (fetal fraction). Samples classified by karyotype analysis as trisomies for FIG. 13A (Chromosome 21), FIG. 13B (Chromosome 13), or FIG. 13C (Chromosome 18) are shown in dark grey. Unaffected samples for each aneuploidy condition are shown in light grey. Horizontal lines in each plot represents the respective classification cutoff for each chromosome (z=3 for chromosome 21, z=3.95 for chromosomes 13 and 18). Dashed vertical lines in each panel represents a robust linear fit of affected samples. Dashed horizontal lines in each panel represents a robust linear fit of all unaffected samples.

Libraries prepared and sequenced in 4-plex during a previous study were sequenced in 12-plex to determine the feasibility of increased multiplexing. Illumina v3 flow cells and sequencing biochemistry, in combination with HCS software improvements, produced a 2.23-fold increase (from 72 to 161 million) in total read counts per lane. We sequenced and analyzed 1900 libraries in 12-plex including 1629 euploid samples, 205 trisomy 21 samples, 54 trisomy 18 samples, and 12 trisomy 13 samples (TABLE 7) and compared the z-scores for chromosomes 21, 18, and 13 to 4-plex results (FIG. 12). Since previous studies had indicated an increase in assay performance using an elevated z-score cutoff, classification was based upon z=3.95 for chromosomes 18 and 13. The classification for chromosome 21 remained at z=3. Using these classification cutoffs, there were a total of 7 discordant classification results between 4-plex and 12 plex sequencing. For chromosome 21, two samples previously misclassified (1 false positive, 1 false negative) were correctly classified while a previously noted true positive was not detected. Four samples were misclassified as false positive samples for chromosome 18 whereas they had previously been correctly classified; each of these libraries was highly GC biased. All samples were concordant for trisomy 13 classification. When sequencing in 12-plex, 99.3% of aneuploid samples (204/205 trisomy 21, 54/54 trisomy 18, and 11/12 trisomy 13) were detected with a false-positive rate of 0% (0/1900), 0.26% (5/1900), and 0.16% (3/1900) for trisomies 21, 18, and 13, respectively (TABLE 8). Overall, these data suggest that the performance of the assay when executed with 12-plex multiplexing is similar to previously obtained results.

A verification study was performed using the optimized library preparation method coupled to 12-plex sequencing (high-throughput assay configuration) to ensure process integrity. Sequencing results from a total of 2856 samples, 1269 of which had a known karyotype were analyzed. These 1269 clinical samples were comprised of 1093 euploid, 134 trisomy 21, 36 trisomy 18, and 6 trisomy 13 samples (TABLE 7). The median fetal DNA fraction for samples was 0.14 (range: 0.04-0.46). The median library concentration of libraries was 28.21 nM (range: 7.53-42.19 nM), resulting in a total yield similar to other methods described herein. Finally, the median number of aligned autosomal reads per sample was 16,291,390 (range: 8,825,886-35,259,563).

Initial comparison of the data generated from the 1269 samples with known fetal karyotype to a distinct plasma aliquot previously sequenced from the same subject revealed a decrease in the discriminatory distance (difference between the 95th percentile of euploid samples and the 5th percentile of trisomy 21 samples) from 4.9 to 3.09 when analyzed using previously established methods which normalize for GC content and remove reads overlapping with repeat regions (e.g., GCRM). To mitigate this effect concomitant with decreasing overall analysis time, a new bioinformatic algorithm specific to the high-throughput assay data was developed. These methods base calculations for classification upon only those 50 kbp genomic segments with stable representation across individuals. When applied to the same high-throughput data set, the discriminatory distance between euploid and trisomy 21 samples increased to 6.49. Overall, new bioinformatic approaches result in an increase in discriminatory distance between euploid and trisomy 21 samples relative to previously described methods.

The results from the high-throughput assay were analyzed using the new analysis methods for 67 control and 1269 patient samples. Thirty three libraries prepared from pooled euploid plasma (0% T21 library), 17 control libraries containing 4% trisomy 21 DNA, and 17 control libraries containing 13% trisomy 21 DNA were sequenced. In all cases, the pooled euploid samples had a z-score less than 3 while the 4% and 13% trisomy 21 control samples had a z-score greater than 3. The classification accuracy of the 1269 patient samples with known karyotype information was then compared. Based upon the classification limits described above (z-score=3 for chromosome 21, z-score=3.95 for chromosomes 18 and 13), all confirmed fetal aneuploidies (134 trisomy 21, 36 trisomy 18, 6 trisomy 13) were detected with a false positive rate of 0.08%, 0%, and 0.08% for trisomies 21, 18, and 13, respectively (FIG. 13; TABLE 8). There was a positive correlation between fetal fraction and the magnitude of the z-score while there is no correlation between these metrics for euploid samples.

Figure 14:
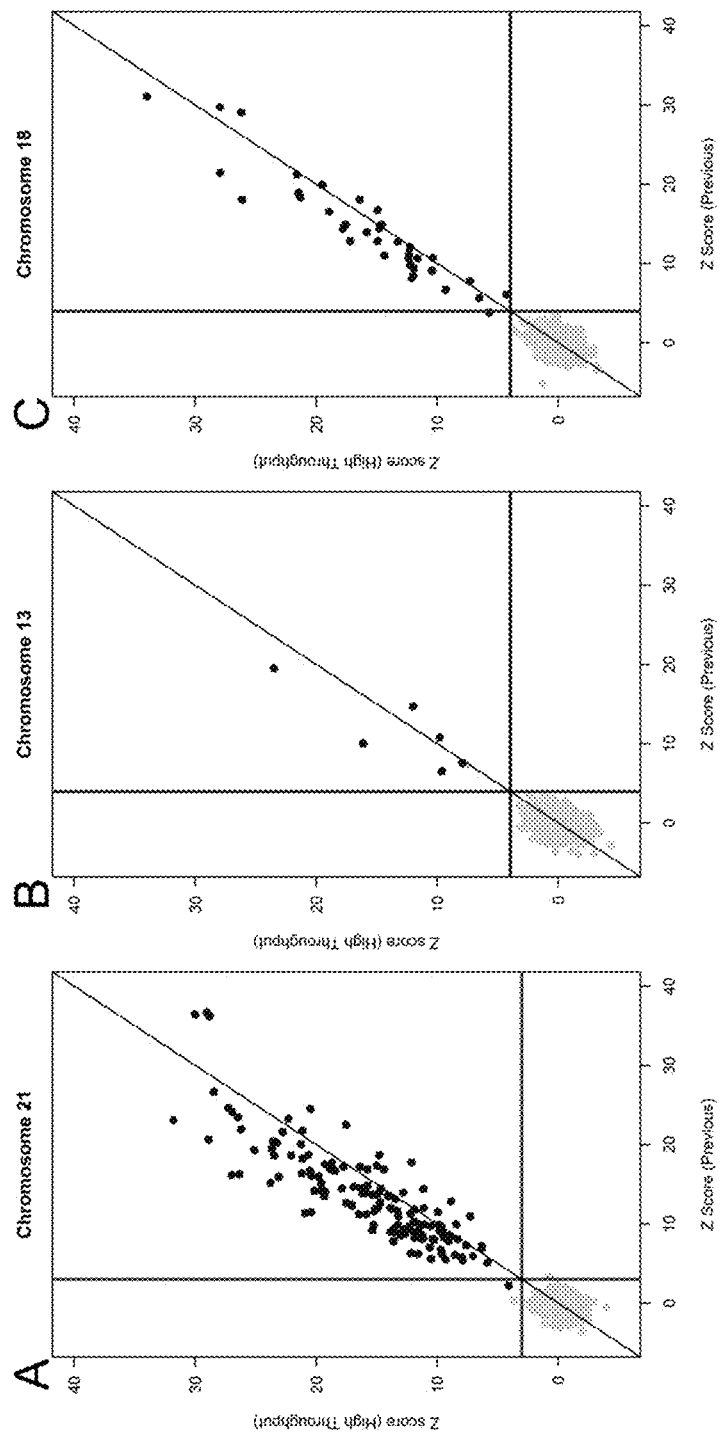
FIG. 14 shows a paired comparison of z-scores. Z-scores were calculated for 1269 paired samples with previously described GC normalized, repeat masked z-scores on the x-axis and z-scores from the high-throughput assay on the y-axis. Samples classified by karyotype analysis as trisomies for FIG. 14A (Chromosome 21), FIG. 14B (Chromosome 13), or FIG. 14C (Chromosome 18) are shown in dark grey. Unaffected samples for each aneuploidy condition are shown in light grey. Horizontal and vertical lines in each plot represent the respective classification cutoff for that chromosome (z=3 for chromosome 21, z=3.95 for chromosomes 13 and 18).
Figure 15:
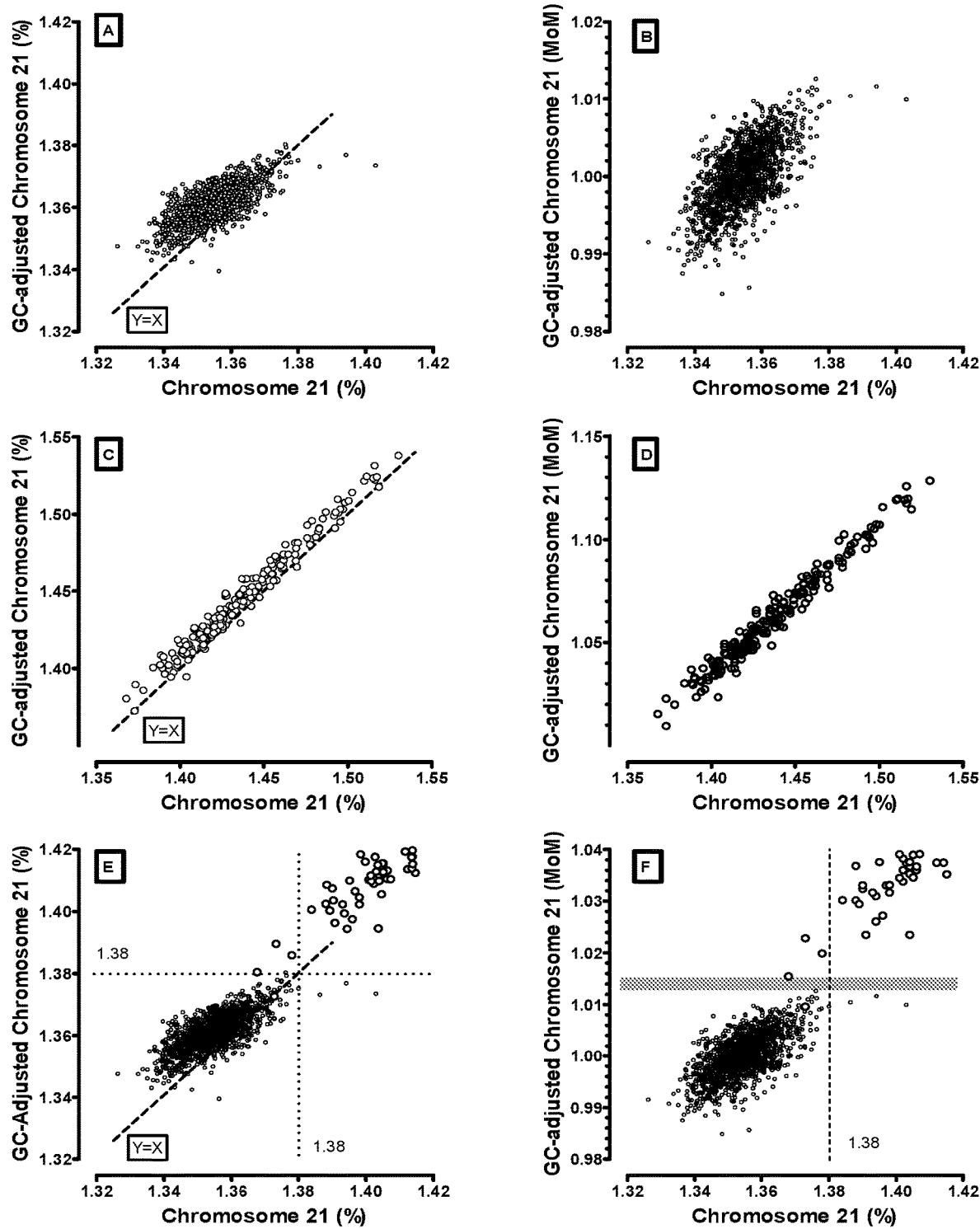
FIG. 15 graphically illustrates the impact of adjusting chromosome 21 percent representation scores for GC content and plate based experimental conditions. Panel A shows C21% before (x-axis) and after (y-axis) GC adjustment in euploid samples, while panel B also accounts for plate to plate differences by converting GC-adjusted C21% results to multiples of the plate median (MoM). Panels C and D show the same analysis for test results from pregnancies with Down syndrome. In both sets of Figures, the GC adjustment reduced the presence of high (and low) outliers among the euploid pregnancies, while reducing the spread of data. Panels E and F show the same two adjustments, but with both euploid and Down syndrome samples in the same panels. These panels focus on the area of overlap, so not all Down syndrome samples are shown. Without any adjustments (x-axis), a cut-off of 1.38% (vertical line) results in four false negatives and three false positive results. With GC adjustment (panel E, y-axis), two of the four false negatives and all three false positive results are resolved using the same cut-off of 1.38% (horizontal line). However, one of the false negative results and a new false positive result fall on the cut-off line. The interpretation of the remaining, fourth, false negative is unchanged. By adding the plate adjustment to create the MoM (panel F, y-axis), all three false positives and three of four false negatives are potentially resolved by any cut-off falling within the grey zone horizontal rectangle.
Figure 16:
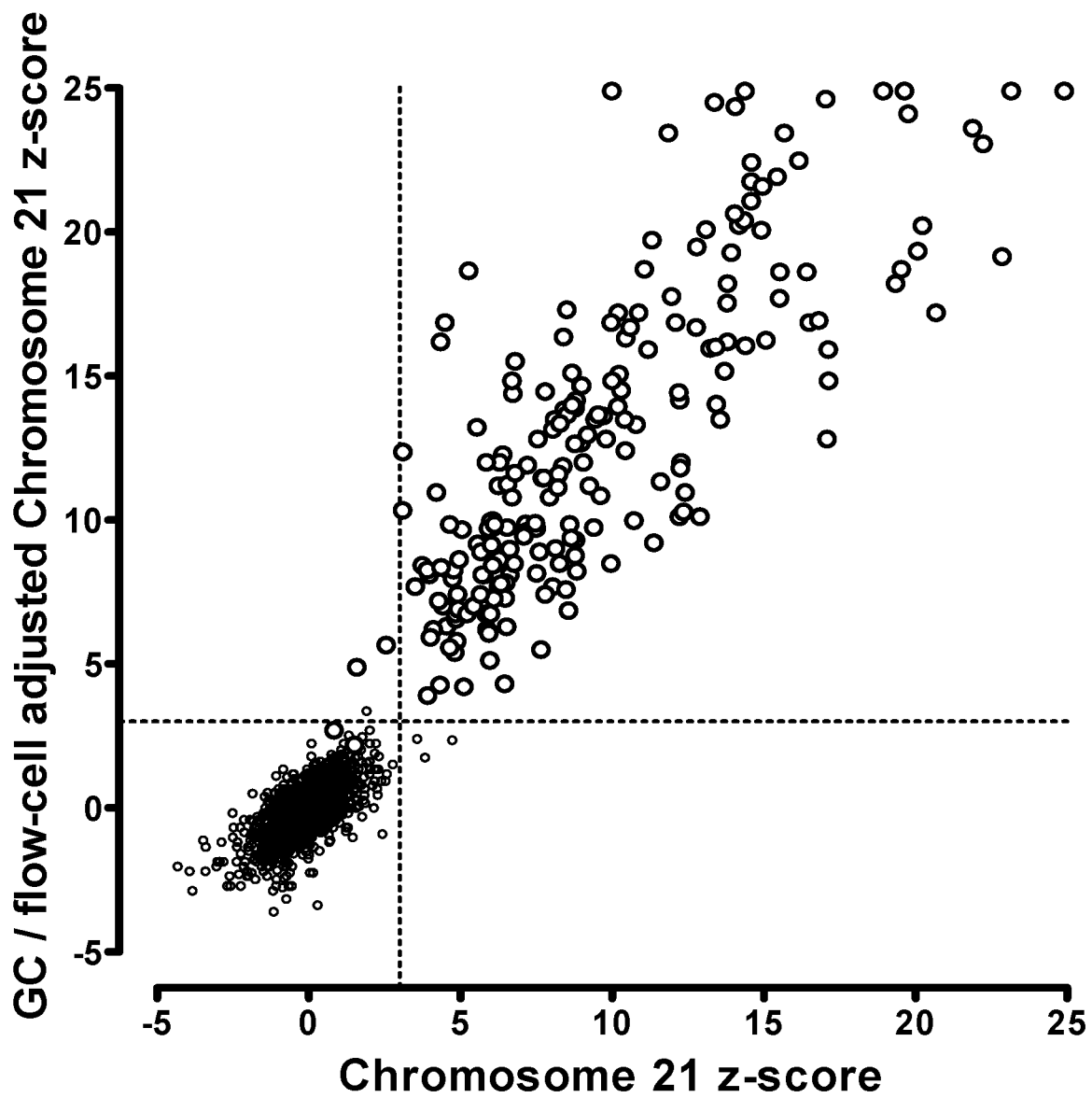
FIG. 16 graphically illustrates the impact of adjusting chromosome 21 z-scores for GC content and plate based experimental conditions. The original chromosome 21 z-score is shown on the x-axis. The results are based on a flow cell specific adjustment for processing variability. The results on the y-axis are also adjusted for GC base content and repeat masked. Results are shown for 1,471 euploid (small open circles) and 212 Down syndrome cases (large open circles). The use of chromosome 21 z-scores adjusted for GC content and flow-cell variability leads to the resolution of two false negative and the three original false positives using the z-score cut-off 3 (equivalent to the con-line' calling algorithm). However, one new false positive is generated. This figure is comparable to the data on FIG. 15, panel F.

Distinct plasma samples from each of the 1269 donors were previously sequenced and thus serve as a comparison for performance. To ensure a comparable evaluation, z-scores from the previously studies were calculated using GCRM values and a population size (for median and MAD calculations) of 96 samples, equivalent to the sample number used for median calculations using high-throughput analysis. Comparison of the two studies revealed the correct classification of a previously reported false negative trisomy 21 sample and a previously reported false positive trisomy 21 sample; however, there was one additional false positive during this study (FIG. 14). There were no discordant samples when comparing trisomy 13 classification and the correct classification of a single trisomy 18 sample with a previous z-score slightly below 3.95. Evaluation of paired z-scores for aneuploid samples revealed a mean difference of 2.19 for trisomy 21, 1.56 for trisomy 18, and 1.64 for trisomy 13 reflecting an increase in z-score for affected samples using the high-throughput methods. There was a statistically significant increase in z-score for confirmed trisomy 21 and trisomy 18 samples using the high-throughput assay (p=4.24e-12 and p=0.0002, respectively; paired wilcox test) relative to the previous study, but no significant difference in z-scores for confirmed trisomy 13 samples (p=0.31; paired wilcox test). There were no statistically significant differences in chromosome 21, chromosome 18, or chromosome 13 z-scores for non-aneuploid samples (p=0.06, p=0.90, p=0.82, respectively; paired wilcox test). This significant increase in aneuploid z-scores without significantly impacting euploid samples further indicates an expansion of the analytical distance between euploid and aneuploid samples for chromosomes 21 and 18 when using the high-throughput assay configuration and new bioinformatic methods.

Discussion

The development presented here was preceded by research activities and followed by additional verification and validation studies conducted in a CLIA-certified laboratory. In total, the entire process of bringing a new laboratory test from research through validation was supported by data from over 5000 tested samples. In this study, more than 3400 samples we sequenced during research, optimization and development. A clinical evaluation study was then performed utilizing 1269 samples, of which we detected all 176 aneuploid samples while maintaining a false positive rate of 0.08% or less for each trisomy.

An assay was developed which enables a 4-fold increase in library preparation throughput and coupled that to a 3-fold increase in sample multiplexing to allow for high-throughput ccf DNA sample processing. While using these methods in combination with improved analytics, sensitivity and specificity for noninvasive aneuploidy detection was improved while decreasing technician and instrument requirements. Overall, these data suggest that the developed high-throughput assay is technically robust and clinically accurate enabling detection of all tested fetal aneuploidies (176/176) with a low false positive rate (0.08%).

TABLE 7

Summary of sample types utilized for each of the studies performed.

| | Number of Samples By Karyotype | | | | |
|---|---|---|---|---|---|
| Study Description | Unknown | Euploid | Trisomy 21 | Trisomy 13 | Trisomy 18 |
| Library Optimization | 0 | 83 | 10 | 0 | 0 |
| 12plex Sequencing | 0 | 1629 | 205 | 12 | 54 |
| Verification | 1587 | 1093 | 134 | 6 | 36 |

TABLE 8

Summary of analysis results for each of the studies performed.

| | Analysis Results By Chromosome | | | | | | |
|---|---|---|---|---|---|---|---|
| Study Description | Spec Chr21 | Sens Chr21 | Spec Chr13 | Sens Chr13 | Spec Chr 18 | Sens Chr18 | Analysis Method |
| Library Optimization | 100 | 100 | NA | NA | NA | NA | GCRM |
| 12plex Sequencing | 100 | 99.5 | 99.84 | 91.7 | 99.74 | 100 | GCRM |
| Verification | 99.92 | 100 | 99.92 | 100 | 100 | 100 | New |

Sens = sensitivity;
Spec = specificity;
NA = Not applicable

Example 5

Examples of Embodiments

A1. A method for detecting the presence or absence of a fetal aneuploidy, comprising:
 (a) obtaining nucleotide sequence reads from sample nucleic acid comprising circulating, cell-free nucleic acid from a pregnant female;
 (b) mapping the nucleotide sequence reads to reference genome sections;
 (c) counting the number of nucleotide sequence reads mapped to each reference genome section, thereby obtaining counts;
 (d) normalizing the counts for a first genome section, or normalizing a derivative of the counts for the first genome section, according to an expected count, or derivative of the expected count, thereby obtaining a normalized sample count,
 which expected count, or derivative of the expected count, is obtained for a group comprising samples, references, or samples and references, exposed to one or more common experimental conditions; and (e) providing an outcome determinative of the presence or absence of a fetal aneuploidy based on the normalized sample count.

A2. A method for detecting the presence or absence of a fetal aneuploidy, comprising:
  (a) obtaining a sample comprising circulating, cell-free nucleic acid from a pregnant female;
  (b) isolating sample nucleic acid from the sample;
  (c) obtaining nucleotide sequence reads from a sample nucleic acid;
  (d) mapping the nucleotide sequence reads to reference genome sections,
  (e) counting the number of nucleotide sequence reads mapped to each reference genome section, thereby obtaining counts;
  (f) normalizing the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (g) providing an outcome determinative of the presence or absence of a fetal aneuploidy based on the normalized sample count.

A3. A method for detecting the presence or absence of a fetal aneuploidy, comprising:
  (a) mapping to reference genome sections nucleotide sequence reads obtained from sample nucleic acid comprising circulating, cell-free nucleic acid from a pregnant female;
  (b) counting the number of nucleotide sequence reads mapped to each reference genome section, thereby obtaining counts;
  (c) normalizing the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (d) providing an outcome determinative of the presence or absence of a fetal aneuploidy based on the normalized sample count.

A3.1. A method for detecting the presence or absence of a fetal aneuploidy, comprising:
  (a) obtaining counts of nucleotide sequence reads mapped to reference genome sections, wherein the nucleotide sequence reads are obtained from sample nucleic acid comprising circulating, cell-free nucleic acid from a pregnant female;
  (b) normalizing the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (c) detecting the presence or absence of a fetal aneuploidy based on the normalized sample count.

A4. The method of any one of embodiments A1 to A3.1, wherein the sample nucleic acid is from blood plasma from the pregnant female.

A5. The method of any one of embodiments A1 to A3.1, wherein the sample nucleic acid is from blood serum from the pregnant female.

A6. The method of any one of embodiments A1 to A3.1, wherein the fetal aneuploidy is trisomy 13.

A7. The method of any one of embodiments A1 to A3.1, wherein the fetal aneuploidy is trisomy 18.

A8. The method of any one of embodiments A1 to A3.1, wherein the fetal aneuploidy is trisomy 21.

A9. The method of any one of embodiments A1 to A3.1, wherein the sequence reads of the cell-free sample nucleic acid are in the form of polynucleotide fragments.

A10. The method of embodiment A9, wherein the polynucleotide fragments are between about 20 and about 50 nucleotides in length.

A11. The method of embodiment A10, wherein the polynucleotides are between about 30 to about 40 nucleotides in length.

A12. The method of any one of embodiments A1 to A11, wherein the expected count is a median count.

A13. The method of any one of embodiments A1 to A11, wherein the expected count is a trimmed or truncated mean, Winsorized mean or bootstrapped estimate.

A14. The method of any one of embodiments A1 to A13, wherein the counts are normalized by GC content, bin-wise normalization, GC LOESS, PERUN, GCRM, or combinations thereof.

A15. The method of any one of embodiments A1 to A14, wherein the counts are normalized by a normalization module.

A16. The method of any one of embodiments A1 to A15, wherein the nucleic acid sequence reads are generated by a sequencing module.

A17. The method of any one of embodiments A1 to A16, which comprises mapping the nucleic acid sequence reads to the genomic sections of a reference genome or to an entire reference genome.

A18. The method of embodiment A17, wherein the nucleic acid sequence reads are mapped by a mapping module.

A19. The method of any one of embodiments A1 to A18, wherein the nucleic acid sequence reads mapped to the genomic sections of the reference genome are counted by a counting module.

A20. The method of embodiment A18 or A19, wherein the sequence reads are transferred to the mapping module from the sequencing module.

A21. The method of embodiment A19 or A20, wherein the nucleic acid sequence reads mapped to the genomic sections of the reference genome are transferred to the counting module from the mapping module.

A22. The method of any one of embodiments A19 to A21, wherein the counts of the nucleic acid sequence reads mapped to the genomic sections of the reference genome are transferred to the normalization module from the counting module.

A23. The method of any one of embodiments A1 to A22, wherein the normalizing the counts comprises determining a percent representation.

A24. The method of any one of embodiments A1 to A23, wherein the normalized count is a z-score.

A25. The method of any one of embodiments A1 to A24, wherein the normalized count is a robust z-score.

A26. The method of any one of embodiments A1 to A25, wherein the derivative of the counts for the first genomic section is a percent representation of the first genomic section.

A27. The method of any one of embodiments A12 to A26, wherein the median is a median of a percent representation.

A28. The method of any one of embodiments A23 to A27, wherein the percent representation is a chromosomal representation.

B1. A method for detecting the presence or absence of a genetic variation, comprising:
  (a) obtaining nucleotide sequence reads from sample nucleic acid comprising circulating, cell-free nucleic acid from a test subject;
  (b) mapping the nucleotide sequence reads to reference genome sections;
  (c) counting the number of nucleotide sequence reads mapped to each reference genome section, thereby obtaining counts;
  (d) normalizing the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (e) providing an outcome determinative of the presence or absence of a genetic variation in the test subject based on the normalized sample count.

B2. A method for detecting the presence or absence of a genetic variation, comprising:
  (a) obtaining a sample comprising circulating, cell-free nucleic acid from a test subject;
  (b) isolating sample nucleic acid from the sample;
  (c) obtaining nucleotide sequence reads from a sample nucleic acid;
  (d) mapping the nucleotide sequence reads to reference genome sections,
  (e) counting the number of nucleotide sequence reads mapped to each reference genome section, thereby obtaining counts;
  (f) normalizing the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (g) providing an outcome determinative of the presence or absence of a genetic variation in the test subject based on the normalized sample count.

B3. A method for detecting the presence or absence of a genetic variation, comprising:
  (a) mapping to reference genome sections nucleotide sequence reads obtained from sample nucleic acid comprising circulating, cell-free nucleic acid from a test subject;
  (b) counting the number of nucleotide sequence reads mapped to each reference genome section, thereby obtaining counts;
  (c) normalizing the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (d) providing an outcome determinative of the presence or absence of a genetic variation in the test subject based on the normalized sample count.

B3.1. A method for detecting the presence or absence of a genetic variation, comprising:
  (a) obtaining counts of nucleotide sequence reads mapped to a reference genome section, wherein the reads are obtained from sample nucleic acid comprising circulating, cell-free nucleic acid from a test subject;
  (c) normalizing the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (d) providing an outcome determinative of the presence or absence of a genetic variation in the test subject based on the normalized sample count.

B4. The method of any one of embodiments B1 to B3.1, wherein the sample nucleic acid is from blood plasma from the test subject.

B5. The method of any one of embodiments B1 to B3.1, wherein the sample nucleic acid is from blood serum from the test subject.

B6. The method of any one of embodiments B1 to B5, wherein the genetic variation is associated with a medical condition.

B7. The method of embodiment B6, wherein the medical condition is cancer.

B8. The method of embodiment B6, wherein the medical condition is an aneuploidy.

B9. The method of any one of embodiments B1 to B5, wherein the test subject is chosen from a human, an animal, and a plant.

B10. The method of embodiment B9, wherein a human test subject comprises a female, a pregnant female, a male, a fetus, or a newborn.

B11. The method of any one of embodiments B1 to B5, wherein the sequence reads of the cell-free sample nucleic acid are in the form of polynucleotide fragments.

B12. The method of embodiment B11, wherein the polynucleotide fragments are between about 20 and about 50 nucleotides in length.

B13. The method of embodiment B12, wherein the polynucleotides are between about 30 to about 40 nucleotides in length.

B14. The method of any one of embodiments B1 to B13, wherein the expected count is a median count.

B15. The method of any one of embodiments B1 to B13, wherein the expected count is a trimmed or truncated mean, Winsorized mean or bootstrapped estimate.

B14. The method of any one of embodiments B1 to B13, wherein the counts are normalized by GC content, bin-wise normalization, GC LOESS, PERUN, GCRM, or combinations thereof.

B15. The method of any one of embodiments B1 to B14, wherein the counts are normalized by a normalization module.

B16. The method of any one of embodiments B1 to B15, wherein the nucleic acid sequence reads are generated by a sequencing module.

B17. The method of any one of embodiments B1 to B16, which comprises mapping the nucleic acid sequence reads to the genomic sections of a reference genome or to an entire reference genome.

B18. The method of embodiment B17, wherein the nucleic acid sequence reads are mapped by a mapping module.

B19. The method of any one of embodiments B1 to B18, wherein the nucleic acid sequence reads mapped to the genomic sections of the reference genome are counted by a counting module.

B20. The method of embodiment B18 or B19, wherein the sequence reads are transferred to the mapping module from the sequencing module.

B21. The method of embodiment B19 or B20, wherein the nucleic acid sequence reads mapped to the genomic sections of the reference genome are transferred to the counting module from the mapping module.

B22. The method of any one of embodiments B19 to B21, wherein the counts of the nucleic acid sequence reads mapped to the genomic sections of the reference genome are transferred to the normalization module from the counting module.

B23. The method of any one of embodiments B1 to B22, wherein the normalizing the counts comprises determining a percent representation.

B24. The method of any one of embodiments B1 to B23, wherein the normalized count is a z-score.

B25. The method of any one of embodiments B1 to B24, wherein the normalized count is a robust z-score.

B26. The method of any one of embodiments B1 to B25, wherein the derivative of the counts for the first genomic section is a percent representation of the first genomic section.

B27. The method of any one of embodiments B12 to B26, wherein the median is a median of a percent representation.

B28. The method of any one of embodiments B23 to B27, wherein the percent representation is a chromosomal representation.

C1. A method for detecting the presence or absence of a genetic variation, comprising:
(a) obtaining nucleotide sequence reads from sample nucleic acid comprising circulating, cell-free nucleic acid from a test subject;
(b) mapping the nucleotide sequence reads to reference genome sections;
(c) counting the number of nucleotide sequence reads mapped to each reference genome section, thereby obtaining counts;
(d) adjusting the counted, mapped sequence reads in (c) according to a selected variable or feature,
which selected feature or variable minimizes or eliminates the effect of repetitive sequences and/or over or under represented sequences;
(e) normalizing the remaining counts in (d) for a first genome section, or normalizing a derivative of the counts for the first genome section, according to an expected count, or derivative of the expected count, thereby obtaining a normalized sample count,
which expected count, or derivative of the expected count, is obtained for a group comprising samples, references, or samples and references, exposed to one or more common experimental conditions;
(f) evaluating the statistical significance of differences between the normalized counts or a derivative of the normalized counts for the test subject and reference subjects for one or more selected genomic sections; and
(g) providing an outcome determinative of the presence or absence of a genetic variation in the test subject based on the evaluation in (f).

C2. A method for detecting the presence or absence of a genetic variation, comprising:
(a) obtaining a sample comprising circulating, cell-free nucleic acid from a test subject;
(b) isolating sample nucleic acid from the sample;
(c) obtaining nucleotide sequence reads from a sample nucleic acid;
(d) mapping the nucleotide sequence reads to reference genome sections,
(e) counting the number of nucleotide sequence reads mapped to each reference genome section, thereby obtaining counts;
(f) adjusting the counted, mapped sequence reads in (e) according to a selected variable or feature,
which selected feature or variable minimizes or eliminates the effect of repetitive sequences and/or over or under represented sequences;
(g) normalizing the remaining counts in (f) for a first genome section, or normalizing a derivative of the counts for the first genome section, according to an expected count, or derivative of the expected count, thereby obtaining a normalized sample count,
which expected count, or derivative of the expected count, is obtained for a group comprising samples, references, or samples and references, exposed to one or more common experimental conditions;
(h) evaluating the statistical significance of differences between the normalized counts or a derivative of the normalized counts for the test subject and reference subjects for one or more selected genomic sections; and
(i) providing an outcome determinative of the presence or absence of a genetic variation in the test subject based on the evaluation in (h).

C3. A method for detecting the presence or absence of a genetic variation, comprising:
(a) mapping to reference genome sections nucleotide sequence reads obtained from sample nucleic acid comprising circulating, cell-free nucleic acid from a test subject;
(b) counting the number of nucleotide sequence reads mapped to each reference genome section, thereby obtaining counts;
(c) adjusting the counted, mapped sequence reads in (b) according to a selected variable or feature,
which selected feature or variable minimizes or eliminates the effect of repetitive sequences and/or over or under represented sequences;
(d) normalizing the remaining counts in (c) for a first genome section, or normalizing a derivative of the counts for the first genome section, according to an expected count, or derivative of the expected count, thereby obtaining a normalized sample count,
which expected count, or derivative of the expected count, is obtained for a group comprising samples, references, or samples and references, exposed to one or more common experimental conditions;
(e) evaluating the statistical significance of differences between the normalized counts or a derivative of the normalized counts for the test subject and reference subjects for one or more selected genomic sections; and
(f) providing an outcome determinative of the presence or absence of a genetic variation in the test subject based on the evaluation in (e).

C3.1 A method for detecting the presence or absence of a genetic variation, comprising:
(a) obtaining counts of nucleotide sequence reads mapped to a reference genome section, wherein the reads are obtained from sample nucleic acid comprising circulating, cell-free nucleic acid from a test subject;
(b) adjusting the counted, mapped sequence reads in (a) according to a selected variable or feature, which selected feature or variable minimizes or eliminates the effect of repetitive sequences and/or over or under represented sequences;
(c) normalizing the remaining counts in (b) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions;
(d) evaluating the statistical significance of differences between the normalized counts or a derivative of the normalized counts for the test subject and reference subjects for one or more selected genomic sections; and
(e) providing an outcome determinative of the presence or absence of a genetic variation in the test subject based on the evaluation in (d).

C4. The method of any one of embodiments C1 to C3.1, wherein the adjusted, counted, mapped sequence reads are further adjusted for one or more experimental conditions prior to normalizing the remaining counts.

C5. The method of any one of embodiments C1 to C4, wherein the genetic variation is a microdeletion.

C6. The method of embodiment C5, wherein the microdeletion is on Chromosome 22.

C7. The method of embodiment C6, wherein the microdeletion occurs in Chromosome 22 region 22q11.2.

C8. The method of embodiment C6, wherein the microdeletion occurs on Chromosome 22 between nucleotide positions 19,000,000 and 22,000,000 according to reference genome hg19.

C9. The method of anyone of embodiments C1 to C8, wherein a derivative of the normalized counts is a Z-score.

C10. The method of embodiment C9, wherein the Z-score is a robust Z-score.

C11. The method of any one of embodiments C1 to C10, wherein the sample nucleic acid is from blood plasma from the test subject.

C12. The method of any one of embodiments C1 to C10, wherein the sample nucleic acid is from blood serum from the test subject.

C13. The method of any one of embodiments C1 to C12, wherein the genetic variation is associated with a medical condition.

C14. The method of embodiment C13, wherein the medical condition is cancer.

C15. The method of embodiment C13, wherein the medical condition is an aneuploidy.

C16. The method of any one of embodiments C1 to C12, wherein the test subject is chosen from a human, an animal, and a plant.

C17. The method of embodiment C16, wherein a human test subject comprises a female, a pregnant female, a male, a fetus, or a newborn.

C18. The method of any one of embodiments C1 to C12, wherein the sequence reads of the cell-free sample nucleic acid are in the form of polynucleotide fragments.

C19. The method of embodiment C18, wherein the polynucleotide fragments are between about 20 and about 50 nucleotides in length.

C20. The method of embodiment C19, wherein the polynucleotides are between about 30 to about 40 nucleotides in length.

C21. The method of any one of embodiments C1 to C20, wherein the expected count is a median count.

C22. The method of any one of embodiments C1 to C20, wherein the expected count is a trimmed or truncated mean, Winsorized mean or bootstrapped estimate.

C23. The method of any one of embodiments C1 to C22, wherein the counts are normalized by GC content, bin-wise normalization, GC LOESS, PERUN, GCRM, or combinations thereof.

C24. The method of any one of embodiments C1 to C23, wherein the counts are normalized by a normalization module.

C25. The method of any one of embodiments C1 to C24, wherein the nucleic acid sequence reads are generated by a sequencing module.

C26. The method of any one of embodiments C1 to C25, which comprises mapping the nucleic acid sequence reads to the genomic sections of a reference genome or to an entire reference genome.

C27. The method of embodiment C26, wherein the nucleic acid sequence reads are mapped by a mapping module.

C28. The method of any one of embodiments C1 to C27, wherein the nucleic acid sequence reads mapped to the genomic sections of the reference genome are counted by a counting module.

C29. The method of embodiment C27 or C28, wherein the sequence reads are transferred to the mapping module from the sequencing module.

C30. The method of embodiment C28 or C29, wherein the nucleic acid sequence reads mapped to the genomic sections of the reference genome are transferred to the counting module from the mapping module.

C31. The method of any one of embodiments C28 to C30, wherein the counts of the nucleic acid sequence reads mapped to the genomic sections of the reference genome are transferred to the normalization module from the counting module.

C32. The method of any one of embodiments C1 to C31, wherein the normalizing the counts comprises determining a percent representation.

C33. The method of any one of embodiments C1 to C32, wherein the normalized count is a z-score.

C34. The method of any one of embodiments C1 to C33, wherein the normalized count is a robust z-score.

C35. The method of any one of embodiments C1 to C34, wherein the derivative of the counts for the first genomic section is a percent representation of the first genomic section.

C36. The method of any one of embodiments C21 to C35, wherein the median is a median of a percent representation.

C37. The method of any one of embodiments C32 to C36, wherein the percent representation is a chromosomal representation.

D1. A method for detecting the presence or absence of a microdeletion, comprising:
- (a) obtaining nucleotide sequence reads from sample nucleic acid comprising circulating, cell-free nucleic acid from a test subject;
- (b) mapping the nucleotide sequence reads to reference genome sections;
- (c) counting the number of nucleotide sequence reads mapped to each reference genome section, thereby obtaining counts;
- (d) adjusting the counted, mapped sequence reads in (c) according to a selected variable or feature, which selected feature or variable minimizes or eliminates the effect of repetitive sequences and/or over or under represented sequences;
- (e) normalizing the remaining counts in (d) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions;
- (f) evaluating the statistical significance of differences between the normalized counts or a derivative of the normalized counts for the test subject and reference subjects for one or more selected genomic sections; and
- (g) providing an outcome determinative of the presence or absence of a genetic variation in the test subject based on the evaluation in (f).

D2. A method for detecting the presence or absence of a microdeletion, comprising:
- (a) obtaining a sample comprising circulating, cell-free nucleic acid from a test subject;
- (b) isolating sample nucleic acid from the sample;
- (c) obtaining nucleotide sequence reads from a sample nucleic acid;
- (d) mapping the nucleotide sequence reads to reference genome sections,
- (e) counting the number of nucleotide sequence reads mapped to each reference genome section, thereby obtaining counts;
- (f) adjusting the counted, mapped sequence reads in (e) according to a selected variable or feature, which selected feature or variable minimizes or eliminates the effect of repetitive sequences and/or over or under represented sequences;
- (g) normalizing the remaining counts in (f) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions;
- (h) evaluating the statistical significance of differences between the normalized counts or a derivative of the normalized counts for the test subject and reference subjects for one or more selected genomic sections; and
- (i) providing an outcome determinative of the presence or absence of a genetic variation in the test subject based on the evaluation in (h).

D3. A method for detecting the presence or absence of a microdeletion, comprising:
- (a) mapping to reference genome sections nucleotide sequence reads obtained from sample nucleic acid comprising circulating, cell-free nucleic acid from a test subject;
- (b) counting the number of nucleotide sequence reads mapped to each reference genome section, thereby obtaining counts;
- (c) adjusting the counted, mapped sequence reads in (b) according to a selected variable or feature, which selected feature or variable minimizes or eliminates the effect of repetitive sequences and/or over or under represented sequences;
- (d) normalizing the remaining counts in (c) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions;
- (e) evaluating the statistical significance of differences between the normalized counts or a derivative of the normalized counts for the test subject and reference subjects for one or more selected genomic sections; and
- (f) providing an outcome determinative of the presence or absence of a genetic variation in the test subject based on the evaluation in (e).

D3.1. A method for detecting the presence or absence of a microdeletion, comprising:
- (a) obtaining counts of nucleotide sequence reads mapped to a reference genome section, wherein the nucleotide sequence reads are obtained from sample nucleic acid comprising circulating, cell-free nucleic acid from a test subject;
- (b) adjusting the counted, mapped sequence reads in (a) according to a selected variable or feature, which selected feature or variable minimizes or eliminates the effect of repetitive sequences and/or over or under represented sequences;
- (c) normalizing the remaining counts in (b) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions;
- (d) evaluating the statistical significance of differences between the normalized counts or a derivative of the normalized counts for the test subject and reference subjects for one or more selected genomic sections; and
- (e) providing an outcome determinative of the presence or absence of a genetic variation in the test subject based on the evaluation in (d).

D4. The method of any one of embodiments D1 to D3.1, wherein the adjusted, counted, mapped sequence reads are further adjusted for one or more experimental conditions prior to normalizing the remaining counts.

D5. The method of embodiment D4, wherein the microdeletion is on Chromosome 22.

D6. The method of embodiment D5, wherein the microdeletion occurs in Chromosome 22 region 22q11.2.

D7. The method of embodiment D5, wherein the microdeletion occurs on Chromosome 22 between nucleotide positions 19,000,000 and 22,000,000 according to reference genome hg19.

D8. The method of anyone of embodiments D1 to D8, wherein a derivative of the normalized counts is a Z-score.

D9. The method of embodiment D8, wherein the Z-score is a robust Z-score.

D10. The method of any one of embodiments D1 to D9, wherein the sample nucleic acid is from blood plasma from the test subject.

D11. The method of any one of embodiments D1 to D9, wherein the sample nucleic acid is from blood serum from the test subject.

D12. The method of any one of embodiments D1 to D11, wherein the genetic variation is associated with a medical condition.

D13. The method of embodiment D12, wherein the medical condition is cancer.

D14. The method of embodiment D12, wherein the medical condition is an aneuploidy.

D15. The method of any one of embodiments D1 to D11, wherein the test subject is chosen from a human, an animal, and a plant.

D16. The method of embodiment D15, wherein a human test subject comprises a female, a pregnant female, a male, a fetus, or a newborn.

D17. The method of any one of embodiments D1 to D11, wherein the sequence reads of the cell-free sample nucleic acid are in the form of polynucleotide fragments.

D18. The method of embodiment D17, wherein the polynucleotide fragments are between about 20 and about 50 nucleotides in length.

D19. The method of embodiment D18, wherein the polynucleotides are between about 30 to about 40 nucleotides in length.

D20. The method of any one of embodiments D1 to D19, wherein the expected count is a median count.

D21. The method of any one of embodiments D1 to D19, wherein the expected count is a trimmed or truncated mean, Winsorized mean or bootstrapped estimate.

D22. The method of any one of embodiments D1 to D21, wherein the counts are normalized by GC content, bin-wise normalization, GC LOESS, PERUN, GCRM, or combinations thereof.

D23. The method of any one of embodiments D1 to D22, wherein the counts are normalized by a normalization module.

D24. The method of any one of embodiments D1 to D23, wherein the nucleic acid sequence reads are generated by a sequencing module.

D25. The method of any one of embodiments D1 to D24, which comprises mapping the nucleic acid sequence reads to the genomic sections of a reference genome or to an entire reference genome.

D26. The method of embodiment D25, wherein the nucleic acid sequence reads are mapped by a mapping module.

D27. The method of any one of embodiments D1 to D26, wherein the nucleic acid sequence reads mapped to the genomic sections of the reference genome are counted by a counting module.

D28. The method of embodiment D26 or D27, wherein the sequence reads are transferred to the mapping module from the sequencing module.

D29. The method of embodiment D27 or D28, wherein the nucleic acid sequence reads mapped to the genomic sections of the reference genome are transferred to the counting module from the mapping module.

D30. The method of any one of embodiments D27 to D29, wherein the counts of the nucleic acid sequence reads mapped to the genomic sections of the reference genome are transferred to the normalization module from the counting module.

D31. The method of any one of embodiments D1 to D30, wherein the normalizing the counts comprises determining a percent representation.

D32. The method of any one of embodiments D1 to D31, wherein the normalized count is a z-score.

D33. The method of any one of embodiments D1 to D32, wherein the normalized count is a robust z-score.

D34. The method of any one of embodiments D1 to D33, wherein the derivative of the counts for the first genomic section is a percent representation of the first genomic section.

D35. The method of any one of embodiments D20 to D34, wherein the median is a median of a percent representation.

D36. The method of any one of embodiments D31 to D35, wherein the percent representation is a chromosomal representation.

E1. The method of any one of embodiments A1 to D21, wherein the normalized sample count is obtained by a process that comprises normalizing the derivative of the counts for the first genome section, which derivative is a first genome section count representation determined by dividing the counts for the first genome section by the counts for multiple genome sections that include the first genome section.

E2. The method of embodiment E1, wherein the derivative of the counts for the first genome section is normalized according to a derivative of the expected count, which derivative of the expected count is an expected first genome section count representation determined by dividing the expected count for the first genome section by the expected count for multiple genome sections that include the first genome section.

E3. The method of any one of embodiments A1 to E2, wherein the first genome section is a chromosome or part of a chromosome and the multiple genome sections comprises autosomes.

E4. The method of embodiment E3, wherein the chromosome is chromosome 21, chromosome 18 or chromosome 13.

E5. The method of any one of embodiments A1 to D21, E3 and E4, wherein the normalized sample count is obtained by a process comprising subtracting the expected count from the counts for the first genome section, thereby generating a subtraction value, and dividing the subtraction value by an estimate of the variability of the count.

E5.1. The method of embodiment E5, wherein the estimate of the variability of the expected count is a median absolute deviation (MAD) of the count.

E5.2. The method of embodiment E5, wherein the estimate of the variability of the count is an alternative to MAD as introduced by Rousseeuw and Croux or a bootstrapped estimate.

E5.3. The method of any one of embodiments E5 to E5.2, wherein the estimate of the variability is obtained for sample data generated from one or more common experimental conditions.

E5.4. The method of any one of embodiments E5 to E5.2, wherein the estimate of the variability is obtained for sample data not generated from one or more common experimental conditions.

E5.5 The method of any one of embodiments E5 to E5.4, wherein the estimate of the variability and the expected count is obtained for sample data generated from one or more common experimental conditions.

E6. The method of any one of embodiments A1 to E4, wherein the normalized sample count is obtained by a process comprising subtracting the expected first genome section count representation from the first genome section count representation, thereby generating a subtraction value, and dividing the subtraction value by an estimate of the variability of the first genome section count representation.

E6.1. The method of embodiment E6, wherein the estimate of the variability of the expected count representation is a median absolute deviation (MAD) of the count representation.

E6.2. The method of embodiment E6, wherein the estimate of the variability of the count representation is an alternative to MAD as introduced by Rousseeuw and Crous or a bootstrapped estimate.

E6.3. The method of any one of embodiment E6 to E6.2, wherein the estimate of the variability of the expected count representation is obtained for sample data generated from one or more common experimental conditions.

E6.4. The method of any one of embodiment E6 to E6.2, wherein the estimate of the variability of the expected count representation is obtained for sample data not generated from one or more common experimental conditions.

E6.5 The method of any one of embodiment E6 to E6.4, wherein the estimate of the variability of the expected count representation and the expected first genome section count representation is obtained for sample data generated from one or more common experimental conditions.

E7. The method of any one of embodiments A1 to E6.6, wherein the one or more common experimental conditions comprise a flow cell.

E8. The method of any one of embodiments A1 to E6.6, wherein the one or more common experimental conditions comprise a channel in a flow cell.

E9. The method of any one of embodiments A1 to E6.6, wherein the one or more common experimental conditions comprise a reagent plate.

E9.1. The method of embodiment E9, wherein the reagent plate is used to stage nucleic acid for sequencing.

E9.2. The method of embodiment E9, wherein the reagent plate is used to prepare a nucleic acid library for sequencing.

E10. The method of any one of embodiments A1 to E6.6, wherein the one or more common experimental conditions comprise an identification tag index.

E11. The method of any one of embodiments A1 to E10, wherein the normalized sample count is adjusted for guanine and cytosine content of the nucleotide sequence reads or of the sample nucleic acid.

E12. The method of embodiment E11, comprising subjecting the counts or the normalized sample count to a locally weighted polynomial regression.

E12.1 The method of embodiment E12, wherein the locally weighted polynomial regression is a LOESS regression.

E13. The method of any one of embodiments A1 to E12, wherein the normalized sample count is adjusted for nucleotide sequences that repeat in the reference genome sections.

E14. The method of embodiment E13, wherein the counts or the normalized sample count are adjusted for nucleotide sequences that repeat in the reference genome sections.

E15. The method of any one of embodiments A1 to E14, which comprises filtering the counts before obtaining the normalized sample count.

E16. The method of any one of embodiments A1 to E15, wherein the sample nucleic acid comprises single stranded nucleic acid.

E17. The method of any one of embodiments A1 to E15, wherein the sample nucleic acid comprises double stranded nucleic acid.

E18. The method of any one of embodiments A1 to E17, wherein obtaining the nucleotide sequence reads includes subjecting the sample nucleic acid to a sequencing process using a sequencing device.

E19. The method of any one of embodiments A1 to E18, wherein providing an outcome comprises factoring the fraction of fetal nucleic acid in the sample nucleic acid.

E20. The method of any one of embodiments A1 to E19, which comprises determining the fraction of fetal nucleic acid in the sample nucleic acid.

E21. The method of any one of embodiments A1 to E20, wherein the normalized sample count is obtained without adjusting for guanine and cytosine content of the nucleotide sequence reads or of the sample nucleic acid.

E22. The method of any one of embodiments A1 to E20, wherein the normalized sample count is obtained for one experimental condition.

E23. The method of embodiment E22, wherein the experimental condition is flow cell.

E24. The method of any one of embodiments A1 to E20, wherein the normalized sample count is obtained for two experimental conditions.

E25. The method of embodiment E24, wherein the experimental conditions are flow cell and reagent plate.

E26. The method of embodiment E24, wherein the experimental conditions are flow cell and identification tag index.

E27. The method of any one of embodiments A1 to E20, wherein the normalized sample count is obtained for three experimental conditions.

E28. The method of embodiment E27, wherein the experimental conditions are flow cell, reagent plate and identification tag index.

E29. The method of any one of embodiments A1 to E20, wherein the normalized sample count is obtained after (i) adjustment according to guanine and cytosine content, and after (i), (ii) adjustment according to an experimental condition.

E30. The method of embodiment E29, wherein the normalized sample count is obtained after adjustment according to nucleotide sequences that repeat in the reference genome sections prior to (i).

E31. The method of embodiment E29 or E30, wherein (ii) consists of adjustment according to flow cell.

E32. The method of embodiment E29 or E30, wherein (ii) consists of adjustment according to identification tag index and then adjustment according to flow cell.

E33. The method of embodiment E29 or E30, wherein (ii) consists of adjustment according to reagent plate and then adjustment according to flow cell.

E34. The method of embodiment E29 or E30, wherein (ii) consists of adjustment according to identification tag index and reagent plate and then adjustment according to flow cell.

E35. The method of embodiment E21, wherein the normalized sample count is obtained after adjustment according to an experimental condition consisting of adjustment according to flow cell.

E36. The method of embodiment E21, wherein the normalized sample count is obtained after adjustment according to an experimental condition consisting of adjustment according to identification tag index and then adjustment according to flow cell.

E37. The method of embodiment E21, wherein the normalized sample count is obtained after adjustment according to an experimental condition consisting of adjustment according to reagent plate and then adjustment according to flow cell.

E38. The method of embodiment E21, wherein the normalized sample count is obtained after adjustment according to an experimental condition consisting of adjustment according to identification tag index and reagent plate and then adjustment according to flow cell.

E39. The method of any one of embodiments E32 to E38, wherein the normalized sample count is obtained after adjustment according to nucleotide sequences that repeat in the reference genome sections prior to adjustment according to the experimental condition.

E40. The method of any one of embodiments E1 to E38, wherein the normalized sample count is a Z-score.

E41. The method of any one of embodiments E29 to E40, wherein (i) comprises:
  (a) determining a guanine and cytosine (GC) bias for each of the portions of the reference genome for multiple samples from a fitted relation for each sample between (i) the counts of the sequence reads mapped to each of the portions of the reference genome, and (ii) GC content for each of the portions; and
  (b) calculating a genomic section elevation for each of the portions of the reference genome from a fitted relation between (i) the GC bias and (ii) the counts of the sequence reads mapped to each of the portions of the reference genome, thereby providing calculated genomic section elevations, whereby bias in the counts of the sequence reads mapped to each of the portions of the reference genome is reduced in the calculated genomic section elevations.

E42. The method of embodiment E41, wherein the portions of the reference genome are in a chromosome.

E43. The method of embodiment E41, wherein the portions of the reference genome are in a portion of a chromosome.

E44. The method of any one of embodiments E41 to E43, wherein the chromosome is chromosome 21.

E45. The method of any one of embodiments E41 to E43, wherein the chromosome is chromosome 18.

E46. The method of any one of embodiments E41 to E43, wherein the chromosome is chromosome 13.

E47. The method of any one of embodiments E41 to E46, which comprises prior to (b) calculating a measure of error for the counts of sequence reads mapped to some or all of the portions of the reference genome and removing or weighting the counts of sequence reads for certain portions of the reference genome according to a threshold of the measure of error.

E48. The method of embodiment E47, wherein the threshold is selected according to a standard deviation gap between a first genomic section elevation and a second genomic section elevation of 3.5 or greater.

E49. The method of embodiment E47 or E48, wherein the measure of error is an R factor.

E50. The method of embodiment E49, wherein the counts of sequence reads for a portion of the reference genome having an R factor of about 7% to about 10% are removed prior to (b).

E51. The method of any one of embodiments E41 to E50, wherein the fitted relation in (b) is a fitted linear relation.

E52. The method of claim E 51, wherein the slope of the relation is determined by linear regression.

E53. The method of claim E 51 or E52, wherein each GC bias is a GC bias coefficient, which GC bias coefficient is the slope of the linear relationship between (i) the counts of the sequence reads mapped to each of the portions of the reference genome, and (ii) the GC content for each of the portions.

E54. The method of any one of embodiments E 41 to E50, wherein the fitted relation in (b) is a fitted non-linear relation.

E55. The method of embodiment E54, wherein each GC bias comprises a GC curvature estimation.

E56. The method of any one of embodiments E41 to E55, wherein the fitted relation in (c) is linear.

E57. The method of embodiment E56, wherein the slope of the relation is determined by linear regression.

E58. The method of any one of embodiments E41 to E57, wherein the fitted relation in (b) is linear, the fitted relation in (c) is linear and the genomic section elevation $L_i$ is determined for each of the portions of the reference genome according to Equation α:

$$L_i = (m_i - G_i S) I^{-1} \qquad \text{Equation } \alpha$$

wherein $G_i$ is the GC bias, I is the intercept of the fitted relation in (c), S is the slope of the relation in (c), $m_i$ is measured counts mapped to each portion of the reference genome and i is a sample.

E59. The method of any one of embodiments E41 to E58, wherein the number of portions of the reference genome is about 40,000 or more portions.

E60. The method of any one of embodiments E41 to E59, wherein each portion of the reference genome comprises a nucleotide sequence of a predetermined length.

E61. The method of embodiment E60, wherein the predetermined length is about 50 kilobases.

E62. The method of any one of embodiments E41 to E61, wherein the GC bias in (b) is determined by a GC bias module.

F1. A computer program product, comprising a computer usable medium having a computer readable program code embodied therein, the computer readable program code comprising distinct software modules comprising a sequence receiving module, a logic processing module, and a data display organization module, the computer readable program code adapted to be executed to implement a method for identifying the presence or absence of a genetic variation in a sample nucleic acid, the method comprising:
  (a) obtaining, by the sequence receiving module, nucleotide sequence reads from sample nucleic acid;
  (b) mapping, by the logic processing module, the nucleotide sequence reads to reference genome sections;
  (c) counting, by the logic processing module, the number of nucleotide sequence reads mapped to each reference genome section, thereby obtaining counts;
  (d) normalizing, by the logic processing module, the counts for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions;
  (e) generating, by the logic processing module, an outcome determinative of the presence or absence of a genetic variation in the test subject based on the normalized sample count; and (f) organizing, by the data display organization module in response to being determined by the logic processing module, a data display indicating the presence or absence of the genetic variation in the sample nucleic acid.

F2. An apparatus, comprising memory in which a computer program product of embodiment F1 is stored.

F3. The apparatus of embodiment F2, which comprises a processor that implements one or more functions of the computer program product specified in embodiment F1.

F4. A system comprising a nucleic acid sequencing apparatus and a processing apparatus, wherein the sequencing apparatus obtains nucleotide sequence reads from a sample nucleic acid, and the processing apparatus obtains the nucleotide sequence reads from the sequencing apparatus and carries out a method comprising:
  (a) mapping the nucleotide sequence reads to reference genome sections;
  (b) counting the number of nucleotide sequence reads mapped to each reference genome section, thereby obtaining counts;
  (c) normalizing the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (d) providing an outcome determinative of the presence or absence of a genetic variation in the sample nucleic acid based on the normalized sample count.

G1. A method of identifying the presence or absence of a 22q11.2 microdeletion between chromosome 22 nucleotide positions 19,000,000 and 22,000,000 according to human reference genome hg19, the method comprising:
  (a) obtaining a sample comprising circulating, cell-free nucleic acid from a test subject;
  (b) isolating sample nucleic acid from the sample;
  (c) obtaining nucleotide sequence reads from a sample nucleic acid;
  (d) mapping the nucleotide sequence reads to reference genome sections,
  (e) counting the number of nucleotide sequence reads mapped to each reference genome section, thereby obtaining counts;
  (f) adjusting the counted, mapped sequence reads in (e) according to a selected variable or feature,
  which selected feature or variable minimizes or eliminates the effect of repetitive sequences and/or over or under represented sequences;
  (g) normalizing the remaining counts in (f) for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions;
  (h) evaluating the statistical significance of differences between the normalized counts or a derivative of the normalized counts for the test subject and reference subjects for one or more selected genomic sections corresponding to chromosome 22 between nucleotide positions 19,000,000 and 22,000,000; and
  (i) providing an outcome determinative of the presence or absence of a genetic variation in the test subject based on the evaluation in (h).

G2. The method of any one of embodiments F1 to F3, wherein the adjusted, counted, mapped sequence reads are further adjusted for one or more experimental conditions prior to normalizing the remaining counts.

H1. A system comprising one or more processors and memory, which memory comprises instructions executable by the one or more processors and which memory comprises counts of sequence reads mapped to genomic sections of a reference genome, which sequence reads are reads of circulating cell-free nucleic acid from a test sample; and which instructions executable by the one or more processors are configured to:
  (a) normalize the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (b) determine the presence or absence of a fetal aneuploidy based on the normalized sample count.

I1. An apparatus comprising one or more processors and memory, which memory comprises instructions executable by the one or more processors and which memory comprises counts of sequence reads mapped to genomic sections of a reference genome, which sequence reads are reads of circulating cell-free nucleic acid from a test sample; and which instructions executable by the one or more processors are configured to:
  (a) normalize the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (b) determine the presence or absence of a fetal aneuploidy based on the normalized sample count.

J1. A computer program product tangibly embodied on a computer-readable medium, comprising instructions that when executed by one or more processors are configured to:
  (a) access counts of sequence reads mapped to genomic sections of a reference genome, which sequence reads are reads of circulating cell-free nucleic acid from a test sample;
  (b) normalize the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
  (c) determine the presence or absence of a fetal aneuploidy based on the normalized sample count.

K1. A system comprising one or more processors and memory, which memory comprises instructions executable by the one or more processors and which memory comprises counts of sequence reads mapped to genomic sections of a reference genome, which sequence reads are reads of circulating cell-free nucleic acid from a pregnant female bearing a fetus; and which instructions executable by the one or more processors are configured to:
- (a) normalize the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
- (b) determine the presence or absence of a genetic variation in the test subject based on the normalized sample count.

L1. An apparatus comprising one or more processors and memory,
which memory comprises instructions executable by the one or more processors and which memory comprises counts of sequence reads mapped to genomic sections of a reference genome, which sequence reads are reads of circulating cell-free nucleic acid from a pregnant female bearing a fetus; and
which instructions executable by the one or more processors are configured to:
- (a) normalize the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
- (b) determine the presence or absence of a genetic variation in the test subject based on the normalized sample count.

M1. A computer program product tangibly embodied on a computer-readable medium, comprising instructions that when executed by one or more processors are configured to:
- (a) access counts of sequence reads mapped to genomic sections of a reference genome, which sequence reads are reads of circulating cell-free nucleic acid from a pregnant female bearing a fetus;
- (b) normalize the counts for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions; and
- (c) determine the presence or absence of a genetic variation in the test subject based on the normalized sample count.

N1. A system comprising one or more processors and memory,
which memory comprises instructions executable by the one or more processors and which memory comprises counts of sequence reads mapped to genomic sections of a reference genome, which sequence reads are reads of circulating cell-free nucleic acid from a pregnant female bearing a fetus; and
which instructions executable by the one or more processors are configured to:
- (a) adjust the counted, mapped sequence reads in according to a selected variable or feature,
  which selected feature or variable minimizes or eliminates the effect of repetitive sequences and/or over or under represented sequences;
- (b) normalize the remaining counts in (a) for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions;
- (c) evaluate the statistical significance of differences between the normalized counts or a derivative of the normalized counts for the test subject and reference subjects for one or more selected genomic sections; and
- (d) determine the presence or absence of a genetic variation in the test subject based on the evaluation in (c).

O1. An apparatus comprising one or more processors and memory,
which memory comprises instructions executable by the one or more processors and which memory comprises counts of sequence reads mapped to portions of a reference genome, which sequence reads are reads of circulating cell-free nucleic acid from a pregnant female bearing a fetus; and
which instructions executable by the one or more processors are configured to:
- (a) adjust the counted, mapped sequence reads in according to a selected variable or feature,
  which selected feature or variable minimizes or eliminates the effect of repetitive sequences and/or over or under represented sequences;
- (b) normalize the remaining counts in (a) for a first genome section, or normalizing a derivative of the counts for the first genome section, according to an expected count, or derivative of the expected count, thereby obtaining a normalized sample count,
  which expected count, or derivative of the expected count, is obtained for a group comprising samples, references, or samples and references, exposed to one or more common experimental conditions;
- (c) evaluate the statistical significance of differences between the normalized counts or a derivative of the normalized counts for the test subject and reference subjects for one or more selected genomic sections; and
- (d) determine the presence or absence of a genetic variation in the test subject based on the evaluation in (c).

P1. A computer program product tangibly embodied on a computer-readable medium, comprising instructions that when executed by one or more processors are configured to:
- (a) access counts of sequence reads mapped to portions of a reference genome, which sequence reads are reads of circulating cell-free nucleic acid from a test sample;
- (b) adjust the counted, mapped sequence reads in according to a selected variable or feature,
  which selected feature or variable minimizes or eliminates the effect of repetitive sequences and/or over or under represented sequences;
- (c) normalize the remaining counts in (b) for a first genome section, or normalizing a derivative of the counts for the first genome section, according to an expected count, or derivative of the expected count, thereby obtaining a normalized sample count, which expected count, or derivative of the expected count, is obtained for a group comprising samples, references, or samples and references, exposed to one or more common experimental conditions;

(d) evaluate the statistical significance of differences between the normalized counts or a derivative of the normalized counts for the test subject and reference subjects for one or more selected genomic sections; and (e) determine the presence or absence of a genetic variation in the test subject based on the evaluation in (d).

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for sequencing circulating cell-free nucleic acid and adjusting nucleotide sequence read counts comprising:

(a) providing a group of circulating cell-free nucleic acid test samples, wherein each test sample of the group of circulating cell-free nucleic acid test samples is obtained from the blood of a pregnant female to determine the presence or absence of a genetic variation;

(b) sequencing the group of circulating cell-free nucleic acid test samples by a massively parallel sequencer, wherein the group of circulating cell-free nucleic acid test samples is sequenced on a single flow cell, and wherein the group of circulating cell-free nucleic acid test samples is sequenced on the same single flow cell;

(c) generating thousands to millions of nucleotide sequence reads for each test sample of the group of circulating cell-free nucleic acid test samples sequenced on the single flow cell;

(d) mapping the thousands to millions of nucleotide sequence reads for each test sample of the group of circulating cell-free nucleic acid test samples sequenced on the single flow cell to reference genome sections;

(e) counting the thousands to millions of nucleotide sequence reads for each test sample of the group of circulating cell-free nucleic acid test samples sequenced on the single flow cell mapped to the reference genome sections, wherein the reference genome sections are euploid, thereby obtaining counts of the thousands to millions of nucleotide sequence reads mapped to the reference genome sections for each test sample of the group of circulating cell-free nucleic acid test samples sequenced on the single flow cell;

(f) normalizing the counts of the thousands to millions of nucleotide sequence reads for a chromosome for each test sample of the group of circulating cell-free nucleic acid test samples sequenced on the single flow cell according to guanine and cytosine (GC) content, thereby generating a GC-normalized count for the chromosome for each test sample of the group of circulating cell-free nucleic acid test samples sequenced on the single flow cell;

(g) determining an expected count for the chromosome based on the GC-normalized counts obtained in (f), wherein the expected count is a median GC-normalized count for the chromosome for the group of circulating cell-free nucleic acid test samples sequenced on the single flow cell; and (h) adjusting the GC-normalized count for the chromosome for each test sample of the group of circulating cell-free nucleic acid test samples sequenced on the single flow cell according to (1) the GC-normalized count generated in (f), (2) the expected count determined in (g), and (3) a median absolute deviation (MAD) of the expected count, thereby generating an adjusted GC-normalized count for the chromosome, wherein the presence of a genetic variation is determined based on detection of a numerical gain or a numerical loss between the adjusted GC-normalized count for genome sections of the chromosome and the expected count obtained for the reference genome sections of the same chromosome.

2. The method of claim 1, wherein the adjusted GC-normalized count for the chromosome is a z-score or a robust z-score.

3. The method of claim 1, wherein the chromosome is chromosome 21.

4. The method of claim 1, wherein the chromosome is chromosome 18.

5. The method of claim 1, wherein the chromosome is chromosome 13.

\* \* \* \* \*